US011976305B2

(12) United States Patent
Mateo et al.

(10) Patent No.: US 11,976,305 B2

(45) Date of Patent: May 7, 2024

(54) LASSA VACCINE

(71) Applicants: INSTITUT PASTEUR, Paris (FR); CENTRE NATIONAL DE LA RECHERCHE SCIENTIFIQUE, Paris (FR)

(72) Inventors: Mathieu Mateo, Lyons (FR); Sylvain Baize, Lyons (FR); Frédéric Tangy, Les Lilas (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/954,592

(22) PCT Filed: Dec. 20, 2018

(86) PCT No.: PCT/IB2018/001620

§ 371 (c)(1),
(2) Date: Jun. 17, 2020

(87) PCT Pub. No.: WO2019/123018

PCT Pub. Date: Jun. 27, 2019

(65) Prior Publication Data

US 2020/0308555 A1 Oct. 1, 2020

Related U.S. Application Data

(60) Provisional application No. 62/609,155, filed on Dec. 21, 2017.

(51) Int. Cl.

*A61K 39/00* (2006.01)
*A61K 39/165* (2006.01)

(Continued)

(52) U.S. Cl.

CPC .............. *C12N 7/00* (2013.01); *A61K 39/165* (2013.01); *A61P 31/14* (2018.01); *C07K 14/005* (2013.01);

(Continued)

(58) Field of Classification Search

None

See application file for complete search history.

(56) References Cited

U.S. PATENT DOCUMENTS

2005/0227224 A1* 10/2005 Tangy .................... C12N 15/86 435/5
2012/0219576 A1 8/2012 Branco et al.
2019/0117758 A1* 4/2019 Robinson ............ C12N 15/863

FOREIGN PATENT DOCUMENTS

WO WO-2005012538 A2 * 2/2005 ........... C07K 14/005
WO 2013/055418 A2 4/2013

(Continued)

OTHER PUBLICATIONS

Auperin et al., "Nucleotide Sequence of the Lassa Virus (Josiah Strain) S Genome RNA and Amino Acid Sequence Comparison of the N and GPC Proteins to Other Arenaviruses," Virology 168: 421-425 (Year: 1989).*

(Continued)

*Primary Examiner* — M Franco G Salvoza

(74) *Attorney, Agent, or Firm* — Arrigo, Lee, Guttman & Mouta-Bellum LLP

(57) ABSTRACT

The invention relates to recombinant measles virus expressing Lassa virus polypeptides, and concerns in particular immunogenic LASV particles expressed by a measles virus and/or virus like particles (VLPs) that contain proteins of a Lassa virus. These particles are recombinant infectious particles able to replicate in a host after an administration. The invention provides means, in particular nucleic acid constructs, vectors, cells and rescue systems to produce (Continued)

A

ATU1 ATU2 ATU3

B

MeV-GPC$_{LASV}$

MeV-NP +GPC$_{LASV}$

MeV-NP$_{ExoN}$ +GPC$_{LASV}$

Z-MeV-GPC$_{LASV}$

Z-MeV-NP+GPC$_{LASV}$

Z-MeV-NP$_{ExoN}$+GPC$_{LASV}$ these recombinant infectious particles. The invention also relates to the use of these recombinant infectious particles, in particular under the form of a composition, more particularly in a vaccine formulation, for the treatment or prevention of an infection by Lassa virus.

33 Claims, 29 Drawing Sheets

Specification includes a Sequence Listing.

(51) Int. Cl.

| | |
|---|---|
| ***A61P 31/14*** | (2006.01) |
| ***C07K 14/005*** | (2006.01) |
| ***C12N 7/00*** | (2006.01) |
| ***C12N 15/86*** | (2006.01) |

(52) U.S. Cl.

CPC .......... *C12N 15/86* (2013.01); *A61K 2039/54* (2013.01); *A61K 2039/572* (2013.01); *C12N 2760/10022* (2013.01); *C12N 2760/10023* (2013.01); *C12N 2760/10034* (2013.01); *C12N 2760/10043* (2013.01); *C12N 2760/10052* (2013.01); *C12N 2760/10071* (2013.01); *C12N 2760/18423* (2013.01); *C12N 2760/18434* (2013.01); *C12N 2760/18443* (2013.01); *C12N 2760/18452* (2013.01); *C12N 2760/18471* (2013.01)

(56) References Cited

FOREIGN PATENT DOCUMENTS

| | | | |
|---|---|---|---|
| WO | WO-2013055418 A2 * | 4/2013 | ............ A61N 1/327 |
| WO | 2016/198642 A1 | 6/2016 | |
| WO | 2016/115116 A1 | 7/2016 | |

OTHER PUBLICATIONS

Genbank, "Lassa virus S genome encoding the nucleoprotein and glycoprotein mRNAs, complete cds," found at https://www.ncbi.nl.nih.gov/nuccore/J04324 (Year: 1993).*

International Search Report, Application No. PCT/IB2018/001620, dated Jun. 24, 2019.

S. P. Fisher-Hoch et al: "Protection of rhesus monkeys from fatal Lassa fever by vaccination with a recombinant vaccinia virus containing the Lassa virus glycoprotein gene," Proceedings of the National Academy of Sciences of the United States of America, vol. 86, No. 1., Jan. 1, 1989 (Jan. 1, 1989), pp. 317-321.

Xiaohong Jiang et al: "Yellow fever 17D-vectored vaccines expressing Lassa virus GPI and GP2 glycoproteins provide protection against fatal disease in guinea pigs," Vaccine, Elsevier, Amsterdam, NL, vol. 29, No. 6, Nov. 24, 2010 (Nov. 24, 2010), pp. 1248-1257.

Stephan Olschlager et al: "Vaccination Strategies against Highly Pathogenic Arenaviruses: The Next Steps toward Clinical Trials," PLOS Pathogens, vol. 9, No. 4, Apr. 11, 2013 (Apr. 11, 2013), p. e1003212.

Katrin Ramsauer et al: "Chikungunya Virus Vaccines: Viral Vector-Based Approaches," Journal of Infectious Diseases. JID, vol. 214, No. suppl 5, Dec. 5, 2016 (Dec. 5, 2016), pp. S500-S505.

Branco Luis M et al: "Lassa virus-like particles displaying all major immunological determinants as a vaccine candidate for Lassa hemorrhagic fever," Virology Journal, Biomed Central, London, GB, vol. 7, No. 1, Oct. 20, 2010 (Oct. 20, 2010), p. 279.

Phanramphoei N. Frantz et al: "Measles-derived vaccines to prevent emerging viral diseases," Microbes and Infection, vol. 20, No. 9-10, Feb. 1, 2018 (Feb. 1, 2018), pp. 493-500.

Ramsauer and Tangy. Chikungunya virus vaccines: viral vestor-based approaches. Journal of Infectious Diseases, 2016, 214, S500-S505.

Nakayama. Measles Vaccine. Uirusu, 2009, 59(2), 257-266. Abstract only.

* cited by examiner

Figure 1:
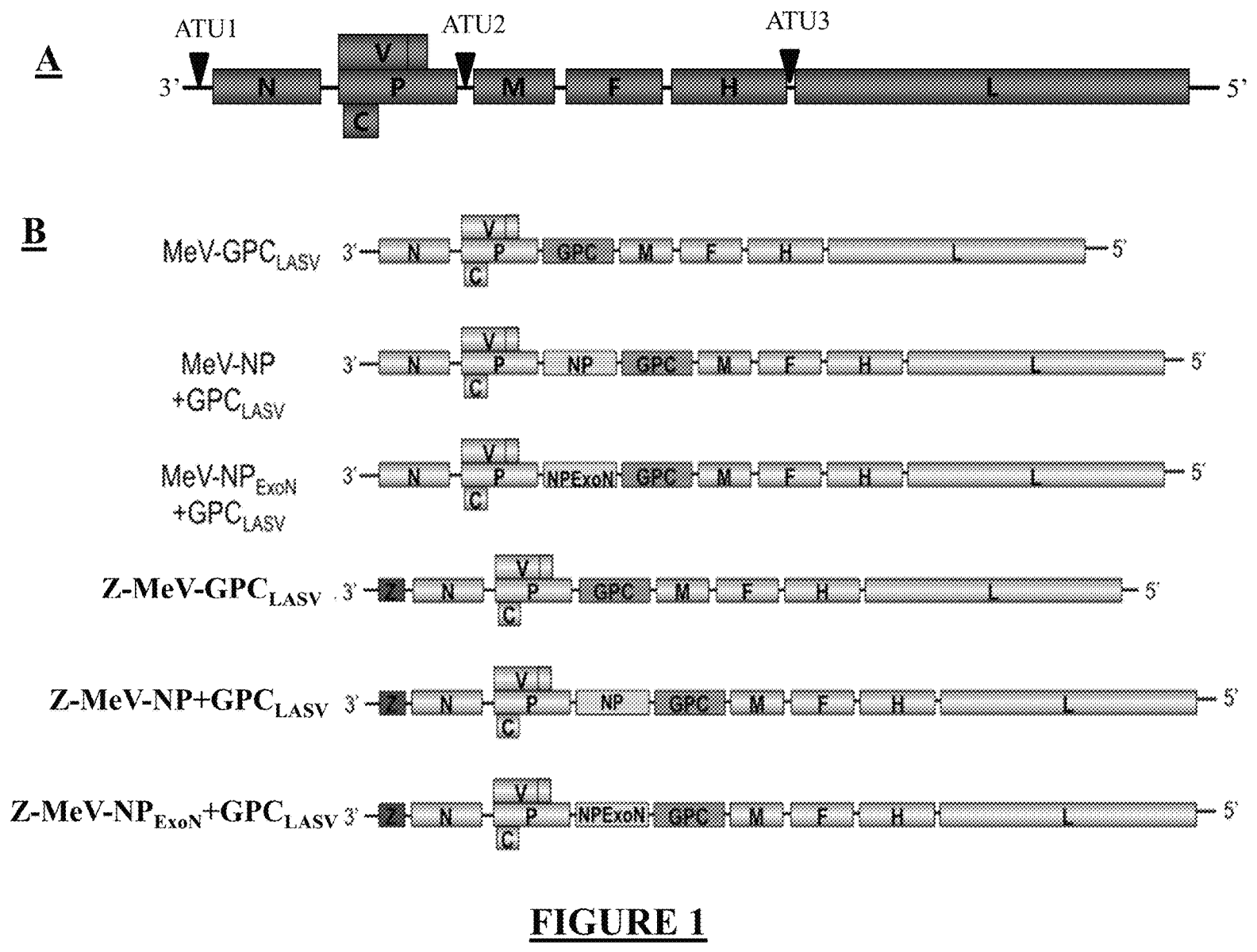

A

ATU1 ATU2 ATU3

3' N V P C M F H L 5'

B

MeV-$GPC_{LASV}$

MeV-NP +$GPC_{LASV}$

MeV-$NP_{ExoN}$ +$GPC_{LASV}$

Z-MeV-$GPC_{LASV}$

Z-MeV-NP+$GPC_{LASV}$

Z-MeV-$NP_{ExoN}$+$GPC_{LASV}$

MeV

Clinical score 0 5 10 15 20

0 5 10 15 20 25 30

Days after challenge

B

MeV-$NP_{ExoN}$+$GPC_{LASV}$ 0 5 10 15 20 25 30

Days after challenge

C

MeV-Z+$GPC_{LASV}$ 0 5 10 15 20 25 30

Days after challenge

MeV

MeV-NP$_{ExoN}$+GPC$_{LASV}$

MeV-Z+GPC$_{LASV}$

A

B

C

RNA copies/mL days post challenge

CHO-K1

CHO-hCD46

$MOPEVAC_{LAS}$ $MeV\text{-}NP_{ExoN}+GPC_{LASV}$

Figure 32:
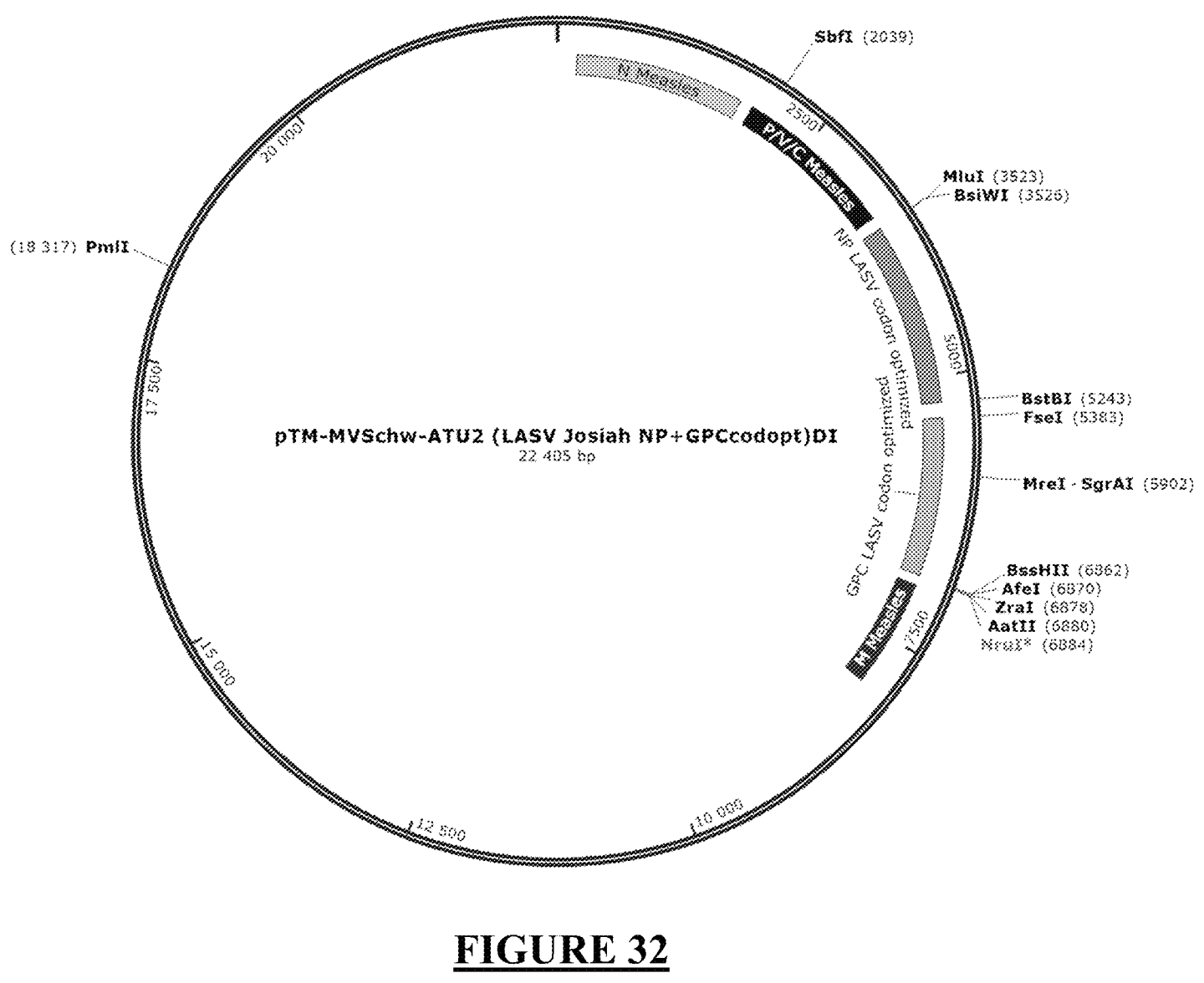

FIGURE 30 pTM-MVSchw-ATU2 (LASV Josiah NP+GPCcodopt)DI
22 405 bp

SbfI (2039)
MluI (3523)
BsiWI (3526)
BstBI (5243)
FseI (5383)
MreI - SgrAI (5902)
BssHII (6862)
AfeI (6870)
ZraI (6878)
AatII (6880)
NruI* (6884)
PmlI (18 317)

N Measles
P/V/C Measles
NP LASV codon optimized
GPC LASV codon optimized
H Measles 2500
5000
7500
10 000
12 500
15 000
17 500
20 000

Figure 33:
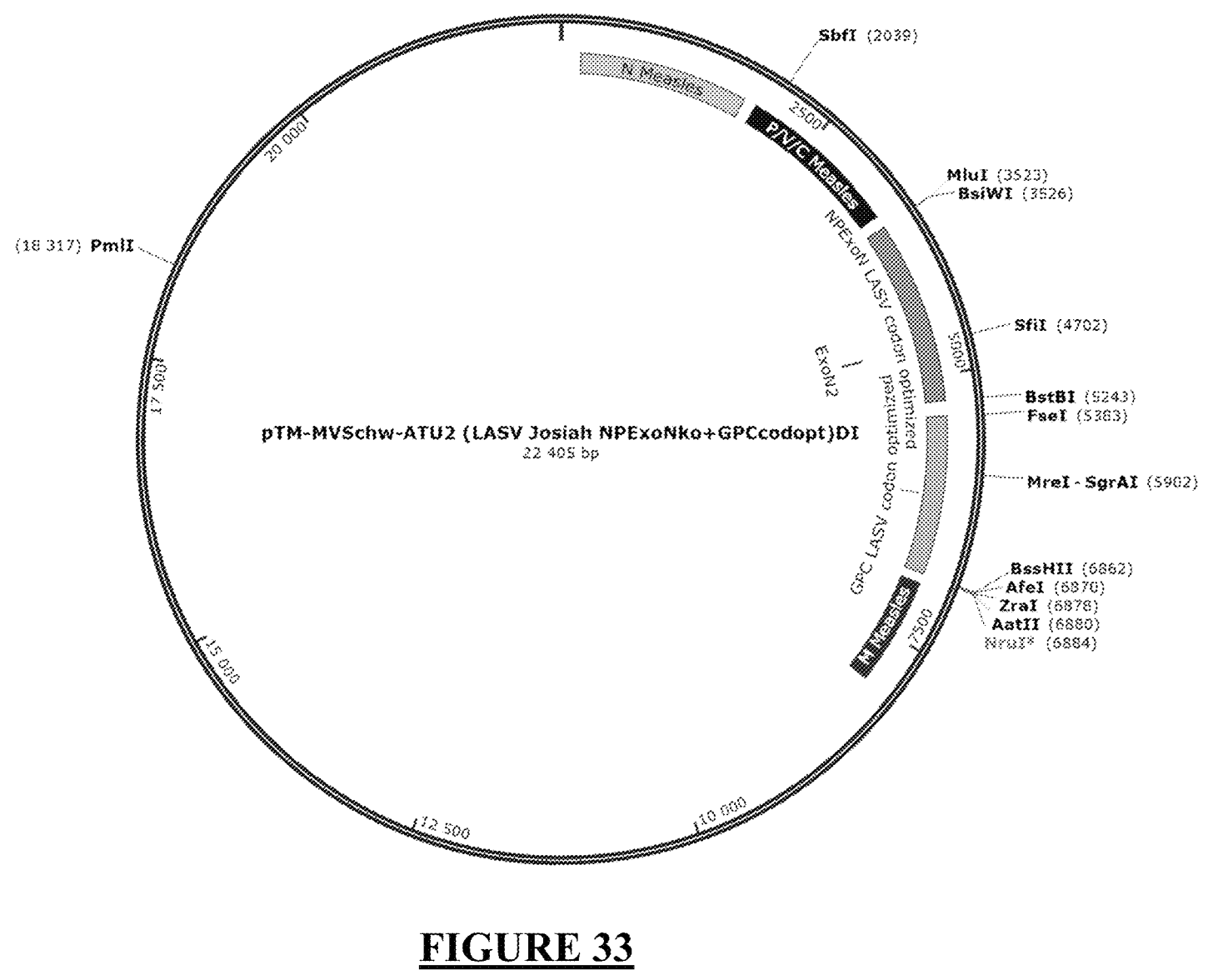

FIGURE 32 pTM-MVSchw-ATU2 (LASV Josiah NPExoNko+GPCcodopt)DI
22 405 bp

SbfI (2039)
MluI (3523)
BsiWI (3526)
SfiI (4702)
BstBI (5243)
FseI (5363)
MreI - SgrAI (5902)
BssHII (6862)
AfeI (6870)
ZraI (6878)
AatII (6880)
NruI* (6884)
PmlI (18 317)

N Measles
P/V/C Measles
NPExoN LASV codon optimized
ExoN2
GPC LASV codon optimized
M Measles 2500
5000
7500
10 000
12 500
15 000
17 500
20 000

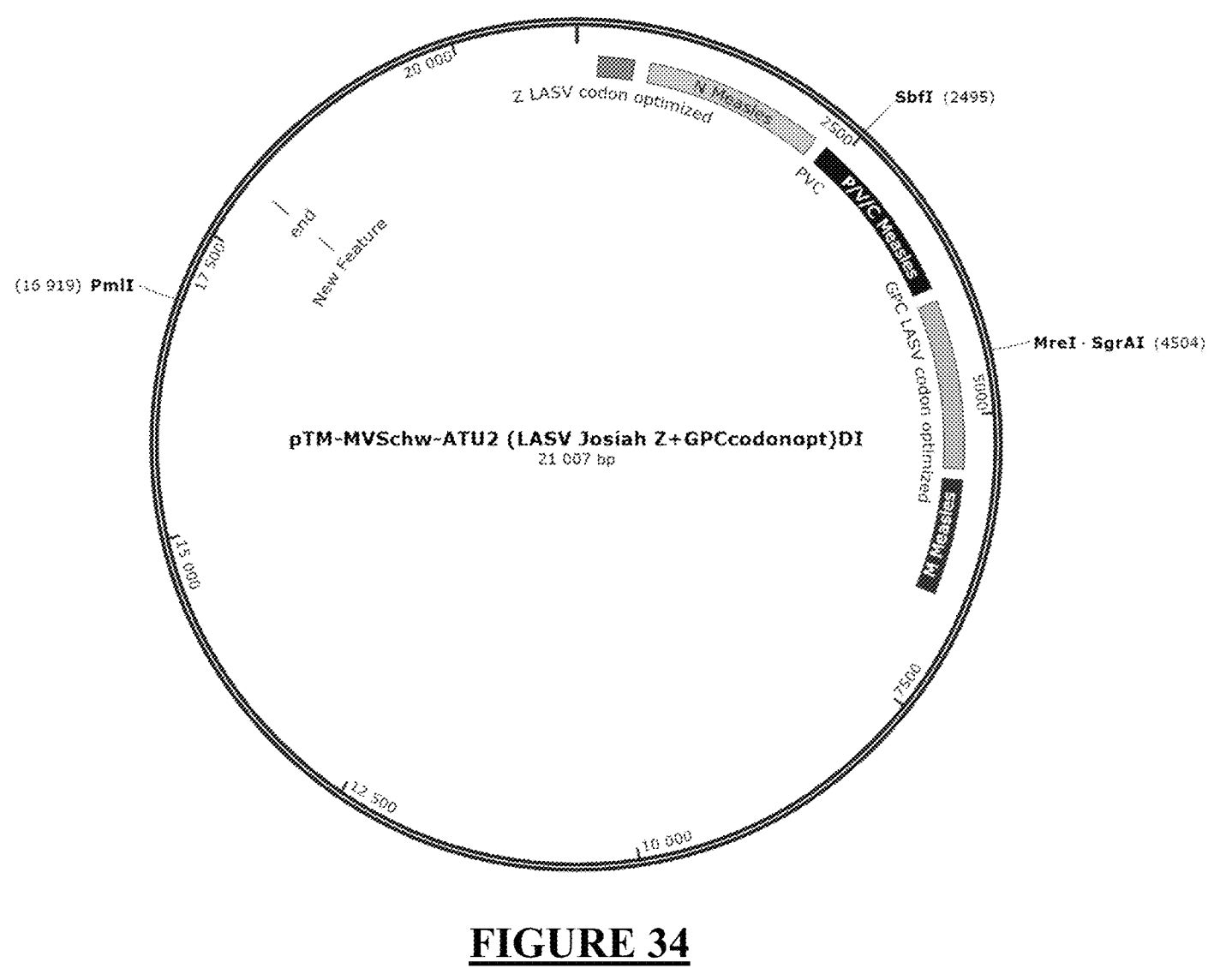

FIGURE 33 pTM-MVSchw-ATU2 (LASV Josiah Z+GPCcodonopt)DI
21 007 bp

MreI · SgrAI (4504)
SbfI (2495)
PmlI (16 919)
P/V/C Measles
PVC
GPC LASV codon optimized
M Measles
N Measles
Z LASV codon optimized
New Feature
end
2500
5000
7500
10 000
12 500
15 000
17 500
20 000

FIGURE 34

LASSA VACCINE

FIELD OF THE INVENTION

The application generally relates to recombinant genetic constructs comprising the recombinant measles virus and expressing at least one Lassa virus polypeptide, protein, antigen, or antigenic fragment thereof. The application also relates to the uses of genetic constructs or viruses, and more particularly their applications for inducing protection against the Lassa virus (LASV), and/or the measles virus (MV or MeV).

The means of the invention are more particularly dedicated to a recombinant nucleic acid construct allowing the expression of at least one of the following polypeptides of the LASV, or a truncated version thereof or an antigenic fragment thereof: the Nucleoprotein (NP), the Glycoprotein precursor (GPC), the zinc-binding protein (Z), or a mutated version of the native NP protein (mutated NP or mNP) wherein the exonuclease activity of the NP protein has been knocked down.

The invention also relates to a recombinant MeV-LASV virus expressing at least one of the previously mentioned LASV polypeptide, antigenic fragment thereof or antigen thereof or a truncated version thereof, namely NP, mNP, GPC and/or Z. The invention also concerns immunogenic particles expressed by the measles virus and comprising a LASV polypeptide, in particular at least the GPC polypeptide, or protein, or antigenic fragment thereof and/or infectious Virus-like particles (VLPs) that contains at least the Z polypeptide, or protein, or antigenic fragment thereof, said immunogenic particles and/or VLPs being able to elicit a cellular and/or humoral response against LASV, in particular a T cell response, in particular a CD4+ and/or CD8+ T cell response.

In particular, the invention is related to the use of these genetic constructs, recombinant nucleic acid constructs, expression vectors like plasmid vectors and the like, recombinant virus infectious particles, VLPs, for inducing an immunogenic or antigenic response within a host.

BACKGROUND OF THE INVENTION

Lassa Virus (LASV) is an old world arenavirus of the Arenaviridae family. LASV are enveloped, single-stranded, bisegmented ambisense RNA viruses. Their genome contains two RNA segments each coding for two proteins, one in each sense, for a total of four viral proteins. The larger segment (approximatively 7 kb) encodes the zinc-binding protein Z. Z protein regulates replication and transcription. The larger segment also encodes the RNA polymerase L. The small segment (approximatively 3.4 kb) encodes the nucleoprotein (NP) and the glycoprotein precursor (GPC), which is posttranslationnaly cleaved into the envelope glycoproteins GP1 and GP2 and the stable signal peptide SSP. These two glycoproteins mediate host cell entry. The synthesis capacity of an arenavirus is contained within the L polymerase protein. This protein uses viral RNA templates consisting in the genomic RNA encapsidated by the NP protein and viral ribonucleoproteins. Upon infection, the virus is delivered into the cytoplasm of the host cell, the L polymerase protein initiates transcription from the genome promoter located at the 3' end of each genomic RNA segment. The primary transcription results in the synthesis of mRNA of the viral genes encoded in the antigenomic orientation, i.e. of NP and L genes. Transcription terminates at the distal end of the stem-loop structure within the intergenomic region. Then, the L polymerase moves across the intergenomic region to generate a complementary antigenomic RNA. This RNA serves as a template for the synthesis of the mRNA of viral genes GPC and Z and for the synthesis of a full length genomic RNA.

LASV is the agent of the Lassa fever, a severe hemorrhagic fever, in humans. The natural reservoir of the virus is the African rodent *Mastomys natalensis*. Lassa virus is transmitted from rodents to humans, but the virus may also be transmitted from human to human, giving rise to local outbreaks.

Between 100.000 and 300.000 patients, and sometimes up to 500.000 patients, are reported with the Lassa fever each year in the endemic regions of west Africa, especially in Guinea, Liberia, Nigeria and Sierra Leone. Therefore, Lassa fever is a major public health concern in these regions. The severity of the disease varies from asymptomatic infection to severe complications leading to fatal hemorrhagic fever. Clinical signs and symptoms include fever, cough, chest pain, dysuria, headache, vomiting, diarrhea, pharyngitis, conjunctivitis, bleeding and facial edema. The mortality rates of patients infected with the LASV is high, with a rate around 10% in some areas where the LASV is distributed. The fatality rate is as high as 50% in young children. Moreover, approximatively 20% of the survivors present long-term complications including hearing deficit. Therefore, the Lassa fever has a serious impact on the population of these regions and is a major health problem. Lately, the distribution of the Lassa fever infections seems to spread in other west African countries, since cases have been reported in *Mali*, Ghana, Ivory Coast and Burkina Faso during the last decade.

Despite its discovery in 1969 in Nigeria, there is currently no preventive or prophylactic treatment against Lassa fever. Most of the patients are treated with Ribavirin, an antiviral drug. Unfortunately, treatment with the drug seems to be the most effective only when administrated early in the course of the illness and it is not fully efficient. The treatment should also be completed with supportive care, like maintenance of blood pressure and oxygenation, fluid and electrolyte balance, and the treatment of any other infections. Therefore, it may be difficult to effectively treat the patients in the endemic regions of west Africa where the Lassa fever spreads.

Whether infection leads to severe illness or death seems to depend on host immune response. Most of the severe cases include a defective cellular response, wherein the dendritic cells and macrophages massively release LASV but are not activated and therefore do not produce cytokines, or not enough. The disease severity, as much as the evolution and spread of the virus into new geographic areas, are a serious health public matter that needs to be fixed.

In this context, the development of a preventive treatment, like a preventive vaccine, is a major priority to meet the needs of these populations. There is therefore a need for a fully efficient treatment able to treat or prevent LASV infections, including to prevent outcomes of LASV primary infection, in particular to prevent the Lassa fever.

One of the most promising therapy for preventing LASV infections is prophylactic vaccination but no such vaccine is currently available. Prophylaxis would be the easiest and safest way to control the LASV infections, and protect the local populations. Despite this urgent need, no vaccine candidate has successfully advanced to clinical trials yet.

Therefore, there is a need for a vaccine and products such as active ingredients for preparing a vaccine, and method for producing these products and vaccine. The vaccine candidate should be safe and efficient when immunizing people in need thereof, without significant side effects, and induces the production of antibodies neutralizing the LASV, and possibly T cells like T helper cells and/or Cytotoxic T cells. In other words, the vaccine should elicit a strong cellular and/or humoral response. Advantageously, the vaccine should confer sterilizing immunity after a single immunization. To this end, there is a need for a vaccine that would enable the LASV proteins and/or LASV VLPs to generate in vivo in infected cells, in particular in infected cells of a host, and thus provide an efficient, long-lasting immunity, especially which induces life-long immunity after only a single, or two, administration steps.

Another need is to facilitate the vaccination of the populations that hardly have access to medical centers or the like. A vaccine candidate that would elicit immunization against two disease agents could enhance global health of these populations. A single vaccination could therefore allow the immunization against several disease agents present in the regions mentioned above. In particular, with the aim to totally eradicate the measles virus (MeV), a vaccine immunizing against both the MeV and the LASV could clearly protect these populations against these two major threats, especially in west Africa.

Measles virus has been isolated in 1954 (Enders, J. F., and T. C. Peebles. 1954. Propagation in tissue cultures of cytopathogenic agents from patients with measles. Proc. Soc. Exp. Biol. Med. 86:277-286.). Measles virus is a member of the order mononegavirales, i.e. viruses with a non-segmented negative-strand RNA genome. The non-segmented genome of MeV has an antimessage polarity which results in a genomic RNA which is neither translated in vivo or in vitro nor infectious when purified. Transcription and replication of non-segmented (−) strand RNA viruses and their assembly into virus particles have been studied and reported especially in Fields virology ($3^{rd}$ edition, vol. 1, 1996, Lippincott—Raven publishers—Fields B N et al.). Transcription and replication of the measles virus do not involve the nucleus of the infected cells but rather take place in the cytoplasm of host cell, just like the LASV. The genome of the MeV comprises genes encoding six major structural proteins designated N, P, M, F, H and L, and an additional two non-structural proteins from the P gene, C and V. The gene order is the following: from the 3' end of the genomic RNA; N, P (including C and V), M, F, H and L large polymerase at the 5' end. The genome furthermore comprises non coding regions in the intergenic region M/F. This non coding region contains approximatively 100 nucleotides of untranslated RNA. The cited genes respectively encode the proteins of the nucleocapsid of the virus or nucleoprotein (N), the phosphoprotein (P), the large protein (L) which together assemble around the genome RNA to provide the nucleocapsid, the hemagglutinin (H), the fusion protein (F) and the matrix protein (M).

Attenuated viruses have been derived from MeV virus to provide vaccine strains and in particular from the Schwarz strain. The Schwarz measles vaccine is a safe and efficient vaccine currently available for preventing measles. Besides providing vaccine, strains attenuated measles virus such as the Schwarz strain have shown to be stable and suitable for the design of efficient delivery vector for immunization against other viruses, like Zika virus or Chikungunya virus. Measles vaccines have been administered to hundreds of millions of children over the last 30 years and have proved its efficiency and safety. It is produced on a large scale in many countries and is distributed at low cost.

SUMMARY OF THE INVENTION

To address, at least partially, the drawbacks of the state of the art, the inventors achieved the production of active components (or ingredients) for vaccines based on recombinant genetic constructs, and especially based on recombinant nucleic acid constructs comprising, within an infectious replicative measles virus, cloned polynucleotide(s) encoding Lassa virus polypeptides, proteins or antigens, or antigenic fragments thereof. Vaccines may be recovered when the recombinant measles virus replicates in the host after administration. The invention thus relates to a LASV vaccine, especially a pediatric vaccine, and relates to active ingredient based on an attenuated measles virus strain such as a known vaccine strain commercially available, especially the widely used Schwarz measles vaccine. For all these reasons, the inventors used attenuated measles viruses to generate recombinant measles virus particles stably expressing structural antigens of LASV, in particular immunogenic particles thereof and/or VLPs. The measles approach of the invention meets all of the relevant criteria of a future LASV vaccine.

One aim of the invention is to provide a genetic construct, in particular recombinant genetic constructs, in particular nucleic acid constructs, for recovering infectious virus from the nucleic acid construct, and in particular a measles virus expressing LASV particles, and optionally also LASV Virus Like Particles (VLPs).

The invention therefor relates to a nucleic acid construct which comprises a cDNA molecule encoding the full-length antigenomic (+) RNA strand of the measles virus, and a first heterologous polynucleotide encoding at least one polypeptide, or at least one protein, or at least one antigen, or at least one antigenic fragment thereof, of the Lassa virus, said at least one polypeptide, or at least one protein, or at least one antigen, or at least one antigenic fragment thereof, being selected from the group consisting of the nucleoprotein (NP), a mutated nucleoprotein (mNP), the Zinc-binding protein (Z) and the glycoprotein precursor (GPC). The first heterologous polynucleotide is operatively cloned within an additional transcription unit (ATU) inserted within the cDNA of the antigenomic (+) RNA strand of the MeV. Particular nucleic acid constructs according to this embodiment are illustrated in FIG. 1 and in FIG. 31 to FIG. 36 and in the examples.

The expression "encodes" in the above definition encompasses the ability of the cDNA to allow transcription of a full length antigenomic (+) RNA, said cDNA serving especially as a template for transcription and where appropriate translation for product expression into cells or cell lines. Hence, when the cDNA is a double stranded molecule, one of the strands has the same nucleotide sequence as the antigenomic (+) RNA of the measles virus with the first heterologous polynucleotide cloned within, except "U" nucleotides that are substituted by "T" nucleotides in the cDNA. The nucleic acid construct of the invention may comprise regulatory elements controlling the transcription of the coding sequences, in particular promoters and termination sequences for the transcription, and possibly enhancer and other cis-acting elements. These regulatory elements may be heterologous with respect to the heterologous polynucleotide issued or derived from LASV gene(s), in particular may be the regulatory elements of the measles virus strain.

The expression "operatively cloned", which can be substituted by the expression "operatively linked", refers to the functional cloning, or insertion, of a heterologous polynucleotide within the nucleic acid construct of the invention such that said polynucleotide and nucleic acid construct are effectively, or efficiently, transcribed and if appropriate translated, in particular in cells, cell line, host cell used as a part of a rescue system for the production of recombinant infectious MeV particles or MeV expressing at least one polypeptide, or at least one protein, or at least one antigen, or at least an antigenic fragment thereof, of LASV. In other words, the nucleic acid construct of the invention allows the production, when placed in appropriate conditions, of an infectious antigenomic (+) RNA capable of producing at least one polypeptide, or at least one protein, or at least one antigen, or at least an antigenic fragment thereof, of LASV.

In a particular embodiment of the invention, the nucleic acid construct comprising the cDNA encoding the nucleotides of the full-length infectious antigenomic (+) RNA strand of MeV but without the operatively cloned heterologous polynucleotide complies with the rule of six (6) of the measles virus genome. In other words, the cDNA encoding the nucleotides of the full-length, infectious antigenomic (+) RNA strand of MeV is a polyhexameric cDNA.

The organization of the genome of measles viruses and their replication and transcription process have been fully identified in the prior art and are especially disclosed in Horikami S. M. and Moyer S. A. (Curr. Top. Microbiol. Immunol. (1995) 191, 35-50 or in Combredet C. et al (Journal of Virology, November 2003, p 11546-11554) for the Schwarz vaccination strain of the virus or for broadly considered negative-sense RNA viruses, in Neumann G. et al (Journal of General Virology (2002) 83, 2635-2662).

The "rule of six" is expressed in the fact that the total number of nucleotides present in a nucleic acid representing the MeV (+) strand RNA genome or in the nucleic acid constructs comprising the same is a multiple of six. The "rule of six" has been acknowledged in the state of the art as a requirement regarding the total number of nucleotides in the genome of the measles virus, which enables efficient or optimized replication of the MeV genomic RNA. In the embodiments of the present invention defining a nucleic acid construct that meets the rule of six, said rule applies to the nucleic acid construct specifying the cDNA encoding the full-length MV (+) strand RNA genome. In this regard the rule of six applies individually to the cDNA encoding the nucleotide sequence of the full-length infectious antigenomic (+) RNA strand of the measles virus, possibly but not necessarily to the polynucleotide cloned into said cDNA and encoding at least one polypeptide of the LASV.

The nucleic acid construct of the invention is in particular a purified DNA molecule, obtained or obtainable by recombination of at least one polynucleotide of MeV and at least one, or several, polynucleotide of the LASV, operably cloned or linked together.

According to the invention, the nucleic acid construct is prepared by cloning a polynucleotide, or several polynucleotides, encoding at least one polypeptide, or a protein, or an antigen, or an antigenic fragment thereof, selected from the group consisting of the GPC protein, the NP protein, the mNP protein and the Z protein of the LASV in the cDNA encoding the full-length antigenomic (+) RNA of the measles virus. The MeV genome is illustrated on FIG. 1A, while several nucleic acid constructs according to the invention are illustrated on FIG. 1B and on FIG. 31 to FIG. 36. Alternatively, a nucleic acid construct of the invention may be prepared using steps of synthesis of nucleic acid fragments or polymerization from a template, including by PCR. The polynucleotide(s) and nucleic acid construct of the invention may rather be prepared in accordance with any known method in the art and in particular may be cloned, obtained by polymerization especially using PCR methods or may be synthesized.

The heterologous polynucleotide may be issued from the fusion of several other polynucleotides, each encoding a particular polypeptide, or a particular protein, antigen or an antigenic fragment thereof, of LASV. For example, the heterologous polynucleotide may be issued from the fusion of polynucleotides each encoding a single protein, the GPC protein and the NP protein or the mNP protein for example, these two polynucleotides being linked within the nucleic acid construct by a linker sequence. A linker sequence is well known in the art and can be a short nucleotide sequence comprising or consisting in a regulatory sequence of the measles virus.

Accordingly, the heterologous polynucleotide may encode a single polypeptide, two different polypeptides, two identical polypeptides, three different polypeptides, two identical polypeptides and another polypeptide, four different polypeptides, two identical polypeptides and two others identical polypeptides, two identical polypeptides and two others different polypeptides, three identical polypeptides and another different polypeptide. Any one of these polynucleotides encoding at least two (identical or different) polypeptides may be issued from the fusion of several polynucleotides, or prepared using steps of synthesis of nucleic acid fragments or polymerization from a template, including by PCR. Alternatively, any one of these polynucleotides may be a cDNA issued from the genomic RNA of the Lassa virus, after retrotranscription, said cDNA being either the full genomic cDNA or a fragment thereof, and encoding a polypeptide of the LASV.

The heterologous polynucleotide, in particular LASV gene(s), is/are cloned within an additional transcription unit (ATU) inserted in the cDNA of the MeV. ATU sequences are known from the skilled person and comprise, for use in steps of cloning into cDNA of MeV, cis-acting sequences necessary for MeV-dependent expression of a transgene, such as a promoter of the gene preceding, in MeV cDNA, the insert represented by the polynucleotide encoding the LASV polypeptide(s) inserted into a multiple cloning sites cassette. The ATU may be further defined as disclosed by Billeter et al. in WO 97/06270. Three ATUs are represented on FIG. 1A. An ATU may also be defined as multiple cloning cassette inserted within the cDNA of the MeV, in particular between the N-P intergenic region of the MeV genome, and/or between the intergenic H-L region of the MeV genome. An ATU may contain cis-acting sequences necessary for the transcription of the P gene of MeV. The different ATUs in particular ATU1 and ATU2 may be identical regarding their nucleic acid sequence. ATUs are generally localized between two CTT codons corresponding respectively to the start and stop codons of the polymerase. ATUs may further comprise a ATG and a TAG codons corresponding respectively to the start and stop codons for translation of the heterologous polynucleotide cloned within the ATU. Alternatively, ATUs are localized between a ATG and a TAG codons corresponding respectively to the start and stop codons for translation of the heterologous polynucleotide cloned within the ATU. ATUs may further comprise a ATG and a TAG codons corresponding respectively to the start and stop codons for translation of the heterologous polynucleotide cloned within the ATU. In a preferred embodiment of the invention, an ATU is a polynucleotide comprising or consisting of SEQ ID No: 16.

SEQ ID No: 16

SEQ ID No: 16 is an ATU sequence localized within the cDNA molecule encoding a full-length antigenomic (+) RNA strand of a measles virus. CTT codons corresponding respectively to the start and stop codons of the polymerase are in bold. ATG and TAG codons corresponding to the start and stop codons for translation of the heterologous polynucleotide cloned within the ATU are underlined.

CTTAGGAACCAGGTCCACACAGCCGCCAGCCCA TCAacgcgtacgATG*TAGg cgcgcagcgcttagacgtctcgcgaTCGATACTAGTACAACCTAAATCCATTATAAAAA ACTT wherein the * corresponds to the heterologous codon-optimized sequence polynucleotide encoding at least one LASV polypeptide.

An ATU with a heterologous polynucleotide encoding the GPC polypeptide is for example localized between amino acid residues 3487 and 5071 on SEQ ID No: 9. SEQ ID No: 17 corresponds to an ATU comprising as a cloned insert a codon-optimized heterologous polynucleotide encoding the GPC protein.

An ATU (known under reference ATU2) is localized between the P and M genes of the MeV. Another ATU (known under reference ATU1) is located upstream the gene N of the MeV. Another ATU (known under reference ATU3) is located between the genes H and L of MeV. It has been observed that the transcription of the viral RNA of MeV follows a gradient from the 5' to the 3' end. This explains that, depending on where the heterologous polynucleotide is inserted, its level of expression will vary and be more or less efficient if inserted within ATU1, ATU2 or ATU3.

The term "polypeptide" is used interchangeably with the terms "antigen" or "protein" or "antigenic fragment" and defines a molecule resulting from a concatenation of amino acid residues. In particular, the polypeptides disclosed in the application originate from the LASV and are antigens, proteins, structural proteins, or antigenic fragments thereof, that may be identical to native proteins or alternatively that may be derived thereof by mutation, including by substitution (in particular by conservative amino acid residues) or by addition of amino acid residues or by secondary modification after translation or by deletion of portions of the native proteins(s) resulting in fragments having a shortened size with respect to the native protein of reference. Fragments are encompassed within the present invention to the extent that they bear epitopes of the native protein suitable for the elicitation of an immune response in a host in particular in a human host, including a child host, preferably a response that enables the protection against a LASV infection or against a LASV associated disease. Epitopes are in particular of the type of T epitopes involved in elicitation of Cell Mediated Immune response (CMI response). T epitopes are involved in the stimulation of T cells through presentation of some parts of the T-cell epitope which can bind on MHC class II molecules, leading to the activation of T cells. Epitopes may alternatively be of type B, involved in the activation of the production of antibodies in a host to whom the protein has been administered or in whom it is expressed following administration of the infectious replicative particles of the invention. Fragments may have a size representing more than 50% of the amino-acid sequence size of the native protein of LASV strain Josiah, preferably at least 90% or 95%. Polypeptide may have at least 50% identity with the native protein of LASV strain Josiah, preferably at least 60%, preferably at least 70%, preferably at least 85% or at least 95%.

In a particular embodiment of the invention, each polynucleotide operatively cloned within the cDNA of the antigenomic (+) RNA encodes polypeptides comprising epitopes localized within any one of the LASV polypeptide(s). According to this embodiment, the epitope sequence(s) share(s) 100% identity with the epitope sequence(s) of the native LASV proteins. Such epitopes are listed in the Immune Epitope database and analysis resource (www.iedb.or). Within the polypeptide(s) of the LASV encoded by the polynucleotide and having an epitope sequence(s) as defined herein, amino acid residue that does not belong to any epitope may be different from the sequence of the native LASV protein(s).

By "polypeptide of LASV" is meant a "polypeptide" as defined herein (either a polypeptide, an antigen, a protein, or an antigenic fragment thereof), the amino acid sequence of which is identical to a counterpart in a strain of LASV, especially LASV strain Josiah, including a polypeptide which is a native mature or precursor of protein of LASV or is an antigenic fragment thereof or a mutant thereof as defined herein in particular an antigenic fragment or a mutant having at least 50%, at least 80%, in particular advantageously at least 90% or preferably at least 95% amino acid sequence identity to a naturally occurring LASV GPC, NP or Z protein. Amino acid sequence identity can be determined by alignment by one of skill in the art using manual alignments or using the numerous alignment programs available (for example, BLASTP—http://blast.ncbi.nlm.nih.gov/). Fragments or mutants of LASV polypeptides of the invention may be defined with respect to the particular amino acid sequences illustrated herein, especially the amino acid sequences from the group consisting of SEQ ID No: 1, SEQ ID No: 3, SEQ ID No: 5 and SEQ ID No: 7. In a particular embodiment of the invention, the polypeptides share at least 50%, at least 80%, in particular advantageously at least 90% or preferably at least 95% amino acid sequence identity with their native proteins of the LASV strain Josiah, or with the polypeptides of SEQ ID No.: 1; SEQ ID No.: 3; SEQ ID No.: 5; or SEQ ID No.: 7.

According to one aspect of the invention, a polynucleotide encoding at least one polypeptide of LASV is issued or derived from the genome of isolated and purified wild strain(s) of LASV, including any Lassa strain whose genome has been fully or partially sequenced. At least some of these sequences may be found in the NCBI nucleotide database. In particular, the polynucleotide encoding at least one LASV polypeptide may be derived or issued from any Lassa strain sequenced and referenced in *Clinical Sequencing Uncovers Origins and Evolution of Lassa Virus* (Andersen Kristian G et al.; 2015; Cell. 2015 Aug. 13; 162(4): 738-750. doi: 10.1016/j.cell.2015.07.020), especially in the supplementary data of the publication wherein the name of the strains and corresponding accession reference of the sequences are listed. Preferentially, the polynucleotide is issued or derived from the strain Josiah whose genomic sequences of the two RNA segments may be found under GenBank accession no. J04324.1 for the short genomic RNA encoding NP protein and GPC protein, and under European Nucleotide Archive accession no. U73034.2 for the long genomic RNA encoding the Z protein and the L protein. Native protein of LASV strain Josiah may be defined as having the sequences issued from RNA segments found under GenBank accession no. J04324.1 for the short genomic RNA encoding NP protein and GPC protein, and under European Nucleotide Archive accession no. U73034.2 for the long genomic RNA. The term "derive" appearing in the definition of the polynucleotides merely specifies that the sequence of said polynucleotide may be identical to the corresponding sequence in a LASV strain or may vary to the extent that it encodes polypeptides, antigens, proteins, or fragments thereof, of LASV that meet(s) the definition of the "polypeptide" according to the present invention. In particular, a polynucleotide derives from the nucleic acid of a LASV strain when it is codon-optimized with respect to such sequence. Accordingly, the term does not restrict the production mode of the polynucleotide.

Alternatively, fragments may be short polypeptides with at least 10 amino acid residues, which harbor epitope(s) of the native protein listed in the Immune Epitope database and analysis resource (www.iedb.org). Fragments in this respect also include polyepitopes.

According to another embodiment of the invention, the nucleic acid construct further comprises a second heterologous polynucleotide encoding at least one polypeptide, or an antigenic fragment thereof, of the LASV, said at least one polypeptide or antigenic fragment thereof being selected from the group consisting of the GPC protein, the NP protein, the mNP protein and Z protein, the second heterologous nucleotide being operatively cloned within another ATU at a location distinct from the location of the first cloned heterologous polynucleotide, preferentially upstream the N gene of the MeV, said another ATU being in particular the ATU1 inserted upstream the N gene of the MeV. The second heterologous polynucleotide or antigenic fragment thereof encodes in particular at least one polypeptide or antigenic fragment thereof different from the polypeptide(s) encoded by the first heterologous polynucleotide.

According to this embodiment, another ATU (known under reference ATU1) is advantageously located in the N-terminal sequence of the cDNA molecule encoding the full-length (+) RNA strand of the antigenome of the MeV upstream the N gene of MeV, while the other ATU (ATU2) is preferentially located between the P and M genes of the virus. Since the transcription of the viral RNA of MeV follows a gradient from the 5' to the 3' end, the inventors found that cloning two polynucleotides at different locations within the cDNA encoding the full-length antigenomic (+) RNA of the measles virus may lead to the production of higher yield of antigenic particles and/or LASV virus like particles (VLPs) when the Z protein is encoded by at least one heterologous polynucleotide, while this production may be less important when the polynucleotides are all cloned within a single and same location. Furthermore, cloning the heterologous polynucleotides at different locations may reduce the attenuation of the expression of the encoded polypeptides. Indeed, when several genes are cloned within a single ATU, it may lead to reduction of the expression of the encoded polypeptides. Particular nucleic acid constructs according to this embodiment are illustrated in FIGS. 1*b* and 1*n* the examples.

Within the other ATU, the second polynucleotide may encode any one of the previously listed polypeptide, or antigenic fragment thereof, of the LASV. Accordingly, the second polynucleotide localized within the other ATU may encode the same polypeptide(s) than the first polynucleotide inserted within the first ATU, or the second polynucleotide may encode at least one common polypeptide with the polypeptide(s) encoded by the first polynucleotide. In a preferred embodiment of the invention, the first polynucleotide and the second polynucleotide encodes at least one different polypeptide, or an antigenic fragment thereof.

The cDNA molecule encoding the full-length antigenomic (+) RNA strand of the MeV may be characteristic of or may be obtained from an attenuated strain of MeV. An "attenuated strain" of MeV is defined as a strain that is avirulent or less virulent than the parent strain in the same host, while maintaining immunogenicity and possibly adjuvanticity when administered in a host for preserving immunodominant T and B cell epitopes and possibly the adjuvanticity such as the induction of T cell costimulatory proteins or cytokine IL-12.

An attenuated strain of a measles virus accordingly refers to a strain which has been serially passaged on selected cells and, possibly, adapted to other cells to produce seed strains suitable for the preparation of human vaccine strains, harboring a stable genome which would not allow reversion to pathogenicity nor integration in host chromosomes. As a particular "attenuated strain", an approved strain for a vaccine is an attenuated strain suitable for the invention when it meets the criteria defined by the FDA (US Food and Drug Administration); i.e. it meets safety, efficacy, quality and reproducibility criteria, after rigorous reviews of laboratory and clinical data (www.fda.gov/cber/vaccine/vacappr.htm).

In particular, the cDNA molecule encoding the full-length antigenomic (+) RNA strand of the MeV is obtained from an attenuated virus strain selected from the group comprising of consisting of the Schwarz strain, the Zagreb strain, the AIK-C strain, the Moraten strain, the Philips strain, the Beckenham 4A strain, the Beckenham 16 strain, the Edmonston seed A strain, the Edmonston seed B strain, the CAM-70 strain, the TD 97 strain, the Leningrad-16 strain, the Shanghai 191 strain and the Belgrade strain. All these strains have been described in the prior art. The invention uses in particular strains that have been allowed for use as commercial vaccines. In particular, the cDNA molecule encoding the full length antigenomic (+) RNA strand of the MeV is obtained from the Schwarz strain.

According to a particular embodiment of the invention, the cDNA molecule is placed under the control of heterologous expression control sequences.

The insertion of such a control for the expression of the cDNA, is favorable when the expression of this cDNA is sought in cell types which do not enable full transcription of the cDNA with its native control sequences.

According to a particular embodiment of the invention, the heterologous expression control sequence comprises the T7 promoter and T7 terminator sequences. These sequences are respectively located 5' and 3' of the coding sequence for the full length antigenomic (+) RNA strand of MeV and from the adjacent sequences around this coding sequence.

In a particular embodiment of the invention, the cDNA molecule, which is defined here above is modified, i.e. comprises additional nucleotide sequences or motifs.

In a preferred embodiment, the cDNA molecule used according to the invention further comprises, at its 5'-end, adjacent to the first nucleotide of the nucleotide sequence encoding the full-length antigenomic (+) RNA strand of the MeV approved vaccine strain, a GGG motif followed by a hammerhead ribozyme sequence and comprises, at its 3'-end, adjacent to the last nucleotide of said nucleotide sequence encoding the full-length anti-genomic (+) RNA strand, the sequence of a ribozyme. The Hepatitis delta virus ribozyme (6) is appropriate to carry out this preferred embodiment.

The GGG motif placed at the 5' end, adjacent to the first nucleotide of the above coding sequence improves the efficiency of the transcription of said cDNA coding sequence. As a requirement for the proper assembly of measles virus particles is the fact that the cDNA encoding the antigenomic (+) RNA complies with the rule of six, when the GGG motif is added, a ribozyme is also added at the 5' end of the coding sequence of the cDNA, 3' from the GGG motif, in order to enable cleavage of the transcript at the first coding nucleotide of the full-length antigenomic (+) RNA strand of MeV.

In order to prepare the nucleic acid construct of the invention, the preparation of a cDNA molecule encoding the full-length antigenomic (+) RNA of a measles virus disclosed in the prior art is achieved by known methods. The obtained cDNA provides especially the basis for the genome vector involved in the rescue of recombinant measles virus particles when it is inserted in a vector such as a plasmid.

A particular cDNA molecule suitable for the preparation of the nucleic acid construct of the invention is the one obtained using the Schwarz strain of measles virus. Plasmid pTM-MVSchw, which contains an infectious MeV cDNA corresponding to the anti-genome of the Schwarz MV vaccine strain and is used for preparation of recombinant vectors encompassing the heterologous polynucleotides of the invention, has been described elsewhere (Combredet, C., et al., A molecularly cloned Schwarz strain of measles virus vaccine induces strong immune responses in macaques and transgenic mice. J Virol, 2003. 77(21): p. 11546-54). Accordingly, the cDNA used within the present invention may be obtained as disclosed in WO2004/000876 or may be obtained from plasmid pTM-MVSchw deposited by Institut Pasteur at the CNCM under No I-2889 on Jun. 12, 2002, the sequence of which is disclosed in WO2004/000876 incorporated herein by reference. The plasmid pTM-MVSchw has been obtained from a Bluescript plasmid and comprises the polynucleotide coding for the full-length measles virus (+) RNA strand of the Schwarz strain placed under the control of the promoter of the T7 RNA polymerase. It has 18967 nucleotides and a sequence represented as SEQ ID NO: 15. cDNA molecules (also designated cDNA of the measles virus or MeV cDNA for convenience) from other MeV strains may be similarly obtained starting from the nucleic acid purified from viral particles of attenuated MeV such as those described herein. An additional transcription unit may be a multiple-cloning site cassette previously inserted in the vector, as explained in Combredet et al., 2003. An ATU may comprise cis-acting sequences necessary for the transcription of the inserted LASV genes. The heterologous polynucleotide(s) are cloned or inserted within additional transcription units (ATU) as defined here above.

The heterologous polynucleotide may also be cloned or inserted within another ATU. As an example, a third ATU may be inserted between the H gene and the L gene of the MeV, and the first or second heterologous polynucleotide may be cloned or inserted within this third ATU. In a particular embodiment of the invention, the nucleic acid construct may comprise a first heterologous polynucleotide inserted within a first ATU, a second heterologous polynucleotide sequence inserted into a second ATU at a distinct location from the first ATU, and a third heterologous polynucleotide inserted within a third ATU at a distinct location from the first and second ATUs.

In a preferred embodiment, the nucleic acid construct comprises heterologous polynucleotide(s) encoding a particular mutated NP protein, or an antigenic fragment thereof. The native NP protein may be mutated to knock down the exonuclease activity of the NP protein. A NP protein knocked down for its exonuclease activity may be determined by luciferase assay using a reporter luciferase gene placed under the control of an IRF3 dependent promoter as described in PMID: 21085117 and illustrated on FIG. 29. NP is involved in the virus-induced inhibition of type I IFN signaling (Martinez-Sobrido, 2006). This activity is linked to the C-terminal domain of the native NP protein. Functional analysis confirmed the exonuclease activity of LASV NP, which has been proven to be a critical step for its type I IFN counteracting function (Qi, 2010). Hence, the inventors introduced two mutations within the exonuclease domain of the NP protein. The exonuclease domain of the NP protein is localized within the C-terminal domain of the NP protein, especially between amino acid residues 341 and 569 of SEQ ID no: 3. Accordingly, a mutated NP protein is in particular issued from a native NP protein mutated (by deletion(s) and/or addition(s) and/or substitution(s) of any amino acid residue) within the exonuclease domain as defined here above, and having its exonuclease activity knocked down according to the luciferase assay described here above. In particular, substitution(s) of at least one amino acid residue D389, E391, D466, D533 and H528 of SEQ ID No: 3 may lead to a mutated NP protein without exonuclease activity. In particular, the amino acid residue at position 389 of SEQ ID No: 3 may be mutated, for example by substituting the Aspartic acid by an Alanine. Alternatively, amino acid residue at position 392 of SEQ ID No: 3 may be mutated, for example by substitution of the Glycine by an Alanine. In a preferred embodiment, both amino acids residues at position 389 and 392 of SEQ ID No. 3 are mutated by substitution. In a more preferred embodiment, the mNP protein has the sequence of SEQ ID No: 5.

According to this embodiment, the mNP polypeptide encoded by the polynucleotide(s) allows the induction of type I IFN. In other words, the immune suppressive function of the native NP is shut down in mNP. Therefore, it is provided nucleic acid constructs comprising polynucleotide(s) which increase the efficiency of chimeric recombinant MeV-LASV infectious particles immunogenicity.

According to a preferred embodiment, the invention also concerns modification and in particular optimization of the polynucleotides to allow an efficient expression of the LASV polypeptides, proteins, antigens, or fragments thereof, in a host cell.

Accordingly, optimization of the polynucleotide sequence can be operated avoiding cis-active domains of nucleic acid molecules: internal TATA-boxes, chi-sites and ribosomal entry sites; AT-rich or GC-rich sequence stretches; ARE, INS, CRS sequence elements; repeat sequences and RNA secondary structures; cryptic splice donor and acceptor sites, branch points.

The optimized polynucleotides may also be codon optimized for expression in a specific cell type, in particular may be modified for the Maccaca codon usage or for the human codon usage. This optimization allows increasing the efficiency of chimeric infectious particles production in cells without impacting the amino acid composition of the expressed protein(s).

In particular, the optimization of the polynucleotide encoding the LASV polypeptide(s) may be performed by modification of the wobble position in codons without impacting the identity of the amino acid residue translated from said codon with respect to the original one.

Optimization is also performed to avoid editing-like sequences from Measles virus. The editing of transcript of measles virus is a process which occurs in particular in the transcript encoded by the P gene of measles virus. This editing, by the insertion of extra G residues at a specific site within the P transcript, gives rise to a new protein truncated compared to the P protein. Addition of only a single G residue results in the expression of the V protein, which contains a unique carboxyl terminus (Cattaneo R et al., Cell. 1989 Mar. 10; 56(5):759-64).

In the polynucleotides according to this particular embodiment of the invention, the following editing-like sequences from measles virus can be mutated: AAAGGG, AAAAGG, GGGAAA, GGGGAA, as well as their complementary sequence: TTTCCC, TTTTCC, CCCTTT, CCCCTT. For example, AAAGGG can be mutated in AAAGGC, AAAAGG can be mutated in AGAAGG or in TAAAGG or in GAAAGG, and GGGAAA in GCGAAA.

Hence, the heterologous polynucleotide(s) may comprise any one of the following sequences, or a plurality of the following sequences, or at least two of the following sequences, or at least three of the following sequences, or the four following sequences:

SEQ ID No: 2 which encodes the GPC protein; and/or
SEQ ID No: 4 which encodes the NP protein; and/or
SEQ ID No: 6 which encodes the mNP protein; and/or
SEQ ID No: 8 which encodes the Z protein.

Within the heterologous polynucleotide(s), each sequence defined here above may be present a single time, or a plurality of times. In a preferred embodiment of the invention, each sequence is present a single time within a single heterologous polynucleotide, or is present a single time within the heterologous polynucleotides taken together.

According to any one of the particular embodiments of the invention, it is provided nucleic acid constructs comprising polynucleotide(s) which increase the efficiency of chimeric recombinant MeV-LASV infectious particles production.

Alternatively, or complementarily, the heterologous polynucleotide(s) may encode any one of the following polypeptides, or an antigenic fragment thereof, or at least two of the following polypeptides, or at least three of the following polypeptides, or the four following polypeptides:

the GPC protein of SEQ ID No: 1 or an antigenic fragment thereof; and/or
the NP protein of SEQ ID No: 3 or an antigenic fragment thereof; and/or
the mNP protein of SEQ ID No: 5 or an antigenic fragment thereof; and/or
the Z protein of SEQ ID No: 7 or an antigenic fragment thereof.

It should be noted that the polynucleotide(s) may encode a polypeptide as defined here above a single time or a several times. In a preferred embodiment, each polypeptide is encoded a single time within a single heterologous polynucleotide, and more preferentially, each polypeptide is encoded a single time within the plurality of polypeptides. According to a particular embodiment of the invention, several polynucleotides wherein each polynucleotide encodes at least one LASV protein are combined or fused to form a polynucleotide encoding several proteins of the LASV. These polynucleotides may distinguish from each other by the fact that they code for proteins of various strains of the LASV, or for different proteins of a LASV strain.

In a particular embodiment, the nucleic acid construct of the invention comprises from the 5' to 3' end the following polynucleotides:

(a) a polynucleotide encoding the N protein of the MeV;
(b) a polynucleotide encoding the P protein of the MeV;
(c) the first heterologous polynucleotide encoding at least one polypeptide selected from the group consisting of the GPC protein, the NP protein, the mNP protein and the Z protein of the LASV, or an antigenic fragment thereof, in particular encoding a single polypeptide which is the GPC protein or an antigenic fragment thereof, or encoding at least two polypeptides, which are the GPC protein or an antigenic fragment thereof and either the NP protein or the mNP protein, or an antigenic fragment thereof, in particular encoding the GPC protein and the mNP protein, wherein the first polynucleotide is in particular operatively cloned within an ATU, in particular ATU2;
(d) a polynucleotide encoding the M protein of the MeV;
(e) a polynucleotide encoding the F protein of the MeV;
(f) a polynucleotide encoding the H protein of the MeV;
(g) a polynucleotide encoding the L protein of the MeV;

and wherein said polynucleotides are operatively linked within the nucleic acid construct and under the control of a viral replication and transcriptional regulatory elements such as MeV leader and trailer sequence(s).

Several examples of this embodiment obtained according to the invention are schematically illustrated on FIG. 1B: the constructs named MeV-$GPC_{LASV}$; MeV-NP+$GPC_{LASV}$; MeV-$NP_{ExoN}$+$GPC_{LASV}$ belong to this particular embodiment, but other construct not illustrated on FIG. 1B are also included, like for example MeV-$GPC_{LASV}$+NP; MeV-$GPC_{LASV}$+$NP_{ExoN}$; MeV-Z+$GPC_{LASV}$; MeV-$GPC_{LASV}$+Z; MeV-Z+NP; MeV-Z+$NP_{ExoN}$; MeV-NP+Z; MeV-$NP_{ExoN}$+Z; MeV-Z+$GPC_{LASV}$+NP; MeV-Z+$GPC_{LASV}$+$NP_{ExoN}$; MeV-Z-NP-$GPC_{LASV}$; MeV-Z-$NP_{ExoN}$-$GPC_{LASV}$; MeV-$GPC_{LASV}$+NP+Z; MeV-$GPC_{LASV}$+$NP_{ExoN}$+Z; MeV-$GPC_{LASV}$+Z+NP; MeV-$GPC_{LASV}$+Z+$NP_{ExoN}$; MeV-NP+$GPC_{LASV}$+Z; MeV-NP-Z+$GPC_{LASV}$; MeV-$NP_{ExoN}$+$GPC_{LASV}$+Z; MeV-$NP_{ExoN}$-Z+$GPC_{LASV}$;

wherein

MeV corresponds to the cDNA molecule encoding the full-length antigenomic (+) RNA strand of the measles virus (MeV);

$GPC_{LASV}$ corresponds to a polynucleotide encoding a polypeptide of the GPC protein, or an antigenic fragment thereof;

NP corresponds to a polynucleotide encoding a polypeptide of the NP protein, or an antigenic fragment thereof;

$NP_{ExoN}$ corresponds to a polynucleotide encoding a polypeptide of the mNP protein, or an antigenic fragment thereof;

Z corresponds to a polynucleotide encoding a polypeptide of the Z protein, or an antigenic fragment thereof;

The expressions "N protein", "P protein", "M protein", "F protein", "H protein" and "L protein" refer respectively to the nucleoprotein (N), the phosphoprotein (P), the matrix protein (M), the fusion protein (F), the hemagglutinin protein (H) and the RNA polymerase large protein (L) of a measles virus and encompass reference to the respective polypeptides or antigenic fragments thereof. These components have been identified in the prior art and are especially disclosed in Fields, Virology (Knipe & Howley, 2001).

In another particular embodiment of the invention, the nucleic acid construct comprises from the 5' to 3' end the following polynucleotides:

(a) the second heterologous polynucleotide encoding at least one polypeptide selected from the group consisting of the GPC protein, the NP protein, the mNP protein and the Z protein of the LASV, or an antigenic fragment thereof, in particular encoding the Z protein, or an antigenic fragment thereof, wherein the second polynucleotide is operatively cloned within an ATU localized upstream the N gene of the MeV, in particular within the ATU1;
(b) a polynucleotide encoding the N protein of the MeV;
(c) a polynucleotide encoding the P protein of the MeV;
(d) the first heterologous polynucleotide encoding at least one polypeptide selected from the group consisting of the GPC protein, the NP protein, the mNP protein and the Z protein of the LASV, or an antigenic fragment thereof, in particular encoding a single polypeptide which is the GPC protein or an antigenic fragment thereof, or encoding at least two polypeptides, which are the GPC protein or an antigenic fragment thereof and either the NP protein or the mNP protein, or an antigenic fragment thereof, in particular encoding the GPC protein and the mNP protein, wherein the first polynucleotide is in particular operatively cloned within an ATU, in particular ATU2;

(e) a polynucleotide encoding the M protein of the MeV;

(f) a polynucleotide encoding the F protein of the MeV;

(g) a polynucleotide encoding the H protein of the MeV;

(h) a polynucleotide encoding the L protein of the MeV, and wherein said polynucleotides are operatively linked within the nucleic acid construct and under the control of a viral replication and transcriptional regulatory elements such as MeV leader and trailer sequence(s).

Several examples of this embodiment are schematically illustrated on FIG. 1B: the constructs named Z-MeV-$GPC_{LASV}$; Z-MeV-NP+$GPC_{LASV}$; Z-MeV-$NP_{ExoN}$+$GPC_{LASV}$ are encompassed within this particular embodiment. When the protein of LASV is named before MeV, said protein is cloned within the additional transcription unit localized upstream the N gene of the MeV. It should be noted that several non-represented constructs are also encompassed by this embodiment. As an example, a heterologous polynucleotide may be cloned within the third ATU. Nucleic acid constructs corresponding to Z-MeV-$GPC_{LASV}$(ATU2)+NP (ATU3), or Z-MeV-NP(ATU2)-$GPC_{LASV}$(ATU3), or Z-MeV-$GPC_{LASV}$(ATU2)+mNP(ATU3), or Z-MeV-mNP (ATU2)-$GPC_{LASV}$(ATU3) are also encompassed by the present invention. It should be noted that a heterologous polynucleotide encoding at least one or any one of the Z polypeptide, the GPC polypeptide and/or the NP or mNP polypeptide could be inserted within ATU3. The various terms used therein have the same meaning as the one used in the previous particular embodiments.

In a particular embodiment of the invention, the nucleic acid construct comprises within the first heterologous polynucleotide a nucleic acid encoding the NP protein, preferentially the NP protein of SEQ ID No: 3, or an antigenic fragment thereof; and a nucleic acid encoding the GPC protein, preferentially the GPC protein of SEQ ID No: 1. In a preferred embodiment, this first heterologous polynucleotide is cloned between the P and M genes of the MeV, preferentially within ATU2 as defined here above.

In a particular embodiment of the invention, the nucleic acid construct comprises within the first heterologous polynucleotide a nucleic acid of SEQ ID No: 4 encoding the NP protein, and a nucleic acid of SEQ ID No: 2 encoding the GPC protein, preferentially these two nucleic acids are separated by a linker sequence. In a preferred embodiment, the nucleic acid of SEQ ID No: 4 is localized upstream the nucleic acid of SEQ ID No: 2. This is for example illustrated on FIG. 1B with the construct named MeV-NP+$GPC_{LASV}$.

In a particular embodiment of the invention, the nucleic acid construct comprises within the first heterologous polynucleotide a nucleic acid encoding the mNP protein, preferentially the mNP protein of SEQ ID No: 5, or an antigenic fragment thereof; and a nucleic acid encoding the GPC protein, preferentially the GPC protein of SEQ ID No: 1.

In a particular embodiment of the invention, the nucleic acid construct comprises within the first heterologous polynucleotide a nucleic acid of SEQ ID No: 6 encoding the mNP protein, and a nucleic acid of SEQ ID No: 2 encoding the GPC protein, preferentially these two nucleic acids are separated by a linker sequence. In a preferred embodiment, the nucleic acid of SEQ ID No: 6 is located upstream (towards the 5' end of the construct) the nucleic acid of SEQ ID No: 2, as illustrated in FIG. 1B with the construct named MeV-$NP_{ExoN}$+$GPC_{LASV}$. In a preferred embodiment, this first heterologous polynucleotide is cloned between the P and M genes of the MeV, preferentially within ATU2 as defined here above.

In a particular embodiment of the invention, the nucleic acid construct comprises the first heterologous polynucleotide and the second heterologous polynucleotide, and:

the second heterologous polynucleotide comprises a nucleic acid encoding the Z protein, or an antigenic fragment thereof, preferentially the Z protein of SEQ ID No: 7; the second heterologous polynucleotide being preferentially cloned within ATU1 as defined here above, and the first heterologous polynucleotide comprises a nucleic acid encoding the GPC protein, or an antigenic fragment thereof, preferentially the GPC protein of SEQ ID No: 1, the first heterologous polynucleotide being preferentially cloned within ATU2 as defined here above.

In a particular embodiment of the invention, the nucleic acid construct comprises the first heterologous polynucleotide and the second heterologous polynucleotide, and:

the second heterologous polynucleotide comprises a nucleic acid of SEQ ID No: 8 encoding the Z protein, the second heterologous polynucleotide being preferentially cloned within ATU1 as defined here above, and the first heterologous polynucleotide comprises a nucleic acid of SEQ ID No: 2 encoding the GPC protein, the first heterologous polynucleotide being preferentially cloned within ATU2 as defined here above.

In a particular embodiment of the invention, the nucleic acid construct comprises a recombinant cDNA whose sequence is selected from the group consisting of: SEQ ID No: 9 (MeV-GPC);

SEQ ID No: 10 (MeV-NP-GPC);

SEQ ID No: 11 (MeV-mNP-GPC);

SEQ ID No: 12 (Z-MeV-GPC);

SEQ ID No: 13 (Z-MeV-NP-GPC); and

SEQ ID No: 14 (Z-MeV-mNP-GPC), wherein said sequences are described as follows:

SEQ ID NO: 9

SEQ ID No: 9 is the sequence of a nucleic acid construct according to a particular embodiment of the invention wherein said construct contains the pTM1-MVSchwarz vector wherein the sequence encoding the GPC protein of LASV strain Josiah has been cloned within the Additional Transcription Unit 2.

SEQ ID NO: 10

SEQ ID No: 10 is the sequence of a nucleic acid construct according to another particular embodiment of the invention wherein said construct contains the pTM1-MVSchwarz vector wherein the sequence encoding the GPC protein of LASV strain Josiah has been cloned within the Additional Transcription Unit 2, and wherein the sequence encoding the NP protein of LASV strain Josiah has been cloned within the Additional Transcription Unit 2.

SEQ ID NO: 11

SEQ ID No: 11 is the sequence of a nucleic acid construct according to another particular embodiment of the invention wherein said construct contains the pTM1-MVSchwarz vector wherein the sequence encoding the GPC protein of LASV strain Josiah has been cloned within the Additional Transcription Unit 2, and wherein the sequence encoding the mutated NP protein of LASV strain Josiah has been cloned within the Additional Transcription Unit 2.

SEQ ID NO: 12

SEQ ID No: 12 is the sequence of a nucleic acid construct according to another particular embodiment of the invention wherein said construct contains the pTM1-MVSchwarz vector wherein the sequence encoding the GPC protein of LASV strain Josiah has been cloned within the Additional Transcription Unit 2, and wherein the sequence encoding the Z protein of LASV strain Josiah has been cloned within the Additional Transcription Unit 1.

SEQ ID NO: 13

SEQ ID No: 13 is the sequence of a nucleic acid construct according to another particular embodiment of the invention wherein said construct contains the pTM1-MVSchwarz vector wherein the sequence encoding the GPC protein of LASV strain Josiah has been cloned within the Additional Transcription Unit 2, and wherein the sequence encoding the NP protein of LASV strain Josiah has been cloned within the Additional Transcription Unit 2, and wherein the sequence encoding the Z protein of LASV strain Josiah has been cloned within the Additional Transcription Unit 1.

SEQ ID NO: 14

SEQ ID No: 14 is the sequence of a nucleic acid construct according to another particular embodiment of the invention wherein said construct contains the pTM1-MVSchwarz vector wherein the sequence encoding the GPC protein of LASV strain Josiah has been cloned within the Additional Transcription Unit 2, and wherein the sequence encoding the mutated NP protein of LASV strain Josiah has been cloned within the Additional Transcription Unit 2, and wherein the sequence encoding the Z protein of LASV strain Josiah has been cloned within the Additional Transcription Unit 1.

The invention also relates to a transfer vector, which may be used for the preparation of recombinant MeV-LASV particles when rescued from helper cells or production cells. Several transfer vectors are illustrated on FIG. 31 to 36. In a preferred embodiment of the invention, the transfer vector is a transfer vector plasmid suitable for the transfection of helper cells or of production cells, and comprising the nucleic acid construct according to the invention. The transfer vector plasmid may be obtained from a Bluescript plasmid and may be obtained by cloning the heterologous polynucleotide(s) of the invention in the pTM-MVSchw plasmid described here above. In particular embodiments of the invention, the transfer plasmid vector has the sequence of SEQ ID No: 9, SEQ ID No: 10, SEQ ID No: 11, SEQ ID No: 12, SEQ ID No: 13 or SEQ ID No: 14.

The invention also concerns the use of a transfer plasmid vector or the use of the nucleic acid construct according to the invention to transform cells suitable for the rescue of recombinant viral MeV-LASV particles, in particular to transfect or to transduce such cells respectively with plasmids or with viral vectors harboring the nucleic acid construct of the invention, said cells being selected for their capacity to express required measles virus proteins for appropriate replication, transcription and encapsidation of the recombinant genome of the virus corresponding to the nucleic acid construct of the invention in recombinant, infectious, replicative recombinant MeV-LASV particles.

The nucleic acid construct of the invention and the transfer plasmid vector are suitable and intended for the preparation of recombinant infectious replicative recombinant measles—Lassa virus (MeV-LASV) and accordingly said nucleic acid construct and transfer plasmid vector are intended for insertion in a transfer genome vector that as a result comprises the cDNA molecule of the measles virus, especially of the Schwarz strain, for the production of said recombinant MeV-LASV virus and expression of LASV polypeptide(s), possibly as LASV VLPs when the Z protein is encoded by at least one heterologous polynucleotide. The pTM-MVSchw plasmid is suitable to prepare the transfer vector, by insertion of the heterologous polynucleotide(s) as described herein necessary for the expression of LASV polypeptide(s), protein(s), antigen(s), or antigenic fragment(s) thereof. As used herein, the term "virus-like particle" (VLP) refers to a structure that in at least one attribute resembles a virus but which has not been demonstrated to be infectious as such. Virus Like Particles in accordance with the invention do not carry genetic information encoding the proteins of the Virus Like Particles, in general, virus-like particles lack a viral genome and, therefore, are noninfectious and non-replicative. In accordance with the present invention, Virus Like Particles can be produced in large quantities and are expressed together with MeV-LASV recombinant particles.

The invention also relates to the cells or cell lines thus transformed by the transfer vector of the invention and by further polynucleotides providing helper functions and proteins. Polynucleotides are thus present in said cells, which encode proteins that include in particular the N, P and L proteins of a measles virus (i.e., native MeV proteins or functional variants thereof capable of forming ribonucleoprotein (RNP) complexes), preferably as stably expressed proteins at least for the N and P proteins functional in the transcription and replication of the recombinant viral MeV-LASV particles. The N and P proteins may be expressed in the cells from a plasmid comprising their coding sequences or may be expressed from a DNA molecule inserted in the genome of the cell. The L protein may be expressed from a different plasmid. It may be expressed transitory. The helper cell is also capable of expressing a RNA polymerase suitable to enable the synthesis of the recombinant RNA derived from the nucleic acid construct of the invention, possibly as a stably expressed RNA polymerase. The RNA polymerase may be the T7 phage polymerase or its nuclear form (nlsT7).

In an embodiment, the cDNA clone of a measles virus is from the same measles virus strain as the N protein and/or the P protein and/or the L protein. In another embodiment, the cDNA clone of a measles virus is from a different strain of virus than the N protein and/or the P protein and/or the L protein.

The cells transformed or transfected with a nucleic acid construct according to the invention are able to produce recombinant measles viruses and and/or LASV VLPs when the Z protein is encoded by at least one heterologous polynucleotide. Accordingly, the recombinant measles virus comprises in its genome the nucleic acid construct of the invention and is able to express at least one polypeptide, protein or antigenic fragment thereof, of the LASV. Hence, the measles virus of the invention is able to express the GPC protein, or the GPC polypeptide, or an antigenic fragment thereof; and/or the NP protein, or the NP polypeptide, or an antigenic fragment thereof; and/or the mNP protein, or the mNP polypeptide, or an antigenic fragment thereof; and/or the Z protein, or the Z polypeptide, or an antigenic fragment thereof. LASV VLPs comprise at least the Z protein, or an antigenic fragment thereof, and may further comprise one other polypeptide of LASV; the GPC protein, a fragment of the GPC protein like GP1 or GP2, the NP protein and/or the mNP protein. In a preferred embodiment, the LASV VLPs comprise the Z protein, or an antigenic fragment thereof, and the GPC protein, or an antigenic fragment thereof, or a fragment of the GPC protein like GP1 and/or GP2. In another preferred embodiment, the LASV VLPs comprise the Z protein, or an antigenic fragment thereof, the GPC protein, or an antigenic fragment thereof, and the mNP protein or the NP protein, or an antigenic fragment thereof.

In a preferred embodiment of the invention, the recombinant measles virus expresses the GPC protein and the mNP protein of the LASV. In another preferred embodiment of the invention, the recombinant measles virus expresses the GPC protein and the Z protein of LASV.

Furthermore, according to some embodiments of the invention, the recombinant measles virus also expresses at least one polypeptide or protein, or an antigenic fragment thereof, of the measles virus. In other words, the recombinant measles virus expresses at least one of the following polypeptides: the N protein, the P protein, the M protein, the F protein, the H protein and the L protein of the MeV.

According to this embodiment, the recombinant virus expresses recombinant antigenic particles of the measles virus and the Lassa virus, allowing the elicitation of cellular response, or a humoral response, or a cellular and humoral response against polypeptides of the LASV and against polypeptides of the MeV.

In particular embodiments of the invention, the elicitation of the cellular response comprises elicitation of a T cell response, in particular CD4+ and/or CD8+ T cells response.

The invention thus relates to a process for the preparation of recombinant infectious measles virus particles comprising:

(a) transfecting cells, in particular helper cells, in particular HEK293 helper cells, stably expressing T7 RNA polymerase and measles N and P proteins with the nucleic acid construct according to the invention or with the transfer plasmid vector according to the invention;
(b) maintaining the transfected cells in conditions suitable for the production of recombinant measles virus and/or LASV VLPs;
(c) infecting cells enabling propagation of the recombinant measles virus and/or the LASV VLPs by co-cultivating them with the transfected cells of step (b);
(d) harvesting the recombinant measles virus expressing at least one LASV protein, preferentially at least the GPC protein and optionally the NP protein, the mNP protein and/or the Z protein, preferentially expressing the GPC protein and the mNP protein, and/or the LASV VLPs expressing at least the Z protein and possibly another LASV protein selected from the group consisting of the GPC protein, the NP protein and/or the mNP protein.

According to a particular embodiment, the invention relates to a process for the preparation of recombinant infectious measles virus particles comprising:

a) transferring, in particular transfecting, the nucleic acid construct of the invention or the transfer vector containing such nucleic acid construct in a helper cell line which also expresses proteins necessary for transcription, replication and encapsidation of the antigenomic (+) RNA sequence of MeV from its cDNA and under conditions enabling viral particles assembly and
b) recovering the recombinant infectious MeV-LASV virus expressing at least one polypeptide or protein of LASV, or an antigenic fragment thereof.

According to a particular embodiment of the invention, the process comprises:

a) transfecting helper cells with a nucleic acid construct according to the invention with a transfer plasmid vector, wherein said helper cells are capable of expressing helper functions to express an RNA polymerase, and to express the N, P and L proteins of a MeV virus;
b) co-cultivating said transfected helper cells of step 1) with passaged cells suitable for the passage of the MeV attenuated strain from which the cDNA originates;
c) recovering the recombinant infectious MeV-LASV virus expressing at least one polypeptide of the LASV.

According to another particular embodiment of the invention the method for the production of recombinant infectious MeV-LASV comprises:

a) recombining a cell or a culture of cells stably producing a RNA polymerase, the nucleoprotein (N) of a measles virus and the polymerase cofactor phosphoprotein (P) of a measles virus, with a nucleic acid construct of the invention and with a vector comprising a nucleic acid encoding a RNA polymerase large protein (L) of a measles virus, and
b) recovering the infectious, MeV-LASV virus from said recombinant cell or culture of recombinant cells.

According to a particular embodiment of the process, recombinant MeV are produced, which express LASV protein(s) comprising at least the GPC protein and/or LASV VLPs comprising at least the Z protein, and wherein the recombinant MeV and/or VLPs may express at least one other LASV proteins, or antigen, or an antigenic fragment thereof, e.g. GPC or a fragment thereof, especially GP1 and/or GP2, and optionally mNP of LASV. In other embodiment, the LASV VLPs comprise the Z protein or a fragment thereof, and optionally the GPC protein, and possibly GP1 and/or GP2. In a preferred embodiment of the invention, the LASV VLPs comprise the Z protein, or antigenic fragment thereof, and the GPC protein, or an antigenic fragment thereof. As an illustration, a process to rescue recombinant MeV expressing LASV proteins, in particular LASV VLPs comprises the steps of:

1) cotransfecting helper cells, in particular HEK293 helper cells, that stably express T7 RNA polymerase, and measles N and P proteins with (i) a transfer vector, in particular a plasmid, comprising cDNA encoding the full-length antigenomic (+) RNA of a measles virus recombined with at least one polynucleotide encoding at least one LASV protein, for example encoding the GPC protein, the NP protein, the mNP protein and/or the Z protein, and with (ii) a vector, especially a plasmid, encoding the MeV L polymerase cDNA;
2) cultivating said cotransfected helper cells in conditions enabling the production of MV-LASV recombinant virus;
3) propagating the thus produced recombinant virus by co-cultivating said helper cells of step 2) with cells enabling said propagation such as Vero cells;
4) recovering replicating MeV-LASV recombinant virus and LASV protein(s), in particular LASV Virus Like Particles.

As used herein, “recombining” means introducing at least one polynucleotide into a cell, for example under the form of a vector, said polynucleotide integrating (entirely or partially) or not integrating into the cell. According to a particular embodiment, recombination can be obtained with a first polynucleotide, which is the nucleic acid construct of the invention. Recombination can, also or alternatively, encompasses introducing a polynucleotide, which is a vector encoding a RNA polymerase large protein (L) of a measles virus, whose definition, nature and stability of expression has been described herein.

In accordance with the invention, the cell or cell lines or a culture of cells stably producing a RNA polymerase, a nucleoprotein (N) of a measles virus and a polymerase cofactor phosphoprotein (P) of a measles virus is a cell or cell line as defined in the present specification or a culture of cells as defined in the present specification, i.e., are also recombinant cells to the extent that they have been transformed by the introduction of one or more polynucleotides as defined above. In a particular embodiment of the invention, the cell or cell line or culture of cells, stably producing the RNA polymerase, the N and P proteins, does not produce the L protein of a measles virus or does not stably produce the L protein of a measles virus, e.g., enabling its transitory expression or production. The production of recombinant MeV-LASV virus of the invention may involve a transfer of cells transformed as described herein. "Transfer" as used herein refers to the plating of the recombinant cells onto a different type of cells, and particularly onto monolayers of a different type of cells. These latter cells are competent to sustain both the replication and the production of infectious recombinant MeV-LASV virus i.e., respectively the formation of infectious viruses inside the cell and possibly the release of these infectious viruses outside of the cells possibly with release of LASV immunogenic particles and/or LASV VLPs. This transfer results in the co-culture of the recombinant cells of the invention with competent cells as defined in the previous sentence. The above transfer may be an additional, i.e., optional, step when the recombinant cells are not efficient virus-producing culture i.e., when infectious recombinant MeV-LASV virus cannot be efficiently recovered from these recombinant cells. This step is introduced after further recombination of the recombinant cells of the invention with any nucleic acid construct of the invention, and optionally a vector comprising a nucleic acid encoding a RNA polymerase large protein (L) of a measles virus.

In a particular embodiment of the invention, a transfer step is required since the recombinant cells, usually chosen for their capacity to be easily recombined are not efficient enough in the sustaining and production of recombinant infectious MeV-LASV virus. In said embodiment, the cell or cell line or culture of cells of step 1) of the above-defined methods is a recombinant cell or cell line or culture of recombinant cells according to the invention.

Cells suitable for the preparation of the recombinant cells of the invention are prokaryotic or eukaryotic cells, particularly animal or plant cells, and more particularly mammalian cells such as human cells or non-human mammalian cells or avian cells or yeast cells. In a particular embodiment, cells, before recombination of its genome, are isolated from either a primary culture or a cell line. Cells of the invention may be dividing or non-dividing cells.

According to a preferred embodiment, helper cells are derived from human embryonic kidney cell line 293, which cell line 293 is deposited with the ATCC under No. CRL-1573. Particular cell line 293 is the cell line disclosed in WO2008/078198 and referred to in the following examples as 293T7/N/P. Thus, the invention also relates to a host cell, in particular an avian cell or a mammalian cell, transfected or transformed with the nucleic acid construct according to any embodiment of the invention, or transfected with a transfer plasmid vector. Suitable cells are the VERO NK cells (African green monkey kidney cells), and MRC5 cells (Medical Research Council cell strain 5). According to another aspect of this process, the cells suitable for passage are CEF cells (chick embryo fibroblasts). CEF cells can be prepared from fertilized chicken eggs as obtained from EARL Morizeau (8 rue Moulin, 28190 Dangers, France) or from any other producer of fertilized chicken eggs.

The process which is disclosed according to the present invention is used advantageously for the production of infectious replicative recombinant MeV-LASV virus appropriate for use as immunization compositions. The invention thus relates to a composition, in particular an antigenic composition, whose active principle comprises infection replicative recombinant MeV-LASV virus rescued from the nucleic acid construct of the invention and in particular obtained by the process disclosed. The composition may be a vaccine composition for administration to a human in need thereof, especially children. Said composition may be used for the treatment against LASV infection. Said composition may be used for the protection against LASV. Thus, the composition may be an immunogenic or antigenic composition for the protective or prophylactic treatment against a LASV infection. In particular, the active ingredients or active principles within the composition comprise recombinant MeV-LASV particles, said recombinant MeV-LASV particles being rescued from a transfer plasmid vector according to the invention and being optionally associated with VLPs comprising the Z protein and optionally other protein(s) of LASV, or antigenic fragment(s) thereof. In the context of the invention, the terms "associated" or "in association" refer to the presence, in a single composition, of both MeV-LASV recombinant viral particles and LASV polypeptides or proteins, in particular as VLPs, usually as physically separate entities. In a particular embodiment of the invention, the composition is a vaccine.

The invention also concerns the recombinant MeV-LASV infectious replicating virus particles in association with LASV polypeptide(s) or protein(s), or antigenic fragment(s) thereof, possibly associated LASV VLPs, or any composition according to the invention, for the use in the treatment or the prevention of an infection by Lassa virus in a subject, in particular a human subject, in particular a child.

The invention also concerns recombinant MeV-LASV infectious, replicative virus and associated LASV polypeptide(s) or protein(s), or antigenic fragment(s) thereof, and potentially associated LASV VLPs for use in an administration scheme and according to a dosage regime that elicits an immune response, advantageously a protective immune response, against LASV virus infection or induced disease, in particular in a human subject, in particular a child.

In a particular embodiment of the invention, the composition or the use of the composition is able to elicit immunization of a subject, in particular a human subject, in particular a child, after a single injection. In other words, the composition or the use of the composition may require a single administration of a selected dose of the recombinant MeV-LASV infectious replicative virus. Alternatively, it may require multiple doses administration in a prime-boost regimen. Priming and boosting may be achieved with identical active ingredients consisting of recombinant MeV-LASV infectious, replicative virus and associated LASV polypeptide(s) and protein(s), or antigenic fragment(s) thereof, and/or LASV VLPs.

The invention also concerns an assembly of different active ingredients including as one of these ingredients recombinant MeV-LASV infectious, replicative virus and associated LASV polypeptide(s) or protein(s), and/or LASV VLPs. The assembly of active ingredients is advantageously for use in immunization of a host, in particular a human host.

The inventors have shown that administration of recombinant MeV-LASV infectious, replicative virus elicits an immune response and especially elicits production of neutralizing antibodies against LASV-related polypeptides.

Accordingly, it has been shown that administration of the active ingredients according to the invention elicits immunization of the host. The vaccine according to the invention is safe, leads to immune answer within the host, which encompasses especially CD4+ and CD8+ T cell responses. As shown in the examples, the vaccine according to the invention induces antigen-specific T cell responses. It has also been shown that immunized monkey hosts survive lethal dose challenge of LASV.

After immunization of a host, and LASV challenge, the level of liver enzymes (ALT and AST), lactate deshydrogenase (LDH), C-reactive protein (CRP) and albumin remained normal or slightly increases in immunized monkey hosts, while these levels increase several folds in non-immunized hosts.

The composition according to the invention is able to elicit production of recombinant LASV-specific immunoglobulins, especially IgM and IgG, and neutralizing antibodies. The composition according to the invention is a safe vaccine, immunogenic and efficacious in a host. The compositions and their use confer at least T cell response and confer immunity against a Lassa virus infection in a vaccinated host.

The composition according to the invention may also be able to elicit production of MeV-specific immunoglobulins, especially IgM and IgG, and neutralizing antibodies. The composition according to the invention is a safe vaccine, immunogenic and efficacious in a host. The compositions and their use confer at least T cell response and may confer immunity against a Measles virus infection in a vaccinated host.

The composition according to the invention also concerns recombinant MeV-LASV infectious, replicative virus and associated LASV polypeptide(s) or protein(s), or antigenic fragment(s) thereof, and potentially associated LASV VLPs for use in an administration scheme and according to a dosage regime that elicits an immune response, advantageously a protective immune response, against measles virus infection or induced disease, in particular in a human subject, in particular a child.

The invention also concerns the recombinant MeV-LASV infectious replicating virus particles in association with LASV polypeptide(s) or protein(s), or antigenic fragment(s) thereof, and/or LASV VLPs, or any composition according to the invention, for the use in the treatment or the prevention of an infection by measles virus in a subject, in particular a human subject, in particular a child.

The invention also concerns a heterologous polynucleotide comprising any one of the codon-optimized sequence encoding the GPC protein, the Z protein, the NP protein and/or the mNP protein. Thus, the invention also concerns the codon-optimized polynucleotide comprising or consisting of SEQ ID No: 2; SEQ ID No: 4, SEQ ID No: 6 and/or SEQ ID No: 8.

DESCRIPTION OF THE FIGURES

Some of the figures, to which the present application refers, are in color. The application as filed contains the color print-out of the figures, which can therefore be accessed by inspection of the file of the application at the patent office.

FIG. 1. Schematic representation of nucleic acid constructs. A: MeV vector. B: nucleic acid constructs according to the invention. MeV genes are indicated in grey and LASV genes are indicated in green, blue and red. For the MV genes: N (nucleoprotein); P/V/C (phosphoprotein and V/C proteins); M (matrix); F (Fusion protein); H (hemagglutinin): L (polymerase). For the LASV genes: NP (nucleoprotein); $NP_{ExoN}$ (also referenced $NP_{KO}$ on some figures; mutated sequence encoding a mutated NP with its exonuclease activity knocked down); GPC (glycoprotein precursor); Z (zinc-binding protein). ATUs are indicated by the black arrows. ATU1 is localized on the left, upstream the N gene of MeV while ATU2 is localized centrally, between P and M MeV genes.

FIG. 2. Growth kinetics of viruses on Vero E6 cells. MeV-GFP corresponds to a construct wherein a polynucleotide encoding a Green Fluorescent Protein has been inserted within ATU2. MeV-$GPC_{LASV}$ corresponds to a construct wherein a polynucleotide encoding the GPC protein of LASV has been inserted within ATU2. MeV-NP+$GPC_{LASV}$ corresponds to a construct wherein genes encoding the GPC protein and the NP protein of LASV has been inserted within ATU2. MeV-$NP_{ExoN}$+$GPC_{LASV}$ corresponds to a construct wherein polynucleotide encoding the GPC protein and a mutated NP protein (exonuclease activity knocked down) of LASV has been inserted within ATU2. MeV-Z+$GPC_{LASV}$ corresponds to a construct wherein a polynucleotide encoding the GPC protein has been inserted within ATU2, and wherein a polynucleotide encoding the Z protein has been inserted within ATU1. Titers obtained in typical experiments, measured by $TCID_{50}$ from 3 independent experiments. Means and standard errors are represented.

FIG. 3. Expression of LASV proteins (GPC, NP and Z) and MeV protein (F) in infected Vero E6 cells and in the supernatants of infected Vero E6 cells. The effect of each construct was assessed by Western blot as detailed in the material and method. NI: non-infected cells. ns: non specific.

FIG. 8. Cell surface expression of cluster of differentiation markers CD80, CD86, CD83 and CD40 in human primary dendritic cells infected with different MeV-LASV vectors. Flow cytometry for the cell surface expression of co-activation molecules 48 h post-infection.

FIG. 10. LASV antigens-specific CD4 and CD8 T cells responses in vaccinated cynomolgus monkeys (*Macaca fascicularis*). Flow cytometry after stimulation of whole blood by overlapping peptides specific to GPC, NP and Z.

FIG. 11. Clinical scores in cynomolgus monkeys (*Macaca fascicularis*) after challenge with a lethal dose of LASV strain Josiah. Clinical score is based on body temperature, body weight, capacity to feed and hydrate normally, behavior, clinical signs. A score of 15 is the endpoint for killing. Lethal dose of LASV strain consists in 1.500 FFU of LASV strain Josiah subcutaneously injected to the animals.

FIG. 12. Body temperature in cynomolgus monkeys (*Macaca fascicularis*) challenged with a lethal dose of LASV strain Josiah.

FIG. 13. Liver enzymes (AST and ALT) levels in plasma of immunized cynomolgus monkeys.

FIG. 16. Viral RNA quantification in the nasal (A) and oral secretions (B) and in the urine (C) of cynomolgus monkeys challenged with a lethal dose of LASV strain Josiah. RNA quantification by qPCR.

FIG. 17. LASV RNA levels detected in organs of challenged cynomolgus monkeys previously immunized with different MeV-LASV.

FIG. 18. LASV infectious titers detected in organs of challenged cynomolgus monkeys previously immunized with different MeV-LASV.

FIG. 19. IgM and IgG responses against LASV in cynomolgus monkeys challenged with a lethal dose of LASV strain Josiah. A. IgM LASV specific. B: IgG LASV specific. Immunoglobulin levels measured by ELISA. Optical density calculated according to the absorbance at 450 nM.

FIG. 20. LASV GP- and NP-specific CD8+ and CD4+ T cell responses after immunization. The percentage of CD8+ and CD4+ T cells that produced IFNg, TNFa and/or IL-2 after stimulation with overlapping peptides covering the whole LASV GP and NP have been determined using flow cytometry.

FIG. 23. LASV GP- and NP-specific CD8+ T cell responses after LASV challenge. The percentage of CD8+ T cells that produced IFNg, TNFa and/or IL-2 after LASV challenge with overlapping peptides covering the whole LASV GP (23A) and NP (23B) have been determined with flow cytometry. The proportion of different sub-populations of responding T cells is presented using pie chart.

FIG. 24. LASV GP- and NP-specific CD4+ T cell responses after LASV challenge. The percentage of CD4+ T cells that produced IFNg, TNFa and/or IL-2 after LASV challenge with overlapping peptides covering the whole LASV GP (23A) and NP (23B) have been determined with flow cytometry. The proportion of different sub-populations of responding T cells is presented using pie chart.

FIG. 28. IgM and IgG responses against MeV in cynomolgus monkeys challenged with a lethal dose of LASV strain Josiah. A: IgM MeV specific. B: IgG MeV specific. IgG and IgM MeV-specific were not measures at days 7 and 14 for the monkeys immunized with the MeV construct.

FIG. 29. Determination of the Exonuclease activity of native and mutated NP protein. Fold induction of Luciferase activity virus-induced and immunostimulatory RNAs-induced interferon-beta activation. CT: control. $NP_{LASV}$: native NP protein. $NP_{ExoNLASV}$: mutated NP protein of SEQ ID No: 5. SeV: Sendai virus at moi=1.

FIG. 30. Analysis of MeV-$NP_{ExoN}$-$GPC_{LASV}$ tropism. CHO cell lines were infected with either a Mopeia virus pseudotyped with LASV GPC or with MeV-$NP_{ExoN}$-$GPC_{LASV}$. Expression of GPC was analyzed by staining with an anti-GP1 antibody. The nuclei are in blue, while the anti-GP1 stained is in green.

FIG. 32. Schematic representation of transfer vector plasmid according to a second embodiment of the invention. The transfer vector has the sequence of SEQ ID No: 10. The measles gene encoding the N protein is localized between nucleotides 190 and 1767. The measles gene encoding the P protein is localized between nucleotides 1889 and 3412. The codon-optimized heterologous polynucleotide of SEQ ID No: 4 encoding the NP protein is localized between nucleotides 3532 and 5241. The codon-optimized heterologous polynucleotide of SEQ ID No: 2 encoding the GPC is localized between nucleotides 5386 and 6861. A linker sequence comprising regulatory sequence of the measles virus is localized between nucleotides 5242 and 5385. ATU2 is localized between nucleotides 3487 and 6925 minus the heterologous polynucleotide insert and the linker sequence. The measles gene encoding the M protein is localized between nucleotides 6958 and 7965.

FIG. 33. Schematic representation of transfer vector plasmid according to a third embodiment of the invention. The transfer vector has the sequence of SEQ ID No: 11. The measles gene encoding the N protein is localized between nucleotides between 190 and 1767. The measles gene encoding the P protein is localized between nucleotides 1889 and 3412. The codon-optimized heterologous polynucleotide of SEQ ID No: 6 encoding the mutated NP protein is localized between nucleotides 3532 and 5241. The codon-optimized heterologous polynucleotide of SEQ ID No: 2 encoding the GPC is localized between nucleotides 5386 and 6861. A linker sequence comprising regulatory sequence of the measles virus is localized between nucleotides 5242 and 5385. ATU2 is localized between nucleotides 3487 and 6925 minus the heterologous polynucleotide insert and the linker sequence. The measles gene encoding the M protein is localized between nucleotides 6958 and 7965.

FIG. 34. Schematic representation of transfer vector plasmid according to a fourth embodiment of the invention. The transfer vector has the sequence of SEQ ID No: 12. The codon-optimized heterologous polynucleotide of SEQ ID No: 8 encoding the Z protein is localized between nucleotides 193 and 504. The measles gene encoding the N protein is localized between nucleotides 646 and 2223. The measles gene encoding the P protein is localized between nucleotides 2345 and 3868. The codon-optimized heterologous polynucleotide of SEQ ID No: 2 encoding the GPC is localized between nucleotides 3988 and 5463. The measles gene encoding the M protein is localized between nucleotides 5560 and 6567.

EXAMPLES

Materials and Methods

Cells and Viruses

Figure 4:
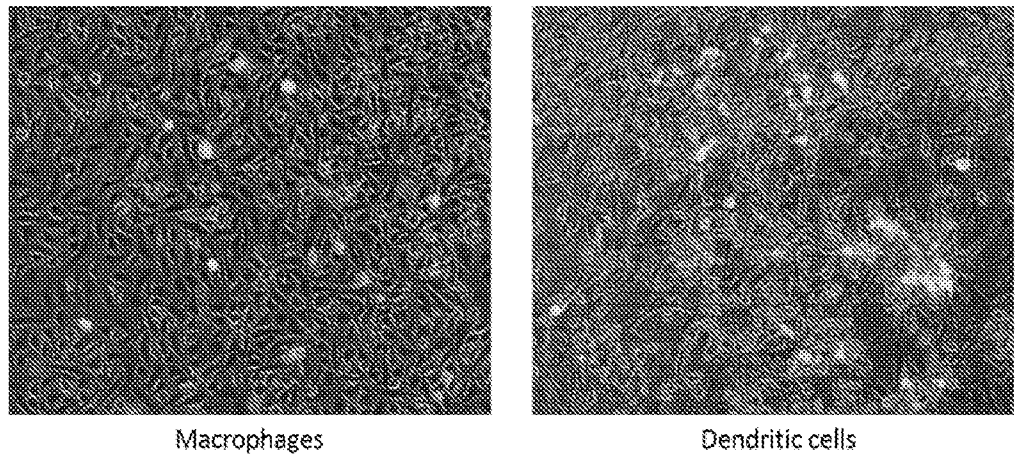
FIG. 4. MeV-GFP entry and replication in immune antigen presenting cells derived from human peripheral blood mononuclear cells.

293T7/N/P cells expressing stably the T7 polymerase and the measles N and P proteins were used to rescue recombinant measles viruses and were maintained as described before {Combredet, 2003 #76}. Vero NK cells were grown in Glutamax Dulbecco Modified Eagle's Medium (DMEM, Life Technologies) supplemented with 5% FCS, and 0.5% Penicillin-Streptomycin. Blood samples were obtained from the Etablissement Frangais du Sang (EFS, Lyon, France). Mononuclear cells were purified by Ficoll density gradient centrifugation (GE Healthcare). Monocytes were first separated from peripheral blood mononuclear cells by centrifugation on a cushion of 50% Percoll (GE Healthcare, Velizy, France) in PBS and then purified using the Monocyte isolation kit II according to the manufacturer's instructions (Miltenyi Biotec, Paris, France). Macrophages were obtained by incubating monocytes for 6 days in RPMI, 10% SVF, 10% autologous serum supplemented with 50 ng/mL of M-CSF. M-CSF was added every 2 days and 40% of the culture medium was replaced.

Plasmid Constructs

Codon-optimized ORF of LASV GPC, NP and Z (LASV strain Josiah) were cloned in the pTM1-MVSchwarz vector in additional transcriptional units (ATU) placed upstream of Nucleoprotein (N) (ATU1 for Z) or between the phosphoprotein (P) and the matrix (M) genes of the Schwarz MV genome (ATU2, GPC alone or NP+GPC) like previously described (Combredet, C., et al., A molecularly cloned Schwarz strain of measles virus vaccine induces strong immune responses in macaques and transgenic mice. J Virol, 2003. 77(21): p. 11546-54). All plasmid constructs were verified by sequencing.

Western Blot and Antibodies

Vero NK cells infected with recombinant MeV-GFP, MeV-$GPC_{LASV}$, MeV-NP+$GPC_{LASV}$, MeV-$NP_{ExoN}$+$GPC_{LASV}$ or MeV-Z+$GPC_{LASV}$ were lysed in Co-IP buffer and cleared by centrifugation. Lysates and culture supernatants were then separated on 4-12% precast gels (Biorad) under denaturing conditions and transferred to PVDF membrane. Membranes were stained with primary antibodies to GP1 (in house mouse monoclonal production), NP (mouse anti-LASV serum), Z (in house rabbit polyclonal production) or F (rabbit polyclonal Fcyt, a kind gift of R. Cattaneo). Cell lysates were also stained with an anti-actin antibody coupled to the horseradish peroxidase (HRP). After staining with secondary antibodies coupled to HRP, membranes were revealed using West Dura substrate (Pierce) and photographed using a LAS4000 imager (GE Healthcare).

Virus Rescue and Titration

Recombinant measles viruses expressing LASV antigens were rescued as previously described (Combredet, 2003; Radecke, F., et al., Rescue of measles viruses from cloned DNA. Embo J, 1995. 14(23): p. 5773-84; WO2008/078198). Briefly, 293T7/N/P cells were transfected with plasmids encoding the measles L polymerase and the antigenomic segment of the desired MeV vector. Clonal syncytia were picked and used to infect Vero NK cells in 6-well plates. When syncytia has reached about 50% of the well superficy, cells were detached and overlaid on Vero NK cells in 10 cm dishes to produce passage 1 (P1) stocks. To prepare higher passage virus stocks, Vero NK cells were infected at a multiplicity of infection (MOI) of 0.01 and then incubated at 32° C. for 2 to 3 days. To harvest virus, cells were scraped into Opti-MEM I reduced-serum medium and freeze-thawed twice. Titers were determined by 50% tissue culture infective dose (TCID50) titration on Vero NK cells.

Quantitative RNA Analysis

For RT-qPCR experiments, total RNA was isolated from mock or infected cells using the Rneasy Mini Kit (Qiagen, Courtaboeuf, France), according to the manufacturer's instructions, and a supplementary DNase step added using the Turbo DNA free kit Ambion (Thermo Fisher Scientific). Synthesis of cDNA was performed using SuperScript III and amplification was performed using the Gene Expression Master Mix kit (Applied Biosystems, Thermo Fisher Scientific). For type I IFN, the primer/probe mix was developed in house. Runs of qPCR assays were performed in a LightCycler 480 (Roche Diagnostics, Meylan, France). The expression of all genes was standardized to that of the GAPDH gene, and expressed as fold induction relative to GAPDH. For viral RNA quantification, an RNA probe of the 771-934 pb region of the NP ORF was cloned into the pGEM vector (Promega) to generate T7 polymerase driven transcripts. The RNA probe was DNAse treated, purified, and quantified (Dropsense96, Trinean, Gent, Belgium). Quantitative PCR for viral RNA was performed with the EuroBioGreen qPCR Mix Lo-ROX (Eurobio, Les Ulis, France), using LASV specific primers.

Flow Cytometry for MP Activation, T Cell Activation and Proliferation

Mock and MOI 1-infected MP were detached 48 h after infection, saturated with human IgG and surface stained with antibodies to CD40, CD83, CD80, and CD86 (BD Biosciences, Le-Pont-de-Claix, France) before final fixation in PBS/1% PFA. LASV antigen-specific T cells were analysed from fresh whole blood. Cells were incubated with a pool of GPC, NP or Z overlapping peptides in the presence of CD28 and CD49d antibodies (2 μg/ml) and Brefeldin A (10 μg/ml) for 6 h at 37° C. SEA (1 μg/ml) or PBS were respectively used as positive or negative control of activation. Peptides are 15-mer amino acids long (1 μg/ml each) with an overlap of 11 residues and spanned the complete GPC, NP or Z ORF of LASV strain Josiah. PBS-EDTA 20 mM was added to samples before cell-surface staining for CD3, CD4 and CD8 (BD Biosciences). Red blood cells were then lysed using PharmLyse (BD Biosciences). Cells were then fixed and permeabilized for intracellular staining with antibodies to IFNγ (Biolegend). For proliferation and activation, wells were stained using antibodies to Ki67 or Granzyme B. Cells were analysed by flow cytometry using an LSR Fortessa cytometer (BD Biosciences) or a 10-color Gallios cytometer (Beckman Coulter). Data were analysed using Kaluza software (Beckman Coulter).

Cynomolgus Monkey Challenge with LASV

Groups of 4 male cynomolgus monkeys (*Macaca Fascicularis,* 32-39 month-old, 3-4 kg) were immunized in A2 facilities (SILABE, France) by subcutaneous injection of 2.106 TCID50 of MeV-$NP_{ExoN}$+$GPC_{LASV}$ or MeV-Z+$GPC_{LASV}$, respectively. Another control group of 3 monkeys was immunized with the MeV vaccine strain Schwarz. Blood draws, oral and nasal swabs and urine sampling were performed every 2-3 days during the first two weeks then once a week up to day 37 in order to assess vaccine replication and shedding, IgM and IgG responses and T cell responses against LASV GPC, NP or Z. After 37 days, monkeys were transported to BSL-4 facilities (Laboratoire P4-Inserm Jean Merieux) where they were challenged subcutaneously using 1,500 FFU of LASV strain Josiah. Animals were followed for clinical signs of the disease and were euthanized according to scoring made based on body temperature, body weight, feeding, hydrating, behaviour and clinical signs. Experimentation endpoint was placed at day 28 post challenge and all animals that had survived to this point were euthanized according to validated experimental procedures. Blood draws, oral and nasal swabs and urine sampling were performed every 2-3 days during the first two weeks then once a week up to day 28 in order to assess LASV virus replication and shedding, IgM and IgG responses and T cell responses against LASV GPC, NP or Z. This study has been approved by the Comite Regional d'Ethique en Matiere d'Experimentation Animale de Strasbourg (APAFIS #6543-20160826144775) and by the Comite Regional d'Ethique pour l'Experimentation Animale Rhone Alpes (CECCAPP 20161110143954).

Determination of the Exonuclease Activity of Native and Mutated NP Protein (FIG. 29):

293T cells were cotransfected using calcium phosphate with 100 ng of a vector that expresses the firefly luciferase (Fluc) reporter gene from a known functional promoter sequence of the IFN-beta gene (pIFNbeta-LUC), variable amounts of either native (wild type) or mutant LASV NP vectors, and 50 ng of a 1-gal-expressing plasmid for transfection normalization. At 24 h post-transfection, cells were infected with Sendai virus (at moi=1) in order to induce IFN-β expression. At 24 hpi, cell lysates were prepared for luciferase and 1-gal assays. Fluc activities were normalized by the 1-gal values. To determine whether NP has an exonuclease activity or not, its effect on the suppression of the immunostimulatory RNAs-induced IFN production is analysed, HEK293 cells were transfected with pIFNbeta-LUC, variable amounts of either native (WT) or mutant LASV NP vectors, and a beta-gal-expressing plasmid for transfection normalization. 18 h later, cells were transfected with either 1 μg of Poly(I:C) or 250 ng of Pichinde virion RNAs by lipofectamine 2000. Luciferase activity was determined at 18 h after the immunostimulatory RNA transfection and normalized by the beta-gal activity. A mutated NP protein with its exonuclease activity knocked down does not suppress the immunostimulatory RNAs-induced IFN production.

Example 1—Generation of Recombinant MeV Viruses Expressing LASV Antigens

In order to determine what is the best combination of LASV antigens to introduce in the MeV vector to get the best immunogenicity, we have generated several MeV/LASV vaccine candidates using the Schwarz MeV vaccine platform (FIG. 1A) expressing GPC alone or in combination with NP (mutated or not in the exonuclease domain to abrogate the immunosuppressive function contained in the LASV NP) or GPC and Z in order to produce antigenic LASV virus-like particles (VLPs) in vivo. We also made constructs expressing Z, GPC and NP mutated or not in the exonuclease domain. The GPC and NP genes were cloned between the MeV P and M genes in the additional transcriptional unit 2 (ATU2).

Figures 2, 3:
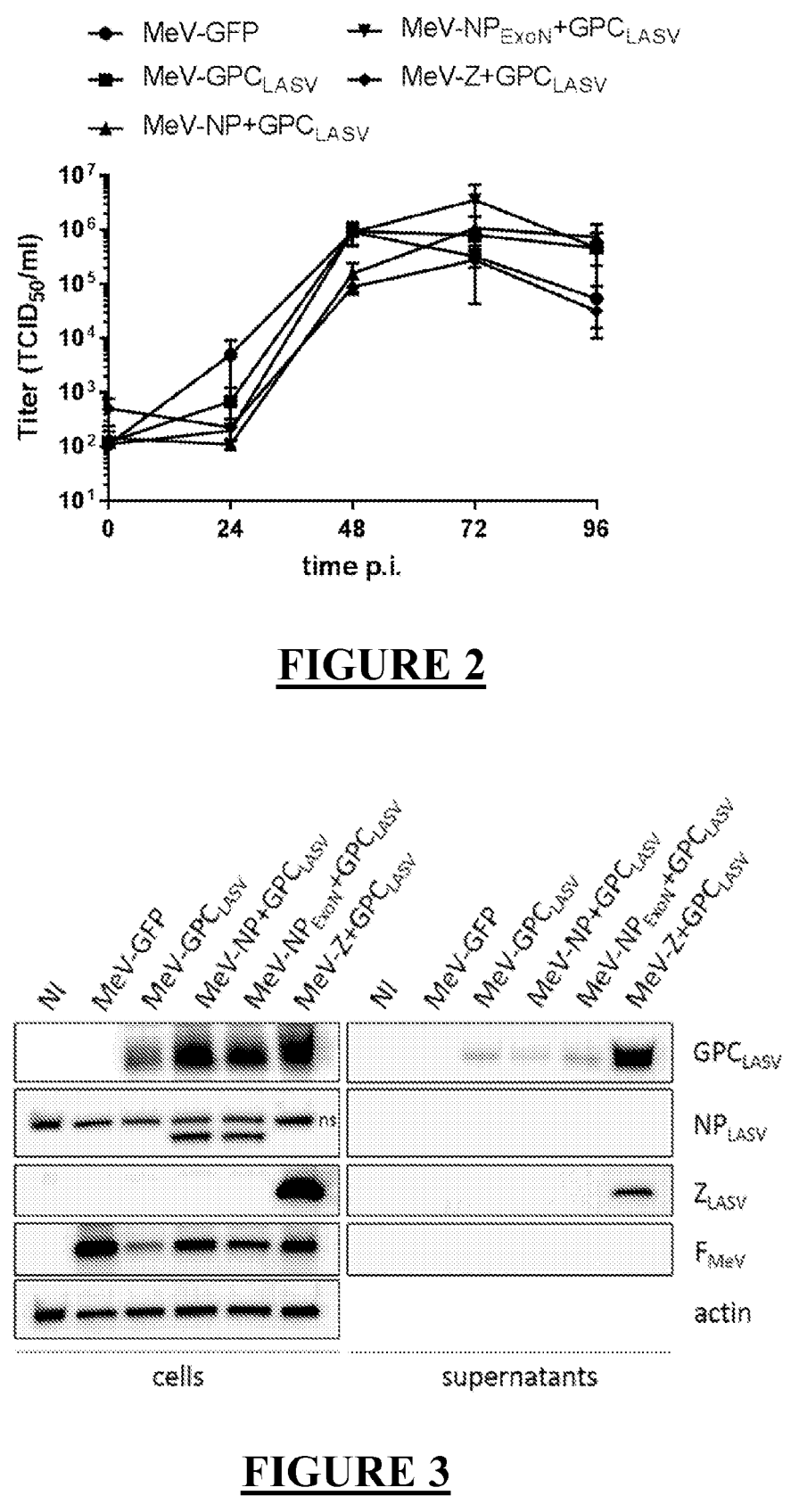

The Z gene was cloned upstream of the N gene in the ATU1 (FIG. 1B). All viruses were rescued and grew to similar titers on Vero E6 cells than a control MeV-GFP expressing GFP from ATU2 (FIG. 2), except for the MeV/LASV-Z+GPC that was attenuated by about a log compared to other constructs. Expression of the different LASV antigens was controlled by western blot using specific antibodies against LASV GPC, NP or Z, or against the measles fusion protein F (FIG. 3). Expression of GPC was detected in MeV-$GPC_{LASV}$, MeV-NP+$GPC_{LASV}$, MeV-$NP_{ExoN}$+$GPC_{LASV}$ and MeV-Z+$GPC_{LASV}$ infected Vero E6 cells; expression of NP in MeV-NP+$GPC_{LASV}$, MeV-$NP_{ExoN}$+$GPC_{LASV}$ and MeV-Z+$GPC_{LASV}$ infected Vero E6 cells; expression of Z only in MeV-Z+$GPC_{LASV}$ infected cells. MeV F expression was detected in all MeV infected cells. As expected, GPC was also detected in the supernatants of MeV-Z+$GPC_{LASV}$ infected cells along with Z, supporting the release of GPC along with Z under the form of VLPs. All vectors were passaged 10 times without loss of LASV antigens expression.

Example 2—Immunogenicity of MeV Viruses Expressing LASV Antigens in Human Primary Antigen Presenting Cells To characterize the immunogenic properties of the different MeV vectors in human immune cells, we infected monocyte derived macrophages and dendritic cells. MeV enters and replicate in these cells, as shown by the expression of GFP on FIG. 4. However, viruses did not replicate efficiently in these cells as infectious titers were barely detectable at day 1 post infection and did not increase over time, likely due to the induction of an antiviral innate response.

Figure 5:
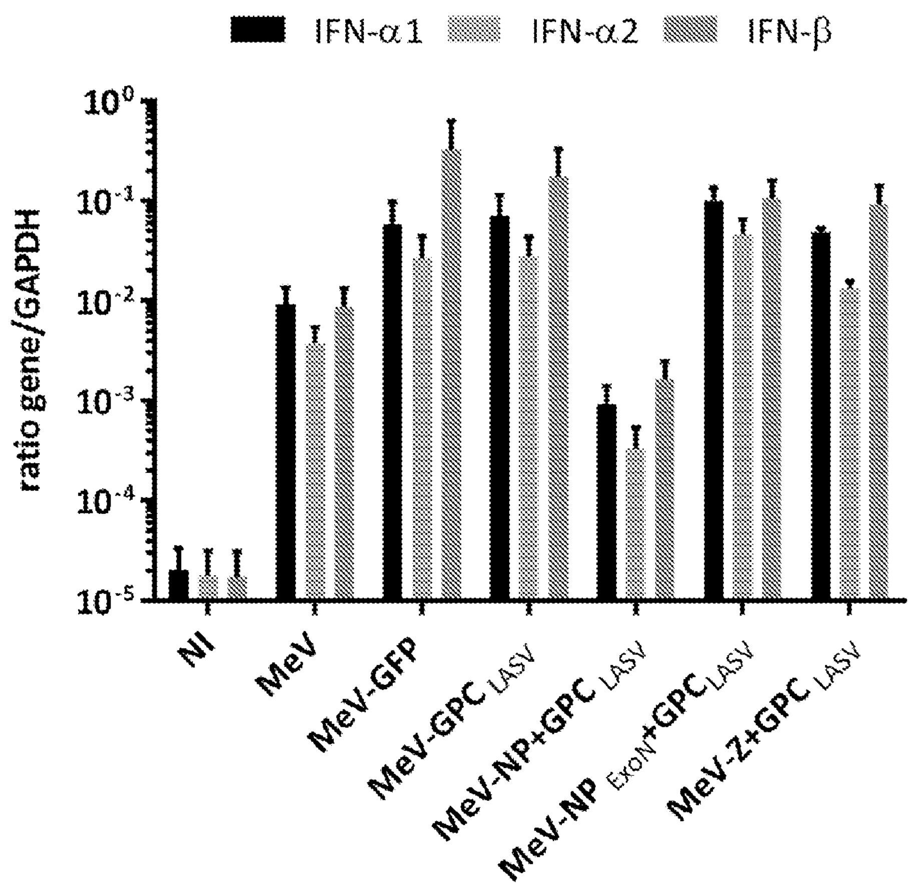
FIG. 5. Expression of type I IFN in human primary macrophages infected with different MeV-LASV vectors. Quantitative RNA analysis by qPCR analyses of type I IFN response (quantitative expression of IFNa1, IFNa2 and IFNb). Expression 24 h post-infection. All results are normalized to GAPDH gene and expressed as fold induction relative to GAPDH.
Figure 6:
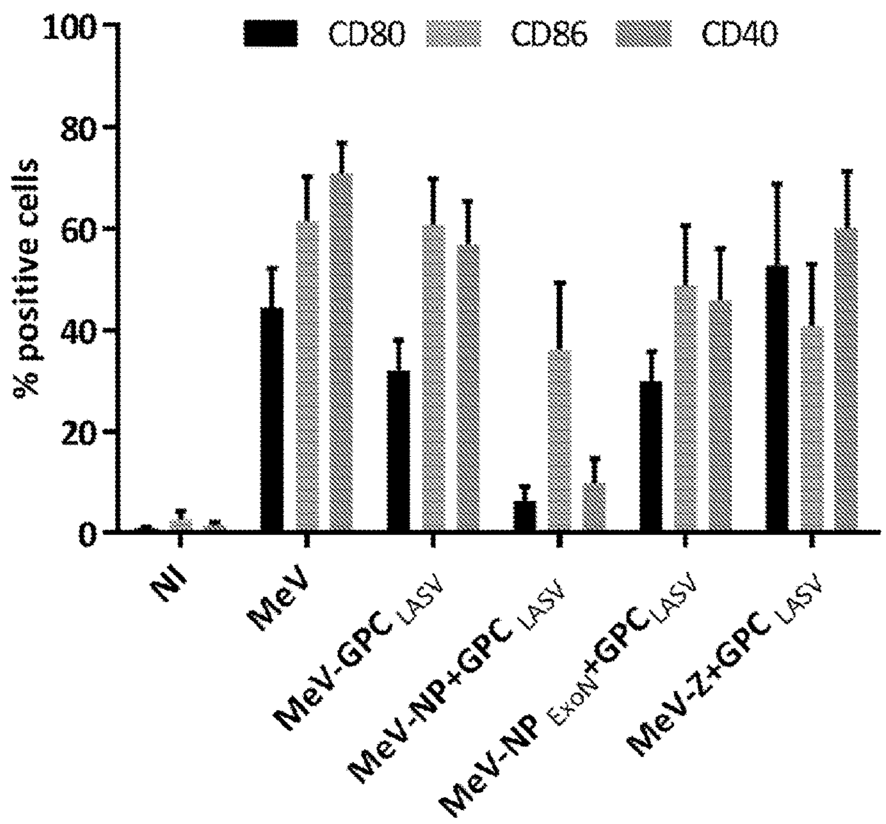
FIG. 6. Cell surface expression of cluster of differentiation markers CD80, CD86 and CD83 CD40 in macrophages infected with different MeV-LASV vectors. Flow cytometry for the cell surface expression of co-activation molecules 48 h post-infection.

We analysed the immune responses of macrophages and dendritic cells to the different recombinant viruses by combining flow cytometry analyses of activation markers and qPCR analyses of the type 1 IFN response. We analysed the type I IFN responses induced by the different vectors by qPCR at 24 hrs post infection (FIG. 5). In macrophages, MeV-GPC$_{LASV}$ and MeV-Z+GPC$_{LASV}$ induced the same levels of IFN alpha-1, alpha-2 and beta than the control MeV-GFP. However, addition of the LASV NP reduced by almost 3 logs the induction of type I IFN (MeV-NP+GPC$_{LASV}$) but mutation of the ExoN domain of LASV NP (MeV-NP$_{ExoN}$+GPC$_{LASV}$) restored the induction of type I IFN to levels comparable to MeV-GFP and -GPC$_{LASV}$. This results demonstrate that the LASV NP can control the induction of type I IFN through its ExoN activity, likely by digesting dsRNA molecules expressed during MeV replication (Son, 2015). We then looked at the induction of co-activation molecules by the different vectors at 48 hrs post infection in macrophages (FIG. 6). Importantly, cell surface expression of co-activation molecules is critical to activate the T cell responses. As shown on FIG. 6, all vectors induced strong cell surface expression of CD80, CD86 and CD83. Notably, expression was reduced in MeV-NP+GPC$_{LASV}$ infected macrophages compared the expression in macrophages infected by the other vectors but was restored when the ExoN domain of LASV NP was mutated.

Figure 7:
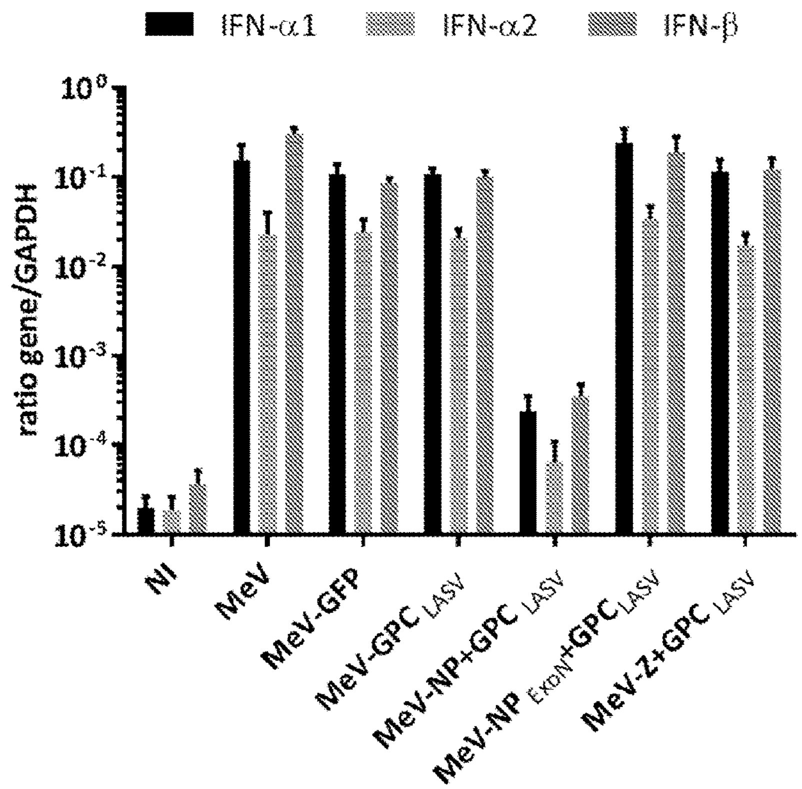
FIG. 7. Expression of type I IFN in human primary dendritic cells infected with different MeV-LASV vectors. Quantitative RNA analysis by qPCR analyses of type I IFN responses (quantitative expression of IFNa1, IFNa2 and IFNb). Expression 24 h post-infection. All results are normalized to GAPDH gene and expressed as fold induction relative to GAPDH.
Figure 8:
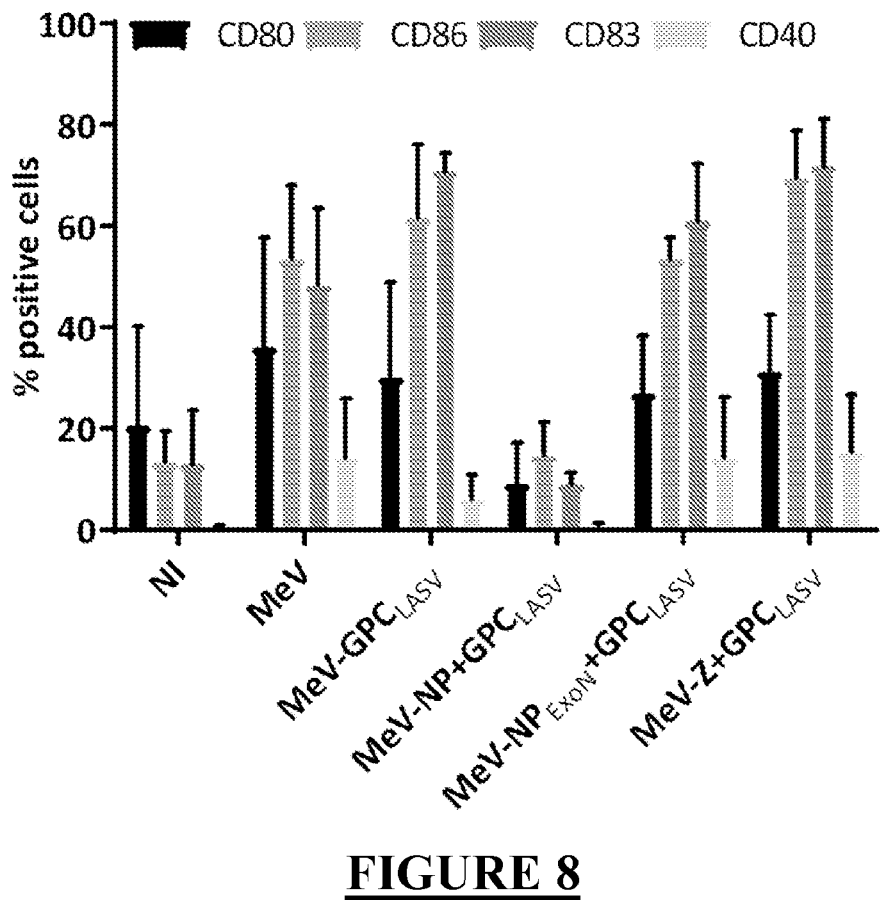

Similar experiments were performed on dendritic cells (FIGS. 7 and 8). As observed in macrophages, MeV-GPC$_{LASV}$ and MeV-Z+GPC$_{LASV}$ induced the same levels of IFN alpha-1, alpha-2 and beta than the control MeV-GFP (FIG. 7). Addition of LASV NP also reduced the induction of type I IFN, but mutation of the ExoN domain of LASV NP restored the induction of type I IFN to levels comparable to MeV-GFP, MeV-Z+GPC$_{LASV}$ and MeV-GPC$_{LASV}$. The expression of the co-activation molecules CD80, CD86, CD83 and CD40 were also similarly induced in dendritic cells infected with MeV-GFP, MeV-Z+GPC$_{LASV}$ and MeV-GPC$_{LASV}$ (FIG. 8).

The vaccine strains of MeV-LASV induce a type I IFN response and cell surface expression of co-activation molecules; the presence of wild type NP strongly reduces the ability of the vaccine to induce these effects, but mutation within the ExoN domain restore the ability of the vaccine to induce these effects.

Figure 9:
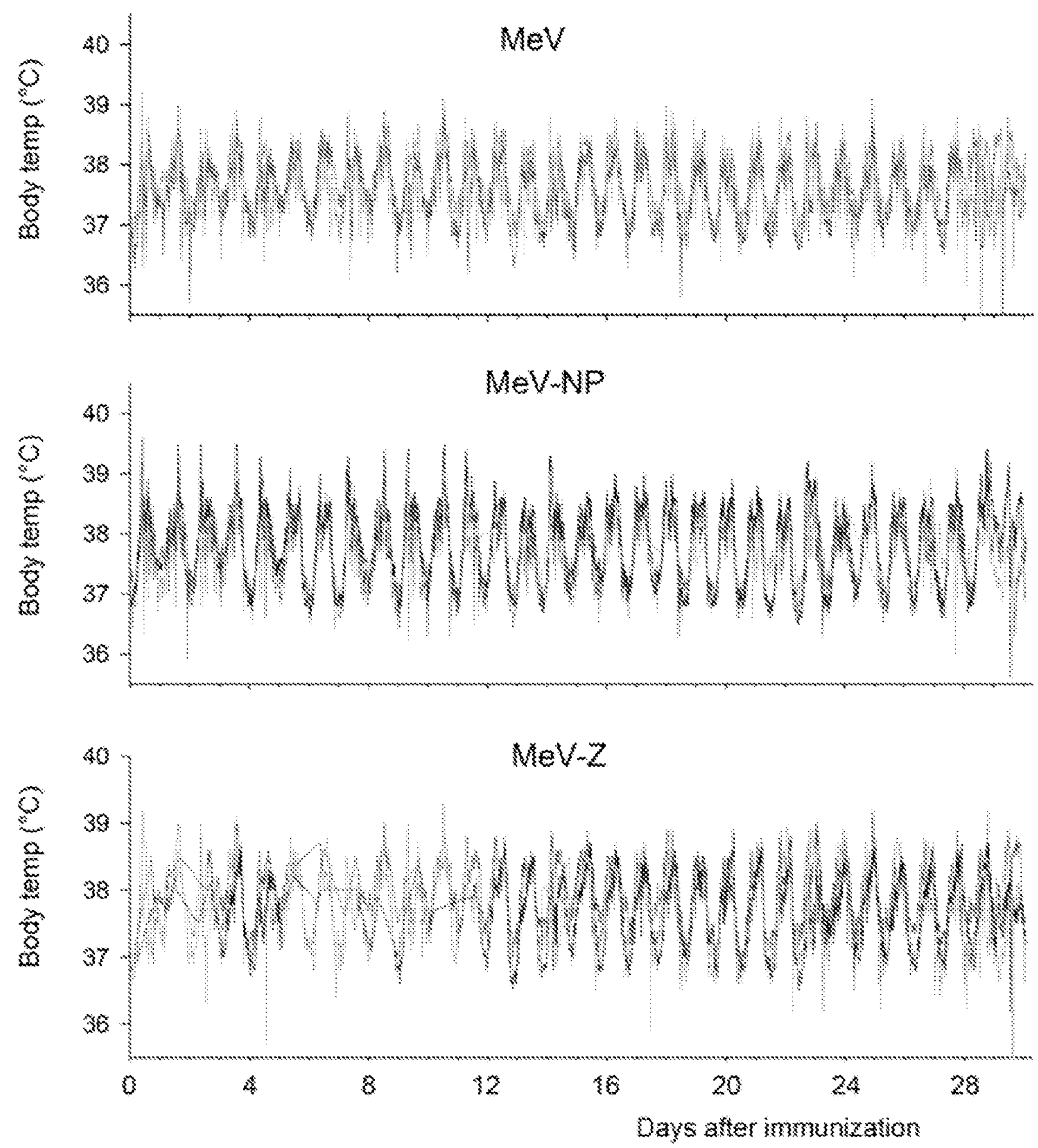
FIG. 9. Body temperature in cynomolgus monkeys (*Macaca fascicularis*) during a 30-day period post immunization. 3, 4 and 4 monkeys were subcutaneously immunized with $2.10^6$ Tissue culture Infective Dose 50 ($TCID_{50}$) of respectively a recombinant MeV strain Schwarz vaccine, a recombinant MeV-$NP_{ExoN}$-GPC vaccine and a recombinant Z-MeV-GPC vaccine.

Example 3—Safety, Immunogenicity and Efficacy of Two Vaccines in Cynomolgus Monkeys Based on the results obtained in human macrophages, we decided to test two vaccine candidates in cynomolgus monkeys, the gold standard model to study LASV pathogenesis. Three control animals were immunized subcutaneously with 2.106 TCID50 of a recombinant MeV strain Schwarz vaccine and two groups of 4 animals were immunized subcutaneously with 2.106 TCID50 of MeV-NP$_{ExoN}$+GPC$_{LASV}$ and MeV-Z+GPC$_{LASV}$, respectively. The health of the animals was then followed for 37 days post immunization (body temperature, body weight, respiratory rate) and no adverse effects were noted. Notably, the body temperature of the animals, continuously monitored thanks to intraperitoneal devices, was not altered by the immunization (FIG. 9).

We also assessed the viremia in immunized animals every 2-3 days during the two weeks following immunization then once a week and could not detect any trace of viral RNA, neither in plasma nor among PBMC. Similarly, we could not detect any viral RNA in the nasal and oral secretions or in the urine of vaccinated animals. Thus, it appears that the vaccine candidates are safe in monkeys and are not shed at any moment post immunization.

Figure 10:
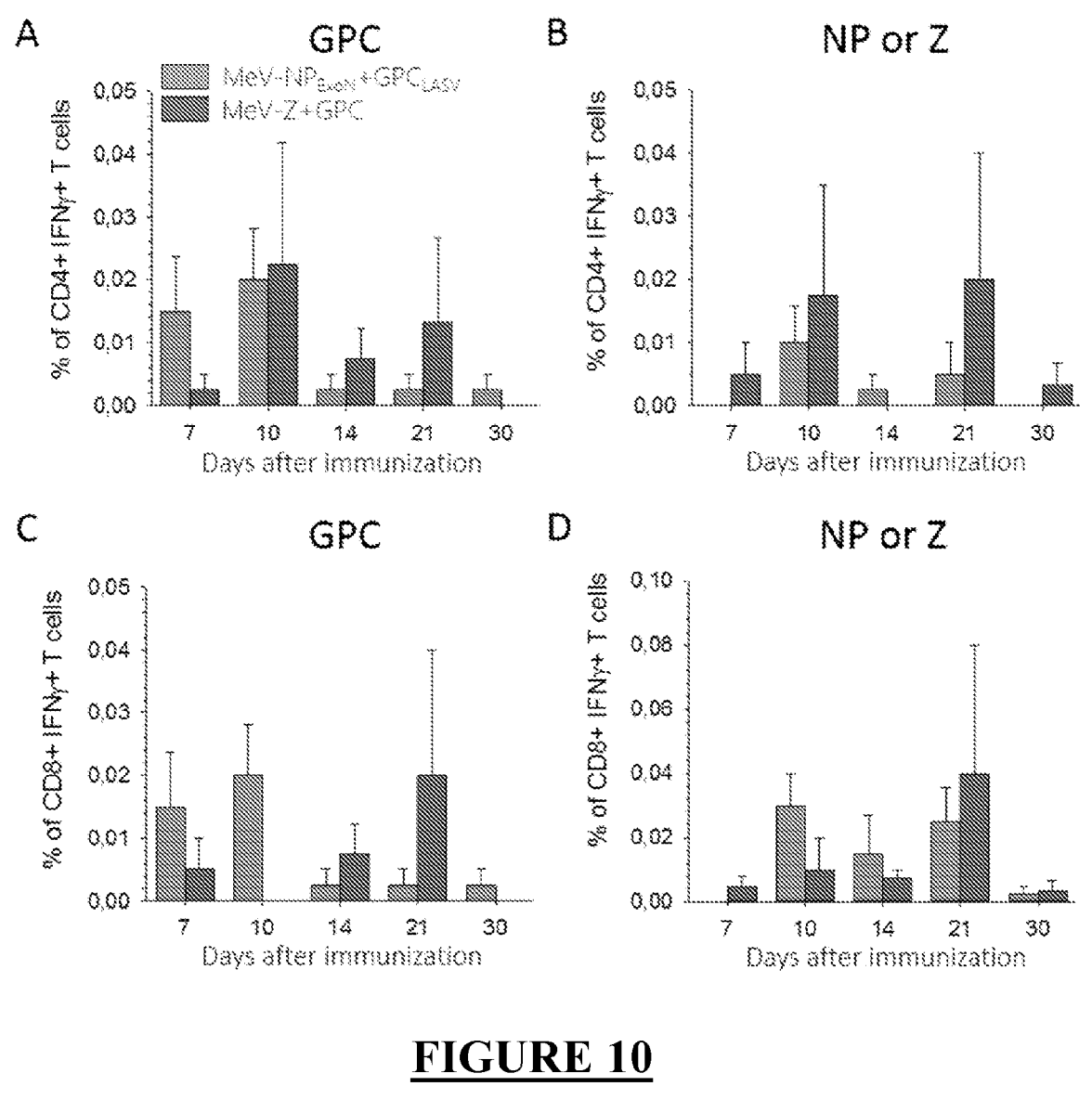

In order to assess the immunogenicity of the vectors, we performed ELISA to detect LASV-specific IgM and IgG. We could not detect specific IgM and IgG in MeV-Z+GPC$_{LASV}$ immunized animals and we only detected low levels of LASV-specific IgG in 3 out of 4 MeV-NP$_{ExoN}$+GPC$_{LASV}$ vaccinated animals at day 37 post immunization. In addition, one MeV-NP$_{ExoN}$+GPC$_{LASV}$ vaccinated animal had neutralizing antibodies as demonstrated by plaque reduction neutralization assay (1:100 titer). We also assessed the LASV-specific T cell responses by flow cytometry after stimulation of whole blood by overlapping peptides specific to GPC, NP or Z. In MeV-NP$_{ExoN}$+GPC$_{LASV}$ vaccinated animals, we detected both CD4 and CD8 T cell responses against GP starting at day 7 and decreasing by day 14 post immunization (FIGS. 10A and 10C, orange bars). In these animals, we also detected both CD4 and CD8 T cell responses against NP between days 10 and day 21 post immunization (FIGS. 10B and 10D, orange bars). In MeV-Z+GPC$_{LASV}$ immunized animals, the CD4 T cell response against GPC was delayed compared to MeV-NP$_{ExoN}$+GPC$_{LASV}$ vaccinated animals, starting by day 10 post immunization but lasting until day 21 post inoculation (FIG. 10A, green bars). GPC-specific CD8 T cell responses started at day 7 at low levels but peaked at day 21 post immunization (FIG. 10C, green bars). Both CD4 and CD8 Z-specific T cell responses were also detected starting at day 7 and until day 30, with a peak at day 21 post immunization (FIGS. 10B and 10D, green bars). Importantly, no T cell responses against LASV antigens were detected in MeV-vaccinated control animals. Thus, both vaccine candidates induce LASV antigen-specific T cell responses, with MeV-NP$_{ExoN}$+GPC$_{LASV}$ inducing earlier responses than MeV-Z+GPC$_{LASV}$.

Example 4—Efficacy of the Vaccines

Figure 11:
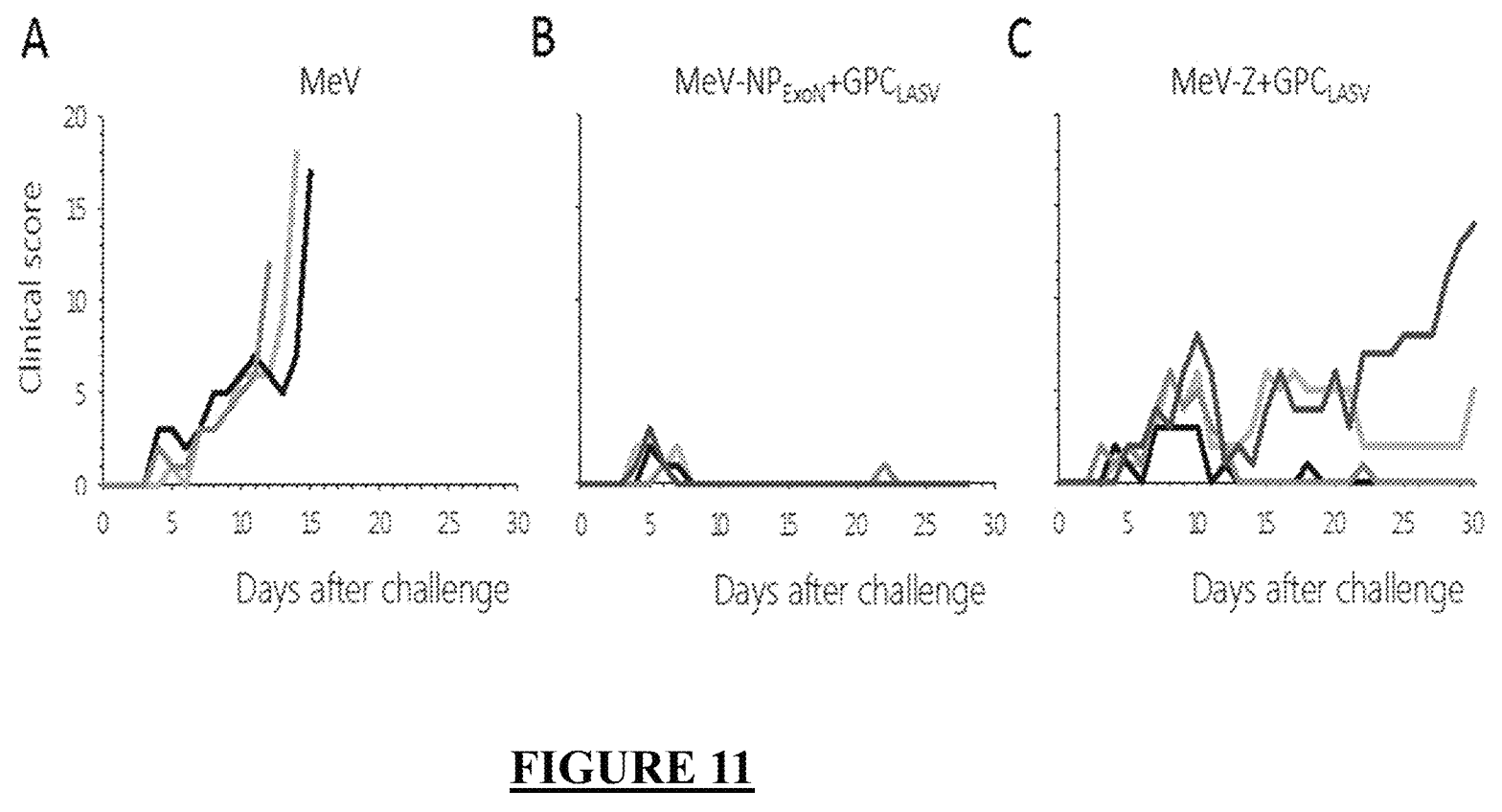

In order to test the efficacy of the vaccine candidates, immunized animals were challenged 37 days post immunization with a lethal dose (1,500 ffu, subcutaneous) of LASV strain Josiah. Animals were then monitored for up to 30 days and were attributed clinical scores based on their body temperature, body weight, capacity to feed and hydrate normally, behaviour, clinical signs, with a score of 15 being the endpoint for killing. The three control animals had scores increasing from day 3 and had to be euthanized respectively at day 12, 14 and 15 post challenge (FIG. 11A).

Figure 12:
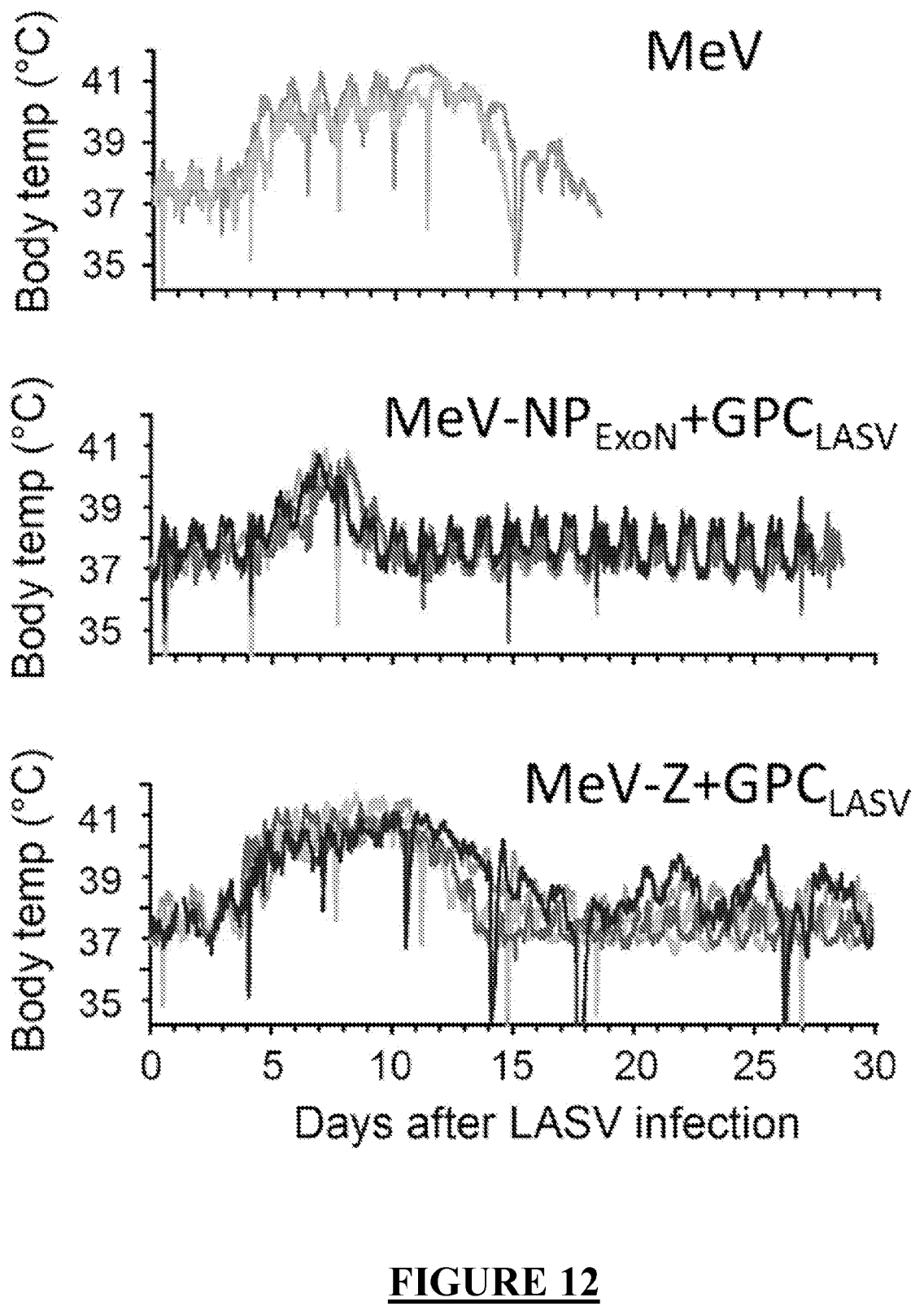

On the contrary, all vaccinated animals survived the LASV infection but the clinical outcomes were different depending on the vaccine. Indeed, MeV-NP$_{ExoN}$+GPC$_{LASV}$ vaccinated animals had a small increase in clinical score by day 5 (max score of 3, FIG. 11B), mainly due to an elevated temperature (see FIG. 12, center graph). On the contrary, MeV-Z+$GPC_{LASV}$ immunized animals experienced severe symptoms such as high fever between day 3 and day 12 (see FIG. 12, lower graph) and while 2 animals totally recovered by day 12, 2 other animals had difficulties feeding and hydrating, showed prostration and one animal had balance issues and lost more than 7.5% of his body weight by day 30, reaching a score of 14 (FIG. 11C).

Figure 13:
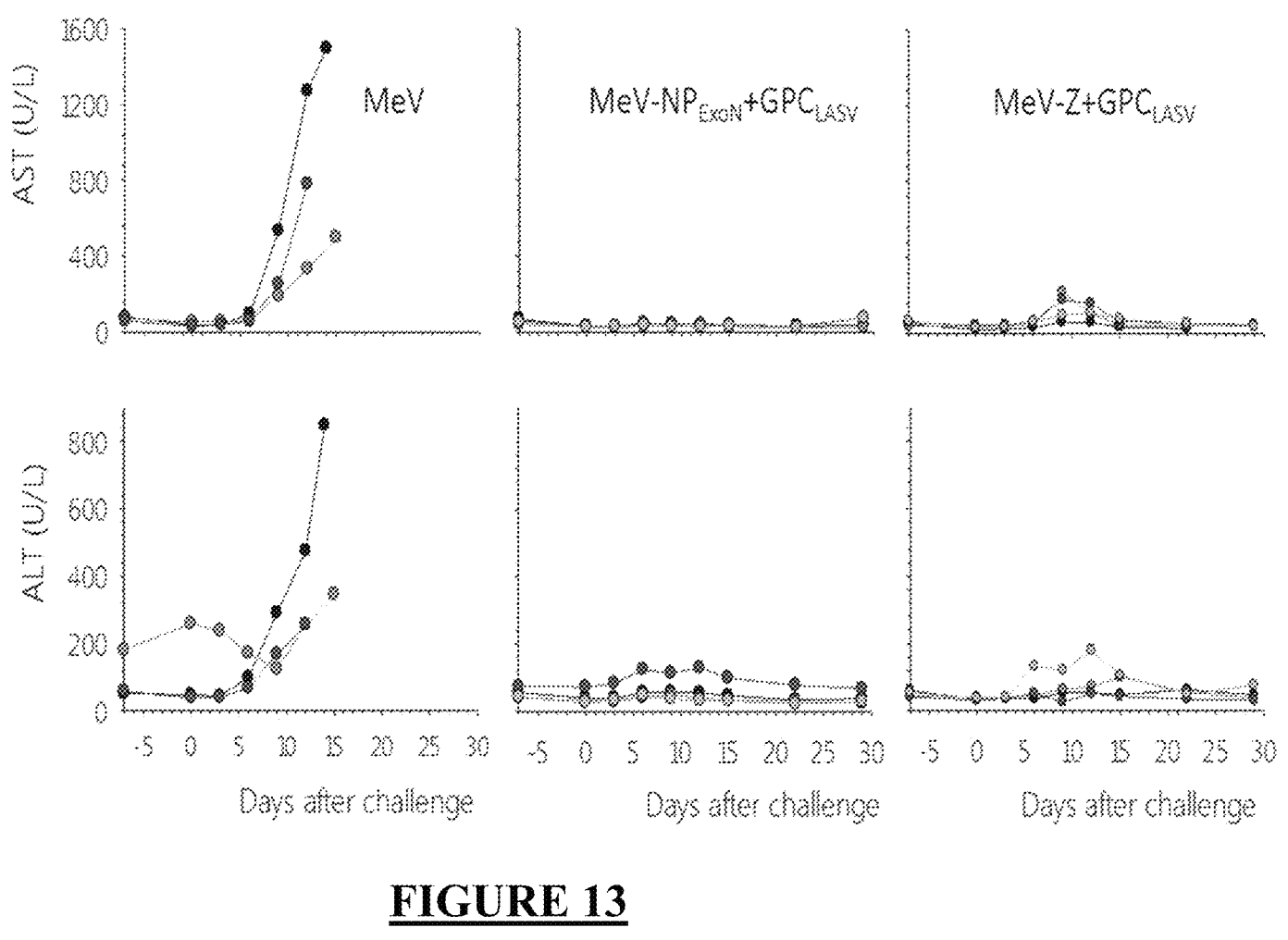

We also followed several biological parameters in plasma over the course of the infection, such as liver enzymes levels (ALT and AST), lactate deshydrogenase (LDH), C-reactive protein (CRP) and albumin, among other parameters. In control animals, the levels of liver enzymes were increasing continuously starting at day 6 and until the death of the animals (FIG. 13, left panels). On the contrary, liver enzyme levels remained normal at any time in MeV-$NP_{ExoN}$+$GPC_{LASV}$ vaccinated animals (FIG. 13, center panels) and only slightly increased in MeV-Z+$GPC_{LASV}$ immunized animals between day 6 and 15 (FIG. 13, right panels).

Figure 14:
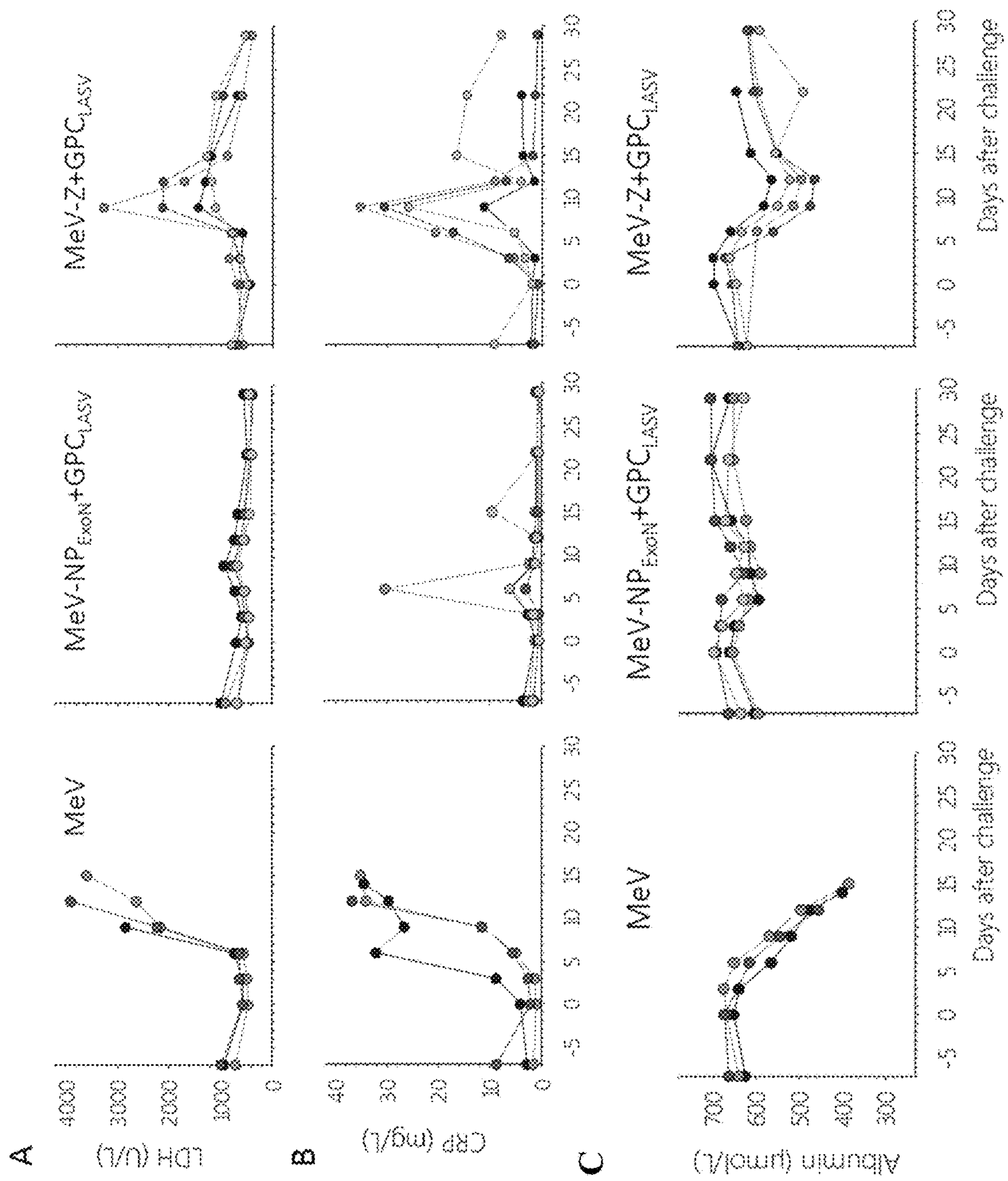
FIG. 14. Plasma level of LDH (A), CRP (B) and albumin (C) in cynomolgus monkeys (*Macaca fascicularis*) challenged with a lethal dose of LASV strain Josiah.

The plasma levels of LDH are a marker of tissue damages. In control animals, LDH levels started to increase at day 6 post challenge and thus till the end of the animals (FIG. 14A, left panel). No increase was noted in MeV-$NP_{ExoN}$+$GPC_{LASV}$ vaccinated animals over the course of the infection (FIG. 14A, center panel). However, LDH levels were elevated in MeV-Z+$GPC_{LASV}$ immunized animals between day 6 and day 15, especially for two animals having LDH values similar to the control animals at day 9 (FIG. 14A, right panel), suggesting some tissular damage in these animals. The levels of CRP, a marker of inflammation, also rapidly increased in control animals until death (FIG. 14B, left panel). CRP values remained low in the MeV-$NP_{ExoN}$+$GPC_{LASV}$ group except for one animal that showed a transient increase in CRP levels by day 6 (FIG. 14B, center panel). On the contrary, all the animals from the MeV-Z+$GPC_{LASV}$ group had increased CRP levels between day 3 and day 15 (FIG. 14B, right panel). In this group, one animal showed a second wave of CRP synthesis between day 15 and day 30, suggesting that LASV virus was still replicating in this animal (FIG. 14B, right panel, light green). We also followed the plasma levels of albumin, a marker of kidney and liver dysfunction, in immunized monkeys. On control animals, albumin levels constantly decreased starting at day 3 (FIG. 14C, left panel) while these levels remained steady in MeV-$NP_{ExoN}$+$GPC_{LASV}$ immunized animals (FIG. 14C, center panel). In the MeV-Z+$GPC_{LASV}$ group, all animals experienced a decrease in albumin plasma levels between day 3 and day 12 but these levels eventually went back to normal by day 15 (FIG. 14C, right panel).

Figure 15:
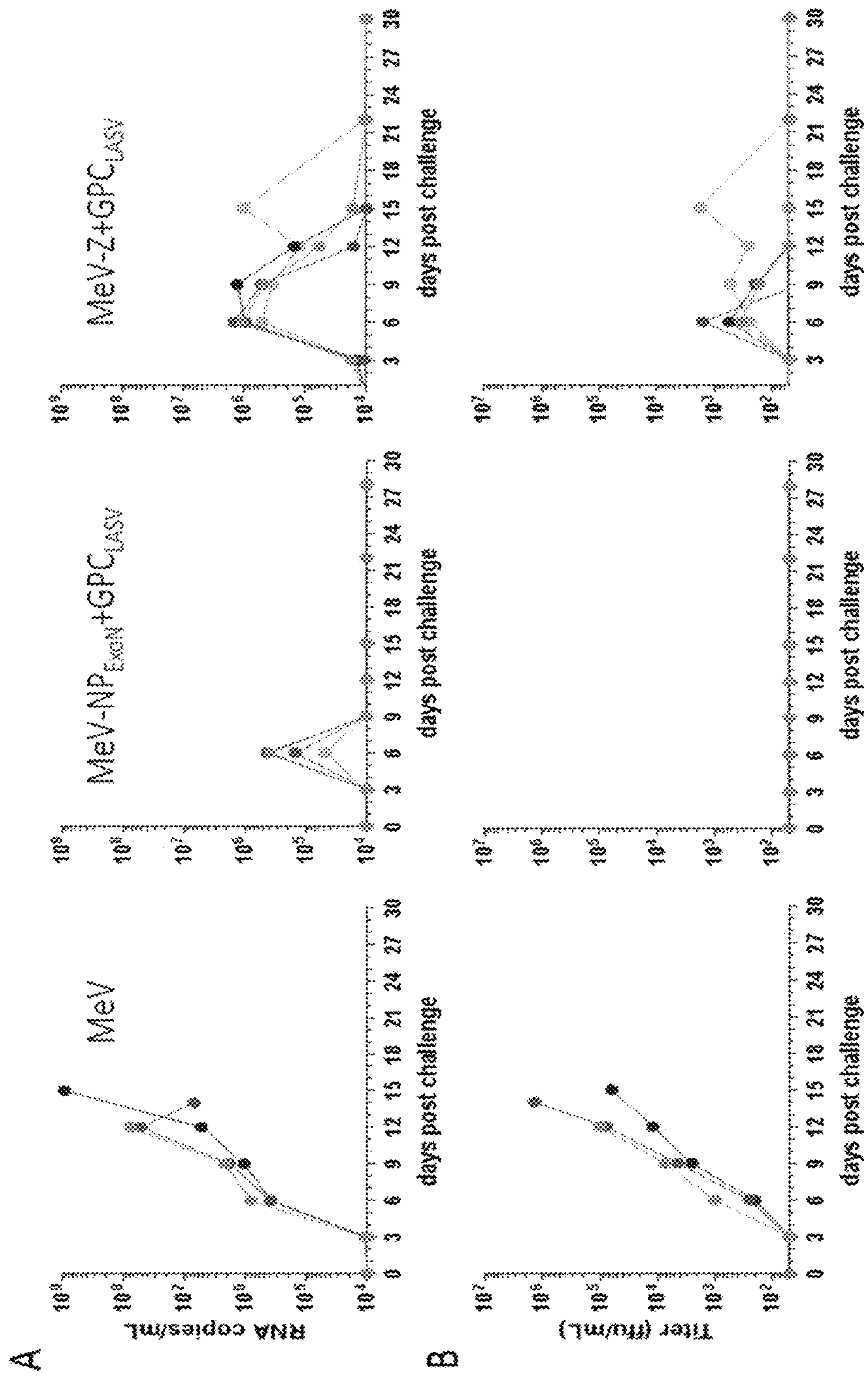
FIG. 15. Viremia (RNA(A) and Titer (B)) in cynomolgus monkeys challenged with a lethal dose of LASV strain Josiah. RNA quantification by qPCR. Titration according to known method in the art.

The viremia in challenged animals was also monitored after challenge by both qRT-PCR and titration. As shown on FIG. 15A, the levels of RNA levels in the blood of the infected controls increased relentlessly from day 3 to the day of killing, peaking at 109 RNA copies per mL at day 15 for one animal (left panel). Infectious titers were also detected in these animals (FIG. 15B, left panel). In MeV-$NP_{ExoN}$+$GPC_{LASV}$ vaccinated animals, viral RNA was only detected at day 6 post challenge and at low levels compared to control animals (FIG. 15A, center panel) and no associated viremia was detected (FIG. 15B, center panel). The levels of viral RNA were higher in MeV-Z+$GPC_{LASV}$ immunized animals, peaking at day 6 around 106 RNA copies per mL and decreasing until day 15 (FIG. 15A, right panel). Notably, one animal had a rebound in the number of RNA copies in the blood by day 15 (FIG. 15A, right panel, light green), which can be correlated with the rebound in CRP observed in the same animal (FIG. 14B, right panel). In addition, infectious titers were detected in all animals at day 6 and up to day 15 for the animal showing prolonged RNA levels in the blood (FIG. 15B, right panel).

Figure 16:
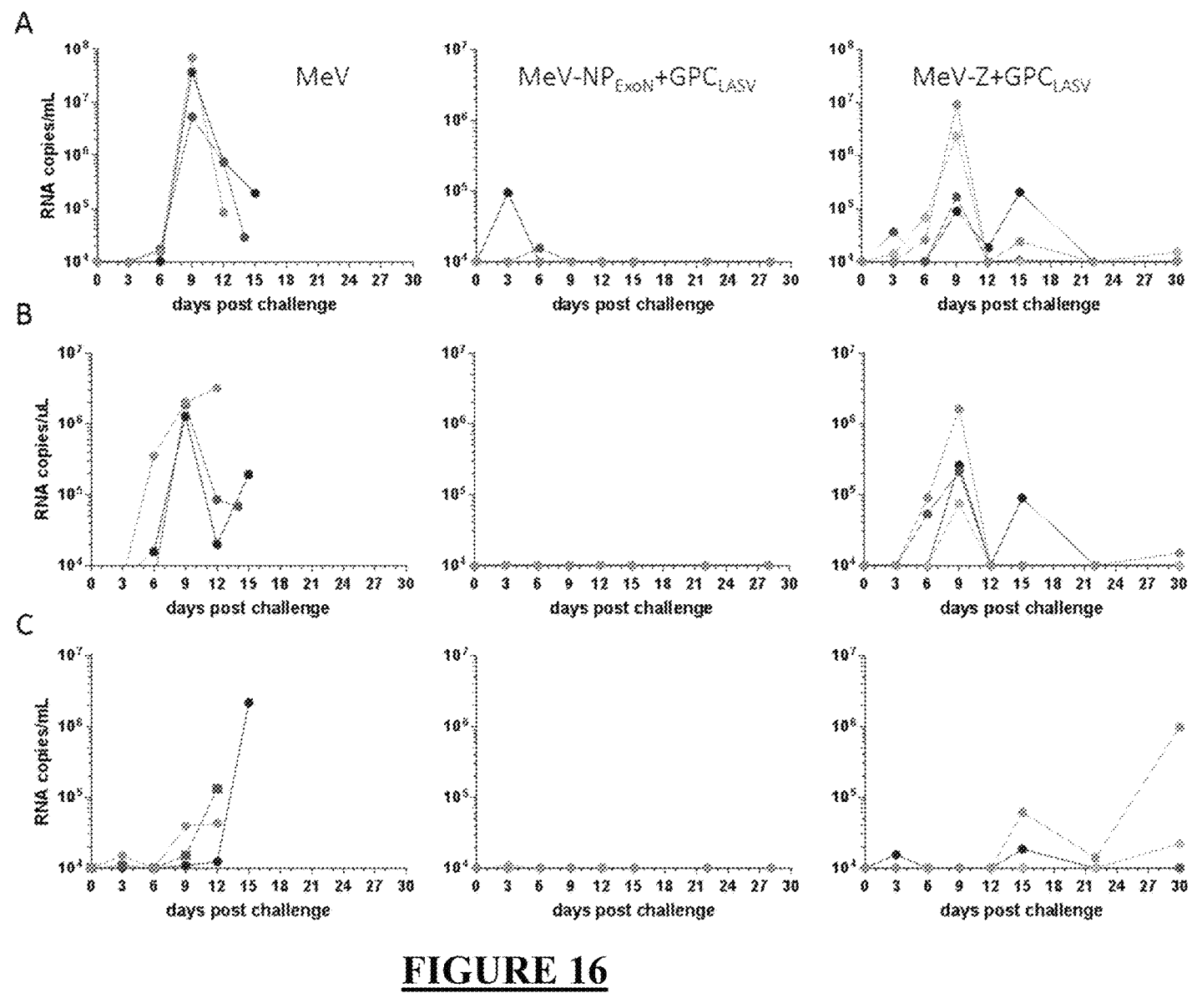

In addition to viremia, we assessed the presence of viral RNA in nasal and oral swabs of challenged animals. As shown on FIG. 16, levels of viral RNA peaked at day 9 in the nasal and oral secretions of control animals (FIGS. 16A and B, left panels) and decreased but were still detectable at the time of death. Similarly, levels of viral RNA peaked at day 9 in these secretions for MeV-Z+$GPC_{LASV}$ immunized animals, with a rebound for one or two animals by day 15 (FIGS. 16A and B, right panels). On the contrary, only small amount of LASV RNA was detected in the nasal swab of one animal at day 3 and another animal at day 6 (FIGS. 16A and B, center panels) and was not associated with the presence of infectious virus (data not shown). In addition, we followed shedding of viral RNA in the urine of challenged animals. LASV RNA levels were only detected in control and MeV-Z+$GPC_{LASV}$ immunized animals, respectively starting at day 9 or day 15 post challenge (FIG. 16C).

Figures 17, 18:
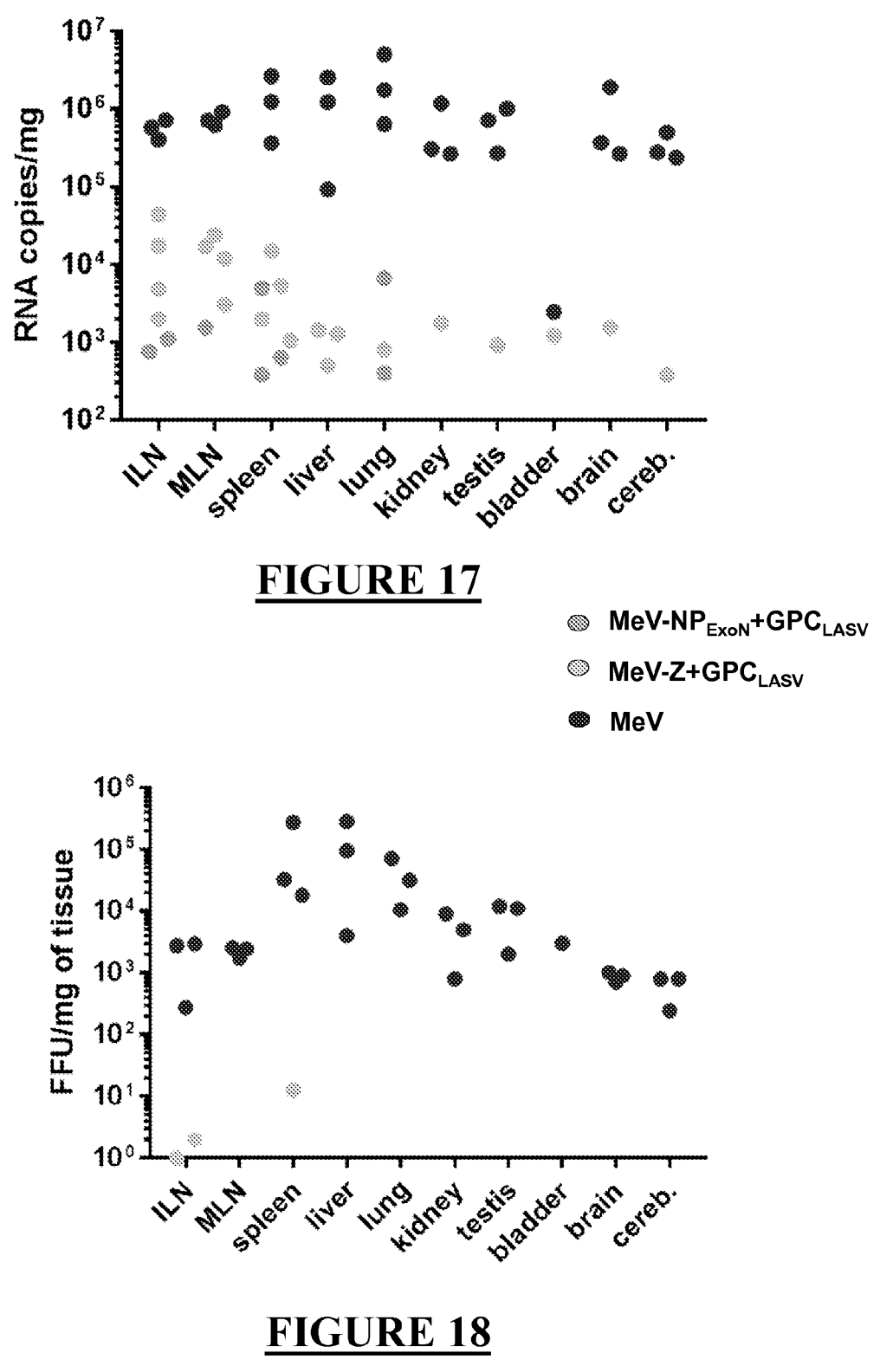

The amount of LASV RNA (FIG. 17), as well as the LASV infectious titers (FIG. 18), have been analysed in different organs collected at the time of necropsy of animals immunized with MeV, MeV-$NP_{ExoN}$-$GPC_{LASV}$ and MeV-Z-$GPC_{LASV}$. All MeV control animals presented a detectable amount of LASV RNA and a high virus titer in each organ tested, except in the bladder wherein only a single animal presented a detectable amount of LASV RNA. Highest infectious titers were found in the spleen, the liver and the lung. In all animals immunized with MeV-Z+$GPC_{LASV}$, detectable amount of LASV RNA has been found in inguinal lymph node, mesenteric lymph and spleen, and detectable amount of LASV RNA has been detected in all organs, but never in a single animal, within this group. Two animals presented infectious titers of Lassa virus in the inguinal lymph node, while one animal presented infectious titer of Lassa virus in the spleen, but the other organs were free of infectious virus. In the group of animals immunized with MeV-$NP_{ExoN}$+$GPC_{LASV}$, detectable amount of LASV RNA was found in the lymphoid organs and in the lung of one to three animals, but the presence of RNA was not associated with the presence of infectious Lassa virus.

Example 5—Immune Response to LASV

Figures 19, 20:
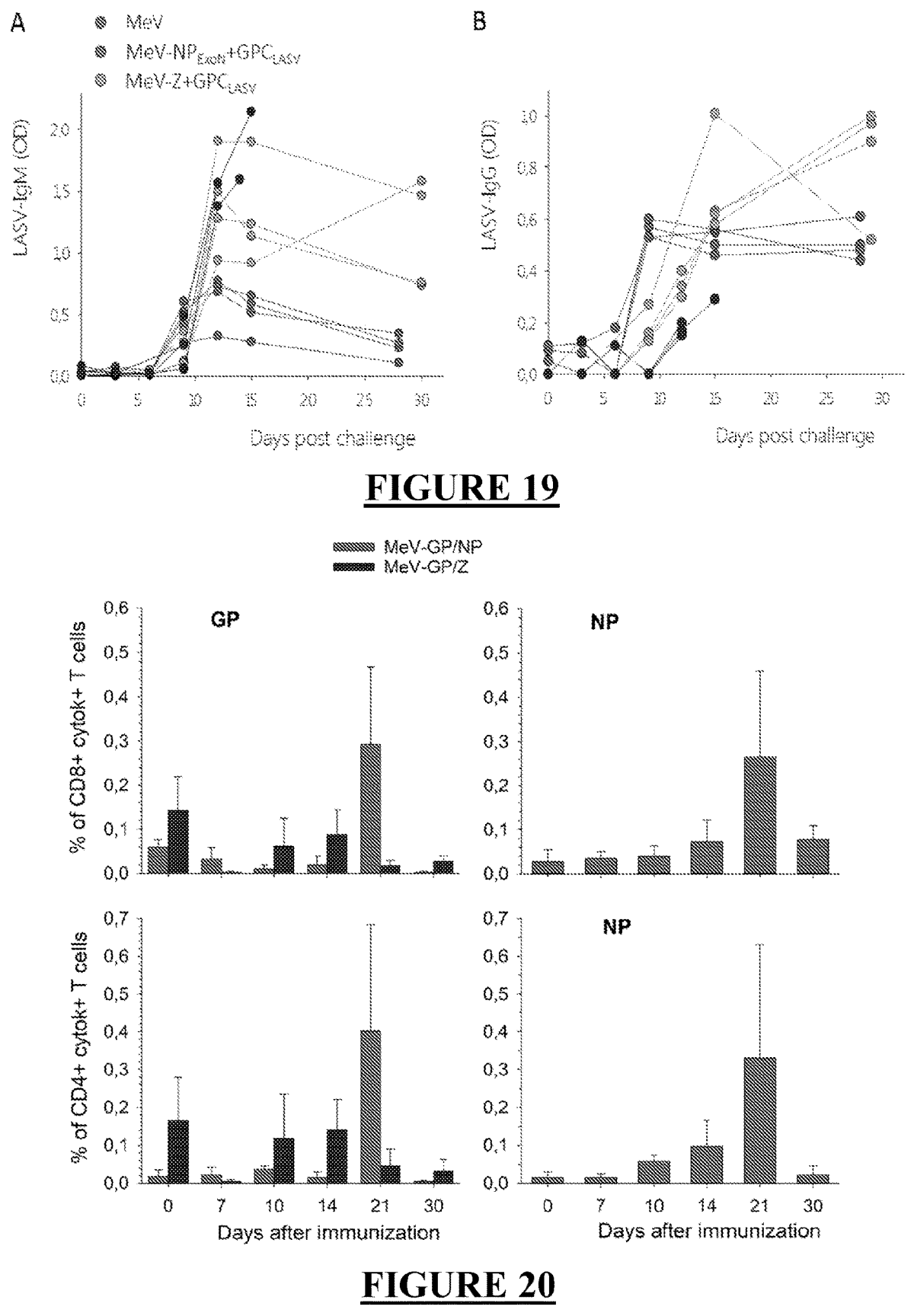

In order to determine the immune response to infection, we first measured the levels of LASV-specific immunoglobulins produced after the challenge with LASV. The IgM response started at day 9 in all animals, and peaked at day 12 (FIG. 19A). Interestingly, IgM levels were higher at day 12 in animals from the control group and from the MeV-Z+$GPC_{LASV}$ group, suggesting that the level IgM response does not positively correlate with the protection but rather with the viral load. In terms of IgG responses, we noted a strong induction of LASV-IgG in all MeV-$NP_{ExoN}$+$GPC_{LASV}$ vaccinated animals by day 9, while the IgG response in MeV-Z+$GPC_{LASV}$ immunized animals only reached similar levels at day 15 (FIG. 19B). The levels of LASV-specific IgG in control animals remained very low at any time point. In addition, the seroneutralisation titers have been determined in the plasma of immunized monkeys with MeV-$NP_{ExoN}$-$GPC_{LASV}$, MeV-Z+$GPC_{LASV}$ and MeV at different time points post-immunization (results are illustrated in table 1). At the time of challenge (i.e. 37 days post-immunization, J0 in table 1), at least one animal per group had a neutralization titer of 1/100e. Fifteen days post-challenge, and until the day of necropsy, all animal vaccinated with MeV-NP$_{ExoN}$-GPC$_{LASV}$ and MeV-Z+GPC$_{LASV}$ had neutralizing antibodies between 1/100e and 1/500e, on the contrary to the animals vaccinated with MeV. Monkeys vaccinated with MeV-Z+GPC$_{LASV}$ had the highest titer at day 30. Neutralizing antibodies have been detected in all animals except in control animals.

Figure 22:
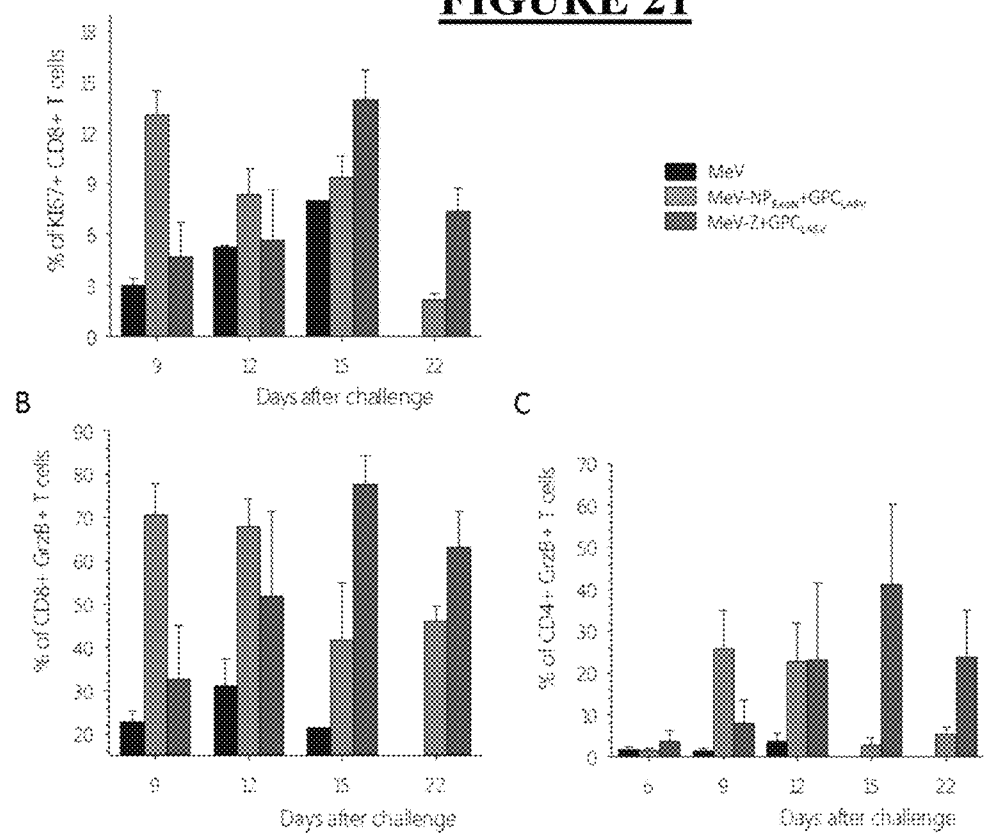
FIG. 22. Proliferation and activation of CD4 and CD8 T cells in of cynomolgus monkeys challenged with a lethal dose of LASV strain Josiah. CD8 proliferation assessed by Ki67 staining (A). CD4 (B) and CD8 (C) Activation assessed by quantification of granzyme B expression.

15 (compare orange bars with red and green bars, respectively). This proliferation was also associated with cytotoxic phenotypes of the CD8 and CD4 T cell response, as shown by the early and robust expression of granzyme B in MeV-NP$_{ExoN}$+GPC$_{LASV}$ immunized animals and the delayed response in control animals and MeV-Z+GPC$_{LASV}$ immunized animals (FIGS. 22B and C, compare orange bars and green bars).

TABLE 1

Seroneutralisation titers measured in the plasma of challenged monkeys

| | MeV-NP$_{ExoN}$-GPC$_{LASV}$ | | | | MeV-Z + GPC$_{LASV}$ | | | |
|---|---|---|---|---|---|---|---|---|
| | CDE031 | CDE041 | CDF053 | CDI009 | CDK026 | CDK086 | CDK106 | CDG058 |
| J0 | No | No | 1/100 | No | 1/100 | No | No | No |
| J6 | No | No | 1/100 | No | No | No | No | 1/100 |
| J15 | 1/100 | 1/100 | 1/500 | 1/100 | 1/500 | 1/500 | 1/500 | 1/500 |
| J28 | 1/500 | 1/500 | 1/100 | 1/100 | | | | |
| J30 | | | | | 1/100 | 1/100 | 1/100 | 1/100 |

| | MeV | | |
|---|---|---|---|
| | CDH011 | CDH028 | CDG058 |
| J0 | No | No | No |
| J6 | No | No | No |
| J15 | No | No | No |
| J28 | | | |
| J30 | | | |

The induction of CD8+ and CD4+ T cells specific for LASV antigens was also monitored by quantifying the percentage of T cells producing IFNg, TNFa and/or IL-2 in response to overlapping peptides covering the whole LASV GP, NP and Z proteins (FIG. 20) after immunization. T cells failed to respond to Z peptide (data not shown). The number of cytokine-producing T cells in response to GP and NP peptides was only modestly increased in comparison with baseline levels (Day 0) and MeV-control animals, and TNFa was the main cytokine involved in this response. Nevertheless, a non-significant increase in the percentage of GP-specific cytokine-producing CD8+ and CD4+ T cells 21 days after immunization with MeV-NP$_{Exon}$-GPC$_{LASV}$, but not after immunization with MeV-Z+GPC$_{LASV}$, has been observed. Furthermore, NP-specific cytokine-producing CD4+ and CD8+ T cells appeared after 14 days in immunized animals and were still present 22 days after.

Figure 21:
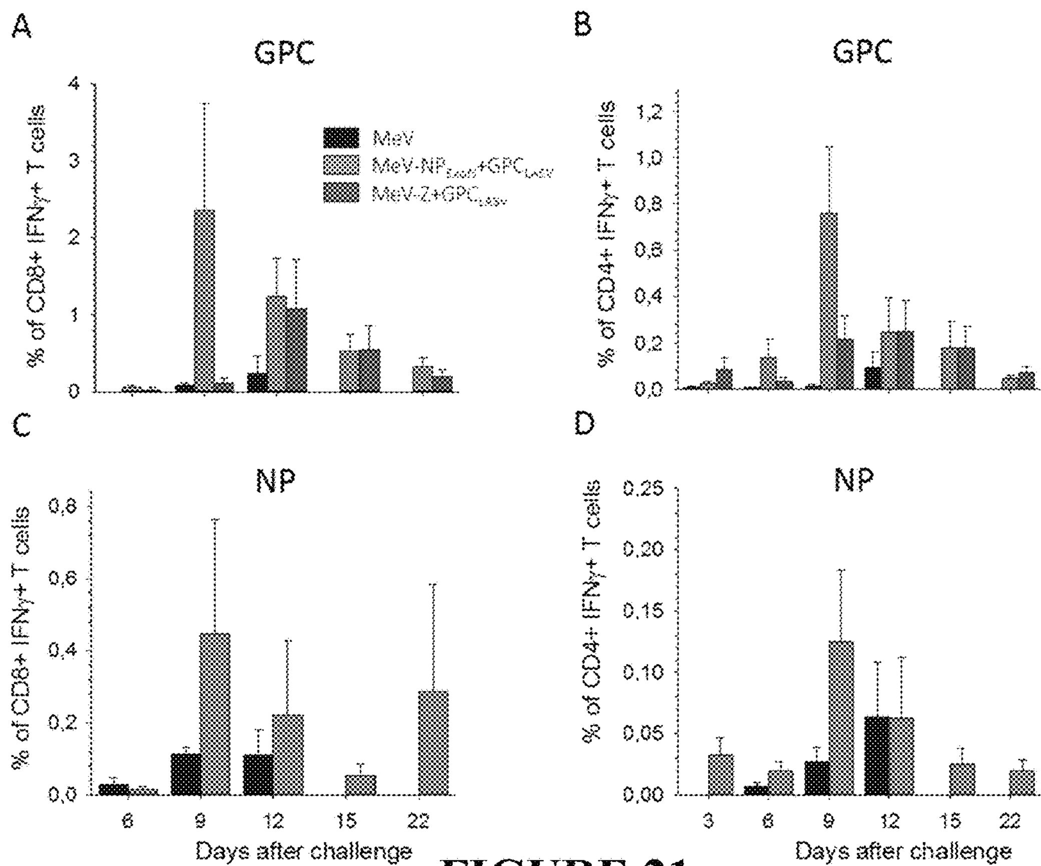
FIG. 21. LASV antigens-specific CD4 and CD8 T cell responses of immunized cynomolgus monkeys challenged with a lethal dose of LASV strain Josiah. Flow cytometry after stimulation of whole blood by overlapping peptides specific to GPC and NP.

Similarly, we followed the T cell response to LASV GPC, NP or Z after challenge in T cell activation assay using overlapping peptides. The CD8 and CD4 response against GPC and NP were early and robust in MeV-NP$_{ExoN}$+GPC$_{LASV}$ vaccinated animals, peaking at day 9 then decreasing slowly (FIG. 21, orange bars). The CD8 and CD4 responses against GPC was delayed and less intense in MeV-Z+GPC$_{LASV}$ immunized animals, peaking at day 12 (FIG. 21, green bars). These animals did not present a LASV-Z specific cellular response. Control animals only experienced a very weak and transient CD8 and CD4 responses against GPC and NP between day 6 and 12 (FIG. 21, red bars).

Figure 23:
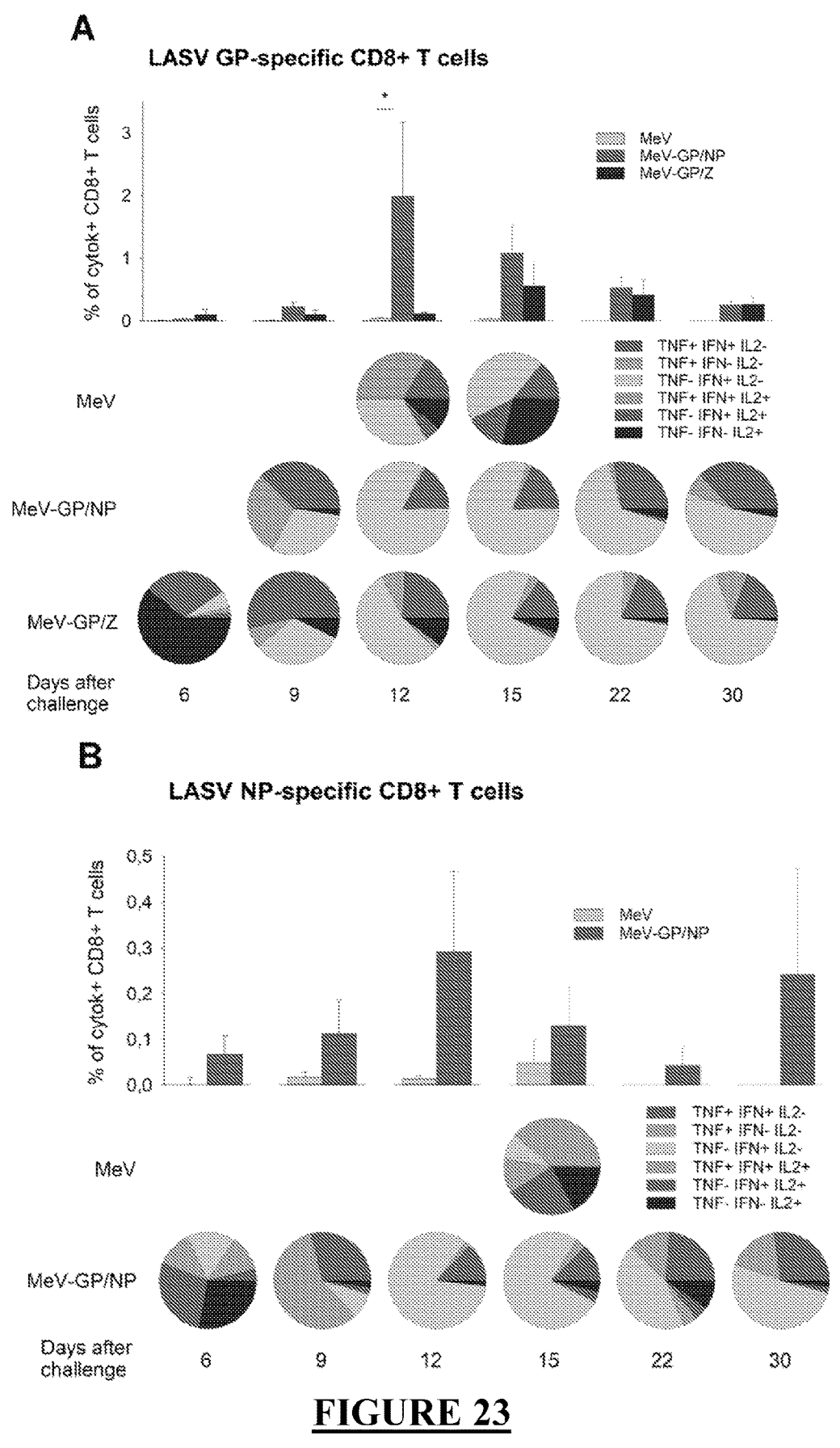
Figure 24:
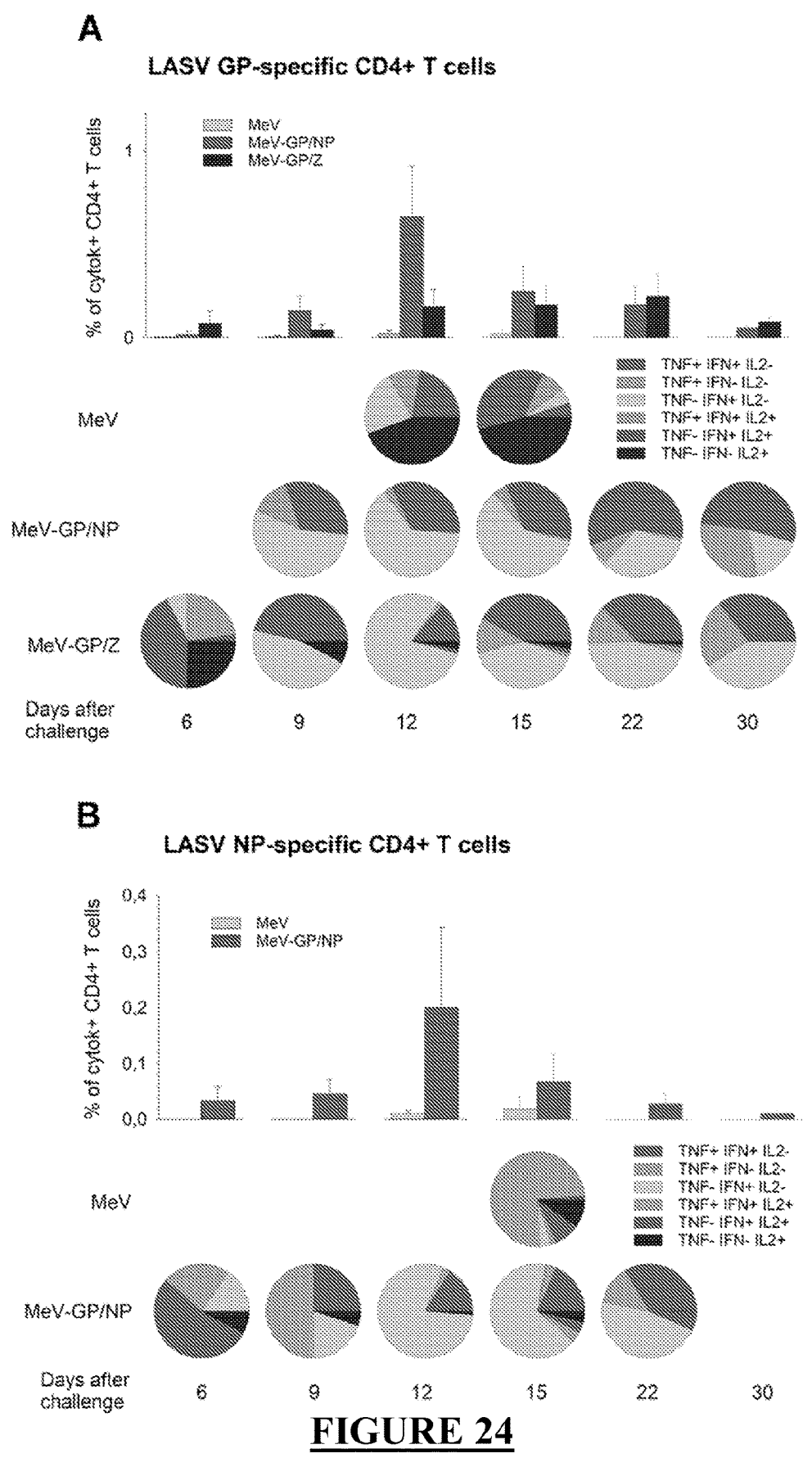

The intensity of the CD8 responses was correlated with the proliferation of these cells as assessed by a Ki67 staining (FIG. 22A), with strong proliferation of CD8 T cells in MeV-NP$_{ExoN}$+GPC$_{LASV}$ immunized animals by day 9 compared to control animals and MeV-Z+GPC$_{LASV}$ immunized animals that had a milder proliferation peaking only at day The induction of LASV GP- and NP-specific T cells in animals challenged with LASV has been monitored. No production of cytokines was observed after stimulation of PBMC with LASV Z peptides after the challenge (data not shown). The data regarding the CD8+ and CD4+ T cells producing cytokines in challenged animals are illustrated on FIGS. 23 and 24 respectively. In animals immunized with MeV, no significant amount of responding cells was found. In response to the LASV GPC peptides in animals immunized with MeV-NP$_{ExoN}$+GPC$_{LASV}$, the percentage of CD8+ and CD4+ T cells producing cytokines in response to GPC peptides rose to 2% and 0.6% respectively at day 12 post challenge, and then returned to basal level by day 22. The main part of T cells produced only IFNg, but the proportion of polyfunctional CD8+ and CD4+ T cells (Pf-T) which produce at least 2 cytokines increased from day 12 to day 30. Within the CD4+ T cells group, the percentage of IFNg-producing cells decreased until day 30 post-challenge, while the opposite was observed for the Pf-T, that rose to 59%. In the animals immunized with MeV-Z+GPC$_{LASV}$, a moderate number of cytokine-producing CD4+ and CD8+ T cells was observed from day 15 and 12 respectively. Most T cells produced only IFNg, and the ratio of Pf-T remained around 20% for CD8+ T cells, but rose up to 40% for CD4+ T cells. At day 30 post-challenge, and for all immunized monkeys, a noticeable part of T cells produced only TNFa.

In response to the LASV NP peptide, trace amounts of cytokine-producing T cells from animals immunized with MeV were only detected 15 days post-challenge. Responding T cells from animals immunized with MeV-Z+GPC$_{LASV}$ were detected as soon as day 6 post-challenge, with a peak response at day 12. The phenotype of T cells was various after 6 days, while at day 9, mainly TNFa-secreting T cells were present. At day 12, IFNg-producing T cells dominated whereas Pf-T proportion increased until day 30.

Figure 25:
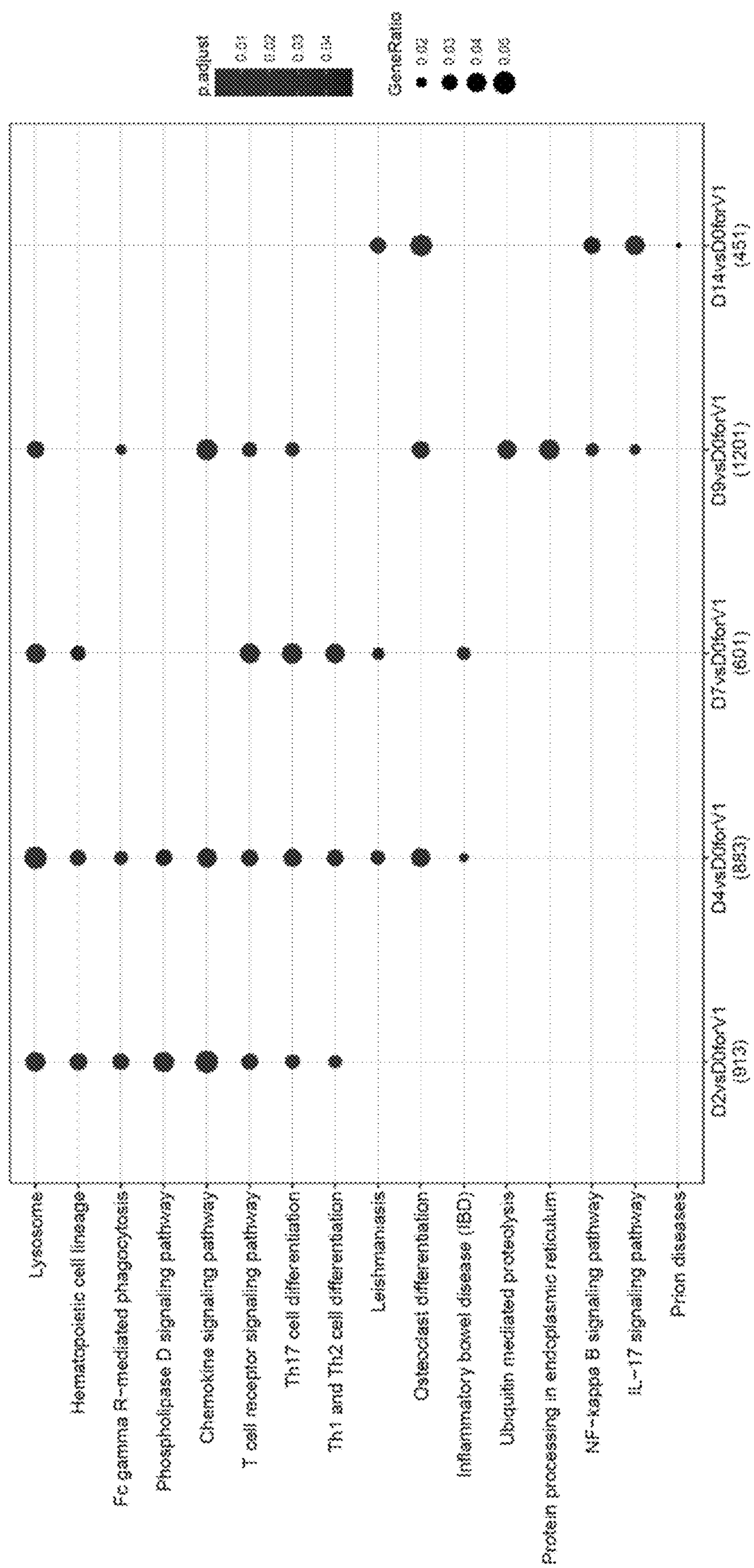
FIG. 25. KEGG pathway analysis performed on the transcriptomic data obtained from cynomolgus monkeys PBMC collected at different time points post-immunization with MeV-$NP_{ExoN}$-$GPC_{LASV}$.
Figure 26:
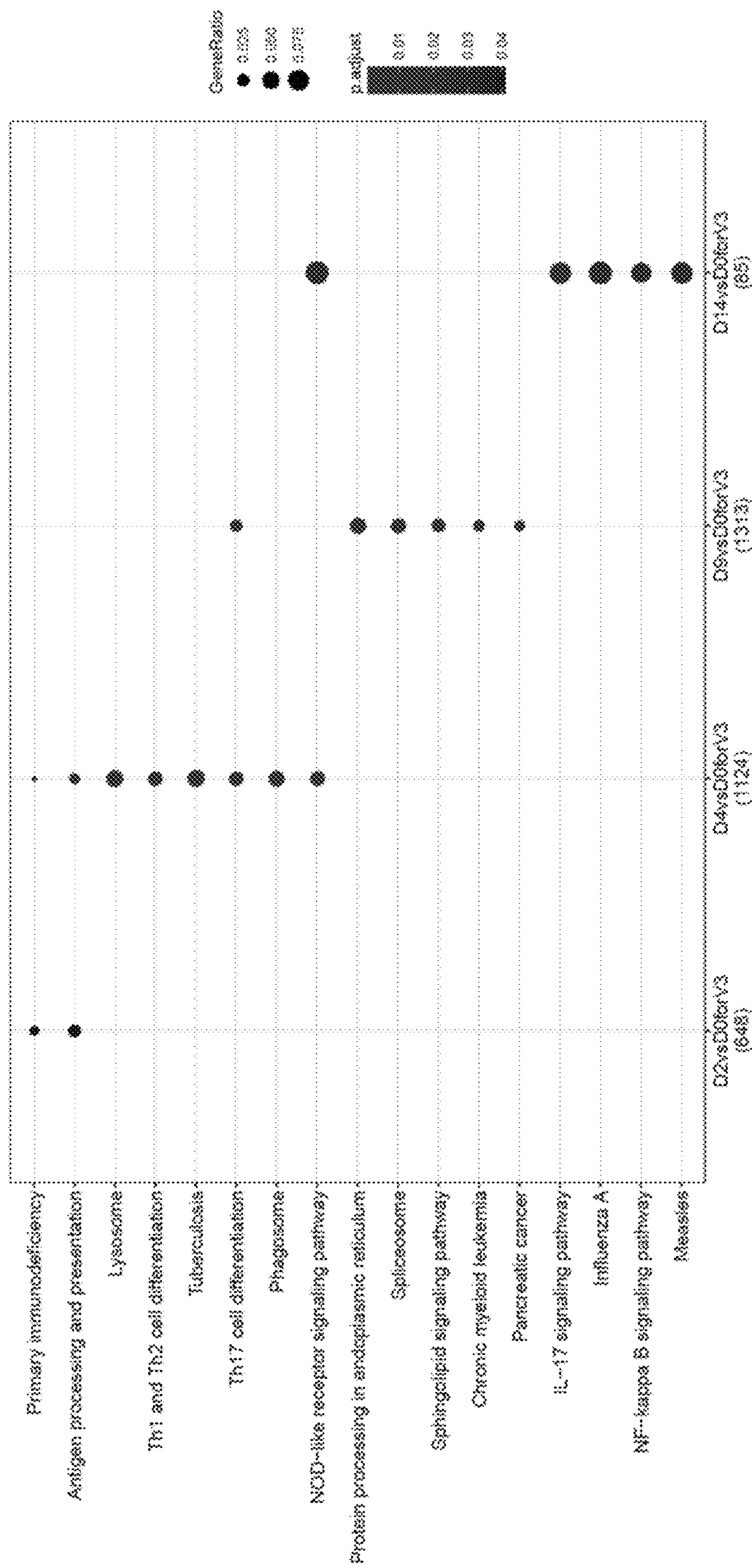
FIG. 26. KEGG pathway analysis performed on the transcriptomic data obtained from cynomolgus monkeys PBMC collected at different time points post-immunization with MeV-Z+$GPC_{LASV}$.

The total cellular RNA content of PBMC of immunized monkeys with MeV-NP$_{ExoN}$+GPC$_{LASV}$ and MeV-Z+GPC$_{LASV}$ has also been extracted at different times post-immunization to perform RNAseq and for analysing the differential expression of genes in PBMC at different time points. An enrichment analysis on differentially expressed genes has been performed using ClusterProfiler (KEGG analysis) in order to identify the pathway associated with those genes. The pathways differentially modulated through time after immunization with MeV-NP$_{ExoN}$+GPC$_{LASV}$ and MeV-Z+GPC$_{LASV}$ are illustrated on FIGS. 25 and 26 respectively. In animals immunized with MeV-NP$_{ExoN}$+GPC$_{LASV}$, pathways involved in immune responses are activated in the first week following immunization (D2 vs D0, D4 vs D0 and D7 vs D0). The activation of the hematopoietic cell lineage and the phospholipase D pathways suggests a strong proliferation of immune cells during the first four days in association with phagocytic functions (FC gamma R-mediated phagocytosis) and chemokine signalling. The increased response of Th1, Th2 and Th17 until the seventh day suggests T cells proliferation. During the second week following immunization, the pathways involved in the modulation of the immune response are activated, notably the ubiquitin-mediated proteolysis, NF-kB signalling and the 11-17 signalling pathway. Immunization with MeV-Z+GPC$_{LASV}$ seems to induce a weaker immune response, with a weak and transient activation of Th1, Th2 and Th17 at day 4 post-immunization and a later activation of the NF-kB and IL-17 signalling pathways (at day 14) as compared to the results observed in animals immunized with MeV-NP$_{ExoN}$+GPC$_{LASV}$. Altogether, the activation of different pathways supports an active and effective cellular response to immunization.

Figure 27:
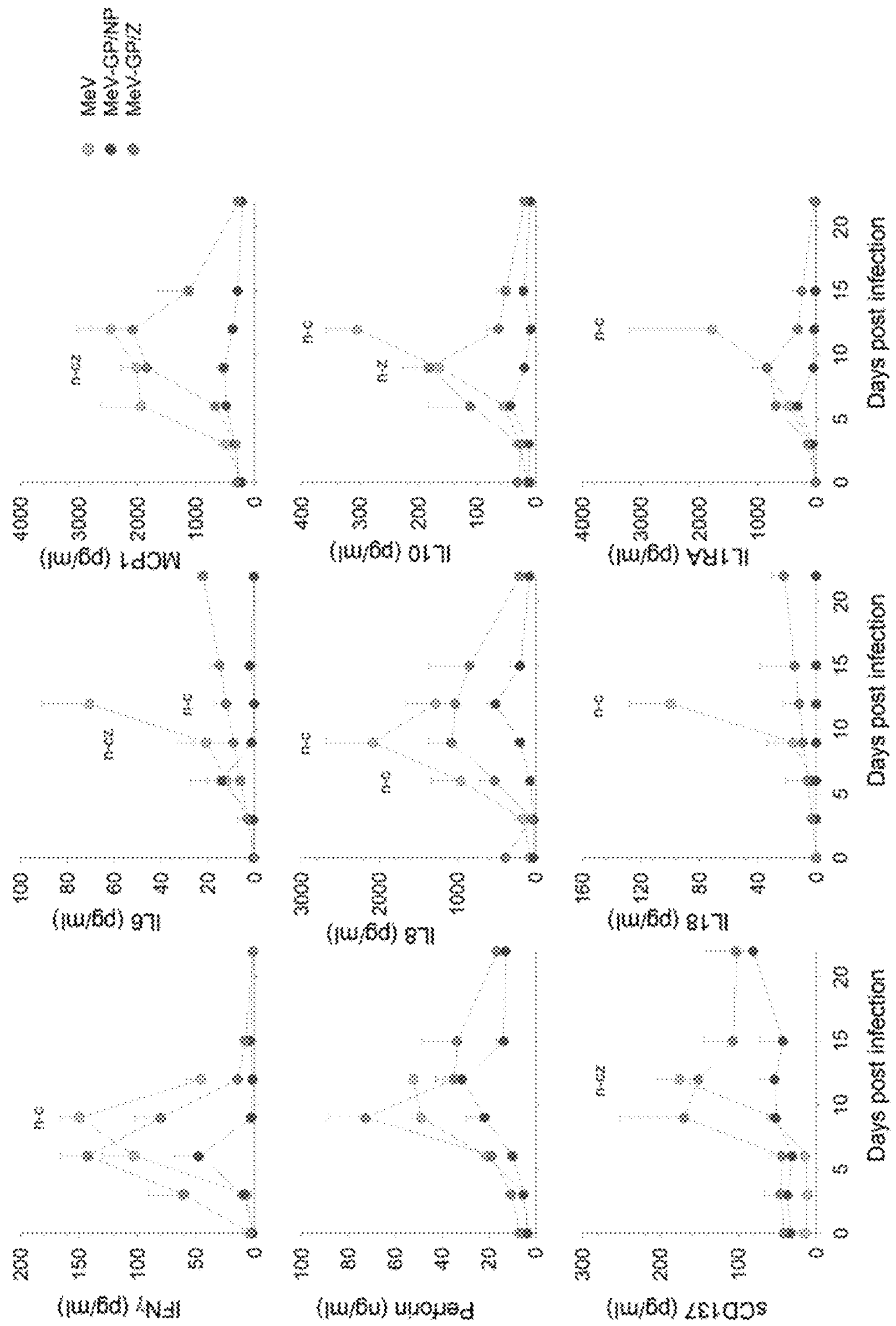
FIG. 27. Quantification of cytokines in the plasma of immunized monkeys after LASV challenge. Different cytokines have been quantified in the plasma of MeV-, MeV-$NP_{ExoN}$-$GPC_{LASV}$, and MeV-Z+$GPC_{LASV}$ immunized cynomolgus monkeys after LASV challenge. Significant differences ($p<0.05$) between different conditions are indicated: n-c (MeV-$NP_{ExoN}$-$GPC_{LASV}$ and MeV), n-z (MeV-$NP_{ExoN}$-$GPC_{LASV}$ and MeV-Z+$GPC_{LASV}$) and n-cz (MeV-$NP_{ExoN}$-$GPC_{LASV}$ and MeV; MeV-$NP_{ExoN}$-$GPC_{LASV}$ and MeV-Z+$GPC_{LASV}$).
Figure 31:
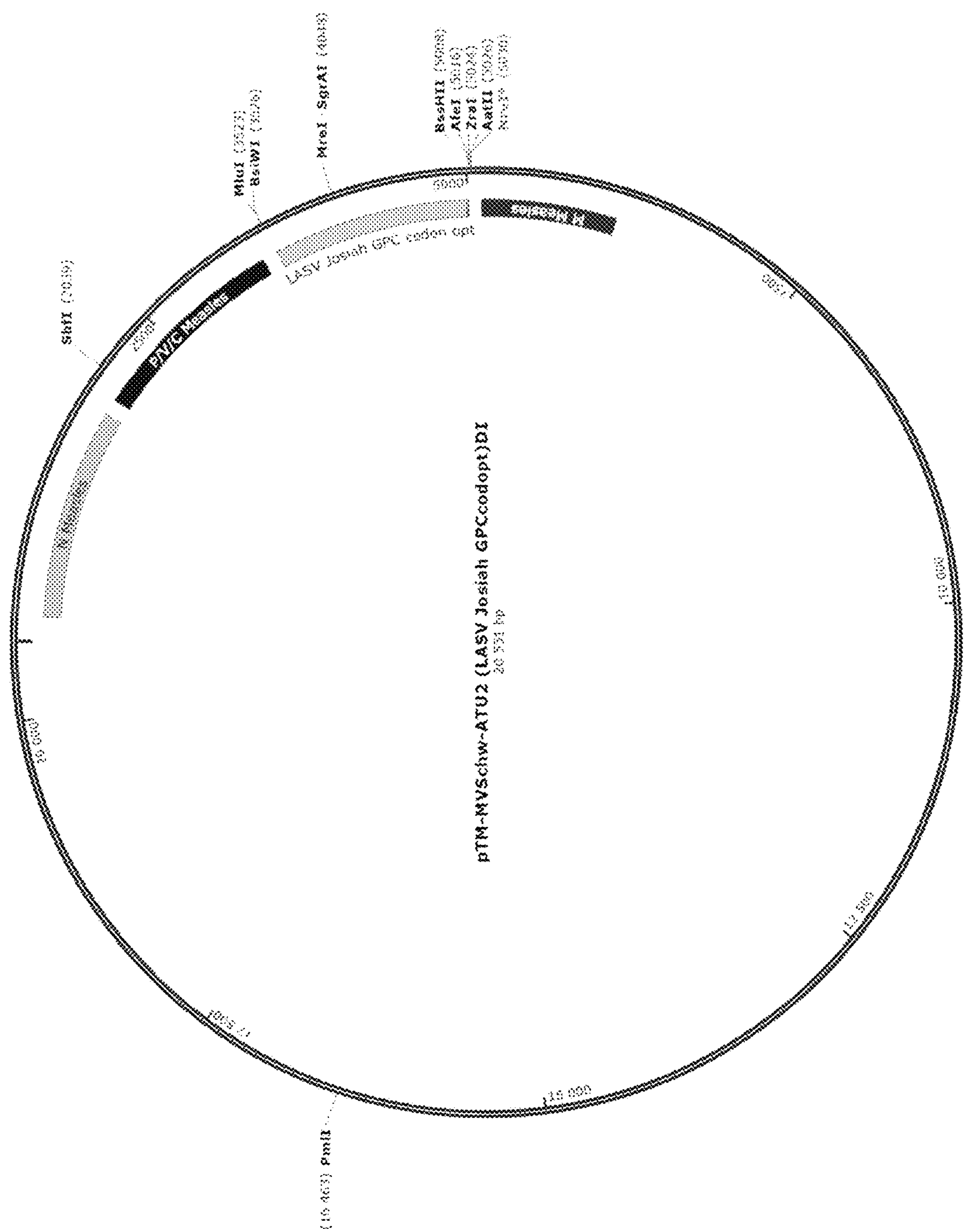
FIG. 31. Schematic representation of transfer vector plasmid according to a first embodiment of the invention. The transfer vector has the sequence of SEQ ID No: 9. The measles gene encoding the N protein is localized between nucleotides 189 and 1767. The measles gene encoding the P protein is localized between nucleotides 1889 and 3412. The codon-optimized heterologous polynucleotide of SEQ ID No: 2 encoding the GPC is localized between nucleotides 3532 and 5007. ATU2 is localized between nucleotides 3487 and 5071 minus the heterologous polynucleotide insert. The measles gene encoding the M protein is localized between nucleotides 5104 and 6111.
Figure 35:
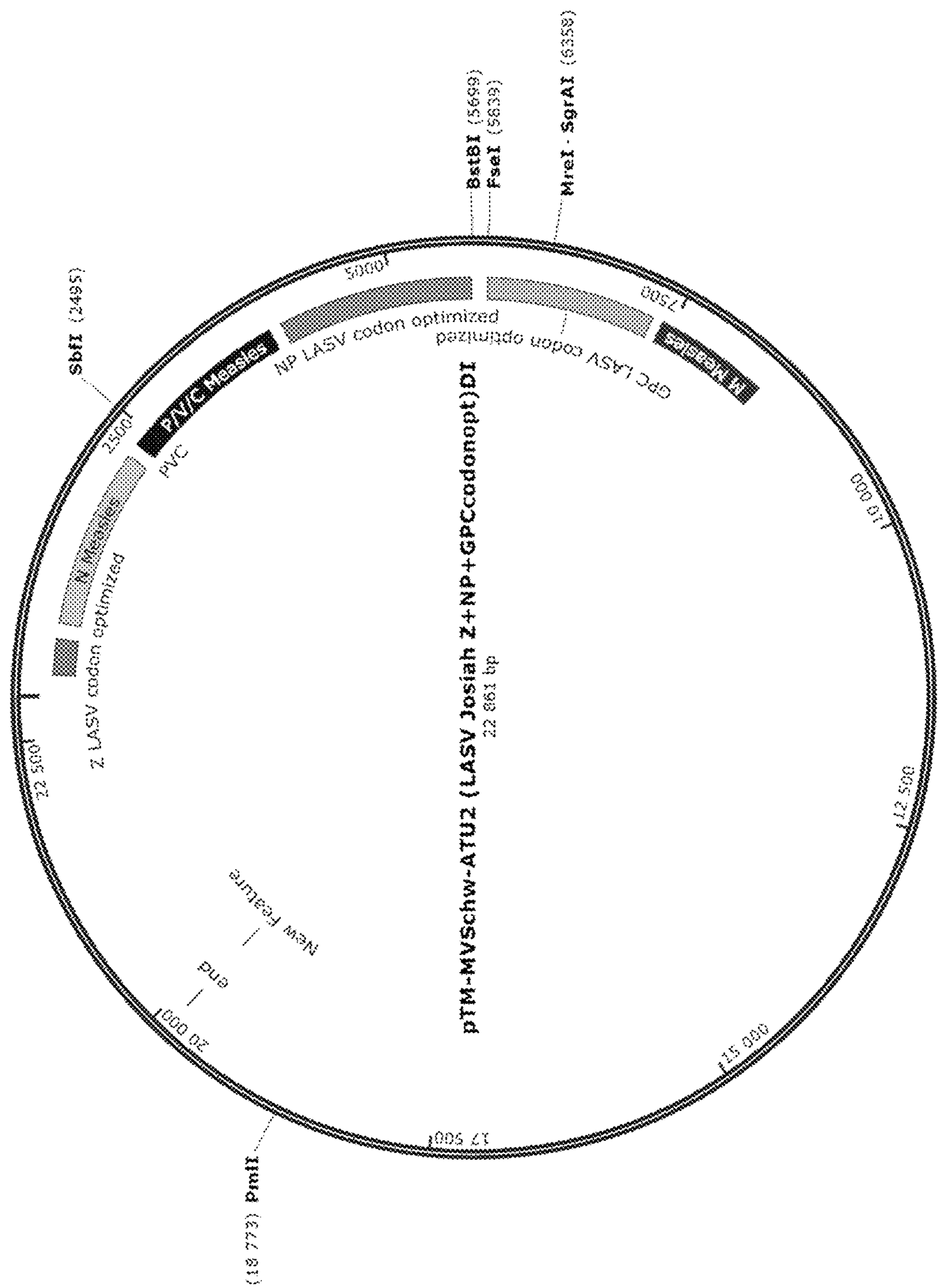
FIG. 35. Schematic representation of transfer vector plasmid according to a fifth embodiment of the invention. The transfer vector has the sequence of SEQ ID No: 13. The codon-optimized heterologous polynucleotide of SEQ ID No: 8 encoding the Z protein is localized between nucleotides 193 and 504. The measles gene encoding the N protein is localized between nucleotides 646 and 2223. The measles gene encoding the P protein is localized between nucleotides 2345 and 3868. The codon-optimized heterologous polynucleotide of SEQ ID No: 4 encoding the NP protein is localized between nucleotides 3988 and 5697. The codon-optimized heterologous polynucleotide of SEQ ID No: 2 encoding the GPC is localized between nucleotides 5842 and 7317 The measles gene encoding the M protein is localized between nucleotides 7414 and 8421.
Figure 36:
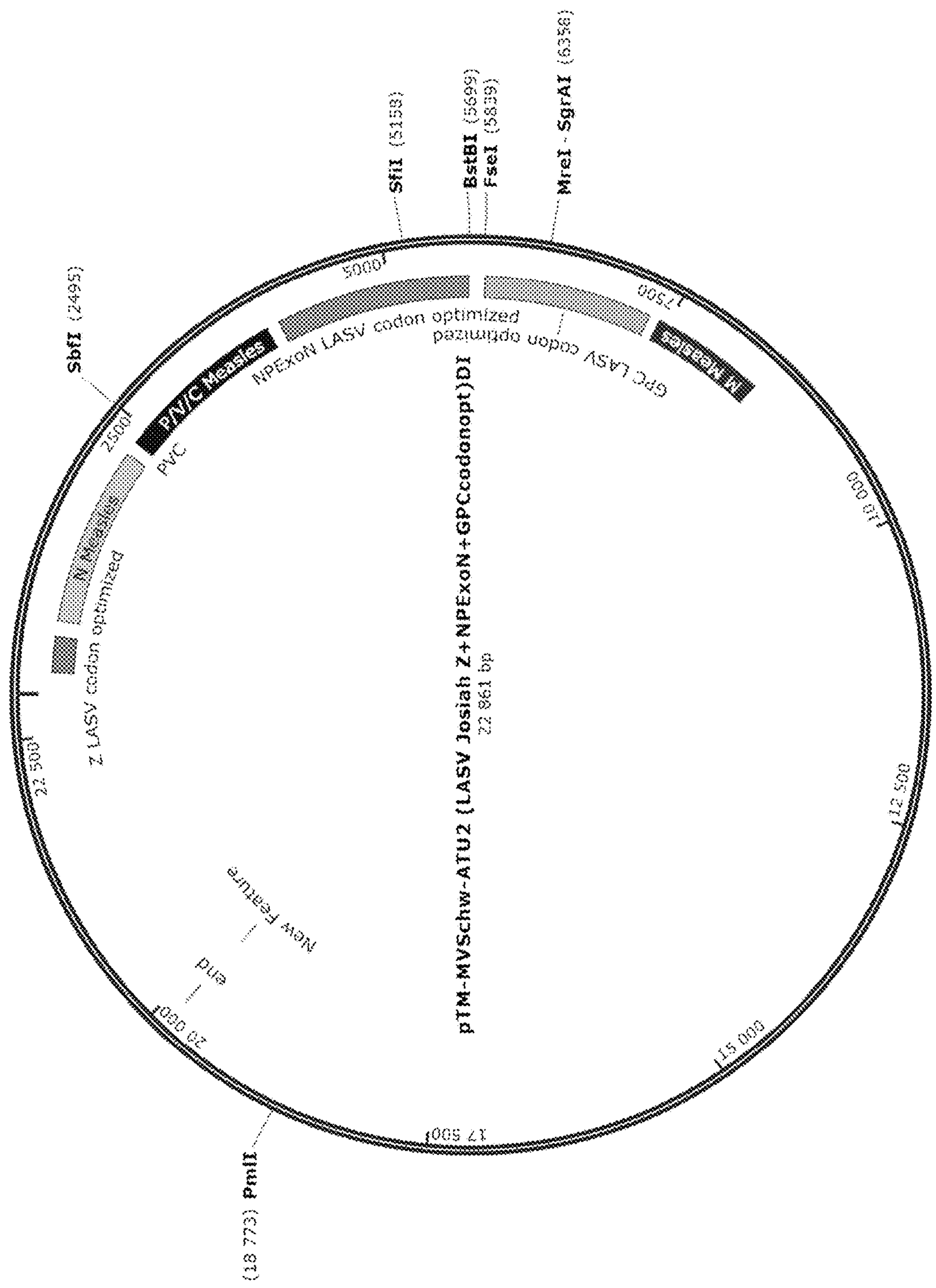
FIG. 36. Schematic representation of transfer vector plasmid according to a sixth embodiment of the invention. The transfer vector has the sequence of SEQ ID No: 14. The codon-optimized heterologous polynucleotide of SEQ ID No: 8 encoding the Z protein is localized between nucleotides 193 and 504. The measles gene encoding the N protein is localized between nucleotides 646 and 2223. The measles gene encoding the P protein is localized between nucleotides 2345 and 3868. The codon-optimized heterologous polynucleotide of SEQ ID No: 6 encoding the mutated NP protein is localized between nucleotides 3988 and 5697. The codon-optimized heterologous polynucleotide of SEQ ID No: 2 encoding the GPC is localized between nucleotides 5842 and 7317 The measles gene encoding the M protein is localized between nucleotides 7414 and 8421.

The release of soluble mediators in plasma of animals after immunization and after LASV challenge has been observed. Among the 29 analytes quantified using Luminex assay, no difference in the levels of soluble mediator was found between animals after immunisation (data not shown). In challenged animals (FIG. 27), a transient release of IFNg was detected in the plasma of all animals, with levels peaking on day 6 and 9 post-infection in immunized animals and MeV-controls respectively. A lower concentration was nevertheless observed in the plasma of monkeys immunized with MeV-NP$_{ExoN}$+GPC$_{LASV}$. Concentrations of perforin rose until day 9 or 12 in all animals, and then decreased to a low level until day 22. Once again, the levels observed in monkeys immunized with MeV-NP$_{ExoN}$+GPC$_{LASV}$ were lower. Elevated soluble CD137 (sCD137) levels were observed in monkeys immunized with MeV and MeV-Z+GPC$_{LASV}$ 9 days after infection, while only moderate concentrations of sCD137 were observed in animals immunized with MeV-NP$_{ExoN}$+GPC$_{LASV}$. IL-6 appeared in the plasma of all animals by day 6, and was still present at day 9 in animals vaccinated with MeV and MeV-Z+GPC$_{LASV}$, while it was not detected anymore in the plasma of animals immunized with MeV-NP$_{ExoN}$+GPC$_{LASV}$. IL-6 levels were still rising in the plasma of MeV-animals, while the increase was moderate in the plasma of animals immunized with MeV-Z+GPC$_{LASV}$. Elevated amount of IL-8 was observed in the plasma of animals immunized with MeV and MeV-Z+GPC$_{LASV}$ from day 6, whereas only low concentrations were detected between day 9 and day 12 in MeV-NP$_{ExoN}$+GPC$_{LASV}$ monkeys. IL-18 was not detected in the plasma of MeV-NP$_{ExoN}$+GPC$_{LASV}$ monkeys, while high levels and low levels was detected in animals immunized with MeV and MeV-Z+GPC$_{LASV}$ respectively. MCP1 remains at basal levels in MeV-NP$_{ExoN}$+GPC$_{LASV}$ monkeys. In contrast, high concentrations were found in MeV and MeV-Z+GPC$_{LASV}$ animals, starting from day 6 and 9 respectively. Levels of IL-10 and IL-1 receptor antagonist (IL-1RA) increased until day 9 in MeV-Z+GPC$_{LASV}$ monkeys, and then decreases to reach a low level at day 22. IL-10 and IL-1RA levels were still rising in MeV animals, while except for small amount detected after 6 days, IL-10 and IL-1 RA were not released in the plasma of animals immunized with MeV-NP$_{ExoN}$+GPC$_{LASV}$.

Example 6: Immune Response to MeV

Figures 28, 29:
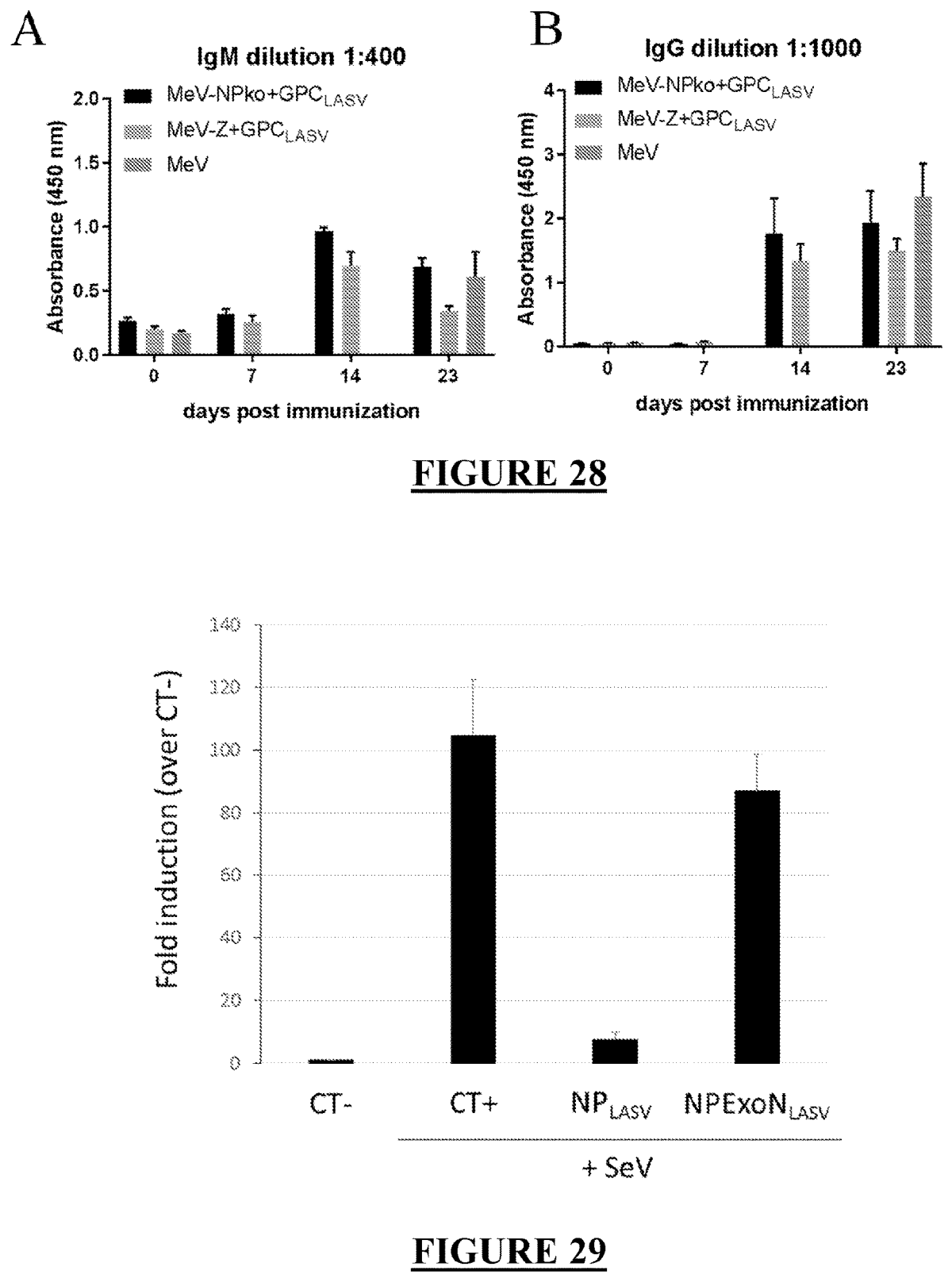

The levels of MeV-specific immunoglobulins produced against MeV-specific immunoglobulins was also assessed post-challenge by ELISA (FIG. 28A: IgM and 28B: IgG). The IgM and IgG MeV-specific are produced in all animals (MeV group, MeV-NP$_{ExoN}$+GPC$_{LASV}$ group; MeV-Z+GPC$_{LASV}$ group). Similar MeV-specific IgM and IgG responses are induced by the MeV-NP$_{ExoN}$-GPC$_{LASV}$, the MeV-Z+GPC$_{LASV}$ and the MeV vaccines (FIG. 28). These animals are vaccinated MeV (FIG. 28), and animals which have been immunized with MeV-NP$_{ExoN}$+GPC$_{LASV}$ or MeV-Z+GPC$_{LASV}$ are vaccinated against LASV (See FIG. 15) and MeV (FIG. 28).

Example 7: Tropism of the Vaccine Strains of MeV-LASV

Figure 30:
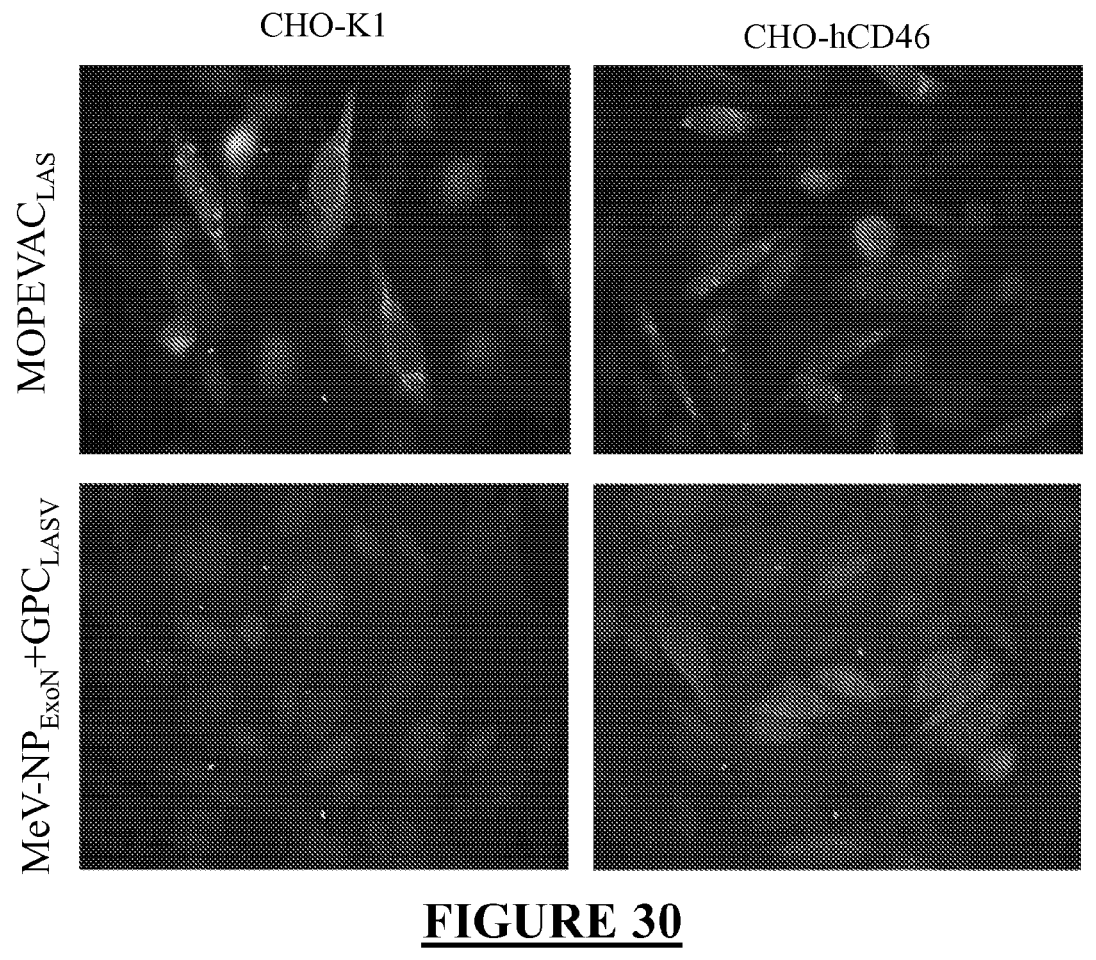

The tropism of MeV-LASV has been analysed. Lassa virus uses α-dystroglycan (α-DG) as a receptor. The vaccine strains of MeV use CD46, SLAM and nectin-4 as receptors. A Mopeia virus has been used as a control to analyse if the introduction of Lassa antigens into the MeV vector has an impact on the tropism of the vaccine strains of MeV. Mopeia virus is an arenavirus closely related to the Lassa virus, and uses the same receptor. A Mopeia virus pseudotyped with the Lassa virus GPC replicates in CHO-K1 cells which express α-DG and in CHO-hCD46 cells which express α-DG and the human CD46, as illustrated on FIG. 30, wherein a staining with an anti-GP1 is positive in both cell lines. On the contrary, MeV-NP$_{ExoN}$+GPC$_{LASV}$ are not able to replicate in CHO-K1 cells, while it replicates in CHO-hCD46 cell line (FIG. 30, bottom pictures). Therefore, the introduction of Lassa antigens into the MeV vector does not extend the tropism the MeV.

CONCLUSION

To conclude, both MeV-NP$_{ExoN}$+GPC$_{LASV}$ and MeV-Z+GPC$_{LASV}$ vaccines were safe, immunogenic and efficacious in non-human primates. Both protected cynomolgus macaques against a lethal challenge with LASV strain Josiah after a single immunization. However, MeV-NP$_{ExoN}$+GPC$_{LASV}$ conferred the best protection with a robust T cell response and a nearly-sterilizing immunity in all vaccinated monkeys. Thus, this vector is a candidate of choice for advance to clinical trials in humans. The immunogenicity of this vector prior challenge could certainly be improved by a prime/boost strategy. Nonetheless, we here bring the proof of principle that a single immunization could protect 100% of challenge animals. In addition, these vectors should protect monkeys against measles and could thus be used, in addition to emergency vaccine, as a bivalent vaccine in endemic countries where both LASV and MeV are major public health issues.

SEQ ID NO: 1

SEQ ID No: 1 corresponds to a recombinant GPC protein of the Lassa Virus strain Josiah encoded by the codon-optimised sequence of SEQ ID No: 2.

MGQIVTFFQEVPHVIEEVMNIVLIALSVLAVLKGLYNFATCGLVGLV

TFLLLCGRSCTTSLYKGVYELQTLELNMETLNMTMPLSCTKNNSHHY

IMVGNETGLELTLTNTSIINHKFCNLSDAHKKNLYDHALMSIISTFH

LSIPNFNQYEAMSCDFNGGKISVQYNLSHSYAGDAANHCGTVANGVL

QTFMRMAWGGSYIALDSGRGNWDCIMTSYQYLIIQNTTWEDHCQFSR

PSPIGYLGLLSQRTRDIYISRRLLGTFTWTLSDSEGKDTPGGYCLTR

WMLIEAELKCFGNTAVAKCNEKHDEEFCDMLRLFDFNKQAIQRLKAE

AQMSIQLINKAVNALINDQLIMKNHLRDIMGIPYCNYSKYWYLNHTT

TGRTSLPKCWLVSNGSYLNETHFSDDIEQQADNMITEMLQKEYMERQ

GKTPLGLVDLFVFSTSFYLISIFLHLVKIPTHRHIVGKSCPKPHRLN

HMGICSCGLYKQPGVPVKWKR*

SEQ ID NO: 2

SEQ ID No: 2 corresponds to a codon-optimized nucleotide sequence encoding the GPC protein of SEQ ID No. 1.

SEQ ID NO: 3

SEQ ID No: 3 corresponds to a recombinant NP protein of the Lassa Virus strain Josiah encoded by the codon-optimised sequence of SEQ ID No: 4.

MSASKEIKSFLWTQSLRRELSGYCSNIKLQVVKDAQALLHGLDFSEV

SNVQRLMRKERRDDNDLKRLRDLNQAVNNLVELKSTQQKSILRVGTL

TSDDLLILAADLEKLKSKVIRTERPLSAGVYMGNLSSQQLDQRRALL

NMIGMSGGNQGARAGRDGVVRVWDVKNAELLNNQFGTMPSLTLACLT

KQGQVDLNDAVQALTDLGLIYTAKYPNTSDLDRLTQSHPILNMIDTK

KSSLNISGYNFSLGAAVKAGACMLDGGNMLETIKVSPQTMDGILKSI

LKVKKALGMFISDTPGERNPYENILYKICLSGDGWPYIASRTSITGR

AWENTVVDLESDGKPQKADSNNSSKSLQSAGFTAGLTYSQLMTLKDA

MLQLDPNAKTWMDIEGRPEDPVEIALYQPSSGCYIHFFREPTDLKQF

```
   1 ATGGGCCAGA TTGTCACATT CTTTCAGGAA GTGCCACACG TCATTGAGGA GGTCATGAAC
  61 ATCGTGCTGA TTGCTCTGTC AGTGCTGGCA GTGCTGAAAG GACTGTACAA CTTCGCTACC
 121 TGTGGACTGG TGGGACTGGT CACATTCCTG CTGCTGTGCG GCAGAAGTTG CACTACCTCA
 181 CTGTACAAAG GAGTGTACGA GCTGCAGACT CTGGAACTGA ACATGGAGAC ACTGAATATG
 241 ACAATGCCTC TGAGCTGCAC CAAGAATAAT AGCCACCACT ATATCATGGT CGGGAACGAA
 301 ACCGGCCTGG AACTGACCCT GACAAACACC AGCATCATTA ACCACAAGTT CTGCAATCTG
 361 AGCGACGCTC ACAAGAAGAA CCTGTATGAC CACGCTCTGA TGTCCATCAT CAGTACCTTT
 421 CACCTGTCCA TCCCCAATTT CAACCAGTAC GAGGCAATGT CATGCGACTT CAACGGGGGC
 481 AAGATCAGTG TCCAGTACAA CCTGAGCCAC TCCTACGCCG GCGACGCAGC CAACCACTGC
 541 GGAACTGTCG CCAATGGCGT GCTGCAGACA TTCATGAGGA TGGCATGGGG GGGATCTTAC
 601 ATCGCACTGG ATAGCGGCAG GGGCAATTGG GATTGCATCA TGACTTCCTA TCAGTATCTG
 661 ATTATCCAGA ATACTACATG GGAGGATCAT TGCCAGTTCA GTCGGCCCAG CCCTATTGGA
 721 TATCTGGGGC TGCTGTCACA GAGAACACGG GATATCTATA TTTCAAGACG CCTGCTGGGC
 781 ACATTCACTT GGACACTGTC AGACAGTGAG GGCAAGGATA CTCCAGGGGG CTACTGCCTG
 841 ACACGATGGA TGCTGATCGA AGCAGAGCTG AAATGCTTCG GCAATACCGC AGTGGCCAAG
 901 TGCAACGAGA AACACGACGA GGAGTTCTGC GACATGCTGA GGCTGTTCGA CTTCAACAAA
 961 CAGGCTATCC AGAGACTGAA GGCAGAAGCC CAGATGTCAA TCCAGCTGAT CAACAAGGCA
1021 GTGAACGCCC TGATCAACGA CCAGCTGATC ATGAAGAACC ACCTGAGAGA CATTATGGGC
1081 ATCCCCTACT GTAATTACAG CAAGTATTGG TACCTGAACC ACACTACAAC CGGGAGAACA
1141 TCCCTGCCCA AGTGCTGGCT GGTCAGCAAT GGGAGTTATC TGAATGAAAC CCATTTCAGC
1201 GACGATATCG AACAGCAGGC TGACAACATG ATCACAGAGA TGCTGCAGAA AGAGTACATG
1261 GAAAGACAGG GCAAGACACC ACTGGGACTG GTCGATCTGT TCGTCTTCTC CACTAGCTTC
1321 TATCTGATTT CCATCTTCCT GCACCTGGTG AAGATCCCCA CTCATAGGCA CATTGTCGGC
1381 AAGAGTTGCC CTAAACCCCA TAGGCTGAAT CACATGGGGA TTTGTAGTTG CGGCCTGTAT
1441 AAGCAGCCTG GCGTGCCTGT GAAATGGAAG AGATGA
```

-continued

KQDAKYSHGIDVTDLFATQPGLTSAVIDALPRNMVITCQGSDDIRKL

LESQGRKDIKLIDIALSKTDSRKYENAVWDQYKDLCHMHTGVVVEKK

KRGGKEEITPHCALMDCIMFDAAVSGGLNTSVLRAVLPRDMVFRTST

PRVVL*

SEQ ID NO: 4

SEQ ID No: 4 corresponds to a codon-optimized nucleotide sequence encoding the NP protein of SEQ ID No. 3.

MSASKEIKSFLWTQSLRRELSGYCSNIKLQVVKDAQALLHGLDFSEV

SNVQRLMRKERRDDNDLKRLRDLNQAVNNLVELKSTQQKSILRVGTL

TSDDLLILAADLEKLKSKVIRTERPLSAGVYMGNLSSQQLDQRRALL

NMIGMSGGNQGARAGRDGVVRVWDVKNAELLNNQFGTMPSLTLACLT

KQGQVDLNDAVQALTDLGLIYTAKYPNTSDLDRLTQSHPILNMIDTK

```
   1 ATGAGTGCCA GCAAAGAAAT CAAGAGCTTC CTGTGGACCC AGAGTCTGCG GAGGGAACTG
  61 AGCGGATACT GTAGCAACAT CAAACTGCAG GTGGTCAAGG ACGCTCAGGC ACTGCTGCAT
 121 GGGCTGGACT TCTCCGAGGT GTCTAATGTG CAGCGGCTGA TGCGGAAAGA ACGGAGGGAC
 181 GATAATGACC TGAAGCGACT GCGCGACCTG AACCAGGCAG TGAACAATCT GGTCGAGCTG
 241 AAGAGCACCC AGCAGAAATC AATCCTGCGG GTCGGGACAC TGACATCTGA CGACCTGCTG
 301 ATCCTGGCTG CAGACCTGGA GAAGCTGAAA TCGAAAGTGA TCCGCACCGA AAGGCCACTG
 361 TCCGCCGGGG TCTACATGGG CAATCTGTCT TCCCAGCAGC TGGACCAGAG GCGGGCTCTG
 421 CTGAACATGA TTGGGATGTC CGGAGGAAAT CAGGGAGCTA GAGCCGGGAG GGACGGAGTC
 481 GTGCGGGTCT GGGACGTGAA GAATGCCGAA CTGCTGAACA ACCAGTTCGG GACCATGCCA
 541 AGTCTGACAC TGGCATGCCT GACTAAACAG GGCCAGGTGG ATCTGAATGA TGCAGTCCAG
 601 GCTCTGACCG ACCTGGGCCT GATCTACACC GCCAAGTACC CCAATACTAG CGACCTGGAT
 661 AGACTGACCC AGAGCCACCC CATCCTGAAC ATGATCGACA CTAAGAAGTC CTCACTGAAC
 721 ATCAGTGGCT ATAATTTCTC CCTGGGGGCA GCAGTCAAGG CTGGCGCATG CATGCTGGAC
 781 GGCGGGAATA TGCTGGAAAC CATCAAAGTG TCTCCCCAGA CCATGGATGG CATCCTGAAA
 841 TCTATTCTGA AAGTCAAGAA GGCCCTGGGA ATGTTTATTT CAGACACCCC CGGCGAGAGG
 901 AATCCATATG AGAACATTCT GTATAAGATT TGCCTGAGTG GCGACGGGTG GCCATACATT
 961 GCAAGCCGGA CATCAATTAC CGGAAGAGCT TGGGAGAATA CAGTCGTGGA CCTGGAAAGC
1021 GACGGCAAGC CCCAGAAGGC CGACTCAAAC AACTCCTCAA AGAGTCTGCA GTCAGCTGGC
1081 TTCACAGCAG GGCTGACTTA CTCCCAGCTG ATGACACTGA AGGACGCAAT GCTGCAGCTG
1141 GACCCAAACG CTAAGACATG GATGGACATC GAGGGACGGC CAGAAGATCC AGTGGAAATC
1201 GCACTGTATC AGCCATCATC CGGATGCTAT ATCCATTTCT TCCGGGAACC AACTGATCTG
1261 AAGCAGTTCA AGCAGGATGC AAAGTACTCC CACGGAATCG ATGTCACCGA TCTGTTCGCA
1321 ACCCAGCCAG GACTGACATC AGCCGTCATC GATGCCCTGC CTAGGAACAT GGTCATTACT
1381 TGCCAGGGCT CCGACGATAT TAGGAAGCTG CTGGAGAGCC AGGGACGGAA GGATATCAAA
1441 CTGATCGATA TTGCCCTGTC TAAGACTGAT AGCCGGAAAT ATGAGAATGC AGTCTGGGAT
1501 CAGTACAAGG ACCTGTGCCA TATGCATACC GGAGTGGTCG TCGAGAAGAA GAAGAGGGGC
1561 GGAAAGGAAG AGATCACACC CCACTGTGCC CTGATGGATT GCATCATGTT CGACGCAGCC
1621 GTGTCCGGGG GCCTGAACAC CTCAGTCCTG AGGGCTGTCC TGCCAAGAGA TATGGTGTTT
1681 AGAACTTCAA CCCCAAGAGT CGTCCTGTAA
```

SEQ ID NO: 5

SEQ ID No: 5 corresponds to a recombinant mutated NP protein of the Lassa Virus strain Josiah encoded by the codon-optimised sequence of SEQ ID No: 6, and wherein the exonuclease activity of the NP protein has been knocked down. Amino acid 388 and amino acid 391 have been mutated (M388D and E391 G).

-continued

KSSLNISGYNFSLGAAVKAGACMLDGGNMLETIKVSPQTMDGILKSI

LKVKKALGMFISDTPGERNPYENILYKICLSGDGWPYIASRTSITGR

AWENTVVDLESDGKPQKADSNNSSKSLQSAGFTAGLTYSQLMTLKDA

MLQLDPNAKTWMAIEARPEDPVEIALYQPSSGCYIHFFREPTDLKQF

-continued

```
KQDAKYSHGIDVTDLFATQPGLTSAVIDALPRNMVITCQGSDDIRKL

LESQGRKDIKLIDIALSKTDSRKYENAVWDQYKDLCHMHTGVVVEKK

KRGGKEEITPHCALMDCIMFDAAVSGGLNTSVLRAVLPRDMVFRTST

PRVVL*
```

SEQ ID NO: 6

SEQ ID No: 6 corresponds to a codon-optimized nucleotide sequence encoding the mutated NP protein of SEQ ID No. 5. Nucleotides 11661 1175 and 1176 has been mutated (C1166A, C1175G and C1176A).

```
   1 ATGAGTGCCA GCAAAGAAAT CAAGAGCTTC CTGTGGACCC AGAGTCTGCG GAGGGAACTG

  61 AGCGGATACT GTAGCAACAT CAAACTGCAG GTGGTCAAGG ACGCTCAGGC ACTGCTGCAT

 121 GGGCTGGACT TCTCCGAGGT GTCTAATGTG CAGCGGCTGA TGCGGAAAGA ACGGAGGGAC

 181 GATAATGACC TGAAGCGACT GCGCGACCTG AACCAGGCAG TGAACAATCT GGTCGAGCTG

 241 AAGAGCACCC AGCAGAAATC AATCCTGCGG GTCGGGACAC TGACATCTGA CGACCTGCTG

 301 ATCCTGGCTG CAGACCTGGA GAAGCTGAAA TCGAAAGTGA TCCGCACCGA AAGGCCACTG

 361 TCCGCCGGGG TCTACATGGG CAATCTGTCT TCCCAGCAGC TGGACCAGAG GCGGGCTCTG

 421 CTGAACATGA TTGGGATGTC CGGAGGAAAT CAGGGAGCTA GAGCCGGGAG GGACGGAGTC

 481 GTGCGGGTCT GGGACGTGAA GAATGCCGAA CTGCTGAACA ACCAGTTCGG GACCATGCCA

 541 AGTCTGACAC TGGCATGCCT GACTAAACAG GGCCAGGTGG ATCTGAATGA TGCAGTCCAG

 601 GCTCTGACCG ACCTGGGCCT GATCTACACC GCCAAGTACC CCAATACTAG CGACCTGGAT

 661 AGACTGACCC AGAGCCACCC CATCCTGAAC ATGATCGACA CTAAGAAGTC CTCACTGAAC

 721 ATCAGTGGCT ATAATTTCTC CCTGGGGGCA GCAGTCAAGG CTGGCGCATG CATGCTGGAC

 781 GGCGGGAATA TGCTGGAAAC CATCAAAGTG TCTCCCCAGA CCATGGATGG CATCCTGAAA

 841 TCTATTCTGA AAGTCAAGAA GGCCCTGGGA ATGTTTATTT CAGACACCCC CGGCGAGAGG

 901 AATCCATATG AGAACATTCT GTATAAGATT TGCCTGAGTG GCGACGGGTG GCCATACATT

 961 GCAAGCCGGA CATCAATTAC CGGAAGAGCT TGGGAGAATA CAGTCGTGGA CCTGGAAAGC

1021 GACGGCAAGC CCCAGAAGGC CGACTCAAAC AACTCCTCAA AGAGTCTGCA GTCAGCTGGC

1081 TTCACAGCAG GGCTGACTTA CTCCCAGCTG ATGACACTGA AGGACGCAAT GCTGCAGCTG

1141 GACCCAAACG CTAAGACATG GATGGCCATC GAGGCCCGGC CAGAAGATCC AGTGGAAATC

1201 GCACTGTATC AGCCATCATC CGGATGCTAT ATCCATTTCT TCCGGGAACC AACTGATCTG

1261 AAGCAGTTCA AGCAGGATGC AAAGTACTCC CACGGAATCG ATGTCACCGA TCTGTTCGCA

1321 ACCCAGCCAG GACTGACATC AGCCGTCATC GATGCCCTGC CTAGGAACAT GGTCATTACT

1381 TGCCAGGGCT CCGACGATAT TAGGAAGCTG CTGGAGAGCC AGGGACGGAA GGATATCAAA

1441 CTGATCGATA TTGCCCTGTC TAAGACTGAT AGCCGGAAAT ATGAGAATGC AGTCTGGGAT

1501 CAGTACAAGG ACCTGTGCCA TATGCATACC GGAGTGGTCG TCGAGAAGAA GAAGAGGGGC

1561 GGAAAGGAAG AGATCACACC CCACTGTGCC CTGATGGATT GCATCATGTT CGACGCAGCC

1621 GTGTCCGGGG GCCTGAACAC CTCAGTCCTG AGGGCTGTCC TGCCAAGAGA TATGGTGTTT

1681 AGAACTTCAA CCCCAAGAGT CGTCCTGTAA
```

SEQ ID NO: 7

SEQ ID No: 7 corresponds to a recombinant Z protein of the Lassa Virus strain Josiah encoded by the codon-optimised sequence of SEQ ID No: 8.

```
MGNKQAKAPESKDSPRASLIPDATHLGPQFCKSCWFENKGLVECNNH

YLCLNCLTLLLSVSNRCPICKMPLPTKLRPSAAPTAPPTGAADSIRP

PPYSP*
```

SEQ ID NO: 8

SEQ ID No: 8 corresponds to a codon-optimized nucleotide sequence encoding the Z protein of SEQ ID No. 7.

```
  1 ATGGGCAATA AGCAGGCAAA GGCACCCGAA AGCAAGGATT CACCTAGAGC ATCACTGATT

 61 CCCGACGCAA CTCATCTGGG GCCACAGTTC TGCAAATCCT GTTGGTTCGA GAACAAAGGC

121 CTGGTGGAGT GCAATAACCA CTACCTGTGC CTGAACTGTC TGACACTGCT GCTGAGTGTG

181 AGCAACAGAT GCCCAATCTG CAAGATGCCT CTGCCAACAA AGCTGAGGCC TTCTGCTGCA

241 CCCACCGCAC CACCAACTGG AGCCGCAGAC AGCATTAGAC CCCCCCCATA CTCACCATAA
```

BIBLIOGRAPHIC REFERENCES

Brandler, S. et al. A recombinant measles vaccine expressing chikungunya virus-like particles is strongly immunogenic and protects mice from lethal challenge with chikungunya virus. Vaccine 31, 3718-3725, doi:10.1016/J. vaccine.2013.05.086 (2013).

Mateo, M., Navaratnaraja h, C. K., Syed, S. & Cattaneo, R. The measles virus hemagglutinin beta-propeller head beta4-beta5 hydrophobie groove governs functional interactions with nectin-4 and CD46 but not those with the signalling lymphocytic activation molecule. J Virol 87, 9208-9216, doi:10.1128/JVI.01210-13 (2013).

Radecke, F. et al. Rescue of measles viruses from cloned DNA. Embo J 14, 5773-5784 (1995).

Stebbings, R. et al. Immunogenicity of a recombinant measles-HIV-1 clade B candidate vaccine. PLoS One 7, e50397, doi:10.1371/journal.pone.0050397 {2012).

Reyes-del Valle, J., Hodge, G., McChesney, M. B. & Cattaneo, R. Protective anti-hepatitis B virus responses in rhesus monkeys primed with a vectored measles virus and boosted with a single dose of hepatitis B surface antigen. J Virol 83, 9013-9017, doi:10.1128/JVI.00906-09 {2009).

Yoneda, M. et al. Recombinant measles virus vaccine expressing the Nipah virus glycoprotein protects against lethal Nipah virus challenge. PLoS One 8, e58414, doi: 10.1371/journal.pone.0058414 (2013).

Combredet, C. et al. A molecularly cloned Schwarz strain of measles virus vaccine induces strong immune responses in macaques and transgenic mice. J Virol 77, 11546-11554 {2003).

Escriou, N. et al. Protection from SARS coronavirus conferred by live measles vaccine expressing the spike glycoprotein. Virology 452-453, 32-41, doi:10.1016/j.virol.2014.01.002 {2014).

Lorin, C. et al. Toxicology, biodistribution and shedding profile of a recombinant measles vaccine vector expressing HIV-1 antigens, in cynomolgus macaques. Naunyn Schmiedebergs Arch Pharmacol 385, 1211-1225, doi: 10.1007/s00210-012-0793-4 {2012).

Brandler, S. et al. Measles vaccine expressing the secreted form of West Nile virus envelope glycoprotein induces protective immunity in squirrel monkeys, a new model of West Nile virus infection. J Infect Dis 206, 212-219, doi:10.1093/infdis/jis328 (2012).

Brandler, S. et al. Pediatric measles vaccine expressing a dengue tetravalent antigen elicits neutralizing antibodies against all four dengue viruses. Vaccine 28, 6730-6739, doi:10.1016/j.vaccine.2010.07.073 (2010).

Guerbois, M. et al. Live attenuated measles vaccine expressing HIV-1 Gag virus like particles covered with gp160DeltaV1V2 is strongly immunogenic. Virology 388, 191-203, doi:10.1016/j.virol.2009.02.047 (2009).

Brandler, S. et al. Pediatric measles vaccine expressing a dengue antigen induces durable serotype-specific neutralizing antibodies to dengue virus. PLoS Negl Trop Dis 1, e96, doi:10.1371/journal.pntd.0000096 (2007).

Lorin, C. et al. A recombinant live attenuated measles vaccine vector primes effective HLA-A0201-restricted cytotoxic T lymphocytes and broadly neutralizing antibodies against HIV-1 conserved epitopes. Vaccine 23, 4463-4472, doi:10.1016/j.vaccine.2005.04.024 (2005).

The invention claimed is:

1. A nucleic acid construct which comprises:

a cDNA molecule encoding a full length antigenomic (+) RNA strand of a measles virus (MeV); and a first heterologous polynucleotide comprising at least one of SEQ ID NO: 2, SEQ ID NO: 4, and SEQ ID NO: 6, wherein the first heterologous polynucleotide is operatively cloned within an additional transcription unit (ATU) inserted within the cDNA of the antigenomic (+) RNA.

2. The nucleic acid construct according to claim 1, further comprising a second heterologous polynucleotide encoding at least one polypeptide, or an antigenic fragment thereof, of Lassa virus (LASV), said at least one polypeptide being selected from the group consisting of GPC protein, NP protein, and mNP protein, the second heterologous polynucleotide being operatively cloned within another ATU at a location distinct from the location of the first heterologous polynucleotide.

3. The nucleic acid construct according to claim 1, wherein the first heterologous polynucleotide comprises SEQ ID NO: 2.

4. The nucleic acid construct according to claim 2, wherein the first and/or second heterologous polynucleotide(s) encode(s) the mNP protein, or an antigenic fragment thereof, wherein the mNP protein has a mutated exonuclease domain, wherein the amino acid sequence of the encoded mNP protein is mutated on amino acid residue 389 and/or 392, by substitution on amino acid residues 389 and 392, of SEQ ID NO: 3.

5. The nucleic acid construct according to claim 2, wherein the first and second heterologous polynucleotides are cloned into an ATU selected from additional transcription unit 2 (ATU2) and additional transcription unit 3 (ATU3).

6. The nucleic acid construct according to claim 1, wherein the first heterologous polynucleotide comprises SEQ ID NO: 4.

7. The nucleic acid construct according to claim 1, comprising from 5' to 3' end the following polynucleotides:

(a) a polynucleotide encoding the N protein of the MeV;
(b) a polynucleotide encoding the P protein of the MeV;
(c) the first heterologous polynucleotide comprising at least one of SEQ ID NO:
2, SEQ ID NO: 4, and SEQ ID NO: 6 wherein the first polynucleotide is operatively cloned within ATU2;
(d) a polynucleotide encoding the M protein of the MeV;
(e) a polynucleotide encoding the F protein of the MeV;
(f) a polynucleotide encoding the H protein of the MeV;
(g) a polynucleotide encoding the L protein of the MeV;
and wherein said polynucleotides are operatively linked within the nucleic acid construct and under the control of a viral replication and transcriptional regulatory elements.

8. The nucleic acid construct according to claim 1, comprising from 5' to 3' end the following polynucleotides:

(a) a second heterologous polynucleotide encoding at least one polypeptide selected from the group consisting of GPC protein, NP protein, and mNP protein of LASV, or an antigenic fragment thereof, wherein the second polynucleotide is operatively cloned within an ATU localized upstream the N gene of the MeV, in additional transcription unit 1 (ATU1);
(b) a polynucleotide encoding the N protein of the MeV;
(c) a polynucleotide encoding the P protein of the MeV;
(d) the first heterologous polynucleotide comprising at least one of SEQ ID NO:
2, SEQ ID NO: 4, and SEQ ID NO: 6, wherein the first polynucleotide is operatively cloned within ATU2;
(e) a polynucleotide encoding the M protein of the MeV;
(f) a polynucleotide encoding the F protein of the MeV;
(g) a polynucleotide encoding the H protein of the MeV;
(h) a polynucleotide encoding the L protein of the MeV,
and wherein said polynucleotides are operatively linked within the nucleic acid construct and under the control of a viral replication and transcriptional regulatory elements.

9. The nucleic acid construct according to claim 1, wherein the first heterologous polynucleotide comprises from 5' to 3' end:

(a) a nucleic acid comprising SEQ ID NO: 4 or SEQ ID NO: 6;
and a nucleic acid comprising SEQ ID NO: 2; wherein the first heterologous polynucleotide is operatively cloned between the P gene and the M gene of the MeV, in ATU2.

10. The nucleic acid construct according to claim 1, wherein the first heterologous polynucleotide comprises from 5' to 3' end:

(a) the nucleic acid of SEQ ID NO:6; and
(b) the nucleic acid of SEQ ID NO: 2;
and wherein the first heterologous polynucleotide sequence is operatively cloned between the gene P and the gene M of the MeV, in ATU2.

11. The nucleic acid construct according to claim 2, wherein the second heterologous polynucleotide encodes Z protein of LASV, or an antigenic fragment thereof, and wherein the first heterologous polynucleotide encodes the GPC protein of LASV, or an antigenic fragment thereof, wherein the sequence of the second heterologous polynucleotide comprises the sequence of SEQ ID NO: 8 and the sequence of the first heterologous polynucleotide comprises the sequence of SEQ ID NO: 2.

12. The nucleic acid construct according to claim 11, wherein the first heterologous polynucleotide is operatively cloned within ATU2 and the second heterologous polynucleotide is operatively cloned within ATU1.

13. The nucleic acid construct according to claim 1, wherein the measles virus is an attenuated virus strain selected from the group consisting of the Schwarz strain, the Zagreb strain, the AIK-C strain, the Moraten strain, the Philips strain, the Beckenham 4A strain, the Beckenham 16 strain, the Edmonston seed A strain, the Edmonston seed B strain, the CAM-70 strain, the TD 97 strain, the Leningrad-16 strain, the Shanghai 191 strain and the Belgrade strain.

14. The nucleic acid construct according to claim 1, wherein the first heterologous polynucleotide comprises SEQ ID NO: 6.

15. The nucleic acid construct according to claim 1, whose recombinant cDNA sequence is selected from the group consisting of:

SEQ ID NO: 9 (construct MeV-GPC);
SEQ ID NO: 10 (construct MeV-NP-GPC); and
SEQ ID NO: 11 (construct MeV-mNP-GPC).

16. A transfer plasm id vector comprising the nucleic acid construct according to claim 1 comprising a sequence selected from the group consisting of:

SEQ ID NO: 9 (Plasm MeV-GPC);
SEQ ID NO: 10 (Plasm MeV-NP-GPC); and
SEQ ID NO: 11 (Plasm MeV-mNP-GPC).

17. A recombinant measles virus, said virus comprising in its genome a nucleic acid construct according to claim 1.

18. A recombinant measles virus, wherein the virus comprises in its genome a nucleic acid construct according to claim 2.

19. The recombinant measles virus according to claim 17 expressing GPC protein and mNP protein of LASV, or antigenic fragments thereof.

20. The recombinant measles virus according to claim 18 expressing GPC protein and Z protein of LASV, or antigenic fragments thereof.

21. The recombinant measles virus according to claim 17, which elicits a cellular and/or humoral and cellular response after a single immunization, against antigenic fragment(s) of the GPC protein, the NP protein, and/or the mNP protein of LASV.

22. An isolated host cell transfected with the nucleic acid construct according to claim 1 selected from a mammalian cell, a VERO NK cells, CEF cells, human embryonic kidney cell line 293 or MRC5 cells.

23. Recombinant virus like particles (VLPs) comprising a Z protein and optionally a GPC protein and/or a NP protein and/or a mNP protein, or an antigenic fragment thereof, of Lassa virus (LASV), wherein the protein(s) or antigenic fragments thereof is(are) encoded by the first and/or second heterologous polynucleotide(s) of the nucleic acid construct according to claim 2.

24. An immunogenic composition comprising the recombinant VLPs according to claim 23.

25. A process for rescuing recombinant Lassa virus (LASV) like particles (VLPs) and/or recombinant measles virus expressing at least one of polypeptide selected from the group consisting of GPC protein, NP protein, mNP protein and Z protein of LASV, or an antigenic fragment thereof, comprising:

(a) transfecting cells, stably expressing T7 RNA polymerase and measles virus N and P proteins with the nucleic acid construct according to claim 1;

(b) maintaining the transfected cells in conditions suitable for the production of recombinant measles virus and/or LASV VLPs;

(c) infecting cells enabling propagation of the recombinant measles virus and/or the LASV VLPs by co-cultivating them with the transfected cells of step (b);

(d) harvesting the recombinant measles virus expressing at least one of the GPC protein, the NP protein, the mNP protein and/or the Z protein of LASV.

26. A method for preventing a Lassa virus related disease, said method comprising the immunization of a human by injection of recombinant Lassa virus VLPs according to claim 24.

27. A method for treating a Lassa virus related disease, said method comprising the immunization of a human by the injection of recombinant Lassa virus VLPs according to claim 24.

28. The nucleic acid construct of claim 2, wherein the first heterologous polynucleotide is operatively cloned within ATU2 located between the P gene and the M gene of the MeV and the second heterologous polynucleotide is operatively cloned within ATU3 located between the genes H and L of MeV.

29. The nucleic acid construct of claim 2, wherein the first heterologous polynucleotide encodes glycoprotein precursor (GPC) of LASV operatively cloned within ATU2 located between the P gene and the M gene of the MeV and the second heterologous polynucleotide encodes a mutated nucleoprotein (mNP) of LASV operatively cloned within ATU3 located between the genes H and L of MeV.

30. The nucleic acid construct of claim 2, wherein the first heterologous polynucleotide encodes nucleoprotein (NP) of LASV operatively cloned within ATU2 located between the P gene and the M gene of the MeV and the second heterologous polynucleotide encodes glycoprotein precursor (GPC) of LASV operatively cloned within ATU3 located between the genes H and L of MeV.

31. The nucleic acid construct of claim 2, wherein the first heterologous polynucleotide encodes the mutated nucleoprotein (mNP) of LASV operatively cloned within ATU2 located between the P gene and the M gene of the MeV and the second heterologous polynucleotide encodes glycoprotein precursor (GPC) of LASV operatively cloned within ATU3 located between the genes H and L of MeV.

32. The nucleic acid construct of claim 2, wherein the first heterologous polynucleotide encodes the glycoprotein precursor (GPC) and nucleoprotein (NP) of LASV operatively cloned within ATU2 located between the P gene and the M gene of the MeV.

33. The nucleic acid construct of claim 2, wherein the first heterologous polynucleotide encodes glycoprotein precursor (GPC) and mutated nucleoprotein (mNP) of LASV operatively cloned within ATU2 located between the P gene and the M gene of the MeV.

* * * * *

SEQUENCE LISTING

```
<160> NUMBER OF SEQ ID NOS: 17

<210> SEQ ID NO 1
<211> LENGTH: 491
<212> TYPE: PRT
<213> ORGANISM: Artificial Sequence
<220> FEATURE:
<223> OTHER INFORMATION: Protein GPC

<400> SEQUENCE: 1

Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
            20                  25                  30

Lys Gly Leu Tyr Asn Phe Ala Thr Cys Gly Leu Val Gly Leu Val Thr
        35                  40                  45

Phe Leu Leu Leu Cys Gly Arg Ser Cys Thr Thr Ser Leu Tyr Lys Gly
    50                  55                  60
```

```
Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
            100                 105                 110

Ile Asn His Lys Phe Cys Asn Leu Ser Asp Ala His Lys Lys Asn Leu
        115                 120                 125

Tyr Asp His Ala Leu Met Ser Ile Ile Ser Thr Phe His Leu Ser Ile
    130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
            180                 185                 190

Arg Met Ala Trp Gly Gly Ser Tyr Ile Ala Leu Asp Ser Gly Arg Gly
        195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
        275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320

Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
        355                 360                 365

Tyr Trp Tyr Leu Asn His Thr Thr Thr Gly Arg Thr Ser Leu Pro Lys
    370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
            420                 425                 430

Leu Phe Val Phe Ser Thr Ser Phe Tyr Leu Ile Ser Ile Phe Leu His
        435                 440                 445

Leu Val Lys Ile Pro Thr His Arg His Ile Val Gly Lys Ser Cys Pro
    450                 455                 460

Lys Pro His Arg Leu Asn His Met Gly Ile Cys Ser Cys Gly Leu Tyr
465                 470                 475                 480
```

```
Lys Gln Pro Gly Val Pro Val Lys Trp Lys Arg
                485                 490


<210> SEQ ID NO 2
<211> LENGTH: 1476
<212> TYPE: DNA
<213> ORGANISM: Artificial Sequence
<220> FEATURE:
<223> OTHER INFORMATION: Codon-optimized cDNA GPC

<400> SEQUENCE: 2

atgggccaga ttgtcacatt ctttcaggaa gtgccacacg tcattgagga ggtcatgaac      60

atcgtgctga ttgctctgtc agtgctggca gtgctgaaag gactgtacaa cttcgctacc     120

tgtggactgg tgggactggt cacattcctg ctgctgtgcg gcagaagttg cactacctca     180

ctgtacaaag gagtgtacga gctgcagact ctggaactga acatggagac actgaatatg     240

acaatgcctc tgagctgcac caagaataat agccaccact atatcatggt cgggaacgaa     300

accggcctgg aactgaccct gacaaacacc agcatcatta accacaagtt ctgcaatctg     360

agcgacgctc acaagaagaa cctgtatgac cacgctctga tgtccatcat cagtaccttt     420

cacctgtcca tccccaattt caaccagtac gaggcaatgt catgcgactt caacgggggc     480

aagatcagtg tccagtacaa cctgagccac tcctacgccg gcgacgcagc caaccactgc     540

ggaactgtcg ccaatggcgt gctgcagaca ttcatgagga tggcatgggg gggatcttac     600

atcgcactgg atagcggcag ggcaattgg gattgcatca tgacttccta tcagtatctg      660

attatccaga atactacatg ggaggatcat tgccagttca gtcggcccag ccctattgga     720

tatctggggc tgctgtcaca gagaacacgg gatatctata tttcaagacg cctgctgggc     780

acattcactt ggacactgtc agacagtgag ggcaaggata ctccaggggg ctactgcctg     840

acacgatgga tgctgatcga agcagagctg aaatgcttcg gcaataccgc agtggccaag     900

tgcaacgaga aacacgacga ggagttctgc gacatgctga ggctgttcga cttcaacaaa     960

caggctatcc agagactgaa ggcagaagcc cagatgtcaa tccagctgat caacaaggca    1020

gtgaacgccc tgatcaacga ccagctgatc atgaagaacc acctgagaga cattatgggc    1080

atcccctact gtaattacag caagtattgg tacctgaacc acactacaac cgggagaaca    1140

tccctgccca agtgctggct ggtcagcaat gggagttatc tgaatgaaac ccatttcagc    1200

gacgatatcg aacagcaggc tgacaacatg atcacagaga tgctgcagaa agagtacatg    1260

gaaagacagg gcaagacacc actgggactg gtcgatctgt tcgtcttctc cactagcttc    1320

tatctgattt ccatcttcct gcacctggtg aagatcccca ctcataggca cattgtcggc    1380

aagagttgcc ctaaacccca taggctgaat cacatgggga tttgtagttg cggcctgtat    1440

aagcagcctg gcgtgcctgt gaaatggaag agatga                              1476


<210> SEQ ID NO 3
<211> LENGTH: 569
<212> TYPE: PRT
<213> ORGANISM: Artificial Sequence
<220> FEATURE:
<223> OTHER INFORMATION: Protein NP

<400> SEQUENCE: 3

Met Ser Ala Ser Lys Glu Ile Lys Ser Phe Leu Trp Thr Gln Ser Leu
1               5                   10                  15

Arg Arg Glu Leu Ser Gly Tyr Cys Ser Asn Ile Lys Leu Gln Val Val
            20                  25                  30
```

```
Lys Asp Ala Gln Ala Leu Leu His Gly Leu Asp Phe Ser Glu Val Ser
        35                  40                  45

Asn Val Gln Arg Leu Met Arg Lys Glu Arg Arg Asp Asp Asn Asp Leu
    50                  55                  60

Lys Arg Leu Arg Asp Leu Asn Gln Ala Val Asn Asn Leu Val Glu Leu
65                  70                  75                  80

Lys Ser Thr Gln Gln Lys Ser Ile Leu Arg Val Gly Thr Leu Thr Ser
                85                  90                  95

Asp Asp Leu Leu Ile Leu Ala Ala Asp Leu Glu Lys Leu Lys Ser Lys
            100                 105                 110

Val Ile Arg Thr Glu Arg Pro Leu Ser Ala Gly Val Tyr Met Gly Asn
        115                 120                 125

Leu Ser Ser Gln Gln Leu Asp Gln Arg Arg Ala Leu Leu Asn Met Ile
    130                 135                 140

Gly Met Ser Gly Gly Asn Gln Gly Ala Arg Ala Gly Arg Asp Gly Val
145                 150                 155                 160

Val Arg Val Trp Asp Val Lys Asn Ala Glu Leu Leu Asn Asn Gln Phe
                165                 170                 175

Gly Thr Met Pro Ser Leu Thr Leu Ala Cys Leu Thr Lys Gln Gly Gln
            180                 185                 190

Val Asp Leu Asn Asp Ala Val Gln Ala Leu Thr Asp Leu Gly Leu Ile
        195                 200                 205

Tyr Thr Ala Lys Tyr Pro Asn Thr Ser Asp Leu Asp Arg Leu Thr Gln
    210                 215                 220

Ser His Pro Ile Leu Asn Met Ile Asp Thr Lys Lys Ser Ser Leu Asn
225                 230                 235                 240

Ile Ser Gly Tyr Asn Phe Ser Leu Gly Ala Ala Val Lys Ala Gly Ala
                245                 250                 255

Cys Met Leu Asp Gly Gly Asn Met Leu Glu Thr Ile Lys Val Ser Pro
            260                 265                 270

Gln Thr Met Asp Gly Ile Leu Lys Ser Ile Leu Lys Val Lys Lys Ala
        275                 280                 285

Leu Gly Met Phe Ile Ser Asp Thr Pro Gly Glu Arg Asn Pro Tyr Glu
    290                 295                 300

Asn Ile Leu Tyr Lys Ile Cys Leu Ser Gly Asp Gly Trp Pro Tyr Ile
305                 310                 315                 320

Ala Ser Arg Thr Ser Ile Thr Gly Arg Ala Trp Glu Asn Thr Val Val
                325                 330                 335

Asp Leu Glu Ser Asp Gly Lys Pro Gln Lys Ala Asp Ser Asn Asn Ser
            340                 345                 350

Ser Lys Ser Leu Gln Ser Ala Gly Phe Thr Ala Gly Leu Thr Tyr Ser
        355                 360                 365

Gln Leu Met Thr Leu Lys Asp Ala Met Leu Gln Leu Asp Pro Asn Ala
    370                 375                 380

Lys Thr Trp Met Asp Ile Glu Gly Arg Pro Glu Asp Pro Val Glu Ile
385                 390                 395                 400

Ala Leu Tyr Gln Pro Ser Ser Gly Cys Tyr Ile His Phe Phe Arg Glu
                405                 410                 415

Pro Thr Asp Leu Lys Gln Phe Lys Gln Asp Ala Lys Tyr Ser His Gly
            420                 425                 430

Ile Asp Val Thr Asp Leu Phe Ala Thr Gln Pro Gly Leu Thr Ser Ala
        435                 440                 445

Val Ile Asp Ala Leu Pro Arg Asn Met Val Ile Thr Cys Gln Gly Ser
```

```
    450                 455                 460

Asp Asp Ile Arg Lys Leu Leu Glu Ser Gln Gly Arg Lys Asp Ile Lys
465                 470                 475                 480

Leu Ile Asp Ile Ala Leu Ser Lys Thr Asp Ser Arg Lys Tyr Glu Asn
                485                 490                 495

Ala Val Trp Asp Gln Tyr Lys Asp Leu Cys His Met His Thr Gly Val
            500                 505                 510

Val Val Glu Lys Lys Lys Arg Gly Gly Lys Glu Glu Ile Thr Pro His
        515                 520                 525

Cys Ala Leu Met Asp Cys Ile Met Phe Asp Ala Ala Val Ser Gly Gly
    530                 535                 540

Leu Asn Thr Ser Val Leu Arg Ala Val Leu Pro Arg Asp Met Val Phe
545                 550                 555                 560

Arg Thr Ser Thr Pro Arg Val Val Leu
                565


<210> SEQ ID NO 4
<211> LENGTH: 1710
<212> TYPE: DNA
<213> ORGANISM: Artificial Sequence
<220> FEATURE:
<223> OTHER INFORMATION: Codon-optimized cDNA NP

<400> SEQUENCE: 4

atgagtgcca gcaaagaaat caagagcttc ctgtggaccc agagtctgcg gagggaactg     60

agcggatact gtagcaacat caaactgcag gtggtcaagg acgctcaggc actgctgcat    120

gggctggact tctccgaggt gtctaatgtg cagcggctga tgcggaaaga acggagggac    180

gataatgacc tgaagcgact gcgcgacctg aaccaggcag tgaacaatct ggtcgagctg    240

aagagcaccc agcagaaatc aatcctgcgg gtcgggacac tgacatctga cgacctgctg    300

atcctggctg cagacctgga gaagctgaaa tcgaaagtga tccgcaccga aaggccactg    360

tccgccgggg tctacatggg caatctgtct tcccagcagc tggaccagag gcgggctctg    420

ctgaacatga ttgggatgtc cggaggaaat cagggagcta gagccgggag ggacggagtc    480

gtgcgggtct gggacgtgaa gaatgccgaa ctgctgaaca accagttcgg gaccatgcca    540

agtctgacac tggcatgcct gactaaacag ggccaggtgg atctgaatga tgcagtccag    600

gctctgaccg acctgggcct gatctacacc gccaagtacc ccaatactag cgacctggat    660

agactgaccc agagccaccc catcctgaac atgatcgaca ctaagaagtc ctcactgaac    720

atcagtggct ataatttctc cctgggggca gcagtcaagg ctggcgcatg catgctggac    780

ggcgggaata tgctggaaac catcaaagtg tctccccaga ccatggatgg catcctgaaa    840

tctattctga aagtcaagaa ggccctggga atgtttattt cagacacccc cggcgagagg    900

aatccatatg agaacattct gtataagatt tgcctgagtg gcgacgggtg gccatacatt    960

gcaagccgga catcaattac cggaagagct tgggagaata cagtcgtgga cctggaaagc   1020

gacggcaagc cccagaaggc cgactcaaac aactcctcaa agagtctgca gtcagctggc   1080

ttcacagcag ggctgactta ctcccagctg atgacactga aggacgcaat gctgcagctg   1140

gacccaaacg ctaagacatg gatggacatc gagggacggc cagaagatcc agtggaaatc   1200

gcactgtatc agccatcatc cggatgctat atccatttct tccgggaacc aactgatctg   1260

aagcagttca agcaggatgc aaagtactcc cacggaatcg atgtcaccga tctgttcgca   1320

acccagccag gactgacatc agccgtcatc gatgccctgc ctaggaacat ggtcattact   1380
```

```
tgccagggct ccgacgatat taggaagctg ctggagagcc agggacggaa ggatatcaaa   1440

ctgatcgata ttgccctgtc taagactgat agccggaaat atgagaatgc agtctgggat   1500

cagtacaagg acctgtgcca tatgcatacc ggagtggtcg tcgagaagaa gaagaggggc   1560

ggaaaggaag agatcacacc ccactgtgcc ctgatggatt gcatcatgtt cgacgcagcc   1620

gtgtccgggg gcctgaacac ctcagtcctg agggctgtcc tgccaagaga tatggtgttt   1680

agaacttcaa ccccaagagt cgtcctgtaa                                    1710


<210> SEQ ID NO 5
<211> LENGTH: 569
<212> TYPE: PRT
<213> ORGANISM: Artificial Sequence
<220> FEATURE:
<223> OTHER INFORMATION: mutated Protein NP

<400> SEQUENCE: 5

Met Ser Ala Ser Lys Glu Ile Lys Ser Phe Leu Trp Thr Gln Ser Leu
1               5                   10                  15

Arg Arg Glu Leu Ser Gly Tyr Cys Ser Asn Ile Lys Leu Gln Val Val
            20                  25                  30

Lys Asp Ala Gln Ala Leu Leu His Gly Leu Asp Phe Ser Glu Val Ser
        35                  40                  45

Asn Val Gln Arg Leu Met Arg Lys Glu Arg Arg Asp Asp Asn Asp Leu
    50                  55                  60

Lys Arg Leu Arg Asp Leu Asn Gln Ala Val Asn Asn Leu Val Glu Leu
65                  70                  75                  80

Lys Ser Thr Gln Gln Lys Ser Ile Leu Arg Val Gly Thr Leu Thr Ser
                85                  90                  95

Asp Asp Leu Leu Ile Leu Ala Ala Asp Leu Glu Lys Leu Lys Ser Lys
            100                 105                 110

Val Ile Arg Thr Glu Arg Pro Leu Ser Ala Gly Val Tyr Met Gly Asn
        115                 120                 125

Leu Ser Ser Gln Gln Leu Asp Gln Arg Arg Ala Leu Leu Asn Met Ile
    130                 135                 140

Gly Met Ser Gly Gly Asn Gln Gly Ala Arg Ala Gly Arg Asp Gly Val
145                 150                 155                 160

Val Arg Val Trp Asp Val Lys Asn Ala Glu Leu Leu Asn Asn Gln Phe
                165                 170                 175

Gly Thr Met Pro Ser Leu Thr Leu Ala Cys Leu Thr Lys Gln Gly Gln
            180                 185                 190

Val Asp Leu Asn Asp Ala Val Gln Ala Leu Thr Asp Leu Gly Leu Ile
        195                 200                 205

Tyr Thr Ala Lys Tyr Pro Asn Thr Ser Asp Leu Asp Arg Leu Thr Gln
    210                 215                 220

Ser His Pro Ile Leu Asn Met Ile Asp Thr Lys Lys Ser Ser Leu Asn
225                 230                 235                 240

Ile Ser Gly Tyr Asn Phe Ser Leu Gly Ala Ala Val Lys Ala Gly Ala
                245                 250                 255

Cys Met Leu Asp Gly Gly Asn Met Leu Glu Thr Ile Lys Val Ser Pro
            260                 265                 270

Gln Thr Met Asp Gly Ile Leu Lys Ser Ile Leu Lys Val Lys Lys Ala
        275                 280                 285

Leu Gly Met Phe Ile Ser Asp Thr Pro Gly Glu Arg Asn Pro Tyr Glu
    290                 295                 300
```

```
Asn Ile Leu Tyr Lys Ile Cys Leu Ser Gly Asp Gly Trp Pro Tyr Ile
305                 310                 315                 320

Ala Ser Arg Thr Ser Ile Thr Gly Arg Ala Trp Glu Asn Thr Val Val
                325                 330                 335

Asp Leu Glu Ser Asp Gly Lys Pro Gln Lys Ala Asp Ser Asn Asn Ser
            340                 345                 350

Ser Lys Ser Leu Gln Ser Ala Gly Phe Thr Ala Gly Leu Thr Tyr Ser
        355                 360                 365

Gln Leu Met Thr Leu Lys Asp Ala Met Leu Gln Leu Asp Pro Asn Ala
    370                 375                 380

Lys Thr Trp Met Ala Ile Glu Ala Arg Pro Glu Asp Pro Val Glu Ile
385                 390                 395                 400

Ala Leu Tyr Gln Pro Ser Ser Gly Cys Tyr Ile His Phe Phe Arg Glu
                405                 410                 415

Pro Thr Asp Leu Lys Gln Phe Lys Gln Asp Ala Lys Tyr Ser His Gly
            420                 425                 430

Ile Asp Val Thr Asp Leu Phe Ala Thr Gln Pro Gly Leu Thr Ser Ala
        435                 440                 445

Val Ile Asp Ala Leu Pro Arg Asn Met Val Ile Thr Cys Gln Gly Ser
    450                 455                 460

Asp Asp Ile Arg Lys Leu Leu Glu Ser Gln Gly Arg Lys Asp Ile Lys
465                 470                 475                 480

Leu Ile Asp Ile Ala Leu Ser Lys Thr Asp Ser Arg Lys Tyr Glu Asn
                485                 490                 495

Ala Val Trp Asp Gln Tyr Lys Asp Leu Cys His Met His Thr Gly Val
            500                 505                 510

Val Val Glu Lys Lys Lys Arg Gly Gly Lys Glu Glu Ile Thr Pro His
        515                 520                 525

Cys Ala Leu Met Asp Cys Ile Met Phe Asp Ala Ala Val Ser Gly Gly
    530                 535                 540

Leu Asn Thr Ser Val Leu Arg Ala Val Leu Pro Arg Asp Met Val Phe
545                 550                 555                 560

Arg Thr Ser Thr Pro Arg Val Val Leu
                565
```

<210> SEQ ID NO 6
<211> LENGTH: 1710
<212> TYPE: DNA
<213> ORGANISM: Artificial Sequence
<220> FEATURE:
<223> OTHER INFORMATION: Codon-optimized cDNA mutated NP

<400> SEQUENCE: 6

```
atgagtgcca gcaaagaaat caagagcttc ctgtggaccc agagtctgcg gagggaactg     60

agcggatact gtagcaacat caaactgcag gtggtcaagg acgctcaggc actgctgcat    120

gggctggact tctccgaggt gtctaatgtg cagcggctga tgcggaaaga acggagggac    180

gataatgacc tgaagcgact gcgcgacctg aaccaggcag tgaacaatct ggtcgagctg    240

aagagcaccc agcagaaatc aatcctgcgg gtcgggacac tgacatctga cgacctgctg    300

atcctggctg cagacctgga gaagctgaaa tcgaaagtga tccgcaccga aaggccactg    360

tccgccgggg tctacatggg caatctgtct tcccagcagc tggaccagag gcgggctctg    420

ctgaacatga ttgggatgtc cggaggaaat cagggagcta gagccgggag ggacggagtc    480

gtgcgggtct gggacgtgaa gaatgccgaa ctgctgaaca accagttcgg gaccatgcca    540
```

```
agtctgacac tggcatgcct gactaaacag ggccaggtgg atctgaatga tgcagtccag    600
gctctgaccg acctgggcct gatctacacc gccaagtacc ccaatactag cgacctggat    660
agactgaccc agagccaccc catcctgaac atgatcgaca ctaagaagtc ctcactgaac    720
atcagtggct ataatttctc cctgggggca gcagtcaagg ctggcgcatg catgctggac    780
ggcgggaata tgctggaaac catcaaagtg tctccccaga ccatggatgg catcctgaaa    840
tctattctga aagtcaagaa ggccctggga atgtttattt cagacacccc cggcgagagg    900
aatccatatg agaacattct gtataagatt tgcctgagtg gcgacgggtg gccatacatt    960
gcaagccgga catcaattac cggaagagct tgggagaata cagtcgtgga cctggaaagc   1020
gacggcaagc cccagaaggc cgactcaaac aactcctcaa agagtctgca gtcagctggc   1080
ttcacagcag ggctgactta ctcccagctg atgacactga aggacgcaat gctgcagctg   1140
gacccaaacg ctaagacatg gatggccatc gaggcccggc cagaagatcc agtggaaatc   1200
gcactgtatc agccatcatc cggatgctat atccatttct tccgggaacc aactgatctg   1260
aagcagttca agcaggatgc aaagtactcc cacggaatcg atgtcaccga tctgttcgca   1320
acccagccag gactgacatc agccgtcatc gatgccctgc ctaggaacat ggtcattact   1380
tgccagggct ccgacgatat taggaagctg ctggagagcc agggacggaa ggatatcaaa   1440
ctgatcgata ttgccctgtc taagactgat agccggaaat atgagaatgc agtctgggat   1500
cagtacaagg acctgtgcca tatgcatacc ggagtggtcg tcgagaagaa gaagaggggc   1560
ggaaaggaag agatcacacc ccactgtgcc ctgatggatt gcatcatgtt cgacgcagcc   1620
gtgtccgggg gcctgaacac ctcagtcctg agggctgtcc tgccaagaga tatggtgttt   1680
agaacttcaa ccccaagagt cgtcctgtaa                                    1710
```

<210> SEQ ID NO 7
<211> LENGTH: 99
<212> TYPE: PRT
<213> ORGANISM: Artificial Sequence
<220> FEATURE:
<223> OTHER INFORMATION: Protein Z

<400> SEQUENCE: 7

```
Met Gly Asn Lys Gln Ala Lys Ala Pro Glu Ser Lys Asp Ser Pro Arg
1               5                   10                  15

Ala Ser Leu Ile Pro Asp Ala Thr His Leu Gly Pro Gln Phe Cys Lys
            20                  25                  30

Ser Cys Trp Phe Glu Asn Lys Gly Leu Val Glu Cys Asn Asn His Tyr
        35                  40                  45

Leu Cys Leu Asn Cys Leu Thr Leu Leu Leu Ser Val Ser Asn Arg Cys
    50                  55                  60

Pro Ile Cys Lys Met Pro Leu Pro Thr Lys Leu Arg Pro Ser Ala Ala
65                  70                  75                  80

Pro Thr Ala Pro Pro Thr Gly Ala Ala Asp Ser Ile Arg Pro Pro Pro
                85                  90                  95

Tyr Ser Pro
```

<210> SEQ ID NO 8
<211> LENGTH: 300
<212> TYPE: DNA
<213> ORGANISM: Artificial Sequence
<220> FEATURE:
<223> OTHER INFORMATION: Codon-optimized cDNA Z

<400> SEQUENCE: 8

```
atgggcaata agcaggcaaa ggcacccgaa agcaaggatt cacctagagc atcactgatt     60

cccgacgcaa ctcatctggg gccacagttc tgcaaatcct gttggttcga gaacaaaggc    120

ctggtggagt gcaataacca ctacctgtgc ctgaactgtc tgacactgct gctgagtgtg    180

agcaacagat gcccaatctg caagatgcct ctgccaacaa agctgaggcc ttctgctgca    240

cccaccgcac caccaactgg agccgcagac agcattagac cccccccata ctcaccataa    300


<210> SEQ ID NO 9
<211> LENGTH: 20551
<212> TYPE: DNA
<213> ORGANISM: Artificial Sequence
<220> FEATURE:
<223> OTHER INFORMATION: Plasmide MeV-GPC

<400> SEQUENCE: 9

gcggccgcta atacgactca ctatagggcc aactttgttt ggtctgatga gtccgtgagg     60

acgaaacccg gagtcccggg tcaccaaaca aagttgggta aggatagttc aatcaatgat    120

catcttctag tgcacttagg attcaagatc ctattatcag ggacaagagc aggattaggg    180

atatccgaga tggccacact tttaaggagc ttagcattgt tcaaaagaaa caaggacaaa    240

ccacccatta catcaggatc cggtggagcc atcagaggaa tcaaacacat tattatagta    300

ccaatccctg gagattcctc aattaccact cgatccagac ttctggaccg gttggtgagg    360

ttaattggaa acccggatgt gagcgggccc aaactaacag gggcactaat aggtatatta    420

tccttatttg tggagtctcc aggtcaattg attcagagga tcaccgatga ccctgacgtt    480

agcataaggc tgttagaggt tgtccagagt gaccagtcac aatctggcct taccttcgca    540

tcaagaggta ccaacatgga ggatgaggcg gaccaatact tttcacatga tgatccaatt    600

agtagtgatc aatccaggtt cggatggttc gggaacaagg aaatctcaga tattgaagtg    660

caagaccctg agggattcaa catgattctg ggtaccatcc tagcccaaat ttgggtcttg    720

ctcgcaaagg cggttacggc cccagacacg gcagctgatt cggagctaag aaggtggata    780

aagtacaccc aacaaagaag ggtagttggt gaatttagat tggagagaaa atggttggat    840

gtggtgagga acaggattgc cgaggacctc tccttacgcc gattcatggt cgctctaatc    900

ctggatatca agagaacacc cggaaacaaa cccaggattg ctgaaatgat atgtgacatt    960

gatacatata tcgtagaggc aggattagcc agttttatcc tgactattaa gtttgggata   1020

gaaactatgt atcctgctct tggactgcat gaatttgctg gtgagttatc cacacttgag   1080

tccttgatga acctttacca gcaaatgggg gaaactgcac cctacatggt aatcctggag   1140

aactcaattc agaacaagtt cagtgcagga tcataccctc tgctctggag ctatgccatg   1200

ggagtaggag tggaacttga aaactccatg ggaggtttga actttggccg atcttacttt   1260

gatccagcat attttagatt agggcaagag atggtaagga ggtcagctgg aaaggtcagt   1320

tccacattgg catctgaact cggtatcact gccgaggatg caaggcttgt ttcagagatt   1380

gcaatgcata ctactgagga caagatcagt agagcggttg gacccagaca agcccaagta   1440

tcatttctac acggtgatca aagtgagaat gagctaccga gattgggggg caaggaagat   1500

aggagggtca aacagagtcg aggagaagcc agggagagct acagagaaac cgggcccagc   1560

agagcaagtg atgcgagagc tgcccatctt ccaaccggca cacccctaga cattgacact   1620

gcaacggagt ccagccaaga tccgcaggac agtcgaaggt cagctgacgc cctgcttagg   1680

ctgcaagcca tggcaggaat ctcggaagaa caaggctcag acacggacac ccctatagtg   1740
```

```
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatgggccag   3540
attgtcacat tctttcagga agtgccacac gtcattgagg aggtcatgaa catcgtgctg   3600
attgctctgt cagtgctggc agtgctgaaa ggactgtaca acttcgctac ctgtggactg   3660
gtgggactgg tcacattcct gctgctgtgc ggcagaagtt gcactacctc actgtacaaa   3720
ggagtgtacg agctgcagac tctggaactg aacatggaga cactgaatat gacaatgcct   3780
ctgagctgca ccaagaataa tagccaccac tatatcatgg tcgggaacga aaccggcctg   3840
gaactgaccc tgacaaacac cagcatcatt aaccacaagt tctgcaatct gagcgacgct   3900
cacaagaaga acctgtatga ccacgctctg atgtccatca tcagtacctt tcacctgtcc   3960
atccccaatt tcaaccagta cgaggcaatg tcatgcgact tcaacggggg caagatcagt   4020
gtccagtaca acctgagcca ctcctacgcc ggcgacgcag ccaaccactg cggaactgtc   4080
gccaatggcg tgctgcagac attcatgagg atggcatggg ggggatctta catcgcactg   4140
```

```
gatagcggca ggggcaattg ggattgcatc atgacttcct atcagtatct gattatccag   4200
aatactacat gggaggatca ttgccagttc agtcggccca gccctattgg atatctgggg   4260
ctgctgtcac agagaacacg ggatatctat atttcaagac gcctgctggg cacattcact   4320
tggacactgt cagacagtga gggcaaggat actccagggg gctactgcct gacacgatgg   4380
atgctgatcg aagcagagct gaaatgcttc ggcaataccg cagtggccaa gtgcaacgag   4440
aaacacgacg aggagttctg cgacatgctg aggctgttcg acttcaacaa acaggctatc   4500
cagagactga aggcagaagc ccagatgtca atccagctga tcaacaaggc agtgaacgcc   4560
ctgatcaacg accagctgat catgaagaac cacctgagag acattatggg catcccctac   4620
tgtaattaca gcaagtattg gtacctgaac cacactacaa ccgggagaac atccctgccc   4680
aagtgctggc tggtcagcaa tgggagttat ctgaatgaaa cccatttcag cgacgatatc   4740
gaacagcagg ctgacaacat gatcacagag atgctgcaga aagagtacat ggaaagacag   4800
ggcaagacac cactgggact ggtcgatctg ttcgtcttct ccactagctt ctatctgatt   4860
tccatcttcc tgcacctggt gaagatcccc actcataggc acattgtcgg caagagttgc   4920
cctaaacccc ataggctgaa tcacatgggg atttgtagtt gcggcctgta taagcagcct   4980
ggcgtgcctg tgaaatggaa gagatgagcg cgcagcgctt agacgtctcg cgatcgatac   5040
tagtacaacc taaatccatt ataaaaaact taggagcaaa gtgattgcct cccaaggtcc   5100
acaatgacag agacctacga cttcgacaag tcggcatggg acatcaaagg gtcgatcgct   5160
ccgatacaac ccaccaccta cagtgatggc aggctggtgc cccaggtcag agtcatagat   5220
cctggtctag gcgacaggaa ggatgaatgc tttatgtaca tgtttctgct gggggttgtt   5280
gaggacagcg attccctagg gcctccaatc gggcgagcat ttgggttcct gcccttaggt   5340
gttggcagat ccacagcaaa gcccgaaaaa ctcctcaaag aggccactga gcttgacata   5400
gttgttagac gtacagcagg gctcaatgaa aaactggtgt tctacaacaa caccccacta   5460
actctcctca caccttggag aaaggtccta acaacaggga gtgtcttcaa cgcaaaccaa   5520
gtgtgcaatg cggttaatct gataccgctc gataccccgc agaggttccg tgttgtttat   5580
atgagcatca cccgtctttc ggataacggg tattacaccg ttcctagaag aatgctggaa   5640
ttcagatcgg tcaatgcagt ggccttcaac ctgctggtga cccttaggat tgacaaggcg   5700
ataggccctg ggaagatcat cgacaataca gagcaacttc ctgaggcaac atttatggtc   5760
cacatcggga acttcaggag aaagaagagt gaagtctact ctgccgatta ttgcaaaatg   5820
aaaatcgaaa agatgggcct ggtttttgca cttggtggga tagggggcac cagtcttcac   5880
attagaagca caggcaaaat gagcaagact ctccatgcac aactcgggtt caagaagacc   5940
ttatgttacc cgctgatgga tatcaatgaa gaccttaatc gattactctg gaggagcaga   6000
tgcaagatag taagaatcca ggcagttttg cagccatcag ttcctcaaga attccgcatt   6060
tacgacgacg tgatcataaa tgatgaccaa ggactattca aagttctgta gaccgtagtg   6120
cccagcaatg cccgaaaacg acccccctca caatgacagc cagaaggccc ggacaaaaaa   6180
gcccccctccg aaagactcca cggaccaagc gagaggccag ccagcagccg acggcaagcg   6240
cgaacaccag gcggccccag cacagaacag ccctgacaca aggccaccac cagccacccc   6300
aatctgcatc ctcctcgtgg gacccccgag gaccaacccc caaggctgcc cccgatccaa   6360
accaccaacc gcatccccac cacccccggg aaagaaaccc ccagcaattg gaaggcccct   6420
ccccctcttc ctcaacacaa gaactccaca accgaaccgc acaagcgacc gaggtgaccc   6480
```

-continued

```
aaccgcaggc atccgactcc ctagacagat cctctctccc cggcaaacta aacaaaactt   6540
agggccaagg aacatacaca cccaacagaa cccagacccc ggcccacggc gccgcgcccc   6600
caacccccga caaccagagg gagcccccaa ccaatcccgc cggctccccc ggtgccccaca   6660
ggcagggaca ccaacccccg aacagaccca gcacccaacc atcgacaatc caagacgggg   6720
gggccccccc aaaaaaaggc ccccaggggc cgacagccag caccgcgagg aagcccaccc   6780
accccacaca cgaccacggc aaccaaacca gaacccagac caccctgggc caccagctcc   6840
cagactcggc catcaccccg cagaaaggaa aggccacaac ccgcgcaccc cagccccgat   6900
ccggcgggga gccacccaac ccgaaccagc acccaagagc gatccccgaa ggacccccga   6960
accgcaaagg acatcagtat cccacagcct ctccaagtcc cccggtctcc tcctcttctc   7020
gaagggacca aaagatcaat ccaccacacc cgacgacact caactcccca cccctaaagg   7080
agacaccggg aatcccagaa tcaagactca tccaatgtcc atcatgggtc tcaaggtgaa   7140
cgtctctgcc atattcatgg cagtactgtt aactctccaa acacccaccg gtcaaatcca   7200
ttggggcaat ctctctaaga taggggtggt aggaatagga agtgcaagct acaaagttat   7260
gactcgttcc agccatcaat cattagtcat aaaattaatg cccaatataa ctctcctcaa   7320
taactgcacg agggtagaga ttgcagaata caggagacta ctgagaacag ttttggaacc   7380
aattagagat gcacttaatg caatgaccca gaatataaga ccggttcaga gtgtagcttc   7440
aagtaggaga cacaagagat ttgcgggagt agtcctggca ggtgcggccc taggcgttgc   7500
cacagctgct cagataacag ccggcattgc acttcaccag tccatgctga actctcaagc   7560
catcgacaat ctgagagcga gcctggaaac tactaatcag gcaattgaga caatcagaca   7620
agcagggcag gagatgatat tggctgttca gggtgtccaa gactacatca ataatgagct   7680
gataccgtct atgaaccaac tatcttgtga tttaatcggc cagaagctcg ggctcaaatt   7740
gctcagatac tatacagaaa tcctgtcatt atttggcccc agtttacggg accccatatc   7800
tgcggagata tctatccagg ctttgagcta tgcgcttgga ggagacatca ataaggtgtt   7860
agaaaagctc ggatacagtg gaggtgattt actgggcatc ttagagagcg gaggaataaa   7920
ggcccggata actcacgtcg acacagagtc ctacttcatt gtcctcagta tagcctatcc   7980
gacgctgtcc gagattaagg gggtgattgt ccaccggcta gagggggtct cgtacaacat   8040
aggctctcaa gagtggtata ccactgtgcc caagtatgtt gcaacccaag ggtaccttat   8100
ctcgaatttt gatgagtcat cgtgtacttt catgccagag gggactgtgt gcagccaaaa   8160
tgccttgtac ccgatgagtc ctctgctcca agaatgcctc cgggggtaca ccaagtcctg   8220
tgctcgtaca ctcgtatccg ggtcttttgg gaaccggttc attttatcac aagggaacct   8280
aatagccaat tgtgcatcaa tcctttgcaa gtgttacaca acaggaacga tcattaatca   8340
agaccctgac aagatcctaa catacattgc tgccgatcac tgcccggtag tcgaggtgaa   8400
cggcgtgacc atccaagtcg ggagcaggag gtatccagac gctgtgtact tgcacagaat   8460
tgacctcggt cctcccatat cattggagag gttggacgta gggacaaatc tggggaatgc   8520
aattgctaag ttggaggatg ccaaggaatt gttggagtca tcggaccaga tattgaggag   8580
tatgaaaggt ttatcgagca ctagcatagt ctacatcctg attgcagtgt gtcttggagg   8640
gttgataggg atccccgctt taatatgttg ctgcaggggg cgttgtaaca aaaagggaga   8700
acaagttggt atgtcaagac caggcctaaa gcctgatctt acgggaacat caaaatccta   8760
tgtaaggtcg ctctgatcct ctacaactct tgaaacacaa atgtcccaca agtctcctct   8820
tcgtcatcaa gcaaccaccg cacccagcat caagcccacc tgaaattatc tccggcttcc   8880
```

```
ctctggccga acaatatcgg tagttaatca aaacttaggg tgcaagatca tccacaatgt   8940
caccacaacg agaccggata aatgccttct acaaagataa cccccatccc aagggaagta   9000
ggatagtcat taacagagaa catcttatga ttgatagacc ttatgttttg ctggctgttc   9060
tgtttgtcat gtttctgagc ttgatcgggt tgctagccat tgcaggcatt agacttcatc   9120
gggcagccat ctacaccgca gagatccata aaagcctcag caccaatcta gatgtaacta   9180
actcaatcga gcatcaggtc aaggacgtgc tgacaccact cttcaaaatc atcggtgatg   9240
aagtgggcct gaggacacct cagagattca ctgacctagt gaaattaatc tctgacaaga   9300
ttaaattcct taatccggat agggagtacg acttcagaga tctcacttgg tgtatcaacc   9360
cgccagagag aatcaaattg gattatgatc aatactgtgc agatgtggct gctgaagagc   9420
tcatgaatgc attggtgaac tcaactctac tggagaccag aacaaccaat cagttcctag   9480
ctgtctcaaa gggaaactgc tcagggccca ctacaatcag aggtcaattc tcaaacatgt   9540
cgctgtccct gttagacttg tatttaggtc gaggttacaa tgtgtcatct atagtcacta   9600
tgacatccca gggaatgtat gggggaactt acctagtgga aaagcctaat ctgagcagca   9660
aaaggtcaga gttgtcacaa ctgagcatgt accgagtgtt tgaagtaggt gttatcagaa   9720
atccgggttt gggggctccg gtgttccata tgacaaacta tcttgagcaa ccagtcagta   9780
atgatctcag caactgtatg gtggctttgg gggagctcaa actcgcagcc ctttgtcacg   9840
gggaagattc tatcacaatt ccctatcagg gatcagggaa aggtgtcagc ttccagctcg   9900
tcaagctagg tgtctggaaa tccccaaccg acatgcaatc ctgggtcccc ttatcaacgg   9960
atgatccagt gatagacagg ctttacctct catctcacag aggtgttatc gctgacaatc  10020
aagcaaaatg ggctgtcccg acaacacgaa cagatgacaa gttgcgaatg gagacatgct  10080
tccaacaggc gtgtaagggt aaaatccaag cactctgcga gaatcccgag tgggcaccat  10140
tgaaggataa caggattcct tcatacgggg tcttgtctgt tgatctgagt ctgacagttg  10200
agcttaaaat caaaattgct tcgggattcg ggccattgat cacacacggt tcagggatgg  10260
acctatacaa atccaaccac aacaatgtgt attggctgac tatcccgcca atgaagaacc  10320
tagccttagg tgtaatcaac acattggagt ggataccgag attcaaggtt agtccctacc  10380
tcttcactgt cccaattaag gaagcaggcg aagactgcca tgccccaaca tacctacctg  10440
cggaggtgga tggtgatgtc aaactcagtt ccaatctggt gattctacct ggtcaagatc  10500
tccaatatgt tttggcaacc tacgatactt ccagggttga acatgctgtg gtttattacg  10560
tttacagccc aagccgctca ttttcttact tttatccttt taggttgcct ataaaggggg  10620
tccccatcga attacaagtg gaatgcttca catgggacca aaaactctgg tgccgtcact  10680
tctgtgtgct tgcggactca gaatctggtg gacatatcac tcactctggg atggtgggca  10740
tgggagtcag ctgcacagtc acccgggaag atggaaccaa tcgcagatag ggctgctagt  10800
gaaccaatca catgatgtca cccagacatc aggcataccc actagtgtga aatagacatc  10860
agaattaaga aaaacgtagg gtccaagtgg ttccccgtta tggactcgct atctgtcaac  10920
cagatcttat accctgaagt tcacctagat agcccgatag ttaccaataa gatagtagcc  10980
atcctggagt atgctcgagt ccctcacgct tacagcctgg aggaccctac actgtgtcag  11040
aacatcaagc accgcctaaa aaacggattt tccaaccaaa tgattataaa caatgtggaa  11100
gttgggaatg tcatcaagtc caagcttagg agttatccgg cccactctca tattccatat  11160
ccaaattgta atcaggattt atttaacata gaagacaaag agtcaacgag gaagatccgt  11220
```

gaactcctca aaaaggggaa ttcgctgtac tccaaagtca gtgataaggt tttccaatgc 11280
ttaagggaca ctaactcacg gcttggccta ggctccgaat tgagggagga catcaaggag 11340
aaagttatta acttgggagt ttacatgcac agctcccagt ggtttgagcc ctttctgttt 11400
tggtttacag tcaagactga gatgaggtca gtgattaaat cacaaaccca tacttgccat 11460
aggaggagac acacacctgt attcttcact ggtagttcag ttgagttgct aatctctcgt 11520
gaccttgttg ctataatcag taaagagtct caacatgtat attacctgac atttgaactg 11580
gttttgatgt attgtgatgt catagagggg aggttaatga cagagaccgc tatgactatt 11640
gatgctaggt atacagagct tctaggaaga gtcagataca tgtggaaact gatagatggt 11700
ttcttccctg cactcgggaa tccaacttat caaattgtag ccatgctgga gcctctttca 11760
cttgcttacc tgcagctgag ggatataaca gtagaactca gaggtgcttt ccttaaccac 11820
tgctttactg aaatacatga tgttcttgac caaaacgggt ttctgatga aggtacttat 11880 catgagttaa ctgaagctct agattacatt ttcataactg atgacataca tctgacaggg 11940
gagattttct catttttcag aagtttcggc caccccagac ttgaagcagt aacggctgct 12000
gaaaatgtta ggaaatacat gaatcagcct aaagtcattg tgtatgagac tctgatgaaa 12060
ggtcatgcca tattttgtgg aatcataatc aacggctatc gtgacaggca cggaggcagt 12120
tggccaccgc tgaccctccc cctgcatgct gcagacacaa tccggaatgc tcaagcttca 12180
ggtgaagggt taacacatga gcagtgcgtt gataactgga aatcttttgc tggagtgaaa 12240
tttggctgct ttatgcctct tagcctggat agtgatctga caatgtacct aaaggacaag 12300
gcacttgctg ctctccaaag ggaatgggat tcagtttacc cgaaagagtt cctgcgttac 12360
gaccctccca agggaaccgg gtcacggagg cttgtagatg ttttccttaa tgattcgagc 12420
tttgacccat atgatgtgat aatgtatgtt gtaagtggag cttacctcca tgaccctgag 12480
ttcaacctgt cttacagcct gaaagaaaag gagatcaagg aaacaggtag actttttgct 12540
aaaatgactt acaaaatgag ggcatgccaa gtgattgctg aaaatctaat ctcaaacggg 12600
attggcaaat attttaagga caatgggatg gccaaggatg agcacgattt gactaaggca 12660
ctccacactc tagctgtctc aggagtcccc aaagatctca aagaaagtca caggggggggg 12720 ccagtcttaa aaacctactc ccgaagccca gtccacacaa gtaccaggaa cgtgagagca 12780
gcaaaagggt ttatagggtt ccctcaagta attcggcagg accaagacac tgatcatccg 12840
gagaatatgg aagcttacga gacagtcagt gcatttatca cgactgatct caagaagtac 12900
tgccttaatt ggagatatga gaccatcagc ttgtttgcac agaggctaaa tgagatttac 12960
ggattgccct catttttcca gtggctgcat aagaggcttg agacctctgt cctgtatgta 13020
agtgaccctc attgcccccc cgaccttgac gcccatatcc cgttatataa agtccccaat 13080
gatcaaatct tcattaagta ccctatggga ggtatagaag ggtattgtca gaagctgtgg 13140
accatcagca ccattcccta tctatacctg gctgcttatg agagcggagt aaggattgct 13200
tcgttagtgc aaggggacaa tcagaccata gccgtaacaa aaagggtacc cagcacatgg 13260
ccctacaacc ttaagaaacg ggaagctgct agagtaacta gagattactt tgtaattctt 13320
aggcaaaggc tacatgatat tggccatcac ctcaaggcaa atgagacaat tgtttcatca 13380 cattttttttg tctattcaaa aggaatatat tatgatgggc tacttgtgtc ccaatcactc 13440
aagagcatcg caagatgtgt attctggtca gagactatag ttgatgaaac aagggcagca 13500
tgcagtaata ttgctacaac aatggctaaa agcatcgaga gaggttatga ccgttacctt 13560
gcatattccc tgaacgtcct aaaagtgata cagcaaattc tgatctctct tggcttcaca 13620

```
atcaattcaa ccatgacccg ggatgtagtc ataccccctcc tcacaaacaa cgacctctta  13680
ataaggatgg cactgttgcc cgctcctatt ggggggatga attatctgaa tatgagcagg  13740
ctgtttgtca gaaacatcgg tgatccagta acatcatcaa ttgctgatct caagagaatg  13800
attctcgcct cactaatgcc tgaagagacc ctccatcaag taatgacaca acaaccgggg  13860
gactcttcat tcctagactg ggctagcgac ccttactcag caaatcttgt atgtgtccag  13920
agcatcacta gactcctcaa gaacataact gcaaggtttg tcctgatcca tagtccaaac  13980
ccaatgttaa aaggattatt ccatgatgac agtaaagaag aggacgaggg actggcggca  14040
ttcctcatgg acaggcatat tatagtacct agggcagctc atgaaatcct ggatcatagt  14100
gtcacagggg caagagagtc tattgcaggc atgctggata ccacaaaagg cttgattcga  14160
gccagcatga ggaagggggg gttaacctct cgagtgataa ccagattgtc caattatgac  14220
tatgaacaat tcagagcagg gatggtgcta ttgacaggaa gaaagagaaa tgtcctcatt  14280
gacaaagagt catgttcagt gcagctggcg agagctctaa gaagccatat gtgggcgagg  14340
ctagctcgag gacggcctat ttacggcctt gaggtccctg atgtactaga atctatgcga  14400
ggccacctta ttcggcgtca tgagacatgt gtcatctgcg agtgtggatc agtcaactac  14460
ggatggtttt ttgtcccctc gggttgccaa ctggatgata ttgacaagga aacatcatcc  14520
ttgagagtcc catatattgg ttctaccact gatgagagaa cagacatgaa gcttgccttc  14580
gtaagagccc caagtcgatc cttgcgatct gctgttagaa tagcaacagt gtactcatgg  14640
gcttacggtg atgatgatag ctcttggaac gaagcctggt tgttggctag gcaaagggcc  14700
aatgtgagcc tggaggagct aagggtgatc actcccatct caacttcgac taatttagcg  14760
cataggttga gggatcgtag cactcaagtg aaatactcag gtacatccct tgtccgagtg  14820
gcgaggtata ccacaatctc caacgacaat ctctcatttg tcatatcaga taagaaggtt  14880
gatactaact ttatatacca acaaggaatg cttctagggt tgggtgtttt agaaacattg  14940
tttcgactcg agaaagatac cggatcatct aacacggtat tacatcttca cgtcgaaaca  15000
gattgttgcg tgatcccgat gatagatcat cccaggatac ccagctcccg caagctagag  15060
ctgagggcag agctatgtac caacccattg atatatgata atgcaccttt aattgacaga  15120
gatgcaacaa ggctatacac ccagagccat aggaggcacc ttgtggaatt tgttacatgg  15180
tccacacccc aactatatca cattttagct aagtccacag cactatctat gattgacctg  15240
gtaacaaaat ttgagaagga ccatatgaat gaaatttcag ctctcatagg ggatgacgat  15300
atcaatagtt tcataactga gtttctgctc atagagccaa gattattcac tatctacttg  15360
ggccagtgtg cggccatcaa ttgggcattt gatgtacatt atcatagacc atcagggaaa  15420
tatcagatgg gtgagctgtt gtcatcgttc ctttctagaa tgagcaaagg agtgtttaag  15480
gtgcttgtca atgctctaag ccacccaaag atctacaaga aattctggca ttgtggtatt  15540
atagagccta tccatggtcc ttcacttgat gctcaaaact tgcacacaac tgtgtgcaac  15600
atggtttaca catgctatat gacctacctc gacctgttgt tgaatgaaga gttagaagag  15660
ttcacatttc tcttgtgtga aagcgacgag gatgtagtac cggacagatt cgacaacatc  15720
caggcaaaac acttatgtgt tctggcagat ttgtactgtc aaccagggac ctgcccacca  15780
attcgaggtc taagaccggt agagaaatgt gcagttctaa ccgaccatat caaggcagag  15840
gctatgttat ctccagcagg atcttcgtgg aacataaatc caattattgt agaccattac  15900
tcatgctctc tgacttatct ccggcgagga tcgatcaaac agataagatt gagagttgat  15960
```

```
ccaggattca ttttcgacgc cctcgctgag gtaaatgtca gtcagccaaa gatcggcagc  16020
aacaacatct caaatatgag catcaaggct ttcagacccc cacacgatga tgttgcaaaa  16080
ttgctcaaag atatcaacac aagcaagcac aatcttccca tttcaggggg caatctcgcc  16140
aattatgaaa tccatgcttt ccgcagaatc gggttgaact catctgcttg ctacaaagct  16200
gttgagatat caacattaat taggagatgc cttgagccag gggaggacgg cttgttcttg  16260
ggtgagggat cgggttctat gttgatcact tataaagaga tacttaaact aaacaagtgc  16320
ttctataata gtggggtttc cgccaattct agatctggtc aaagggaatt agcaccctat  16380
ccctccgaag ttggccttgt cgaacacaga atgggagtag gtaatattgt caaagtgctc  16440
tttaacggga ggcccgaagt cacgtgggta ggcagtgtag attgcttcaa tttcatagtt  16500
agtaatatcc ctacctctag tgtggggttt atccattcag atatagagac cttgcctgac  16560
aaagatacta tagagaagct agaggaattg gcagccatct tatcgatggc tctgctcctg  16620
ggcaaaatag gatcaatact ggtgattaag cttatgcctt tcagcgggga ttttgttcag  16680
ggatttataa gttatgtagg gtctcattat agagaagtga accttgtata ccctagatac  16740
agcaacttca tctctactga atcttatttg gttatgacag atctcaaggc taaccggcta  16800
atgaatcctg aaaagattaa gcagcagata attgaatcat ctgtgaggac ttcacctgga  16860
cttataggtc acatcctatc cattaagcaa ctaagctgca tacaagcaat tgtgggagac  16920
gcagttagta gaggtgatat caatcctact ctgaaaaaac ttacacctat agagcaggtg  16980
ctgatcaatt gcgggttggc aattaacgga cctaagctgt gcaaagaatt gatccaccat  17040
gatgttgcct cagggcaaga tggattgctt aattctatac tcatcctcta cagggagttg  17100
gcaagattca aagacaacca aagaagtcaa caagggatgt tccacgctta ccccgtattg  17160
gtaagtagca ggcaacgaga acttatatct aggatcaccc gcaaattctg gggcacatt  17220
cttctttact ccgggaacaa aaagttgata aataagttta tccagaatct caagtccggc  17280
tatctgatac tagacttaca ccagaatatc ttcgttaaga atctatccaa gtcagagaaa  17340
cagattatta tgacgggggg tttgaaacgt gagtgggttt ttaaggtaac agtcaaggag  17400
accaaagaat ggtataagtt agtcggatac agtgccctga ttaaggacta attggttgaa  17460
ctccggaacc ctaatcctgc cctaggtggt taggcattat ttgcaatata ttaaagaaaa  17520
ctttgaaaat acgaagtttc tattcccagc tttgtctggt ggccggcatg gtcccagcct  17580
cctcgctggc gccggctggg caacattccg aggggaccgt cccctcggta atggcgaatg  17640
ggacgcggcc gatccggctg ctaacaaagc ccgaaaggaa gctgagttgg ctgctgccac  17700
cgctgagcaa taactagcat aaccccttgg ggcctctaaa cgggtcttga ggggtttttt  17760
gctgaaagga ggaactatat ccggatgcgg ccgcgggccc tatggtaccc agcttttgtt  17820
ccctttagtg agggttaatt ccgagcttgg cgtaatcatg gtcatagctg tttcctgtgt  17880
gaaattgtta tccgctcaca attccacaca acataggagc cggaagcata aagtgtaaag  17940
cctggggtgc ctaatgagtg aggtaactca cattaattgc gttgcgctca ctgcccgctt  18000
tccagtcggg aaacctgtcg tgccagctgc attaatgaat cggccaacgc gcggggagag  18060
gcggtttgcg tattgggcgc tcttccgctt cctcgctcac tgactcgctg cgctcggtcg  18120
ttcggctgcg gcgagcggta tcagctcact caaaggcggt aatacggtta tccacagaat  18180
caggggataa cgcaggaaag aacatgtgag caaaaggcca gcaaaaggcc aggaaccgta  18240
aaaaggccgc gttgctggcg tttttccata ggctcggccc ccctgacgag catcacaaaa  18300
atcgacgctc aagtcagagg tggcgaaacc cgacaggact ataaagatac caggcgttcc  18360
```

```
ccccctggaag ctccctcgtg cgctctcctg ttccgaccct gccgcttacc ggatacctgt  18420
ccgcctttct cccttcggga agcgtggcgc tttctcaatg ctcacgctgt aggtatctca  18480
gttcggtgta ggtcgttcgc tccaagctgg gctgtgtgca cgaacccccc gttcagcccg  18540
accgctgcgc cttatccggt aactatcgtc ttgagtccaa cccggtaaga cacgacttat  18600
cgccactggc agcagccact ggtaacagga ttagcagagc gaggtatgta ggcggtgcta  18660
cagagttctt gaagtggtgg cctaactacg gctacactag aaggacagta tttggtatct  18720
gcgctctgct gaagccagtt accttcggaa aaagagttgg tagctcttga tccggcaaac  18780
aaaccaccgc tggtagcggt ggtttttttg tttgcaagca gcagattacg cgcagaaaaa  18840
aaggatctca agaagatcct ttgatctttt ctacggggtc tgacgctcag tggaacgaaa  18900
actcacgtta agggattttg gtcatgagat tatcaaaaag gatcttcacc tagatccttt  18960
taaattaaaa atgaagtttt aaatcaatct aaagtatata tgagtaaact tggtctgaca  19020
gttaccaatg cttaatcagt gaggcaccta tctcagcgat ctgtctattt cgttcatcca  19080
tagttgcctg actgcccgtc gtgtagataa ctacgatacg ggagggctta ccatctggcc  19140
ccagtgctgc aatgataccg cgagacccac gctcaccggc tccagattta tcagcaataa  19200
accagccagc cggaagggcc gagcgcagaa gtggtcctgc aactttatcc gcctccatcc  19260
agtctattaa ttgttgccgg gaagctagag taagtagttc gccagttaat agtttgcgca  19320
acgttgttgc cattgctaca ggcatcgtgg tgtcacgctc gtcgtttggt atggcttcat  19380
tcagctccgg ttcccaacga tcaaggcgag ttacatgatc ccccatgttg tgaaaaaaag  19440
cggttagctc cttcggtcct ccgatcgttg tcagaagtaa gttggccgca gtgttatcac  19500
tcatgcttat ggcagcactg cataattctc ttactgtcat gccatccgta agatgctttt  19560
ctgtgactgg tgagtactca accaagtcat tctgagaata gtgtatgcgg cgaccgagtt  19620
gctcttgccc ggcgtcaata cgggataata ccgcgccaca tagcagaact ttaaaagtgc  19680
tcatcattgg aaaacgttct tcggggcgaa aactctcaag gatcttaccg ctgttgagat  19740
ccagttcgat gtaacccact cgtgcaccca actgatcttc agcatctttt actttcacca  19800
gcgtttctgg gtgagcaaaa acaggaaggc aaaatgccgc aaaaaaggga ataagggcga  19860
cacggaaatg ttgaatactc atactcttcc tttttcaata ttattgaagc atttatcagg  19920
gttattgtct catgagcgga tacatatttg aatgtattta gaaaaataaa caaatagggg  19980
ttccgcgcac atttccccga aaagtgccac ctgaaattgt aaacgttaat attttgttaa  20040
aattcgcgtt aaatttttgt taaatcagct cattttttaa ccaataggcc gaaatcggca  20100
aaatccctta taaatcaaaa gaatagaccg agatagggtt gagtgttgtt ccagtttgga  20160
acaagagtcc actattaaag aacgtggact ccaacgtcaa agggcgaaaa accgtctatc  20220
agggcgatgg cccactacgt gaaccatcac cctaatcaag ttttttgggg tcgaggtgcc  20280
gtaaagcact aaatcggaac cctaaaggga gcccccgatt tagagcttga cggggaaagc  20340
cggcgaacgt ggcgagaaag gaagggaaga aagcgaaagg agcgggcgct agggcgctgg  20400
caagtgtagc ggtcacgctg cgcgtaacca ccacacccgc cgcgcttaat gcgccgctac  20460
agggcgcgtc ccattcgcca ttcaggctgc gcaactgttg ggaagggcga tcggtgcggg  20520
cctcttcgct attacgccag ccaccgcggt g                                 20551
```

<210> SEQ ID NO 10
<211> LENGTH: 22405
<212> TYPE: DNA

```
<213> ORGANISM: Artificial Sequence
<220> FEATURE:
<223> OTHER INFORMATION: Plasmide MeV-NP+GPC

<400> SEQUENCE: 10

gcggccgcta atacgactca ctatagggcc aactttgttt ggtctgatga gtccgtgagg     60

acgaaacccg gagtcccggg tcaccaaaca aagttgggta aggatagttc aatcaatgat    120

catcttctag tgcacttagg attcaagatc ctattatcag ggacaagagc aggattaggg    180

atatccgaga tggccacact tttaaggagc ttagcattgt tcaaaagaaa caaggacaaa    240

ccacccatta catcaggatc cggtggagcc atcagaggaa tcaaacacat tattatagta    300

ccaatccctg gagattcctc aattaccact cgatccagac ttctggaccg gttggtgagg    360

ttaattggaa acccggatgt gagcgggccc aaactaacag gggcactaat aggtatatta    420

tccttatttg tggagtctcc aggtcaattg attcagagga tcaccgatga ccctgacgtt    480

agcataaggc tgttagaggt tgtccagagt gaccagtcac aatctggcct taccttcgca    540

tcaagaggta ccaacatgga ggatgaggcg gaccaatact tttcacatga tgatccaatt    600

agtagtgatc aatccaggtt cggatggttc gggaacaagg aaatctcaga tattgaagtg    660

caagaccctg agggattcaa catgattctg ggtaccatcc tagcccaaat ttgggtcttg    720

ctcgcaaagg cggttacggc cccagacacg gcagctgatt cggagctaag aaggtggata    780

aagtacaccc aacaaagaag ggtagttggt gaatttagat tggagagaaa atggttggat    840

gtggtgagga acaggattgc cgaggacctc tccttacgcc gattcatggt cgctctaatc    900

ctggatatca agagaacacc cggaaacaaa cccaggattg ctgaaatgat atgtgacatt    960

gatacatata tcgtagaggc aggattagcc agttttatcc tgactattaa gtttgggata   1020

gaaactatgt atcctgctct tggactgcat gaatttgctg gtgagttatc cacacttgag   1080

tccttgatga acctttacca gcaaatgggg gaaactgcac cctacatggt aatcctggag   1140

aactcaattc agaacaagtt cagtgcagga tcataccctc tgctctggag ctatgccatg   1200

ggagtaggag tggaacttga aaactccatg ggaggtttga actttggccg atcttacttt   1260

gatccagcat attttagatt agggcaagag atggtaagga ggtcagctgg aaaggtcagt   1320

tccacattgg catctgaact cggtatcact gccgaggatg caaggcttgt ttcagagatt   1380

gcaatgcata ctactgagga caagatcagt agagcggttg gacccagaca agcccaagta   1440

tcatttctac acggtgatca aagtgagaat gagctaccga gattgggggg caaggaagat   1500

aggagggtca aacagagtcg aggagaagcc agggagagct acagagaaac cgggcccagc   1560

agagcaagtg atgcgagagc tgcccatctt ccaaccggca caccccctaga cattgacact   1620

gcaacggagt ccagccaaga tccgcaggac agtcgaaggt cagctgacgc cctgcttagg   1680

ctgcaagcca tggcaggaat ctcggaagaa caaggctcag acacggacac ccctatagtg   1740

tacaatgaca gaaatcttct agactaggtg cgagaggccg agggccagaa caacatccgc   1800

ctaccatcca tcattgttat aaaaaactta ggaaccaggt ccacacagcc gccagcccat   1860

caaccatcca ctcccacgat tggagccaat ggcagaagag caggcacgcc atgtcaaaaa   1920

cggactggaa tgcatccggg ctctcaaggc cgagcccatc ggctcactgg ccatcgagga   1980

agctatggca gcatggtcag aaatatcaga caacccagga caggagcgag ccacctgcag   2040

ggaagagaag gcaggcagtt cgggtctcag caaaccatgc ctctcagcaa ttggatcaac   2100

tgaaggcggt gcacctcgca tccgcggtca gggacctgga gagagcgatg acgacgctga   2160

aactttggga atccccccaa gaaatctcca ggcatcaagc actgggttac agtgttatta   2220
```

```
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatgagtgcc   3540
agcaaagaaa tcaagagctt cctgtggacc cagagtctgc ggagggaact gagcggatac   3600
tgtagcaaca tcaaactgca ggtggtcaag gacgctcagg cactgctgca tgggctggac   3660
ttctccgagg tgtctaatgt gcagcggctg atgcggaaag aacggaggga cgataatgac   3720
ctgaagcgac tgcgcgacct gaaccaggca gtgaacaatc tggtcgagct gaagagcacc   3780
cagcagaaat caatcctgcg ggtcgggaca ctgacatctg acgacctgct gatcctggct   3840
gcagacctgg agaagctgaa atcgaaagtg atccgcaccg aaaggccact gtccgccggg   3900
gtctacatgg gcaatctgtc ttcccagcag ctggaccaga ggcgggctct gctgaacatg   3960
attgggatgt ccggaggaaa tcagggagct agagccggga gggacggagt cgtgcgggtc   4020
tgggacgtga agaatgccga actgctgaac aaccagttcg ggaccatgcc aagtctgaca   4080
ctggcatgcc tgactaaaca gggccaggtg gatctgaatg atgcagtcca ggctctgacc   4140
gacctgggcc tgatctacac cgccaagtac cccaatacta gcgacctgga tagactgacc   4200
cagagccacc ccatcctgaa catgatcgac actaagaagt cctcactgaa catcagtggc   4260
tataatttct ccctgggggc agcagtcaag gctggcgcat gcatgctgga cggcgggaat   4320
atgctggaaa ccatcaaagt gtctccccag accatggatg gcatcctgaa atctattctg   4380
aaagtcaaga aggccctggg aatgtttatt tcagacaccc ccggcgagag gaatccatat   4440
gagaacattc tgtataagat ttgcctgagt ggcgacgggt ggccatacat tgcaagccgg   4500
acatcaatta ccggaagagc ttgggagaat acagtcgtgg acctggaaag cgacggcaag   4560
```

```
ccccagaagg ccgactcaaa caactcctca aagagtctgc agtcagctgg cttcacagca   4620

gggctgactt actcccagct gatgacactg aaggacgcaa tgctgcagct ggacccaaac   4680

gctaagacat ggatggacat cgagggacgg ccagaagatc cagtggaaat cgcactgtat   4740

cagccatcat ccggatgcta tatccatttc ttccgggaac caactgatct gaagcagttc   4800

aagcaggatg caaagtactc ccacggaatc gatgtcaccg atctgttcgc aacccagcca   4860

ggactgacat cagccgtcat cgatgccctg cctaggaaca tggtcattac ttgccagggc   4920

tccgacgata ttaggaagct gctggagagc cagggacgga aggatatcaa actgatcgat   4980

attgccctgt ctaagactga tagccggaaa tatgagaatg cagtctggga tcagtacaag   5040

gacctgtgcc atatgcatac cggagtggtc gtcgagaaga agaagagggg cggaaaggaa   5100

gagatcacac cccactgtgc cctgatggat tgcatcatgt tcgacgcagc cgtgtccggg   5160

ggcctgaaca cctcagtcct gagggctgtc ctgccaagag atatggtgtt tagaacttca   5220

accccaagag tcgtcctgta attcgaacta cagctcaact tacctgccaa ccccatgcca   5280

gtcgacccaa ctagtacaac ctaaatccat tataaaaaac ttaggaacca ggtccacaca   5340

gccgccagcc catcaaccat ccactcccac gattggaggc cggccatggg ccagattgtc   5400

acattctttc aggaagtgcc acacgtcatt gaggaggtca tgaacatcgt gctgattgct   5460

ctgtcagtgc tggcagtgct gaaaggactg tacaacttcg ctacctgtgg actggtggga   5520

ctggtcacat tcctgctgct gtgcggcaga agttgcacta cctcactgta caaaggagtg   5580

tacgagctgc agactctgga actgaacatg gagacactga atatgacaat gcctctgagc   5640

tgcaccaaga ataatagcca ccactatatc atggtcggga acgaaaccgg cctggaactg   5700

accctgacaa acaccagcat cattaaccac aagttctgca atctgagcga cgctcacaag   5760

aagaacctgt atgaccacgc tctgatgtcc atcatcagta cctttcacct gtccatcccc   5820

aatttcaacc agtacgaggc aatgtcatgc gacttcaacg ggggcaagat cagtgtccag   5880

tacaacctga gccactccta cgccggcgac gcagccaacc actgcggaac tgtcgccaat   5940

ggcgtgctgc agacattcat gaggatggca tggggggggat cttacatcgc actggatagc   6000

ggcaggggca attgggattg catcatgact tcctatcagt atctgattat ccagaatact   6060

acatgggagg atcattgcca gttcagtcgg cccagcccta ttggatatct ggggctgctg   6120

tcacagagaa cacgggatat ctatatttca agacgcctgc tgggcacatt cacttggaca   6180

ctgtcagaca gtgagggcaa ggatactcca gggggctact gcctgacacg atggatgctg   6240

atcgaagcag agctgaaatg cttcggcaat accgcagtgg ccaagtgcaa cgagaaacac   6300

gacgaggagt tctgcgacat gctgaggctg ttcgacttca acaaacaggc tatccagaga   6360

ctgaaggcag aagcccagat gtcaatccag ctgatcaaca aggcagtgaa cgccctgatc   6420

aacgaccagc tgatcatgaa gaaccacctg agagacatta tgggcatccc ctactgtaat   6480

tacagcaagt attggtacct gaaccacact acaaccggga gaacatccct gcccaagtgc   6540

tggctggtca gcaatgggag ttatctgaat gaaacccatt tcagcgacga tatcgaacag   6600

caggctgaca acatgatcac agagatgctg cagaaagagt acatggaaag acagggcaag   6660

acaccactgg gactggtcga tctgttcgtc ttctccacta gcttctatct gatttccatc   6720

ttcctgcacc tggtgaagat ccccactcat aggcacattg tcggcaagag ttgccctaaa   6780

ccccataggc tgaatcacat ggggatttgt agttgcggcc tgtataagca gcctggcgtg   6840

cctgtgaagt ggaagagatg agcgcgcagc gcttagacgt ctcgcgatcg atactagtac   6900

aacctaaatc cattataaaa aacttaggag caaagtgatt gcctcccaag gtccacaatg   6960
```

```
acagagacct acgacttcga caagtcggca tgggacatca aagggtcgat cgctccgata   7020
caacccacca cctacagtga tggcaggctg gtgccccagg tcagagtcat agatcctggt   7080
ctaggcgaca ggaaggatga atgctttatg tacatgtttc tgctgggggt tgttgaggac   7140
agcgattccc tagggcctcc aatcgggcga gcatttgggt tcctgccctt aggtgttggc   7200
agatccacag caaagcccga aaaactcctc aaagaggcca ctgagcttga catagttgtt   7260
agacgtacag cagggctcaa tgaaaaactg gtgttctaca acaacacccc actaactctc   7320
ctcacacctt ggagaaaggt cctaacaaca gggagtgtct tcaacgcaaa ccaagtgtgc   7380
aatgcggtta atctgatacc gctcgatacc ccgcagaggt tccgtgttgt ttatatgagc   7440
atcacccgtc tttcggataa cgggtattac accgttccta gaagaatgct ggaattcaga   7500
tcggtcaatg cagtggcctt caacctgctg gtgaccctta ggattgacaa ggcgataggc   7560
cctgggaaga tcatcgacaa tacagagcaa cttcctgagg caacatttat ggtccacatc   7620
gggaacttca ggagaaagaa gagtgaagtc tactctgccg attattgcaa aatgaaaatc   7680
gaaaagatgg gcctggtttt tgcacttggt gggatagggg gcaccagtct tcacattaga   7740
agcacaggca aaatgagcaa gactctccat gcacaactcg ggttcaagaa gaccttatgt   7800
tacccgctga tggatatcaa tgaagacctt aatcgattac tctggaggag cagatgcaag   7860
atagtaagaa tccaggcagt tttgcagcca tcagttcctc aagaattccg catttacgac   7920
gacgtgatca taaatgatga ccaaggacta ttcaaagttc tgtagaccgt agtgcccagc   7980
aatgcccgaa aacgaccccc ctcacaatga cagccagaag gcccggacaa aaaagccccc   8040
tccgaaagac tccacggacc aagcgagagg ccagccagca gccgacggca agcgcgaaca   8100
ccaggcggcc ccagcacaga acagccctga cacaaggcca ccaccagcca ccccaatctg   8160
catcctcctc gtgggacccc cgaggaccaa cccccaaggc tgcccccgat ccaaaccacc   8220
aaccgcatcc ccaccacccc cgggaaagaa acccccagca attggaaggc ccctccccct   8280
cttcctcaac acaagaactc cacaaccgaa ccgcacaagc gaccgaggtg acccaaccgc   8340
aggcatccga ctccctagac agatcctctc tccccggcaa actaaacaaa acttagggcc   8400
aaggaacata cacacccaac agaacccaga ccccggccca cggcgccgcg cccccaaccc   8460
ccgacaacca gagggagccc ccaaccaatc ccgccggctc cccccggtgcc cacaggcagg   8520
gacaccaacc cccgaacaga cccagcaccc aaccatcgac aatccaagac ggggggggccc   8580
ccccaaaaaa aggcccccag gggccgacag ccagcaccgc gaggaagccc acccacccca   8640
cacacgacca cggcaaccaa accagaaccc agaccaccct gggccaccag ctcccagact   8700
cggccatcac cccgcagaaa ggaaaggcca caacccgcgc accccagccc cgatccggcg   8760
gggagccacc caacccgaac cagcacccaa gagcgatccc cgaaggaccc ccgaaccgca   8820
aaggacatca gtatcccaca gcctctccaa gtcccccggt ctcctcctct tctcgaaggg   8880
accaaaagat caatccacca cacccgacga cactcaactc cccacccccta aaggagacac   8940
cgggaatccc agaatcaaga ctcatccaat gtccatcatg ggtctcaagg tgaacgtctc   9000
tgccatattc atggcagtac tgttaactct ccaaacaccc accggtcaaa tccattgggg   9060
caatctctct aagatagggg tggtaggaat aggaagtgca agctacaaag ttatgactcg   9120
ttccagccat caatcattag tcataaaatt aatgcccaat ataactctcc tcaataactg   9180
cacgagggta gagattgcag aatacaggag actactgaga acagttttgg aaccaattag   9240
agatgcactt aatgcaatga cccagaatat aagaccggtt cagagtgtag cttcaagtag   9300
```

-continued

```
gagacacaag agatttgcgg gagtagtcct ggcaggtgcg gccctaggcg ttgccacagc   9360
tgctcagata acagccggca ttgcacttca ccagtccatg ctgaactctc aagccatcga   9420
caatctgaga gcgagcctgg aaactactaa tcaggcaatt gagacaatca gacaagcagg   9480
gcaggagatg atattggctg ttcagggtgt ccaagactac atcaataatg agctgatacc   9540
gtctatgaac caactatctt gtgatttaat cggccagaag ctcgggctca aattgctcag   9600
atactataca gaaatcctgt cattatttgg ccccagttta cgggacccca tatctgcgga   9660
gatatctatc caggctttga gctatgcgct tggaggagac atcaataagg tgttagaaaa   9720
gctcggatac agtggaggtg atttactggg catcttagag agcggaggaa taaaggcccg   9780
gataactcac gtcgacacag agtcctactt cattgtcctc agtatagcct atccgacgct   9840
gtccgagatt aagggggtga ttgtccaccg gctagagggg gtctcgtaca acataggctc   9900
tcaagagtgg tataccactg tgcccaagta tgttgcaacc caagggtacc ttatctcgaa   9960
ttttgatgag tcatcgtgta ctttcatgcc agaggggact gtgtgcagcc aaaatgcctt  10020
gtacccgatg agtcctctgc tccaagaatg cctccggggg tacaccaagt cctgtgctcg  10080
tacactcgta tccgggtctt ttgggaaccg gttcatttta tcacaaggga acctaatagc  10140
caattgtgca tcaatccttt gcaagtgtta cacaacagga acgatcatta atcaagaccc  10200
tgacaagatc ctaacataca ttgctgccga tcactgcccg gtagtcgagg tgaacggcgt  10260
gaccatccaa gtcgggagca ggaggtatcc agacgctgtg tacttgcaca gaattgacct  10320
cggtcctccc atatcattgg agaggttgga cgtagggaca aatctgggga atgcaattgc  10380
taagttggag gatgccaagg aattgttgga gtcatcggac cagatattga ggagtatgaa  10440
aggtttatcg agcactagca tagtctacat cctgattgca gtgtgtcttg gagggttgat  10500
agggatcccc gctttaatat gttgctgcag ggggcgttgt aacaaaaagg gagaacaagt  10560
tggtatgtca agaccaggcc taaagcctga tcttacggga acatcaaaat cctatgtaag  10620
gtcgctctga tcctctacaa ctcttgaaac acaaatgtcc cacaagtctc ctcttcgtca  10680
tcaagcaacc accgcaccca gcatcaagcc cacctgaaat tatctccggc ttccctctgg  10740
ccgaacaata tcggtagtta atcaaaactt agggtgcaag atcatccaca atgtcaccac  10800
aacgagaccg gataaatgcc ttctacaaag ataacccca tcccaaggga agtaggatag  10860
tcattaacag agaacatctt atgattgata gaccttatgt tttgctggct gttctgtttg  10920
tcatgtttct gagcttgatc gggttgctag ccattgcagg cattagactt catcgggcag  10980
ccatctacac cgcagagatc cataaaagcc tcagcaccaa tctagatgta actaactcaa  11040
tcgagcatca ggtcaaggac gtgctgacac cactcttcaa aatcatcggt gatgaagtgg  11100
gcctgaggac acctcagaga ttcactgacc tagtgaaatt aatctctgac aagattaaat  11160
tccttaatcc ggatagggag tacgacttca gagatctcac ttggtgtatc aacccgccag  11220
agagaatcaa attggattat gatcaatact gtgcagatgt ggctgctgaa gagctcatga  11280
atgcattggt gaactcaact ctactggaga ccagaacaac caatcagttc ctagctgtct  11340
caaagggaaa ctgctcaggg cccactacaa tcagaggtca attctcaaac atgtcgctgt  11400
ccctgttaga cttgtattta ggtcgaggtt acaatgtgtc atctatagtc actatgacat  11460
cccagggaat gtatggggga acttacctag tggaaaagcc taatctgagc agcaaaaggt  11520
cagagttgtc acaactgagc atgtaccgag tgtttgaagt aggtgttatc agaaatccgg  11580
gtttgggggc tccggtgttc catatgacaa actatcttga gcaaccagtc agtaatgatc  11640
tcagcaactg tatggtggct ttgggggagc tcaaactcgc agccctttgt cacggggaag  11700
```

```
attctatcac aattccctat cagggatcag ggaaaggtgt cagcttccag ctcgtcaagc  11760
taggtgtctg gaaatcccca accgacatgc aatcctgggt ccccttatca acggatgatc  11820
cagtgataga caggctttac ctctcatctc acagaggtgt tatcgctgac aatcaagcaa  11880
aatgggctgt cccgacaaca cgaacagatg acaagttgcg aatggagaca tgcttccaac  11940
aggcgtgtaa gggtaaaatc caagcactct gcgagaatcc cgagtgggca ccattgaagg  12000
ataacaggat tccttcatac ggggtcttgt ctgttgatct gagtctgaca gttgagctta  12060
aaatcaaaat tgcttcggga ttcgggccat tgatcacaca cggttcaggg atggacctat  12120
acaaatccaa ccacaacaat gtgtattggc tgactatccc gccaatgaag aacctagcct  12180
taggtgtaat caacacattg gagtggatac cgagattcaa ggttagtccc tacctcttca  12240
ctgtcccaat taaggaagca ggcgaagact gccatgcccc aacataccta cctgcggagg  12300
tggatggtga tgtcaaactc agttccaatc tggtgattct acctggtcaa gatctccaat  12360
atgttttggc aacctacgat acttccaggg ttgaacatgc tgtggtttat tacgtttaca  12420
gcccaagccg ctcattttct tacttttatc cttttaggtt gcctataaag gggggtcccca  12480
tcgaattaca agtggaatgc ttcacatggg accaaaaact ctggtgccgt cacttctgtg  12540
tgcttgcgga ctcagaatct ggtggacata tcactcactc tgggatggtg ggcatgggag  12600
tcagctgcac agtcacccgg gaagatggaa ccaatcgcag atagggctgc tagtgaacca  12660
atcacatgat gtcacccaga catcaggcat acccactagt gtgaaataga catcagaatt  12720
aagaaaaacg tagggtccaa gtggttcccc gttatggact cgctatctgt caaccagatc  12780
ttataccctg aagttcacct agatagcccg atagttacca ataagatagt agccatcctg  12840
gagtatgctc gagtccctca cgcttacagc ctggaggacc ctacactgtg tcagaacatc  12900
aagcaccgcc taaaaaacgg attttccaac caaatgatta taaacaatgt ggaagttggg  12960
aatgtcatca agtccaagct taggagttat ccggcccact ctcatattcc atatccaaat  13020
tgtaatcagg atttatttaa catagaagac aaagagtcaa cgaggaagat ccgtgaactc  13080
ctcaaaaagg ggaattcgct gtactccaaa gtcagtgata aggttttcca atgcttaagg  13140
gacactaact cacggcttgg cctaggctcc gaattgaggg aggacatcaa ggagaaagtt  13200
attaacttgg gagtttacat gcacagctcc cagtggtttg agccctttct gttttggttt  13260
acagtcaaga ctgagatgag gtcagtgatt aaatcacaaa cccatacttg ccataggagg  13320
agacacacac ctgtattctt cactggtagt tcagttgagt tgctaatctc tcgtgacctt  13380
gttgctataa tcagtaaaga gtctcaacat gtatattacc tgacatttga actggttttg  13440
atgtattgtg atgtcataga ggggaggtta atgacagaga ccgctatgac tattgatgct  13500
aggtatacag agcttctagg aagagtcaga tacatgtgga aactgataga tggtttcttc  13560
cctgcactcg ggaatccaac ttatcaaatt gtagccatgc tggagcctct ttcacttgct  13620
tacctgcagc tgagggatat aacagtagaa ctcagaggtg ctttccttaa ccactgcttt  13680
actgaaatac atgatgttct tgaccaaaac gggttttctg atgaaggtac ttatcatgag  13740
ttaactgaag ctctagatta cattttcata actgatgaca tacatctgac aggggagatt  13800
ttctcatttt tcagaagttt cggccacccc agacttgaag cagtaacggc tgctgaaaat  13860
gttaggaaat acatgaatca gcctaaagtc attgtgtatg agactctgat gaaaggtcat  13920
gccatatttt gtggaatcat aatcaacggc tatcgtgaca ggcacggagg cagttggcca  13980
ccgctgaccc tccccctgca tgctgcagac acaatccgga atgctcaagc ttcaggtgaa  14040
```

```
gggttaacac atgagcagtg cgttgataac tggaaatctt ttgctggagt gaaatttggc  14100
tgctttatgc ctcttagcct ggatagtgat ctgacaatgt acctaaagga caaggcactt  14160
gctgctctcc aaagggaatg ggattcagtt tacccgaaag agttcctgcg ttacgaccct  14220
cccaagggaa ccgggtcacg gaggcttgta gatgttttcc ttaatgattc gagctttgac  14280
ccatatgatg tgataatgta tgttgtaagt ggagcttacc tccatgaccc tgagttcaac  14340
ctgtcttaca gcctgaaaga aaaggagatc aaggaaacag gtagactttt tgctaaaatg  14400
acttacaaaa tgagggcatg ccaagtgatt gctgaaaatc taatctcaaa cgggattggc  14460
aaatatttta aggacaatgg gatggccaag gatgagcacg atttgactaa ggcactccac  14520
actctagctg tctcaggagt ccccaaagat ctcaaagaaa gtcacagggg ggggccagtc  14580
ttaaaaacct actcccgaag cccagtccac acaagtacca ggaacgtgag agcagcaaaa  14640
gggtttatag ggttccctca agtaattcgg caggaccaag acactgatca tccggagaat  14700
atggaagctt acgagacagt cagtgcattt atcacgactg atctcaagaa gtactgcctt  14760
aattggagat atgagaccat cagcttgttt gcacagaggc taaatgagat ttacggattg  14820
ccctcatttt tccagtggct gcataagagg cttgagacct ctgtcctgta tgtaagtgac  14880
cctcattgcc cccccgacct tgacgcccat atcccgttat ataaagtccc caatgatcaa  14940
atcttcatta agtaccctat gggaggtata gaagggtatt gtcagaagct gtggaccatc  15000
agcaccattc cctatctata cctggctgct tatgagagcg gagtaaggat tgcttcgtta  15060
gtgcaagggg acaatcagac catagccgta acaaaaaggg tacccagcac atggccctac  15120
aaccttaaga aacgggaagc tgctagagta actagagatt actttgtaat tcttaggcaa  15180
aggctacatg atattggcca tcacctcaag gcaaatgaga caattgtttc atcacatttt  15240
tttgtctatt caaaaggaat atattatgat gggctacttg tgtcccaatc actcaagagc  15300
atcgcaagat gtgtattctg gtcagagact atagttgatg aaacaagggc agcatgcagt  15360
aatattgcta caacaatggc taaaagcatc gagagaggtt atgaccgtta ccttgcatat  15420
tccctgaacg tcctaaaagt gatacagcaa attctgatct ctcttggctt cacaatcaat  15480
tcaaccatga cccgggatgt agtcataccc ctcctcacaa acaacgacct cttaataagg  15540
atggcactgt tgcccgctcc tattgggggg atgaattatc tgaatatgag caggctgttt  15600
gtcagaaaca tcggtgatcc agtaacatca tcaattgctg atctcaagag aatgattctc  15660
gcctcactaa tgcctgaaga gaccctccat caagtaatga cacaacaacc gggggactct  15720
tcattcctag actgggctag cgacccttac tcagcaaatc ttgtatgtgt ccagagcatc  15780
actagactcc tcaagaacat aactgcaagg tttgtcctga tccatagtcc aaacccaatg  15840
ttaaaaggat tattccatga tgacagtaaa gaagaggacg agggactggc ggcattcctc  15900
atggacaggc atattatagt acctagggca gctcatgaaa tcctggatca tagtgtcaca  15960
ggggcaagag agtctattgc aggcatgctg gataccacaa aaggcttgat tcgagccagc  16020
atgaggaagg gggggttaac ctctcgagtg ataaccagat tgtccaatta tgactatgaa  16080
caattcagag cagggatggt gctattgaca ggaagaaaga gaaatgtcct cattgacaaa  16140
gagtcatgtt cagtgcagct ggcgagagct ctaagaagcc atatgtgggc gaggctagct  16200
cgaggacggc ctatttacgg ccttgaggtc cctgatgtac tagaatctat gcgaggccac  16260
cttattcggc gtcatgagac atgtgtcatc tgcgagtgtg gatcagtcaa ctacggatgg  16320
tttttgtcc cctcgggttg ccaactggat gatattgaca aggaaacatc atccttgaga  16380
gtcccatata ttggttctac cactgatgag agaacagaca tgaagcttgc cttcgtaaga  16440
```

gccccaagtc gatccttgcg atctgctgtt agaatagcaa cagtgtactc atgggcttac 16500
ggtgatgatg atagctcttg gaacgaagcc tggttgttgg ctaggcaaag ggccaatgtg 16560
agcctggagg agctaagggt gatcactccc atctcaactt cgactaattt agcgcatagg 16620
ttgagggatc gtagcactca agtgaaatac tcaggtacat cccttgtccg agtggcgagg 16680
tataccacaa tctccaacga caatctctca tttgtcatat cagataagaa ggttgatact 16740
aactttatat accaacaagg aatgcttcta gggttgggtg ttttagaaac attgtttcga 16800
ctcgagaaag ataccggatc atctaacacg gtattacatc ttcacgtcga aacagattgt 16860
tgcgtgatcc cgatgataga tcatcccagg atacccagct cccgcaagct agagctgagg 16920
gcagagctat gtaccaaccc attgatatat gataatgcac ctttaattga cagagatgca 16980
acaaggctat acacccagag ccataggagg caccttgtgg aatttgttac atggtccaca 17040
ccccaactat atcacatttt agctaagtcc acagcactat ctatgattga cctggtaaca 17100
aaatttgaga aggaccatat gaatgaaatt tcagctctca taggggatga cgatatcaat 17160
agtttcataa ctgagtttct gctcatagag ccaagattat tcactatcta cttgggccag 17220
tgtgcggcca tcaattgggc atttgatgta cattatcata gaccatcagg gaaatatcag 17280
atgggtgagc tgttgtcatc gttcctttct agaatgagca aaggagtgtt taaggtgctt 17340
gtcaatgctc taagccaccc aaagatctac aagaaattct ggcattgtgg tattatagag 17400
cctatccatg gtccttcact tgatgctcaa aacttgcaca caactgtgtg caacatggtt 17460
tacacatgct atatgaccta cctcgacctg ttgttgaatg aagagttaga agagttcaca 17520
tttctcttgt gtgaaagcga cgaggatgta gtaccggaca gattcgacaa catccaggca 17580
aaacacttat gtgttctggc agatttgtac tgtcaaccag ggacctgccc accaattcga 17640
ggtctaagac cggtagagaa atgtgcagtt ctaaccgacc atatcaaggc agaggctatg 17700
ttatctccag caggatcttc gtggaacata aatccaatta ttgtagacca ttactcatgc 17760
tctctgactt atctccggcg aggatcgatc aaacagataa gattgagagt tgatccagga 17820
ttcattttcg acgccctcgc tgaggtaaat gtcagtcagc caaagatcgg cagcaacaac 17880
atctcaaata tgagcatcaa ggctttcaga cccccacacg atgatgttgc aaaattgctc 17940
aaagatatca acacaagcaa gcacaatctt cccatttcag gggggcaatct cgccaattat 18000 gaaatccatg ctttccgcag aatcgggttg aactcatctg cttgctacaa agctgttgag 18060
atatcaacat taattaggag atgccttgag ccaggggagg acggcttgtt cttgggtgag 18120
ggatcgggtt ctatgttgat cacttataaa gagatactta aactaaacaa gtgcttctat 18180
aatagtgggg tttccgccaa ttctagatct ggtcaaaggg aattagcacc ctatccctcc 18240
gaagttggcc ttgtcgaaca cagaatggga gtaggtaata ttgtcaaagt gctctttaac 18300
gggaggcccg aagtcacgtg ggtaggcagt gtagattgct tcaatttcat agttagtaat 18360
atccctacct ctagtgtggg gtttatccat tcagatatag agaccttgcc tgacaaagat 18420
actatagaga agctagagga attggcagcc atcttatcga tggctctgct cctgggcaaa 18480
ataggatcaa tactggtgat taagcttatg cctttcagcg gggattttgt tcagggattt 18540
ataagttatg tagggtctca ttatagagaa gtgaaccttg tataccctag atacagcaac 18600
ttcatctcta ctgaatctta tttggttatg acagatctca aggctaaccg gctaatgaat 18660
cctgaaaaga ttaagcagca gataattgaa tcatctgtga ggacttcacc tggacttata 18720
ggtcacatcc tatccattaa gcaactaagc tgcatacaag caattgtggg agacgcagtt 18780
agtagaggtg atatcaatcc tactctgaaa aaacttacac ctatagagca ggtgctgatc 18840
aattgcgggt tggcaattaa cggacctaag ctgtgcaaag aattgatcca ccatgatgtt 18900
gcctcagggc aagatggatt gcttaattct atactcatcc tctacaggga gttggcaaga 18960
ttcaaagaca accaaagaag tcaacaaggg atgttccacg cttaccccgt attggtaagt 19020
agcaggcaac gagaacttat atctaggatc acccgcaaat tctgggggca cattcttctt 19080
tactccggga acaaaaagtt gataaataag tttatccaga atctcaagtc cggctatctg 19140
atactagact tacaccagaa tatcttcgtt aagaatctat ccaagtcaga gaaacagatt 19200
attatgacgg ggggtttgaa acgtgagtgg gtttttaagg taacagtcaa ggagaccaaa 19260
gaatggtata agttagtcgg atacagtgcc ctgattaagg actaattggt tgaactccgg 19320
aaccctaatc ctgccctagg tggttaggca ttatttgcaa tatattaaag aaaactttga 19380
aaatacgaag tttctattcc cagctttgtc tggtggccgg catggtccca gcctcctcgc 19440
tggcgccggc tgggcaacat tccgagggga ccgtcccctc ggtaatggcg aatgggacgc 19500
ggccgatccg gctgctaaca aagcccgaaa ggaagctgag ttggctgctg ccaccgctga 19560
gcaataacta gcataacccc ttggggcctc taaacgggtc ttgaggggtt ttttgctgaa 19620
aggaggaact atatccggat gcggccgcgg gccctatggt acccagcttt tgttcccttt 19680
agtgagggtt aattccgagc ttggcgtaat catggtcata gctgtttcct gtgtgaaatt 19740
gttatccgct cacaattcca cacaacatag gagccggaag cataaagtgt aaagcctggg 19800
gtgcctaatg agtgaggtaa ctcacattaa ttgcgttgcg ctcactgccc gctttccagt 19860
cgggaaacct gtcgtgccag ctgcattaat gaatcggcca acgcgcgggg agaggcggtt 19920
tgcgtattgg gcgctcttcc gcttcctcgc tcactgactc gctgcgctcg gtcgttcggc 19980
tgcggcgagc ggtatcagct cactcaaagg cggtaatacg gttatccaca gaatcagggg 20040
ataacgcagg aaagaacatg tgagcaaaag gccagcaaaa ggccaggaac cgtaaaaagg 20100
ccgcgttgct ggcgtttttc cataggctcg gcccccctga cgagcatcac aaaaatcgac 20160
gctcaagtca gaggtggcga aacccgacag gactataaag ataccaggcg tttccccctg 20220
gaagctccct cgtgcgctct cctgttccga ccctgccgct taccggatac ctgtccgcct 20280
ttctcccttc gggaagcgtg gcgctttctc aatgctcacg ctgtaggtat ctcagttcgg 20340
tgtaggtcgt tcgctccaag ctgggctgtg tgcacgaacc ccccgttcag cccgaccgct 20400
gcgccttatc cggtaactat cgtcttgagt ccaacccggt aagacacgac ttatcgccac 20460
tggcagcagc cactggtaac aggattagca gagcgaggta tgtaggcggt gctacagagt 20520
tcttgaagtg gtggcctaac tacggctaca ctagaaggac agtatttggt atctgcgctc 20580
tgctgaagcc agttaccttc ggaaaaagag ttggtagctc ttgatccggc aaacaaacca 20640
ccgctggtag cggtggtttt tttgtttgca agcagcagat tacgcgcaga aaaaaaggat 20700
ctcaagaaga tcctttgatc ttttctacgg ggtctgacgc tcagtggaac gaaaactcac 20760
gttaagggat tttggtcatg agattatcaa aaaggatctt cacctagatc cttttaaatt 20820
aaaaatgaag ttttaaatca atctaaagta tatatgagta aacttggtct gacagttacc 20880
aatgcttaat cagtgaggca cctatctcag cgatctgtct atttcgttca tccatagttg 20940
cctgactgcc cgtcgtgtag ataactacga tacgggaggg cttaccatct ggccccagtg 21000
ctgcaatgat accgcgagac ccacgctcac cggctccaga tttatcagca ataaaccagc 21060
cagccggaag ggccgagcgc agaagtggtc ctgcaacttt atccgcctcc atccagtcta 21120
ttaattgttg ccgggaagct agagtaagta gttcgccagt taatagtttg cgcaacgttg 21180
ttgccattgc tacaggcatc gtggtgtcac gctcgtcgtt tggtatggct tcattcagct 21240
ccggttccca acgatcaagg cgagttacat gatcccccat gttgtgaaaa aaagcggtta 21300
gctccttcgg tcctccgatc gttgtcagaa gtaagttggc cgcagtgtta tcactcatgc 21360
ttatggcagc actgcataat tctcttactg tcatgccatc cgtaagatgc ttttctgtga 21420
ctggtgagta ctcaaccaag tcattctgag aatagtgtat gcggcgaccg agttgctctt 21480
gcccggcgtc aatacgggat aataccgcgc cacatagcag aactttaaaa gtgctcatca 21540
ttggaaaacg ttcttcgggg cgaaaactct caaggatctt accgctgttg agatccagtt 21600
cgatgtaacc cactcgtgca cccaactgat cttcagcatc ttttactttc accagcgttt 21660
ctgggtgagc aaaaacagga aggcaaaatg ccgcaaaaaa gggaataagg gcgacacgga 21720
aatgttgaat actcatactc ttcctttttc aatattattg aagcatttat cagggttatt 21780
gtctcatgag cggatacata tttgaatgta tttagaaaaa taaacaaata ggggttccgc 21840
gcacatttcc ccgaaaagtg ccacctgaaa ttgtaaacgt taatattttg ttaaaattcg 21900
cgttaaattt ttgttaaatc agctcatttt ttaaccaata ggccgaaatc ggcaaaatcc 21960
cttataaatc aaaagaatag accgagatag ggttgagtgt tgttccagtt tggaacaaga 22020
gtccactatt aaagaacgtg gactccaacg tcaaagggcg aaaaaccgtc tatcagggcg 22080
atggcccact acgtgaacca tcaccctaat caagtttttt ggggtcgagg tgccgtaaag 22140
cactaaatcg gaaccctaaa gggagccccc gatttagagc ttgacgggga aagccggcga 22200
acgtggcgag aaaggaaggg aagaaagcga aaggagcggg cgctagggcg ctggcaagtg 22260
tagcggtcac gctgcgcgta accaccacac ccgccgcgct taatgcgccg ctacagggcg 22320
cgtcccattc gccattcagg ctgcgcaact gttgggaagg gcgatcggtg cgggcctctt 22380
cgctattacg ccagccaccg cggtg 22405

<210> SEQ ID NO 11
<211> LENGTH: 22405
<212> TYPE: DNA
<213> ORGANISM: Artificial Sequence
<220> FEATURE:
<223> OTHER INFORMATION: Plasmide MeV-mNP+GPC

<400> SEQUENCE: 11
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420
tccttatttg tggagtctcc aggtcaattg attcagagga tcaccgatga ccctgacgtt 480
agcataaggc tgttagaggt tgtccagagt gaccagtcac aatctggcct taccttcgca 540
tcaagaggta ccaacatgga ggatgaggcg gaccaatact tttcacatga tgatccaatt 600
agtagtgatc aatccaggtt cggatggttc gggaacaagg aaatctcaga tattgaagtg 660
caagaccctg agggattcaa catgattctg ggtaccatcc tagcccaaat ttgggtcttg 720
ctcgcaaagg cggttacggc cccagacacg gcagctgatt cggagctaag aaggtggata 780

-continued

```
aagtacaccc aacaaagaag ggtagttggt gaatttagat tggagagaaa atggttggat    840
gtggtgagga acaggattgc cgaggacctc tccttacgcc gattcatggt cgctctaatc    900
ctggatatca agagaacacc cggaaacaaa cccaggattg ctgaaatgat atgtgacatt    960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga acctttacca gcaaatgggg gaaactgcac cctacatggt aatcctggag   1140
aactcaattc agaacaagtt cagtgcagga tcataccctc tgctctggag ctatgccatg   1200
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg gacccagaca agcccaagta   1440
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca cacccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atcccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
```

```
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagc ctaccctcca tcattgttat   3480
aaaaaactta ggaaccaggt ccacacagcc gccagcccat caacgcgtac gatgagtgcc   3540
agcaaagaaa tcaagagctt cctgtggacc cagagtctgc ggagggaact gagcggatac   3600
tgtagcaaca tcaaactgca ggtggtcaag gacgctcagg cactgctgca tgggctggac   3660
ttctccgagg tgtctaatgt gcagcggctg atgcggaaag aacggaggga cgataatgac   3720
ctgaagcgac tgcgcgacct gaaccaggca gtgaacaatc tggtcgagct gaagagcacc   3780
cagcagaaat caatcctgcg ggtcgggaca ctgacatctg acgacctgct gatcctggct   3840
gcagacctgg agaagctgaa atcgaaagtg atccgcaccg aaaggccact gtccgccggg   3900
gtctacatgg gcaatctgtc ttcccagcag ctggaccaga ggcgggctct gctgaacatg   3960
attgggatgt ccggaggaaa tcagggagct agagccggga gggacggagt cgtgcgggtc   4020
tgggacgtga agaatgccga actgctgaac aaccagttcg ggaccatgcc aagtctgaca   4080
ctggcatgcc tgactaaaca gggccaggtg gatctgaatg atgcagtcca ggctctgacc   4140
gacctgggcc tgatctacac cgccaagtac cccaatacta gcgacctgga tagactgacc   4200
cagagccacc ccatcctgaa catgatcgac actaagaagt cctcactgaa catcagtggc   4260
tataatttct ccctgggggc agcagtcaag gctggcgcat gcatgctgga cggcgggaat   4320
atgctggaaa ccatcaaagt gtctccccag accatggatg gcatcctgaa atctattctg   4380
aaagtcaaga aggccctggg aatgtttatt tcagacaccc ccggcgagag gaatccatat   4440
gagaacattc tgtataagat ttgcctgagt ggcgacgggt ggccatacat tgcaagccgg   4500
acatcaatta ccggaagagc ttgggagaat acagtcgtgg acctggaaag cgacggcaag   4560
ccccagaagg ccgactcaaa caactcctca aagagtctgc agtcagctgg cttcacagca   4620
gggctgactt actcccagct gatgacactg aaggacgcaa tgctgcagct ggacccaaac   4680
gctaagacat ggatggccat cgaggcccgg ccagaagatc cagtggaaat cgcactgtat   4740
cagccatcat ccggatgcta tatccatttc ttccgggaac caactgatct gaagcagttc   4800
aagcaggatg caaagtactc ccacggaatc gatgtcaccg atctgttcgc aacccagcca   4860
ggactgacat cagccgtcat cgatgccctg cctaggaaca tggtcattac ttgccagggc   4920
tccgacgata ttaggaagct gctggagagc cagggacgga aggatatcaa actgatcgat   4980
attgccctgt ctaagactga tagccggaaa tatgagaatg cagtctggga tcagtacaag   5040
gacctgtgcc atatgcatac cggagtggtc gtcgagaaga agaagagggg cggaaaggaa   5100
gagatcacac cccactgtgc cctgatggat tgcatcatgt tcgacgcagc cgtgtccggg   5160
ggcctgaaca cctcagtcct gagggctgtc ctgccaagag atatggtgtt tagaacttca   5220
accccaagag tcgtcctgta attcgaacta cagctcaact tacctgccaa ccccatgcca   5280
gtcgacccaa ctagtacaac ctaaatccat tataaaaaac ttaggaacca ggtccacaca   5340
gccgccagcc catcaaccat ccactcccac gattggaggc cggccatggg ccagattgtc   5400
acattctttc aggaagtgcc acacgtcatt gaggaggtca tgaacatcgt gctgattgct   5460
ctgtcagtgc tggcagtgct gaaaggactg tacaacttcg ctacctgtgg actggtggga   5520
```

```
ctggtcacat tcctgctgct gtgcggcaga agttgcacta cctcactgta caaaggagtg   5580
tacgagctgc agactctgga actgaacatg gagacactga atatgacaat gcctctgagc   5640
tgcaccaaga ataatagcca ccactatatc atggtcggga acgaaaccgg cctggaactg   5700
accctgacaa acaccagcat cattaaccac aagttctgca atctgagcga cgctcacaag   5760
aagaacctgt atgaccacgc tctgatgtcc atcatcagta cctttcacct gtccatcccc   5820
aatttcaacc agtacgaggc aatgtcatgc gacttcaacg gggcaagat cagtgtccag    5880
tacaacctga gccactccta cgccggcgac gcagccaacc actgcggaac tgtcgccaat   5940
ggcgtgctgc agacattcat gaggatggca tggggggat cttacatcgc actggatagc    6000
ggcaggggca attgggattg catcatgact tcctatcagt atctgattat ccagaatact   6060
acatgggagg atcattgcca gttcagtcgg cccagcccta ttggatatct ggggctgctg   6120
tcacagagaa cacgggatat ctatatttca agacgcctgc tgggcacatt cacttggaca   6180
ctgtcagaca gtgagggcaa ggatactcca gggggctact gcctgacacg atggatgctg   6240
atcgaagcag agctgaaatg cttcggcaat accgcagtgg ccaagtgcaa cgagaaacac   6300
gacgaggagt tctgcgacat gctgaggctg ttcgacttca acaaacaggc tatccagaga   6360
ctgaaggcag aagcccagat gtcaatccag ctgatcaaca aggcagtgaa cgccctgatc   6420
aacgaccagc tgatcatgaa gaaccacctg agagacatta tgggcatccc ctactgtaat   6480
tacagcaagt attggtacct gaaccacact acaaccggga gaacatccct gcccaagtgc   6540
tggctggtca gcaatgggag ttatctgaat gaaacccatt tcagcgacga tatcgaacag   6600
caggctgaca acatgatcac agagatgctg cagaaagagt acatggaaag acagggcaag   6660
acaccactgg gactggtcga tctgttcgtc ttctccacta gcttctatct gatttccatc   6720
ttcctgcacc tggtgaagat ccccactcat aggcacattg tcggcaagag ttgccctaaa   6780
ccccataggc tgaatcacat ggggatttgt agttgcggcc tgtataagca gcctggcgtg   6840
cctgtgaagt ggaagagatg agcgcgcagc gcttagacgt ctcgcgatcg atactagtac   6900
aacctaaatc cattataaaa aacttaggag caaagtgatt gcctcccaag gtccacaatg   6960
acagagacct acgacttcga caagtcggca tgggacatca aagggtcgat cgctccgata   7020
caacccacca cctacagtga tggcaggctg gtgccccagg tcagagtcat agatcctggt   7080
ctaggcgaca ggaaggatga atgctttatg tacatgtttc tgctgggggt tgttgaggac   7140
agcgattccc tagggcctcc aatcgggcga gcatttgggt tcctgccctt aggtgttggc   7200
agatccacag caaagcccga aaaactcctc aaagaggcca ctgagcttga catagttgtt   7260
agacgtacag cagggctcaa tgaaaaactg gtgttctaca acaacacccc actaactctc   7320
ctcacacctt ggagaaaggt cctaacaaca gggagtgtct tcaacgcaaa ccaagtgtgc   7380
aatgcggtta atctgatacc gctcgatacc ccgcagaggt tccgtgttgt ttatatgagc   7440
atcacccgtc tttcggataa cgggtattac accgttccta gaagaatgct ggaattcaga   7500
tcggtcaatg cagtggcctt caacctgctg gtgaccctta ggattgacaa ggcgataggc   7560
cctgggaaga tcatcgacaa tacagagcaa cttcctgagg caacatttat ggtccacatc   7620
gggaacttca ggagaaagaa gagtgaagtc tactctgccg attattgcaa aatgaaaatc   7680
gaaaagatgg gcctggtttt tgcacttggt gggatagggg gcaccagtct tcacattaga   7740
agcacaggca aaatgagcaa gactctccat gcacaactcg ggttcaagaa gaccttatgt   7800
tacccgctga tggatatcaa tgaagacctt aatcgattac tctggaggag cagatgcaag   7860
atagtaagaa tccaggcagt tttgcagcca tcagttcctc aagaattccg catttacgac   7920
```

```
gacgtgatca taaatgatga ccaaggacta ttcaaagttc tgtagaccgt agtgcccagc   7980
aatgcccgaa aacgaccccc ctcacaatga cagccagaag gcccggacaa aaaagccccc   8040
tccgaaagac tccacggacc aagcgagagg ccagccagca gccgacggca agcgcgaaca   8100
ccaggcggcc ccagcacaga acagccctga cacaaggcca ccaccagcca ccccaatctg   8160
catcctcctc gtgggacccc cgaggaccaa cccccaaggc tgcccccgat ccaaaccacc   8220
aaccgcatcc ccaccacccc cgggaaagaa acccccagca attggaaggc ccctccccct   8280
cttcctcaac acaagaactc cacaaccgaa ccgcacaagc gaccgaggtg acccaaccgc   8340
aggcatccga ctccctagac agatcctctc tccccggcaa actaaacaaa acttagggcc   8400
aaggaacata cacacccaac agaacccaga ccccggccca cggcgccgcg cccccaaccc   8460
ccgacaacca gagggagccc ccaaccaatc ccgccggctc ccccggtgcc cacaggcagg   8520
gacaccaacc cccgaacaga cccagcaccc aaccatcgac aatccaagac ggggggggccc   8580
ccccaaaaaa aggcccccag gggccgacag ccagcaccgc gaggaagccc acccacccca   8640
cacacgacca cggcaaccaa accagaaccc agaccaccct gggccaccag ctcccagact   8700
cggccatcac cccgcagaaa ggaaaggcca caacccgcgc accccagccc cgatccggcg   8760
gggagccacc caacccgaac cagcacccaa gagcgatccc cgaaggaccc ccgaaccgca   8820
aaggacatca gtatcccaca gcctctccaa gtcccccggt ctcctcctct tctcgaaggg   8880
accaaaagat caatccacca cacccgacga cactcaactc cccaccccta aaggagacac   8940
cgggaatccc agaatcaaga ctcatccaat gtccatcatg ggtctcaagg tgaacgtctc   9000
tgccatattc atggcagtac tgttaactct ccaaacaccc accggtcaaa tccattgggg   9060
caatctctct aagatagggg tggtaggaat aggaagtgca agctacaaag ttatgactcg   9120
ttccagccat caatcattag tcataaaatt aatgcccaat ataactctcc tcaataactg   9180
cacgagggta gagattgcag aatacaggag actactgaga acagttttgg aaccaattag   9240
agatgcactt aatgcaatga cccagaatat aagaccggtt cagagtgtag cttcaagtag   9300
gagacacaag agatttgcgg gagtagtcct ggcaggtgcg gccctaggcg ttgccacagc   9360
tgctcagata acagccggca ttgcacttca ccagtccatg ctgaactctc aagccatcga   9420
caatctgaga gcgagcctgg aaactactaa tcaggcaatt gagacaatca gacaagcagg   9480
gcaggagatg atattggctg ttcagggtgt ccaagactac atcaataatg agctgatacc   9540
gtctatgaac caactatctt gtgatttaat cggccagaag ctcgggctca aattgctcag   9600
atactataca gaaatcctgt cattatttgg ccccagttta cgggacccca tatctgcgga   9660
gatatctatc caggctttga gctatgcgct tggaggagac atcaataagg tgttagaaaa   9720
gctcggatac agtggaggtg atttactggg catcttagag agcggaggaa taaaggcccg   9780
gataactcac gtcgacacag agtcctactt cattgtcctc agtatagcct atccgacgct   9840
gtccgagatt aagggggtga ttgtccaccg gctagagggg gtctcgtaca acataggctc   9900
tcaagagtgg tataccactg tgcccaagta tgttgcaacc caagggtacc ttatctcgaa   9960
ttttgatgag tcatcgtgta ctttcatgcc agaggggact gtgtgcagcc aaaatgcctt  10020
gtacccgatg agtcctctgc tccaagaatg cctccggggg tacaccaagt cctgtgctcg  10080
tacactcgta tccgggtctt ttgggaaccg gttcatttta tcacaaggga acctaatagc  10140
caattgtgca tcaatccttt gcaagtgtta cacaacagga acgatcatta atcaagaccc  10200
tgacaagatc ctaacataca ttgctgccga tcactgcccg gtagtcgagg tgaacggcgt  10260
```

-continued

```
gaccatccaa gtcgggagca ggaggtatcc agacgctgtg tacttgcaca gaattgacct  10320
cggtcctccc atatcattgg agaggttgga cgtagggaca aatctgggga atgcaattgc  10380
taagttggag gatgccaagg aattgttgga gtcatcggac cagatattga ggagtatgaa  10440
aggtttatcg agcactagca tagtctacat cctgattgca gtgtgtcttg gagggttgat  10500
agggatcccc gctttaatat gttgctgcag ggggcgttgt aacaaaaagg gagaacaagt  10560
tggtatgtca agaccaggcc taaagcctga tcttacggga acatcaaaat cctatgtaag  10620
gtcgctctga tcctctacaa ctcttgaaac acaaatgtcc cacaagtctc ctcttcgtca  10680
tcaagcaacc accgcaccca gcatcaagcc cacctgaaat tatctccggc ttccctctgg  10740
ccgaacaata tcggtagtta atcaaaactt agggtgcaag atcatccaca atgtcaccac  10800
aacgagaccg gataaatgcc ttctacaaag ataacccccca tcccaaggga agtaggatag  10860
tcattaacag agaacatctt atgattgata gaccttatgt tttgctggct gttctgtttg  10920
tcatgtttct gagcttgatc gggttgctag ccattgcagg cattagactt catcgggcag  10980
ccatctacac cgcagagatc cataaaagcc tcagcaccaa tctagatgta actaactcaa  11040
tcgagcatca ggtcaaggac gtgctgacac cactcttcaa aatcatcggt gatgaagtgg  11100
gcctgaggac acctcagaga ttcactgacc tagtgaaatt aatctctgac aagattaaat  11160
tccttaatcc ggatagggag tacgacttca gagatctcac ttggtgtatc aacccgccag  11220
agagaatcaa attggattat gatcaatact gtgcagatgt ggctgctgaa gagctcatga  11280
atgcattggt gaactcaact ctactggaga ccagaacaac caatcagttc ctagctgtct  11340
caaagggaaa ctgctcaggg cccactacaa tcagaggtca attctcaaac atgtcgctgt  11400
ccctgttaga cttgtattta ggtcgaggtt acaatgtgtc atctatagtc actatgacat  11460
cccagggaat gtatgggggga acttacctag tggaaaagcc taatctgagc agcaaaaggt  11520
cagagttgtc acaactgagc atgtaccgag tgtttgaagt aggtgttatc agaaatccgg  11580
gtttgggggc tccggtgttc catatgacaa actatcttga gcaaccagtc agtaatgatc  11640
tcagcaactg tatggtggct ttgggggagc tcaaactcgc agccctttgt cacggggaag  11700
attctatcac aattccctat cagggatcag ggaaaggtgt cagcttccag ctcgtcaagc  11760
taggtgtctg gaaatcccca accgacatgc aatcctgggt ccccttatca acggatgatc  11820
cagtgataga caggctttac ctctcatctc acagaggtgt tatcgctgac aatcaagcaa  11880
aatgggctgt cccgacaaca cgaacagatg acaagttgcg aatggagaca tgcttccaac  11940
aggcgtgtaa gggtaaaatc caagcactct gcgagaatcc cgagtgggca ccattgaagg  12000
ataacaggat tccttcatac ggggtcttgt ctgttgatct gagtctgaca gttgagctta  12060
aaatcaaaat tgcttcggga ttcgggccat tgatcacaca cggttcaggg atggacctat  12120
acaaatccaa ccacaacaat gtgtattggc tgactatccc gccaatgaag aacctagcct  12180
taggtgtaat caacacattg gagtggatac cgagattcaa ggttagtccc tacctcttca  12240
ctgtcccaat taaggaagca ggcgaagact gccatgcccc aacataccta cctgcggagg  12300
tggatggtga tgtcaaactc agttccaatc tggtgattct acctggtcaa gatctccaat  12360
atgttttggc aacctacgat acttccaggg ttgaacatgc tgtggtttat tacgtttaca  12420
gcccaagccg ctcattttct tacttttatc cttttaggtt gcctataaag ggggtcccca  12480
tcgaattaca agtggaatgc ttcacatggg accaaaaact ctggtgccgt cacttctgtg  12540
tgcttgcgga ctcagaatct ggtggacata tcactcactc tgggatggtg ggcatgggag  12600
tcagctgcac agtcacccgg gaagatggaa ccaatcgcag atagggctgc tagtgaacca  12660
```

```
atcacatgat gtcacccaga catcaggcat acccactagt gtgaaataga catcagaatt  12720

aagaaaaacg tagggtccaa gtggttcccc gttatggact cgctatctgt caaccagatc  12780

ttataccctg aagttcacct agatagcccg atagttacca ataagatagt agccatcctg  12840

gagtatgctc gagtccctca cgcttacagc ctggaggacc ctacactgtg tcagaacatc  12900

aagcaccgcc taaaaaacgg attttccaac caaatgatta taaacaatgt ggaagttggg  12960

aatgtcatca agtccaagct taggagttat ccggcccact ctcatattcc atatccaaat  13020

tgtaatcagg atttatttaa catagaagac aaagagtcaa cgaggaagat ccgtgaactc  13080

ctcaaaaagg ggaattcgct gtactccaaa gtcagtgata aggttttcca atgcttaagg  13140

gacactaact cacggcttgg cctaggctcc gaattgaggg aggacatcaa ggagaaagtt  13200

attaacttgg gagtttacat gcacagctcc cagtggtttg agccctttct gttttggttt  13260

acagtcaaga ctgagatgag gtcagtgatt aaatcacaaa cccatacttg ccataggagg  13320

agacacacac ctgtattctt cactggtagt tcagttgagt tgctaatctc tcgtgacctt  13380

gttgctataa tcagtaaaga gtctcaacat gtatattacc tgacatttga actggttttg  13440

atgtattgtg atgtcataga ggggaggtta atgacagaga ccgctatgac tattgatgct  13500

aggtatacag agcttctagg aagagtcaga tacatgtgga aactgataga tggtttcttc  13560

cctgcactcg ggaatccaac ttatcaaatt gtagccatgc tggagcctct ttcacttgct  13620

tacctgcagc tgagggatat aacagtagaa ctcagaggtg ctttccttaa ccactgcttt  13680

actgaaatac atgatgttct tgaccaaaac gggttttctg atgaaggtac ttatcatgag  13740

ttaactgaag ctctagatta cattttcata actgatgaca tacatctgac aggggagatt  13800

ttctcatttt tcagaagttt cggccacccc agacttgaag cagtaacggc tgctgaaaat  13860

gttaggaaat acatgaatca gcctaaagtc attgtgtatg agactctgat gaaaggtcat  13920

gccatatttt gtggaatcat aatcaacggc tatcgtgaca ggcacggagg cagttggcca  13980

ccgctgaccc tcccccctgca tgctgcagac acaatccgga atgctcaagc ttcaggtgaa  14040

gggttaacac atgagcagtg cgttgataac tggaaatctt ttgctggagt gaaatttggc  14100

tgctttatgc ctcttagcct ggatagtgat ctgacaatgt acctaaagga caaggcactt  14160

gctgctctcc aaagggaatg ggattcagtt tacccgaaag agttcctgcg ttacgaccct  14220

cccaagggaa ccgggtcacg gaggcttgta gatgttttcc ttaatgattc gagctttgac  14280

ccatatgatg tgataatgta tgttgtaagt ggagcttacc tccatgaccc tgagttcaac  14340

ctgtcttaca gcctgaaaga aaaggagatc aaggaaacag gtagactttt tgctaaaatg  14400

acttacaaaa tgagggcatg ccaagtgatt gctgaaaatc taatctcaaa cgggattggc  14460

aaatatttta aggacaatgg gatggccaag gatgagcacg atttgactaa ggcactccac  14520

actctagctg tctcaggagt ccccaaagat ctcaaagaaa gtcacagggg ggggccagtc  14580

ttaaaaacct actcccgaag cccagtccac acaagtacca ggaacgtgag agcagcaaaa  14640

gggtttatag ggttccctca agtaattcgg caggaccaag acactgatca tccggagaat  14700

atggaagctt acgagacagt cagtgcattt atcacgactg atctcaagaa gtactgcctt  14760

aattggagat atgagaccat cagcttgttt gcacagaggc taaatgagat ttacggattg  14820

ccctcatttt tccagtggct gcataagagg cttgagacct ctgtcctgta tgtaagtgac  14880

cctcattgcc cccccgacct tgacgcccat atcccgttat ataaagtccc caatgatcaa  14940

atcttcatta agtaccctat gggaggtata gaagggtatt gtcagaagct gtggaccatc  15000
```

agcaccattc cctatctata cctggctgct tatgagagcg gagtaaggat tgcttcgtta 15060
gtgcaagggg acaatcagac catagccgta acaaaaaggg tacccagcac atggccctac 15120
aaccttaaga aacgggaagc tgctagagta actagagatt actttgtaat tcttaggcaa 15180
aggctacatg atattggcca tcacctcaag gcaaatgaga caattgtttc atcacatttt 15240
tttgtctatt caaaaggaat atattatgat gggctacttg tgtcccaatc actcaagagc 15300
atcgcaagat gtgtattctg gtcagagact atagttgatg aaacaagggc agcatgcagt 15360
aatattgcta caacaatggc taaaagcatc gagagaggtt atgaccgtta ccttgcatat 15420
tccctgaacg tcctaaaagt gatacagcaa attctgatct ctcttggctt cacaatcaat 15480
tcaaccatga cccgggatgt agtcataccc ctcctcacaa acaacgacct cttaataagg 15540
atggcactgt tgcccgctcc tattgggggg atgaattatc tgaatatgag caggctgttt 15600
gtcagaaaca tcggtgatcc agtaacatca tcaattgctg atctcaagag aatgattctc 15660
gcctcactaa tgcctgaaga gaccctccat caagtaatga cacaacaacc ggggggactct 15720
tcattcctag actgggctag cgacccttac tcagcaaatc ttgtatgtgt ccagagcatc 15780
actagactcc tcaagaacat aactgcaagg tttgtcctga tccatagtcc aaacccaatg 15840
ttaaaaggat tattccatga tgacagtaaa gaagaggacg agggactggc ggcattcctc 15900
atggacaggc atattatagt acctagggca gctcatgaaa tcctggatca tagtgtcaca 15960
ggggcaagag agtctattgc aggcatgctg gataccacaa aaggcttgat tcgagccagc 16020
atgaggaagg gggggttaac ctctcgagtg ataaccagat tgtccaatta tgactatgaa 16080
caattcagag cagggatggt gctattgaca ggaagaaaga gaaatgtcct cattgacaaa 16140
gagtcatgtt cagtgcagct ggcgagagct ctaagaagcc atatgtgggc gaggctagct 16200
cgaggacggc ctatttacgg ccttgaggtc cctgatgtac tagaatctat gcgaggccac 16260
cttattcggc gtcatgagac atgtgtcatc tgcgagtgtg gatcagtcaa ctacggatgg 16320
tttttgtcc cctcgggttg ccaactggat gatattgaca aggaaacatc atccttgaga 16380
gtcccatata ttggttctac cactgatgag agaacagaca tgaagcttgc cttcgtaaga 16440
gccccaagtc gatccttgcg atctgctgtt agaatagcaa cagtgtactc atgggcttac 16500
ggtgatgatg atagctcttg gaacgaagcc tggttgttgg ctaggcaaag ggccaatgtg 16560
agcctggagg agctaagggt gatcactccc atctcaactt cgactaattt agcgcatagg 16620
ttgagggatc gtagcactca agtgaaatac tcaggtacat cccttgtccg agtggcgagg 16680
tataccacaa tctccaacga caatctctca tttgtcatat cagataagaa ggttgatact 16740
aactttatat accaacaagg aatgcttcta gggttgggtg ttttagaaac attgtttcga 16800
ctcgagaaag ataccggatc atctaacacg gtattacatc ttcacgtcga aacagattgt 16860
tgcgtgatcc cgatgataga tcatcccagg atacccagct cccgcaagct agagctgagg 16920
gcagagctat gtaccaaccc attgatatat gataatgcac ctttaattga cagagatgca 16980
acaaggctat acacccagag ccataggagg caccttgtgg aatttgttac atggtccaca 17040
ccccaactat atcacatttt agctaagtcc acagcactat ctatgattga cctggtaaca 17100
aaatttgaga aggaccatat gaatgaaatt tcagctctca taggggatga cgatatcaat 17160
agtttcataa ctgagtttct gctcatagag ccaagattat tcactatcta cttgggccag 17220
tgtgcggcca tcaattgggc atttgatgta cattatcata gaccatcagg gaaatatcag 17280
atgggtgagc tgttgtcatc gttcctttct agaatgagca aaggagtgtt taaggtgctt 17340
gtcaatgctc taagccaccc aaagatctac aagaaattct ggcattgtgg tattatagag 17400

```
cctatccatg gtccttcact tgatgctcaa aacttgcaca caactgtgtg caacatggtt  17460
tacacatgct atatgaccta cctcgacctg ttgttgaatg aagagttaga agagttcaca  17520
tttctcttgt gtgaaagcga cgaggatgta gtaccggaca gattcgacaa catccaggca  17580
aaacacttat gtgttctggc agatttgtac tgtcaaccag ggacctgccc accaattcga  17640
ggtctaagac cggtagagaa atgtgcagtt ctaaccgacc atatcaaggc agaggctatg  17700
ttatctccag caggatcttc gtggaacata aatccaatta ttgtagacca ttactcatgc  17760
tctctgactt atctccggcg aggatcgatc aaacagataa gattgagagt tgatccagga  17820
ttcattttcg acgccctcgc tgaggtaaat gtcagtcagc caaagatcgg cagcaacaac  17880
atctcaaata tgagcatcaa ggctttcaga cccccacacg atgatgttgc aaaattgctc  17940
aaagatatca acacaagcaa gcacaatctt cccatttcag gggcaatct cgccaattat  18000
gaaatccatg ctttccgcag aatcgggttg aactcatctg cttgctacaa agctgttgag  18060
atatcaacat taattaggag atgccttgag ccaggggagg acggcttgtt cttgggtgag  18120
ggatcgggtt ctatgttgat cacttataaa gagatactta aactaaacaa gtgcttctat  18180
aatagtgggg tttccgccaa ttctagatct ggtcaaaggg aattagcacc ctatccctcc  18240
gaagttggcc ttgtcgaaca cagaatggga gtaggtaata ttgtcaaagt gctctttaac  18300
gggaggcccg aagtcacgtg ggtaggcagt gtagattgct tcaatttcat agttagtaat  18360
atccctacct ctagtgtggg gtttatccat tcagatatag agaccttgcc tgacaaagat  18420
actatagaga agctagagga attggcagcc atcttatcga tggctctgct cctgggcaaa  18480
ataggatcaa tactggtgat taagcttatg cctttcagcg ggattttgt tcagggattt  18540
ataagttatg tagggtctca ttatagagaa gtgaaccttg tataccctag atacagcaac  18600
ttcatctcta ctgaatctta tttggttatg acagatctca aggctaaccg gctaatgaat  18660
cctgaaaaga ttaagcagca gataattgaa tcatctgtga ggacttcacc tggacttata  18720
ggtcacatcc tatccattaa gcaactaagc tgcatacaag caattgtggg agacgcagtt  18780
agtagaggtg atatcaatcc tactctgaaa aaacttacac ctatagagca ggtgctgatc  18840
aattgcgggt tggcaattaa cggacctaag ctgtgcaaag aattgatcca ccatgatgtt  18900
gcctcagggc aagatggatt gcttaattct atactcatcc tctacaggga gttggcaaga  18960
ttcaaagaca accaaagaag tcaacaaggg atgttccacg cttaccccgt attggtaagt  19020
agcaggcaac gagaacttat atctaggatc acccgcaaat tctgggggca cattcttctt  19080
tactccggga acaaaaagtt gataaataag tttatccaga atctcaagtc cggctatctg  19140
atactagact tacaccagaa tatcttcgtt aagaatctat ccaagtcaga gaaacagatt  19200
attatgacgg ggggtttgaa acgtgagtgg gtttttaagg taacagtcaa ggagaccaaa  19260
gaatggtata agttagtcgg atacagtgcc ctgattaagg actaattggt tgaactccgg  19320
aaccctaatc ctgccctagg tggttaggca ttatttgcaa tatattaaag aaaactttga  19380
aaatacgaag tttctattcc cagctttgtc tggtggccgg catggtccca gcctcctcgc  19440
tggcgccggc tgggcaacat tccgagggga ccgtcccctc ggtaatggcg aatgggacgc  19500
ggccgatccg gctgctaaca aagcccgaaa ggaagctgag ttggctgctg ccaccgctga  19560
gcaataacta gcataacccc ttggggcctc taaacgggtc ttgaggggtt ttttgctgaa  19620
aggaggaact atatccggat gcggccgcgg gccctatggt acccagcttt tgttcccttt  19680
agtgagggtt aattccgagc ttggcgtaat catggtcata gctgtttcct gtgtgaaatt  19740
```

```
gttatccgct cacaattcca cacaacatag gagccggaag cataaagtgt aaagcctggg  19800
gtgcctaatg agtgaggtaa ctcacattaa ttgcgttgcg ctcactgccc gctttccagt  19860
cgggaaacct gtcgtgccag ctgcattaat gaatcggcca acgcgcgggg agaggcggtt  19920
tgcgtattgg gcgctcttcc gcttcctcgc tcactgactc gctgcgctcg gtcgttcggc  19980
tgcggcgagc ggtatcagct cactcaaagg cggtaatacg gttatccaca gaatcagggg  20040
ataacgcagg aaagaacatg tgagcaaaag gccagcaaaa ggccaggaac cgtaaaaagg  20100
ccgcgttgct ggcgtttttc cataggctcg gcccccctga cgagcatcac aaaaatcgac  20160
gctcaagtca gaggtggcga aacccgacag gactataaag ataccaggcg tttccccctg  20220
gaagctccct cgtgcgctct cctgttccga ccctgccgct taccggatac ctgtccgcct  20280
ttctcccttc gggaagcgtg gcgctttctc aatgctcacg ctgtaggtat ctcagttcgg  20340
tgtaggtcgt tcgctccaag ctgggctgtg tgcacgaacc ccccgttcag cccgaccgct  20400
gcgccttatc cggtaactat cgtcttgagt ccaacccggt aagacacgac ttatcgccac  20460
tggcagcagc cactggtaac aggattagca gagcgaggta tgtaggcggt gctacagagt  20520
tcttgaagtg gtggcctaac tacggctaca ctagaaggac agtatttggt atctgcgctc  20580
tgctgaagcc agttaccttc ggaaaaagag ttggtagctc ttgatccggc aaacaaacca  20640
ccgctggtag cggtggtttt tttgtttgca agcagcagat tacgcgcaga aaaaaaggat  20700
ctcaagaaga tcctttgatc ttttctacgg ggtctgacgc tcagtggaac gaaaactcac  20760
gttaagggat tttggtcatg agattatcaa aaaggatctt cacctagatc cttttaaatt  20820
aaaaatgaag ttttaaatca atctaaagta tatatgagta aacttggtct gacagttacc  20880
aatgcttaat cagtgaggca cctatctcag cgatctgtct atttcgttca tccatagttg  20940
cctgactgcc cgtcgtgtag ataactacga tacgggaggg cttaccatct ggccccagtg  21000
ctgcaatgat accgcgagac ccacgctcac cggctccaga tttatcagca ataaaccagc  21060
cagccggaag ggccgagcgc agaagtggtc ctgcaacttt atccgcctcc atccagtcta  21120
ttaattgttg ccgggaagct agagtaagta gttcgccagt taatagtttg cgcaacgttg  21180
ttgccattgc tacaggcatc gtggtgtcac gctcgtcgtt tggtatggct tcattcagct  21240
ccggttccca acgatcaagg cgagttacat gatcccccat gttgtgaaaa aaagcggtta  21300
gctccttcgg tcctccgatc gttgtcagaa gtaagttggc cgcagtgtta tcactcatgc  21360
ttatggcagc actgcataat tctcttactg tcatgccatc cgtaagatgc ttttctgtga  21420
ctggtgagta ctcaaccaag tcattctgag aatagtgtat gcggcgaccg agttgctctt  21480
gcccggcgtc aatacgggat aataccgcgc cacatagcag aactttaaaa gtgctcatca  21540
ttggaaaacg ttcttcgggg cgaaaactct caaggatctt accgctgttg agatccagtt  21600
cgatgtaacc cactcgtgca cccaactgat cttcagcatc ttttactttc accagcgttt  21660
ctgggtgagc aaaaacagga aggcaaaatg ccgcaaaaaa gggaataagg gcgacacgga  21720
aatgttgaat actcatactc ttcctttttc aatattattg aagcatttat cagggttatt  21780
gtctcatgag cggatacata tttgaatgta tttagaaaaa taaacaaata ggggttccgc  21840
gcacatttcc ccgaaaagtg ccacctgaaa ttgtaaacgt taatattttg ttaaaattcg  21900
cgttaaattt ttgttaaatc agctcatttt ttaaccaata ggccgaaatc ggcaaaatcc  21960
cttataaatc aaaagaatag accgagatag ggttgagtgt tgttccagtt tggaacaaga  22020
gtccactatt aaagaacgtg gactccaacg tcaaagggcg aaaaaccgtc tatcagggcg  22080
atggcccact acgtgaacca tcaccctaat caagtttttt ggggtcgagg tgccgtaaag  22140
```

```
cactaaatcg gaaccctaaa gggagccccc gatttagagc ttgacgggga aagccggcga  22200

acgtggcgag aaaggaaggg aagaaagcga aaggagcggg cgctagggcg ctggcaagtg  22260

tagcggtcac gctgcgcgta accaccacac ccgccgcgct taatgcgccg ctacagggcg  22320

cgtcccattc gccattcagg ctgcgcaact gttgggaagg gcgatcggtg cgggcctctt  22380

cgctattacg ccagccaccg cggtg                                        22405
```

```
<210> SEQ ID NO 12
<211> LENGTH: 21007
<212> TYPE: DNA
<213> ORGANISM: Artificial Sequence
<220> FEATURE:
<223> OTHER INFORMATION: Plasmide MeV-Z-GPC

<400> SEQUENCE: 12

gcggccgcta atacgactca ctatagggcc aactttgttt ggtctgatga gtccgtgagg     60

acgaaacccg gagtcccggg tcaccaaaca aagttgggta aggatagttc aatcaatgat    120

catcttctag tgcacttagg attcaagatc ctattatcag ggacaagagc aggattaggg    180

atatccgaga cgcgtacgat gggcaataag caggcaaagg cacccgaaag caaggattca    240

cctagagcat cactgattcc cgacgcaact catctggggc cacagttctg caaatcctgt    300

tggttcgaga acaaaggcct ggtggagtgc aataaccact acctgtgcct gaactgtctg    360

acactgctgc tgagtgtgag caacagatgc ccaatctgca agatgcctct gccaacaaag    420

ctgaggcctt ctgctgcacc caccgcacca ccaactggag ccgcagacag cattagaccc    480

cccccatact caccataagc gcgcagcgct tagacgtctc gcgatcgatt agtgcgagag    540

gccgagggcc agaacaacat ccgcctacca tccatcattg ttataaaaaa cttaggattc    600

aagatcctat tatcagggac aagagcagga ttagggatat ccgagatggc cacactttta    660

aggagcttag cattgttcaa aagaaacaag gacaaaccac ccattacatc aggatccggt    720

ggagccatca gaggaatcaa acacattatt atagtaccaa tccctggaga ttcctcaatt    780

accactcgat ccagacttct ggaccggttg gtgaggttaa ttggaaaccc ggatgtgagc    840

gggcccaaac taacaggggc actaataggt atattatcct tatttgtgga gtctccaggt    900

caattgattc agaggatcac cgatgaccct gacgttagca taaggctgtt agaggttgtc    960

cagagtgacc agtcacaatc tggccttacc ttcgcatcaa gaggtaccaa catggaggat   1020

gaggcggacc aatacttttc acatgatgat ccaattagta gtgatcaatc caggttcgga   1080

tggttcggga acaaggaaat ctcagatatt gaagtgcaag accctgaggg attcaacatg   1140

attctgggta ccatcctagc ccaaatttgg gtcttgctcg caaaggcggt tacggcccca   1200

gacacggcag ctgattcgga gctaagaagg tggataaagt acacccaaca aagaagggta   1260

gttggtgaat ttagattgga gagaaaatgg ttggatgtgg tgaggaacag gattgccgag   1320

gacctctcct tacgccgatt catggtcgct ctaatcctgg atatcaagag aacacccgga   1380

aacaaaccca ggattgctga aatgatatgt gacattgata catatatcgt agaggcagga   1440

ttagccagtt ttatcctgac tattaagttt gggatagaaa ctatgtatcc tgctcttgga   1500

ctgcatgaat ttgctggtga gttatccaca cttgagtcct tgatgaacct ttaccagcaa   1560

atgggggaaa ctgcacccta catggtaatc ctggagaact caattcagaa caagttcagt   1620

gcaggatcat accctctgct ctggagctat gccatgggag taggagtgga acttgaaaac   1680

tccatgggag gtttgaactt tggccgatct tactttgatc cagcatattt tagattaggg   1740
```

-continued

```
caagagatgg taaggaggtc agctggaaag gtcagttcca cattggcatc tgaactcggt   1800
atcactgccg aggatgcaag gcttgtttca gagattgcaa tgcatactac tgaggacaag   1860
atcagtagag cggttggacc cagacaagcc caagtatcat ttctacacgg tgatcaaagt   1920
gagaatgagc taccgagatt ggggggcaag gaagatagga gggtcaaaca gagtcgagga   1980
gaagccaggg agagctacag agaaaccggg cccagcagag caagtgatgc gagagctgcc   2040
catcttccaa ccggcacacc cctagacatt gacactgcaa cggagtccag ccaagatccg   2100
caggacagtc gaaggtcagc tgacgccctg cttaggctgc aagccatggc aggaatctcg   2160
gaagaacaag gctcagacac ggacacccct atagtgtaca atgacagaaa tcttctagac   2220
taggtgcgag aggccgaggg ccagaacaac atccgcctac catccatcat tgttataaaa   2280
aacttaggaa ccaggtccac acagccgcca gcccatcaac catccactcc cacgattgga   2340
gccaatggca gaagagcagg cacgccatgt caaaaacgga ctggaatgca tccgggctct   2400
caaggccgag cccatcggct cactggccat cgaggaagct atggcagcat ggtcagaaat   2460
atcagacaac ccaggacagg agcgagccac ctgcagggaa gagaaggcag gcagttcggg   2520
tctcagcaaa ccatgcctct cagcaattgg atcaactgaa ggcggtgcac ctcgcatccg   2580
cggtcaggga cctggagaga gcgatgacga cgctgaaact ttgggaatcc ccccaagaaa   2640
tctccaggca tcaagcactg ggttacagtg ttattacgtt tatgatcaca gcggtgaagc   2700
ggttaaggga atccaagatg ctgactctat catggttcaa tcaggccttg atggtgatag   2760
caccctctca ggaggagaca atgaatctga aaacagcgat gtggatattg gcgaacctga   2820
taccgaggga tatgctatca ctgaccgggg atctgctccc atctctatgg ggttcagggc   2880
ttctgatgtt gaaactgcag aaggagggga gatccacgag ctcctgagac tccaatccag   2940
aggcaacaac tttccgaagc ttgggaaaac tctcaatgtt cctccgcccc cggaccccgg   3000
tagggccagc acttccggga cacccattaa aaagggcaca gacgcgagat tagcctcatt   3060
tggaacggag atcgcgtctt tattgacagg tggtgcaacc caatgtgctc gaaagtcacc   3120
ctcggaacca tcagggccag gtgcacctgc ggggaatgtc cccgagtgtg tgagcaatgc   3180
cgcactgata caggagtgga cacccgaatc tggtaccaca atctccccga gatcccagaa   3240
taatgaagaa gggggagact attatgatga tgagctgttc tctgatgtcc aagatattaa   3300
aacagccttg gccaaaatac acgaggataa tcagaagata atctccaagc tagaatcact   3360
gctgttattg aagggagaag ttgagtcaat taagaagcag atcaacaggc aaaatatcag   3420
catatccacc ctggaaggac acctctcaag catcatgatc gccattcctg gacttgggaa   3480
ggatcccaac gaccccactg cagatgtcga aatcaatccc gacttgaaac ccatcatagg   3540
cagagattca ggccgagcac tggccgaagt tctcaagaaa cccgttgcca gccgacaact   3600
ccaaggaatg acaaatggac ggaccagttc cagaggacag ctgctgaagg aatttcagct   3660
aaagccgatc gggaaaaaga tgagctcagc cgtcgggttt gttcctgaca ccggccctgc   3720
atcacgcagt gtaatccgct ccattataaa atccagccgg ctagaggagg atcggaagcg   3780
ttacctgatg actctccttg atgatatcaa aggagccaat gatcttgcca agttccacca   3840
gatgctgatg aagataataa tgaagtagct acagctcaac ttacctgcca accccatgcc   3900
agtcgaccca actagcctac cctccatcat tgttataaaa aacttaggaa ccaggtccac   3960
acagccgcca gcccatcaac gcgtacgatg ggccagattg tcacattctt tcaggaagtg   4020
ccacacgtca ttgaggaggt catgaacatc gtgctgattg ctctgtcagt gctggcagtg   4080
ctgaaaggac tgtacaactt cgctacctgt ggactggtgg gactggtcac attcctgctg   4140
```

```
ctgtgcggca gaagttgcac tacctcactg tacaaaggag tgtacgagct gcagactctg   4200
gaactgaaca tggagacact gaatatgaca atgcctctga gctgcaccaa gaataatagc   4260
caccactata tcatggtcgg gaacgaaacc ggcctggaac tgaccctgac aaacaccagc   4320
atcattaacc acaagttctg caatctgagc gacgctcaca agaagaacct gtatgaccac   4380
gctctgatgt ccatcatcag tacctttcac ctgtccatcc ccaatttcaa ccagtacgag   4440
gcaatgtcat gcgacttcaa cgggggcaag atcagtgtcc agtacaacct gagccactcc   4500
tacgccggcg acgcagccaa ccactgcgga actgtcgcca atggcgtgct gcagacattc   4560
atgaggatgg catggggggg atcttacatc gcactggata gcggcagggg caattgggat   4620
tgcatcatga cttcctatca gtatctgatt atccagaata ctacatggga ggatcattgc   4680
cagttcagtc ggcccagccc tattggatat ctggggctgc tgtcacagag aacacgggat   4740
atctatattt caagacgcct gctgggcaca ttcacttgga cactgtcaga cagtgagggc   4800
aaggatactc cagggggcta ctgcctgaca cgatggatgc tgatcgaagc agagctgaaa   4860
tgcttcggca ataccgcagt ggccaagtgc aacgagaaac acgacgagga gttctgcgac   4920
atgctgaggc tgttcgactt caacaaacag gctatccaga gactgaaggc agaagcccag   4980
atgtcaatcc agctgatcaa caaggcagtg aacgccctga tcaacgacca gctgatcatg   5040
aagaaccacc tgagagacat tatgggcatc ccctactgta attacagcaa gtattggtac   5100
ctgaaccaca ctacaaccgg gagaacatcc ctgcccaagt gctggctggt cagcaatggg   5160
agttatctga atgaaaccca tttcagcgac gatatcgaac agcaggctga caacatgatc   5220
acagagatgc tgcagaaaga gtacatggaa agacagggca agacaccact gggactggtc   5280
gatctgttcg tcttctccac tagcttctat ctgatttcca tcttcctgca cctggtgaag   5340
atccccactc ataggcacat tgtcggcaag agttgcccta aaccccatag gctgaatcac   5400
atggggattt gtagttgcgg cctgtataag cagcctggcg tgcctgtgaa gtggaagaga   5460
tgagcgcgca gcgcttagac gtctcgcgat cgatactagt acaacctaaa tccattataa   5520
aaaacttagg agcaaagtga ttgcctccca aggtccacaa tgacagagac ctacgacttc   5580
gacaagtcgg catgggacat caaagggtcg atcgctccga tacaacccac cacctacagt   5640
gatggcaggc tggtgcccca ggtcagagtc atagatcctg gtctaggcga caggaaggat   5700
gaatgcttta tgtacatgtt tctgctgggg gttgttgagg acagcgattc cctagggcct   5760
ccaatcgggc gagcatttgg gttcctgccc ttaggtgttg gcagatccac agcaaagccc   5820
gaaaaactcc tcaaagaggc cactgagctt gacatagttg ttagacgtac agcagggctc   5880
aatgaaaaac tggtgttcta caacaacacc ccactaactc tcctcacacc ttggagaaag   5940
gtcctaacaa cagggagtgt cttcaacgca aaccaagtgt gcaatgcggt taatctgata   6000
ccgctcgata ccccgcagag gttccgtgtt gtttatatga gcatcacccg tctttcggat   6060
aacgggtatt acaccgttcc tagaagaatg ctggaattca gatcggtcaa tgcagtggcc   6120
ttcaacctgc tggtgaccct taggattgac aaggcgatag gccctgggaa gatcatcgac   6180
aatacagagc aacttcctga ggcaacattt atggtccaca tcgggaactt caggagaaag   6240
aagagtgaag tctactctgc cgattattgc aaaatgaaaa tcgaaaagat gggcctggtt   6300
tttgcacttg gtgggatagg gggcaccagt cttcacatta gaagcacagg caaaatgagc   6360
aagactctcc atgcacaact cgggttcaag aagaccttat gttacccgct gatggatatc   6420
aatgaagacc ttaatcgatt actctggagg agcagatgca agatagtaag aatccaggca   6480
```

-continued

```
gttttgcagc catcagttcc tcaagaattc cgcatttacg acgacgtgat cataaatgat   6540
gaccaaggac tattcaaagt tctgtagacc gtagtgccca gcaatgcccg aaaacgaccc   6600
ccctcacaat gacagccaga aggcccggac aaaaaagccc cctccgaaag actccacgga   6660
ccaagcgaga ggccagccag cagccgacgg caagcgcgaa caccaggcgg ccccagcaca   6720
gaacagccct gacacaaggc caccaccagc caccccaatc tgcatcctcc tcgtgggacc   6780
cccgaggacc aacccccaag gctgccccg atccaaacca ccaaccgcat ccccaccacc   6840
cccgggaaag aaacccccag caattggaag gcccctcccc ctcttcctca acacaagaac   6900
tccacaaccg aaccgcacaa gcgaccgagg tgacccaacc gcaggcatcc gactccctag   6960
acagatcctc tctccccggc aaactaaaca aaacttaggg ccaaggaaca tacacaccca   7020
acagaaccca gaccccggcc cacggcgccg cgcccccaac ccccgacaac cagagggagc   7080
ccccaaccaa tcccgccggc tcccccggtg cccacaggca gggacaccaa cccccgaaca   7140
gacccagcac ccaaccatcg acaatccaag acgggggggc ccccccaaaa aaaggccccc   7200
aggggccgac agccagcacc gcgaggaagc ccacccaccc cacacacgac cacggcaacc   7260
aaaccagaac ccagaccacc ctgggccacc agctcccaga ctcggccatc accccgcaga   7320
aaggaaaggc cacaacccgc gcaccccagc cccgatccgg cggggagcca cccaacccga   7380
accagcaccc aagagcgatc cccgaaggac ccccgaaccg caaaggacat cagtatccca   7440
cagcctctcc aagtcccccg gtctcctcct cttctcgaag ggaccaaaag atcaatccac   7500
cacacccgac gacactcaac tccccacccc taaaggagac accgggaatc ccagaatcaa   7560
gactcatcca atgtccatca tgggtctcaa ggtgaacgtc tctgccatat tcatggcagt   7620
actgttaact ctccaaacac ccaccggtca aatccattgg ggcaatctct ctaagatagg   7680
ggtggtagga ataggaagtg caagctacaa agttatgact cgttccagcc atcaatcatt   7740
agtcataaaa ttaatgccca atataactct cctcaataac tgcacgaggg tagagattgc   7800
agaatacagg agactactga gaacagtttt ggaaccaatt agagatgcac ttaatgcaat   7860
gacccagaat ataagaccgg ttcagagtgt agcttcaagt aggagacaca agagatttgc   7920
gggagtagtc ctggcaggtg cggccctagg cgttgccaca gctgctcaga taacagccgg   7980
cattgcactt caccagtcca tgctgaactc tcaagccatc gacaatctga gagcgagcct   8040
ggaaactact aatcaggcaa ttgagacaat cagacaagca gggcaggaga tgatattggc   8100
tgttcagggt gtccaagact acatcaataa tgagctgata ccgtctatga accaactatc   8160
ttgtgattta atcggccaga agctcgggct caaattgctc agatactata cagaaatcct   8220
gtcattattt ggccccagtt tacgggaccc catatctgcg gagatatcta tccaggcttt   8280
gagctatgcg cttggaggag acatcaataa ggtgttagaa aagctcggat acagtggagg   8340
tgatttactg ggcatcttag agagcggagg aataaaggcc cggataactc acgtcgacac   8400
agagtcctac ttcattgtcc tcagtatagc ctatccgacg ctgtccgaga ttaagggggt   8460
gattgtccac cggctagagg gggtctcgta caacataggc tctcaagagt ggtataccac   8520
tgtgcccaag tatgttgcaa cccaagggta ccttatctcg aattttgatg agtcatcgtg   8580
tactttcatg ccagagggga ctgtgtgcag ccaaaatgcc ttgtacccga tgagtcctct   8640
gctccaagaa tgcctccggg ggtacaccaa gtcctgtgct cgtacactcg tatccgggtc   8700
ttttgggaac cggttcattt tatcacaagg gaacctaata gccaattgtg catcaatcct   8760
ttgcaagtgt tacacaacag gaacgatcat taatcaagac cctgacaaga tcctaacata   8820
cattgctgcc gatcactgcc cggtagtcga ggtgaacggc gtgaccatcc aagtcgggag   8880
```

```
caggaggtat ccagacgctg tgtacttgca cagaattgac ctcggtcctc ccatatcatt    8940
ggagaggttg gacgtaggga caaatctggg gaatgcaatt gctaagttgg aggatgccaa    9000
ggaattgttg gagtcatcgg accagatatt gaggagtatg aaaggtttat cgagcactag    9060
catagtctac atcctgattg cagtgtgtct tggagggttg atagggatcc ccgctttaat    9120
atgttgctgc agggggcgtt gtaacaaaaa gggagaacaa gttggtatgt caagaccagg    9180
cctaaagcct gatcttacgg gaacatcaaa atcctatgta aggtcgctct gatcctctac    9240
aactcttgaa acacaaatgt cccacaagtc tcctcttcgt catcaagcaa ccaccgcacc    9300
cagcatcaag cccacctgaa attatctccg gcttccctct ggccgaacaa tatcggtagt    9360
taatcaaaac ttagggtgca agatcatcca caatgtcacc acaacgagac cggataaatg    9420
ccttctacaa agataacccc catcccaagg gaagtaggat agtcattaac agagaacatc    9480
ttatgattga tagaccttat gttttgctgg ctgttctgtt tgtcatgttt ctgagcttga    9540
tcgggttgct agccattgca ggcattagac ttcatcgggc agccatctac accgcagaga    9600
tccataaaag cctcagcacc aatctagatg taactaactc aatcgagcat caggtcaagg    9660
acgtgctgac accactcttc aaaatcatcg gtgatgaagt gggcctgagg acacctcaga    9720
gattcactga cctagtgaaa ttaatctctg acaagattaa attccttaat ccggataggg    9780
agtacgactt cagagatctc acttggtgta tcaacccgcc agagagaatc aaattggatt    9840
atgatcaata ctgtgcagat gtggctgctg aagagctcat gaatgcattg gtgaactcaa    9900
ctctactgga gaccagaaca accaatcagt tcctagctgt ctcaaaggga aactgctcag    9960
ggcccactac aatcagaggt caattctcaa acatgtcgct gtccctgtta gacttgtatt   10020
taggtcgagg ttacaatgtg tcatctatag tcactatgac atcccaggga atgtatgggg   10080
gaacttacct agtggaaaag cctaatctga gcagcaaaag gtcagagttg tcacaactga   10140
gcatgtaccg agtgtttgaa gtaggtgtta tcagaaatcc gggtttgggg gctccggtgt   10200
tccatatgac aaactatctt gagcaaccag tcagtaatga tctcagcaac tgtatggtgg   10260
ctttggggga gctcaaactc gcagcccttt gtcacgggga agattctatc acaattccct   10320
atcagggatc agggaaaggt gtcagcttcc agctcgtcaa gctaggtgtc tggaaatccc   10380
caaccgacat gcaatcctgg gtccccttat caacggatga tccagtgata gacaggcttt   10440
acctctcatc tcacagaggt gttatcgctg acaatcaagc aaaatgggct gtcccgacaa   10500
cacgaacaga tgacaagttg cgaatggaga catgcttcca acaggcgtgt aagggtaaaa   10560
tccaagcact ctgcgagaat cccgagtggg caccattgaa ggataacagg attccttcat   10620
acggggtctt gtctgttgat ctgagtctga cagttgagct taaaatcaaa attgcttcgg   10680
gattcgggcc attgatcaca cacggttcag ggatggacct atacaaatcc aaccacaaca   10740
atgtgtattg gctgactatc ccgccaatga agaacctagc cttaggtgta atcaacacat   10800
tggagtggat accgagattc aaggttagtc cctacctctt cactgtccca attaaggaag   10860
caggcgaaga ctgccatgcc ccaacatacc tacctgcgga ggtggatggt gatgtcaaac   10920
tcagttccaa tctggtgatt ctacctggtc aagatctcca atatgttttg gcaacctacg   10980
atacttccag ggttgaacat gctgtggttt attacgttta cagcccaagc cgctcatttt   11040
cttactttta tccttttagg ttgcctataa agggggtccc catcgaatta caagtggaat   11100
gcttcacatg ggaccaaaaa ctctggtgcc gtcacttctg tgtgcttgcg gactcagaat   11160
ctggtggaca tatcactcac tctgggatgg tgggcatggg agtcagctgc acagtcaccc   11220
```

```
gggaagatgg aaccaatcgc agatagggct gctagtgaac caatcacatg atgtcaccca  11280
gacatcaggc atacccacta gtgtgaaata gacatcagaa ttaagaaaaa cgtagggtcc  11340
aagtggttcc ccgttatgga ctcgctatct gtcaaccaga tcttataccc tgaagttcac  11400
ctagatagcc cgatagttac caataagata gtagccatcc tggagtatgc tcgagtccct  11460
cacgcttaca gcctggagga ccctacactg tgtcagaaca tcaagcaccg cctaaaaaac  11520
ggattttcca accaaatgat tataaacaat gtggaagttg ggaatgtcat caagtccaag  11580
cttaggagtt atccggccca ctctcatatt ccatatccaa attgtaatca ggatttattt  11640
aacatagaag acaaagagtc aacgaggaag atccgtgaac tcctcaaaaa ggggaattcg  11700
ctgtactcca aagtcagtga taaggttttc caatgcttaa gggacactaa ctcacggctt  11760
ggcctaggct ccgaattgag ggaggacatc aaggagaaag ttattaactt gggagtttac  11820
atgcacagct cccagtggtt tgagcccttt ctgttttggt ttacagtcaa gactgagatg  11880
aggtcagtga ttaaatcaca aacccatact tgccatagga ggagacacac acctgtattc  11940
ttcactggta gttcagttga gttgctaatc tctcgtgacc ttgttgctat aatcagtaaa  12000
gagtctcaac atgtatatta cctgacattt gaactggttt tgatgtattg tgatgtcata  12060
gaggggaggt taatgacaga gaccgctatg actattgatg ctaggtatac agagcttcta  12120
ggaagagtca gatacatgtg gaaactgata gatggtttct tccctgcact cgggaatcca  12180
acttatcaaa ttgtagccat gctggagcct ctttcacttg cttacctgca gctgagggat  12240
ataacagtag aactcagagg tgctttcctt aaccactgct ttactgaaat acatgatgtt  12300
cttgaccaaa acgggttttc tgatgaaggt acttatcatg agttaactga agctctagat  12360
tacattttca taactgatga catacatctg acaggggaga ttttctcatt tttcagaagt  12420
ttcggccacc ccagacttga agcagtaacg gctgctgaaa atgttaggaa atacatgaat  12480
cagcctaaag tcattgtgta tgagactctg atgaaaggtc atgccatatt ttgtggaatc  12540
ataatcaacg gctatcgtga caggcacgga ggcagttggc caccgctgac cctccccctg  12600
catgctgcag acacaatccg gaatgctcaa gcttcaggtg aagggttaac acatgagcag  12660
tgcgttgata actggaaatc ttttgctgga gtgaaatttg gctgctttat gcctcttagc  12720
ctggatagtg atctgacaat gtacctaaag gacaaggcac ttgctgctct ccaaagggaa  12780
tgggattcag tttacccgaa agagttcctg cgttacgacc ctcccaaggg aaccgggtca  12840
cggaggcttg tagatgtttt ccttaatgat tcgagctttg acccatatga tgtgataatg  12900
tatgttgtaa gtggagctta cctccatgac cctgagttca acctgtctta cagcctgaaa  12960
gaaaaggaga tcaaggaaac aggtagactt tttgctaaaa tgacttacaa aatgagggca  13020
tgccaagtga ttgctgaaaa tctaatctca aacgggattg gcaaatattt taaggacaat  13080
gggatggcca aggatgagca cgatttgact aaggcactcc acactctagc tgtctcagga  13140
gtccccaaag atctcaaaga aagtcacagg ggggggccag tcttaaaaac ctactcccga  13200
agcccagtcc acacaagtac caggaacgtg agagcagcaa aagggtttat agggttccct  13260
caagtaattc ggcaggacca agacactgat catccggaga atatggaagc ttacgagaca  13320
gtcagtgcat ttatcacgac tgatctcaag aagtactgcc ttaattggag atatgagacc  13380
atcagcttgt ttgcacagag gctaaatgag atttacggat tgccctcatt tttccagtgg  13440
ctgcataaga ggcttgagac ctctgtcctg tatgtaagtg accctcattg cccccccgac  13500
cttgacgccc atatcccgtt atataaagtc cccaatgatc aaatcttcat taagtaccct  13560
atgggaggta tagaagggta ttgtcagaag ctgtggacca tcagcaccat tccctatcta  13620
```

```
tacctggctg cttatgagag cggagtaagg attgcttcgt tagtgcaagg ggacaatcag  13680
accatagccg taacaaaaag ggtacccagc acatggccct acaaccttaa gaaacgggaa  13740
gctgctagag taactagaga ttactttgta attcttaggc aaaggctaca tgatattggc  13800
catcacctca aggcaaatga gacaattgtt tcatcacatt tttttgtcta ttcaaaagga  13860
atatattatg atgggctact tgtgtcccaa tcactcaaga gcatcgcaag atgtgtattc  13920
tggtcagaga ctatagttga tgaaacaagg gcagcatgca gtaatattgc tacaacaatg  13980
gctaaaagca tcgagagagg ttatgaccgt taccttgcat attccctgaa cgtcctaaaa  14040
gtgatacagc aaattctgat ctctcttggc ttcacaatca attcaaccat gacccgggat  14100
gtagtcatac ccctcctcac aaacaacgac ctcttaataa ggatggcact gttgcccgct  14160
cctattgggg ggatgaatta tctgaatatg agcaggctgt ttgtcagaaa catcggtgat  14220
ccagtaacat catcaattgc tgatctcaag agaatgattc tcgcctcact aatgcctgaa  14280
gagaccctcc atcaagtaat gacacaacaa ccgggggact cttcattcct agactgggct  14340
agcgaccctt actcagcaaa tcttgtatgt gtccagagca tcactagact cctcaagaac  14400
ataactgcaa ggtttgtcct gatccatagt ccaaacccaa tgttaaaagg attattccat  14460
gatgacagta aagaagagga cgagggactg gcggcattcc tcatggacag gcatattata  14520
gtacctaggg cagctcatga aatcctggat catagtgtca caggggcaag agagtctatt  14580
gcaggcatgc tggataccac aaaaggcttg attcgagcca gcatgaggaa ggggggggtta  14640
acctctcgag tgataaccag attgtccaat tatgactatg aacaattcag agcagggatg  14700
gtgctattga caggaagaaa gagaaatgtc ctcattgaca aagagtcatg ttcagtgcag  14760
ctggcgagag ctctaagaag ccatatgtgg gcgaggctag ctcgaggacg gcctatttac  14820
ggccttgagg tccctgatgt actagaatct atgcgaggcc accttattcg gcgtcatgag  14880
acatgtgtca tctgcgagtg tggatcagtc aactacggat ggttttttgt cccctcgggt  14940
tgccaactgg atgatattga caaggaaaca tcatccttga gagtcccata tattggttct  15000
accactgatg agagaacaga catgaagctt gccttcgtaa gagccccaag tcgatccttg  15060
cgatctgctg ttagaatagc aacagtgtac tcatgggctt acggtgatga tgatagctct  15120
tggaacgaag cctggttgtt ggctaggcaa agggccaatg tgagcctgga ggagctaagg  15180
gtgatcactc ccatctcaac ttcgactaat ttagcgcata ggttgaggga tcgtagcact  15240
caagtgaaat actcaggtac atcccttgtc cgagtggcga ggtataccac aatctccaac  15300
gacaatctct catttgtcat atcagataag aaggttgata ctaactttat ataccaacaa  15360
ggaatgcttc tagggttggg tgttttagaa acattgtttc gactcgagaa agataccgga  15420
tcatctaaca cggtattaca tcttcacgtc gaaacagatt gttgcgtgat cccgatgata  15480
gatcatccca ggatacccag ctcccgcaag ctagagctga gggcagagct atgtaccaac  15540
ccattgatat atgataatgc acctttaatt gacagagatg caacaaggct atacacccag  15600
agccatagga ggcaccttgt ggaatttgtt acatggtcca caccccaact atatcacatt  15660
ttagctaagt ccacagcact atctatgatt gacctggtaa caaaatttga gaaggaccat  15720
atgaatgaaa tttcagctct catagggggat gacgatatca atagtttcat aactgagttt  15780
ctgctcatag agccaagatt attcactatc tacttgggcc agtgtgcggc catcaattgg  15840
gcatttgatg tacattatca tagaccatca gggaaatatc agatgggtga gctgttgtca  15900
tcgttccttt ctagaatgag caaaggagtg tttaaggtgc ttgtcaatgc tctaagccac  15960
```

```
ccaaagatct acaagaaatt ctggcattgt ggtattatag agcctatcca tggtccttca  16020
cttgatgctc aaaacttgca cacaactgtg tgcaacatgg tttacacatg ctatatgacc  16080
tacctcgacc tgttgttgaa tgaagagtta gaagagttca catttctctt gtgtgaaagc  16140
gacgaggatg tagtaccgga cagattcgac aacatccagg caaaacactt atgtgttctg  16200
gcagatttgt actgtcaacc agggacctgc ccaccaattc gaggtctaag accggtagag  16260
aaatgtgcag ttctaaccga ccatatcaag gcagaggcta tgttatctcc agcaggatct  16320
tcgtggaaca taaatccaat tattgtagac cattactcat gctctctgac ttatctccgg  16380
cgaggatcga tcaaacagat aagattgaga gttgatccag gattcatttt cgacgccctc  16440
gctgaggtaa atgtcagtca gccaaagatc ggcagcaaca acatctcaaa tatgagcatc  16500
aaggctttca gaccccccaca cgatgatgtt gcaaaattgc tcaaagatat caacacaagc  16560
aagcacaatc ttcccatttc agggggcaat ctcgccaatt atgaaatcca tgctttccgc  16620
agaatcgggt tgaactcatc tgcttgctac aaagctgttg agatatcaac attaattagg  16680
agatgccttg agccagggga ggacggcttg ttcttgggtg agggatcggg ttctatgttg  16740
atcacttata aagagatact taaactaaac aagtgcttct ataatagtgg ggtttccgcc  16800
aattctagat ctggtcaaag ggaattagca ccctatccct ccgaagttgg ccttgtcgaa  16860
cacagaatgg gagtaggtaa tattgtcaaa gtgctcttta acgggaggcc cgaagtcacg  16920
tgggtaggca gtgtagattg cttcaatttc atagttagta atatccctac ctctagtgtg  16980
gggtttatcc attcagatat agagaccttg cctgacaaag atactataga gaagctagag  17040
gaattggcag ccatcttatc gatggctctg ctcctgggca aaataggatc aatactggtg  17100
attaagctta tgcctttcag cggggatttt gttcagggat ttataagtta tgtagggtct  17160
cattatagag aagtgaacct tgtataccct agatacagca acttcatctc tactgaatct  17220
tatttggtta tgacagatct caaggctaac cggctaatga atcctgaaaa gattaagcag  17280
cagataattg aatcatctgt gaggacttca cctggactta taggtcacat cctatccatt  17340
aagcaactaa gctgcataca agcaattgtg ggagacgcag ttagtagagg tgatatcaat  17400
cctactctga aaaaacttac acctatagag caggtgctga tcaattgcgg gttggcaatt  17460
aacggaccta agctgtgcaa agaattgatc caccatgatg ttgcctcagg gcaagatgga  17520
ttgcttaatt ctatactcat cctctacagg gagttggcaa gattcaaaga caaccaaaga  17580
agtcaacaag ggatgttcca cgcttacccc gtattggtaa gtagcaggca acgagaactt  17640
atatctagga tcacccgcaa attctggggg cacattcttc tttactccgg gaacaaaaag  17700
ttgataaata agtttatcca gaatctcaag tccggctatc tgatactaga cttacaccag  17760
aatatcttcg ttaagaatct atccaagtca gagaaacaga ttattatgac ggggggtttg  17820
aaacgtgagt gggtttttaa ggtaacagtc aaggagacca aagaatggta taagttagtc  17880
ggatacagtg ccctgattaa ggactaattg gttgaactcc ggaaccctaa tcctgcccta  17940
ggtggttagg cattatttgc aatatattaa agaaaacttt gaaaatacga agtttctatt  18000
cccagctttg tctggtggcc ggcatggtcc cagcctcctc gctggcgccg gctgggcaac  18060
attccgaggg gaccgtcccc tcggtaatgg cgaatgggac gcggccgatc cggctgctaa  18120
caaagcccga aaggaagctg agttggctgc tgccaccgct gagcaataac tagcataacc  18180
ccttggggcc tctaaacggg tcttgagggg ttttttgctg aaaggaggaa ctatatccgg  18240
atgcggccgc gggccctatg gtacccagct tttgttccct ttagtgaggg ttaattccga  18300
gcttggcgta atcatggtca tagctgtttc ctgtgtgaaa ttgttatccg ctcacaattc  18360
```

```
cacacaacat aggagccgga agcataaagt gtaaagcctg gggtgcctaa tgagtgaggt  18420
aactcacatt aattgcgttg cgctcactgc ccgctttcca gtcgggaaac ctgtcgtgcc  18480
agctgcatta atgaatcggc caacgcgcgg ggagaggcgg tttgcgtatt gggcgctctt  18540
ccgcttcctc gctcactgac tcgctgcgct cggtcgttcg gctgcggcga gcggtatcag  18600
ctcactcaaa ggcggtaata cggttatcca cagaatcagg ggataacgca ggaaagaaca  18660
tgtgagcaaa aggccagcaa aaggccagga accgtaaaaa ggccgcgttg ctggcgtttt  18720
tccataggct ccgcccccct gacgagcatc acaaaaatcg acgctcaagt cagaggtggc  18780
gaaacccgac aggactataa agataccagg cgtttccccc tggaagctcc ctcgtgcgct  18840
ctcctgttcc gaccctgccg cttaccggat acctgtccgc ctttctccct tcgggaagcg  18900
tggcgctttc tcaatgctca cgctgtaggt atctcagttc ggtgtaggtc gttcgctcca  18960
agctgggctg tgtgcacgaa ccccccgttc agcccgaccg ctgcgcctta tccggtaact  19020
atcgtcttga gtccaacccg gtaagacacg acttatcgcc actggcagca gccactggta  19080
acaggattag cagagcgagg tatgtaggcg gtgctacaga gttcttgaag tggtggccta  19140
actacggcta cactagaagg acagtatttg gtatctgcgc tctgctgaag ccagttacct  19200
tcggaaaaag agttggtagc tcttgatccg gcaaacaaac caccgctggt agcggtggtt  19260
tttttgtttg caagcagcag attacgcgca gaaaaaaagg atctcaagaa gatcctttga  19320
tcttttctac ggggtctgac gctcagtgga acgaaaactc acgttaaggg attttggtca  19380
tgagattatc aaaaaggatc ttcacctaga tccttttaaa ttaaaaatga agttttaaat  19440
caatctaaag tatatatgag taaacttggt ctgacagtta ccaatgctta atcagtgagg  19500
cacctatctc agcgatctgt ctatttcgtt catccatagt tgcctgactg cccgtcgtgt  19560
agataactac gatacgggag ggcttaccat ctggccccag tgctgcaatg ataccgcgag  19620
acccacgctc accggctcca gatttatcag caataaacca gccagccgga agggccgagc  19680
gcagaagtgg tcctgcaact ttatccgcct ccatccagtc tattaattgt tgccgggaag  19740
ctagagtaag tagttcgcca gttaatagtt tgcgcaacgt tgttgccatt gctacaggca  19800
tcgtggtgtc acgctcgtcg tttggtatgg cttcattcag ctccggttcc caacgatcaa  19860
ggcgagttac atgatccccc atgttgtgaa aaaaagcggt tagctccttc ggtcctccga  19920
tcgttgtcag aagtaagttg gccgcagtgt tatcactcat gcttatggca gcactgcata  19980
attctcttac tgtcatgcca tccgtaagat gcttttctgt gactggtgag tactcaacca  20040
agtcattctg agaatagtgt atgcggcgac cgagttgctc ttgcccggcg tcaatacggg  20100
ataataccgc gccacatagc agaactttaa aagtgctcat cattggaaaa cgttcttcgg  20160
ggcgaaaact ctcaaggatc ttaccgctgt tgagatccag ttcgatgtaa cccactcgtg  20220
cacccaactg atcttcagca tcttttactt tcaccagcgt ttctgggtga gcaaaaacag  20280
gaaggcaaaa tgccgcaaaa aagggaataa gggcgacacg gaaatgttga atactcatac  20340
tcttcctttt tcaatattat tgaagcattt atcagggtta ttgtctcatg agcggataca  20400
tatttgaatg tatttagaaa aataaacaaa taggggttcc gcgcacattt ccccgaaaag  20460
tgccacctga aattgtaaac gttaatattt tgttaaaatt cgcgttaaat ttttgttaaa  20520
tcagctcatt ttttaaccaa taggccgaaa tcggcaaaat cccttataaa tcaaaagaat  20580
agaccgagat agggttgagt gttgttccag tttggaacaa gagtccacta ttaaagaacg  20640
tggactccaa cgtcaaaggg cgaaaaaccg tctatcaggg cgatggccca ctacgtgaac  20700
```

catcacccta atcaagtttt ttggggtcga ggtgccgtaa agcactaaat cggaacccta 20760
aagggagccc ccgatttaga gcttgacggg gaaagccggc gaacgtggcg agaaaggaag 20820
ggaagaaagc gaaaggagcg ggcgctaggg cgctggcaag tgtagcggtc acgctgcgcg 20880
taaccaccac acccgccgcg cttaatgcgc cgctacaggg cgcgtcccat tcgccattca 20940
ggctgcgcaa ctgttgggaa gggcgatcgg tgcgggcctc ttcgctatta cgccagccac 21000
cgcggtg 21007

<210> SEQ ID NO 13
<211> LENGTH: 22861
<212> TYPE: DNA
<213> ORGANISM: Artificial Sequence
<220> FEATURE:
<223> OTHER INFORMATION: Plasmide MeV-Z-NP-GPC

<400> SEQUENCE: 13
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga cgcgtacgat gggcaataag caggcaaagg cacccgaaag caaggattca 240
cctagagcat cactgattcc cgacgcaact catctggggc cacagttctg caaatcctgt 300
tggttcgaga acaaaggcct ggtggagtgc aataaccact acctgtgcct gaactgtctg 360
acactgctgc tgagtgtgag caacagatgc ccaatctgca agatgcctct gccaacaaag 420
ctgaggcctt ctgctgcacc caccgcacca ccaactggag ccgcagacag cattagaccc 480
cccccatact caccataagc gcgcagcgct tagacgtctc gcgatcgatt agtgcgagag 540
gccgagggcc agaacaacat ccgcctacca tccatcattg ttataaaaaa cttaggattc 600
aagatcctat tatcagggac aagagcagga ttagggatat ccgagatggc cacactttta 660
aggagcttag cattgttcaa aagaaacaag gacaaaccac ccattacatc aggatccggt 720
ggagccatca gaggaatcaa acacattatt atagtaccaa tccctggaga ttcctcaatt 780
accactcgat ccagacttct ggaccggttg gtgaggttaa ttggaaaccc ggatgtgagc 840
gggcccaaac taacaggggc actaataggt atattatcct tatttgtgga gtctccaggt 900
caattgattc agaggatcac cgatgaccct gacgttagca taaggctgtt agaggttgtc 960
cagagtgacc agtcacaatc tggccttacc ttcgcatcaa gaggtaccaa catggaggat 1020
gaggcggacc aatacttttc acatgatgat ccaattagta gtgatcaatc caggttcgga 1080
tggttcggga acaaggaaat ctcagatatt gaagtgcaag accctgaggg attcaacatg 1140
attctgggta ccatcctagc ccaaatttgg gtcttgctcg caaaggcggt tacggcccca 1200
gacacggcag ctgattcgga gctaagaagg tggataaagt acacccaaca aagaagggta 1260
gttggtgaat ttagattgga gagaaaatgg ttggatgtgg tgaggaacag gattgccgag 1320
gacctctcct tacgccgatt catggtcgct ctaatcctgg atatcaagag aacacccgga 1380
aacaaaccca ggattgctga aatgatatgt gacattgata catatatcgt agaggcagga 1440
ttagccagtt ttatcctgac tattaagttt gggatagaaa ctatgtatcc tgctcttgga 1500
ctgcatgaat ttgctggtga gttatccaca cttgagtcct tgatgaacct ttaccagcaa 1560
atgggggaaa ctgcacccta catggtaatc ctggagaact caattcagaa caagttcagt 1620
gcaggatcat accctctgct ctggagctat gccatgggag taggagtgga acttgaaaac 1680
tccatgggag gtttgaactt tggccgatct tactttgatc cagcatattt tagattaggg 1740

```
caagagatgg taaggaggtc agctggaaag gtcagttcca cattggcatc tgaactcggt   1800
atcactgccg aggatgcaag gcttgtttca gagattgcaa tgcatactac tgaggacaag   1860
atcagtagag cggttggacc cagacaagcc caagtatcat ttctacacgg tgatcaaagt   1920
gagaatgagc taccgagatt gggggcaag gaagatagga gggtcaaaca gagtcgagga   1980
gaagccaggg agagctacag agaaaccggg cccagcagag caagtgatgc gagagctgcc   2040
catcttccaa ccggcacacc cctagacatt gacactgcaa cggagtccag ccaagatccg   2100
caggacagtc gaaggtcagc tgacgccctg cttaggctgc aagccatggc aggaatctcg   2160
gaagaacaag gctcagacac ggacacccct atagtgtaca atgacagaaa tcttctagac   2220
taggtgcgag aggccgaggg ccagaacaac atccgcctac catccatcat tgttataaaa   2280
aacttaggaa ccaggtccac acagccgcca gcccatcaac catccactcc cacgattgga   2340
gccaatggca gaagagcagg cacgccatgt caaaaacgga ctggaatgca tccgggctct   2400
caaggccgag cccatcggct cactggccat cgaggaagct atggcagcat ggtcagaaat   2460
atcagacaac ccaggacagg agcgagccac ctgcagggaa gagaaggcag gcagttcggg   2520
tctcagcaaa ccatgcctct cagcaattgg atcaactgaa ggcggtgcac ctcgcatccg   2580
cggtcaggga cctggagaga gcgatgacga cgctgaaact ttgggaatcc ccccaagaaa   2640
tctccaggca tcaagcactg ggttacagtg ttattacgtt tatgatcaca gcggtgaagc   2700
ggttaaggga atccaagatg ctgactctat catggttcaa tcaggccttg atggtgatag   2760
caccctctca ggaggagaca atgaatctga aaacagcgat gtggatattg gcgaacctga   2820
taccgaggga tatgctatca ctgaccgggg atctgctccc atctctatgg ggttcagggc   2880
ttctgatgtt gaaactgcag aaggaggga gatccacgag ctcctgagac tccaatccag   2940
aggcaacaac tttccgaagc ttgggaaaac tctcaatgtt cctccgcccc cggaccccgg   3000
tagggccagc acttccggga cacccattaa aaagggcaca gacgcgagat tagcctcatt   3060
tggaacggag atcgcgtctt tattgacagg tggtgcaacc caatgtgctc gaaagtcacc   3120
ctcggaacca tcagggccag gtgcacctgc ggggaatgtc cccgagtgtg tgagcaatgc   3180
cgcactgata caggagtgga cacccgaatc tggtaccaca atctccccga gatcccagaa   3240
taatgaagaa gggggagact attatgatga tgagctgttc tctgatgtcc aagatattaa   3300
aacagccttg gccaaaatac acgaggataa tcagaagata atctccaagc tagaatcact   3360
gctgttattg aagggagaag ttgagtcaat taagaagcag atcaacaggc aaaatatcag   3420
catatccacc ctggaaggac acctctcaag catcatgatc gccattcctg gacttgggaa   3480
ggatcccaac gaccccactg cagatgtcga aatcaatccc gacttgaaac ccatcatagg   3540
cagagattca ggccgagcac tggccgaagt tctcaagaaa cccgttgcca gccgacaact   3600
ccaaggaatg acaaatggac ggaccagttc cagaggacag ctgctgaagg aatttcagct   3660
aaagccgatc gggaaaaaga tgagctcagc cgtcgggttt gttcctgaca ccggccctgc   3720
atcacgcagt gtaatccgct ccattataaa atccagccgg ctagaggagg atcggaagcg   3780
ttacctgatg actctccttg atgatatcaa aggagccaat gatcttgcca agttccacca   3840
gatgctgatg aagataataa tgaagtagct acagctcaac ttacctgcca accccatgcc   3900
agtcgaccca actagcctac cctccatcat tgttataaaa aacttaggaa ccaggtccac   3960
acagccgcca gcccatcaac gcgtacgatg agtgccagca aagaaatcaa gagcttcctg   4020
tggacccaga gtctgcggag ggaactgagc ggatactgta gcaacatcaa actgcaggtg   4080
```

```
gtcaaggacg ctcaggcact gctgcatggg ctggacttct ccgaggtgtc taatgtgcag   4140
cggctgatgc ggaaagaacg gagggacgat aatgacctga agcgactgcg cgacctgaac   4200
caggcagtga acaatctggt cgagctgaag agcacccagc agaaatcaat cctgcgggtc   4260
gggacactga catctgacga cctgctgatc ctggctgcag acctggagaa gctgaaatcg   4320
aaagtgatcc gcaccgaaag gccactgtcc gccggggtct acatgggcaa tctgtcttcc   4380
cagcagctgg accagaggcg ggctctgctg aacatgattg ggatgtccgg aggaaatcag   4440
ggagctagag ccgggaggga cggagtcgtg cgggtctggg acgtgaagaa tgccgaactg   4500
ctgaacaacc agttcgggac catgccaagt ctgacactgg catgcctgac taaacagggc   4560
caggtggatc tgaatgatgc agtccaggct ctgaccgacc tgggcctgat ctacaccgcc   4620
aagtacccca atactagcga cctggataga ctgacccaga gccaccccat cctgaacatg   4680
atcgacacta agaagtcctc actgaacatc agtggctata atttctccct gggggcagca   4740
gtcaaggctg gcgcatgcat gctggacggc gggaatatgc tggaaaccat caaagtgtct   4800
ccccagacca tggatggcat cctgaaatct attctgaaag tcaagaaggc cctgggaatg   4860
tttatttcag acacccccgg cgagaggaat ccatatgaga acattctgta taagatttgc   4920
ctgagtggcg acgggtggcc atacattgca agccggacat caattaccgg aagagcttgg   4980
gagaatacag tcgtggacct ggaaagcgac ggcaagcccc agaaggccga ctcaaacaac   5040
tcctcaaaga gtctgcagtc agctggcttc acagcagggc tgacttactc ccagctgatg   5100
acactgaagg acgcaatgct gcagctggac ccaaacgcta agacatggat ggacatcgag   5160
ggacggccag aagatccagt ggaaatcgca ctgtatcagc catcatccgg atgctatatc   5220
catttcttcc gggaaccaac tgatctgaag cagttcaagc aggatgcaaa gtactcccac   5280
ggaatcgatg tcaccgatct gttcgcaacc cagccaggac tgacatcagc cgtcatcgat   5340
gccctgccta ggaacatggt cattacttgc cagggctccg acgatattag gaagctgctg   5400
gagagccagg gacggaagga tatcaaactg atcgatattg ccctgtctaa gactgatagc   5460
cggaaatatg agaatgcagt ctgggatcag tacaaggacc tgtgccatat gcataccgga   5520
gtggtcgtcg agaagaagaa gaggggcgga aaggaagaga tcacacccca ctgtgccctg   5580
atggattgca tcatgttcga cgcagccgtg tccgggggcc tgaacacctc agtcctgagg   5640
gctgtcctgc caagagatat ggtgtttaga acttcaaccc caagagtcgt cctgtaattc   5700
gaactacagc tcaacttacc tgccaacccc atgccagtcg acccaactag tacaacctaa   5760
atccattata aaaaacttag gaaccaggtc cacacagccg ccagcccatc aaccatccac   5820
tcccacgatt ggaggccggc catgggccag attgtcacat tctttcagga agtgccacac   5880
gtcattgagg aggtcatgaa catcgtgctg attgctctgt cagtgctggc agtgctgaaa   5940
ggactgtaca acttcgctac ctgtggactg gtgggactgg tcacattcct gctgctgtgc   6000
ggcagaagtt gcactacctc actgtacaaa ggagtgtacg agctgcagac tctggaactg   6060
aacatggaga cactgaatat gacaatgcct ctgagctgca ccaagaataa tagccaccac   6120
tatatcatgg tcgggaacga aaccggcctg gaactgaccc tgacaaacac cagcatcatt   6180
aaccacaagt tctgcaatct gagcgacgct cacaagaaga acctgtatga ccacgctctg   6240
atgtccatca tcagtacctt tcacctgtcc atccccaatt tcaaccagta cgaggcaatg   6300
tcatgcgact tcaacggggg caagatcagt gtccagtaca acctgagcca ctcctacgcc   6360
ggcgacgcag ccaaccactg cggaactgtc gccaatggcg tgctgcagac attcatgagg   6420
atggcatggg ggggatctta catcgcactg gatagcggca ggggcaattg ggattgcatc   6480
```

```
atgacttcct atcagtatct gattatccag aatactacat gggaggatca ttgccagttc   6540
agtcggccca gccctattgg atatctgggg ctgctgtcac agagaacacg ggatatctat   6600
atttcaagac gcctgctggg cacattcact tggacactgt cagacagtga gggcaaggat   6660
actccagggg gctactgcct gacacgatgg atgctgatcg aagcagagct gaaatgcttc   6720
ggcaataccg cagtggccaa gtgcaacgag aaacacgacg aggagttctg cgacatgctg   6780
aggctgttcg acttcaacaa acaggctatc cagagactga aggcagaagc ccagatgtca   6840
atccagctga tcaacaaggc agtgaacgcc ctgatcaacg accagctgat catgaagaac   6900
cacctgagag acattatggg catcccctac tgtaattaca gcaagtattg gtacctgaac   6960
cacactacaa ccgggagaac atccctgccc aagtgctggc tggtcagcaa tgggagttat   7020
ctgaatgaaa cccatttcag cgacgatatc gaacagcagg ctgacaacat gatcacagag   7080
atgctgcaga aagagtacat ggaaagacag ggcaagacac cactgggact ggtcgatctg   7140
ttcgtcttct ccactagctt ctatctgatt tccatcttcc tgcacctggt gaagatcccc   7200
actcataggc acattgtcgg caagagttgc cctaaacccc ataggctgaa tcacatgggg   7260
atttgtagtt gcggcctgta taagcagcct ggcgtgcctg tgaagtggaa gagatgagcg   7320
cgcagcgctt agacgtctcg cgatcgatac tagtacaacc taaatccatt ataaaaaact   7380
taggagcaaa gtgattgcct cccaaggtcc acaatgacag agacctacga cttcgacaag   7440
tcggcatggg acatcaaagg gtcgatcgct ccgatacaac ccaccaccta cagtgatggc   7500
aggctggtgc cccaggtcag agtcatagat cctggtctag gcgacaggaa ggatgaatgc   7560
tttatgtaca tgtttctgct gggggttgtt gaggacagcg attccctagg gcctccaatc   7620
gggcgagcat ttgggttcct gcccttaggt gttggcagat ccacagcaaa gcccgaaaaa   7680
ctcctcaaag aggccactga gcttgacata gttgttagac gtacagcagg gctcaatgaa   7740
aaactggtgt tctacaacaa caccccacta actctcctca caccttggag aaaggtccta   7800
acaacaggga gtgtcttcaa cgcaaaccaa gtgtgcaatg cggttaatct gataccgctc   7860
gataccccgc agaggttccg tgttgtttat atgagcatca cccgtctttc ggataacggg   7920
tattacaccg ttcctagaag aatgctggaa ttcagatcgg tcaatgcagt ggccttcaac   7980
ctgctggtga cccttaggat tgacaaggcg ataggccctg ggaagatcat cgacaataca   8040
gagcaacttc ctgaggcaac atttatggtc cacatcggga acttcaggag aaagaagagt   8100
gaagtctact ctgccgatta ttgcaaaatg aaaatcgaaa agatgggcct ggtttttgca   8160
cttggtggga tagggggcac cagtcttcac attagaagca caggcaaaat gagcaagact   8220
ctccatgcac aactcgggtt caagaagacc ttatgttacc cgctgatgga tatcaatgaa   8280
gaccttaatc gattactctg gaggagcaga tgcaagatag taagaatcca ggcagttttg   8340
cagccatcag ttcctcaaga attccgcatt tacgacgacg tgatcataaa tgatgaccaa   8400
ggactattca aagttctgta gaccgtagtg cccagcaatg cccgaaaacg acccccctca   8460
caatgacagc cagaaggccc ggacaaaaaa gccccctccg aaagactcca cggaccaagc   8520
gagaggccag ccagcagccg acggcaagcg cgaacaccag gcggccccag cacagaacag   8580
ccctgacaca aggccaccac cagccacccc aatctgcatc ctcctcgtgg gacccccgag   8640
gaccaacccc caaggctgcc cccgatccaa accaccaacc gcatccccac cacccccggg   8700
aaagaaaccc ccagcaattg gaaggcccct cccccctcttc ctcaacacaa gaactccaca   8760
accgaaccgc acaagcgacc gaggtgaccc aaccgcaggc atccgactcc ctagacagat   8820
```

```
cctctctccc cggcaaacta aacaaaactt agggccaagg aacatacaca cccaacagaa   8880
cccagacccc ggcccacggc gccgcgcccc caaccccega caaccagagg gagcccccaa   8940
ccaatcccgc cggctccccc ggtgcccaca ggcagggaca ccaacccccg aacagaccca   9000
gcacccaacc atcgacaatc caagacgggg gggccccccc aaaaaaaggc ccccaggggc   9060
cgacagccag caccgcgagg aagcccaccc accccacaca cgaccacggc aaccaaacca   9120
gaacccagac caccctgggc caccagctcc cagactcggc catcaccccg cagaaaggaa   9180
aggccacaac ccgcgcaccc cagccccgat ccggcgggga gccacccaac ccgaaccagc   9240
acccaagagc gatccccgaa ggacccccga accgcaaagg acatcagtat cccacagcct   9300
ctccaagtcc cccggtctcc tcctcttctc gaagggacca aaagatcaat ccaccacacc   9360
cgacgacact caactcccca cccctaaagg agacaccggg aatcccagaa tcaagactca   9420
tccaatgtcc atcatgggtc tcaaggtgaa cgtctctgcc atattcatgg cagtactgtt   9480
aactctccaa acacccaccg gtcaaatcca ttggggcaat ctctctaaga taggggtggt   9540
aggaatagga agtgcaagct acaaagttat gactcgttcc agccatcaat cattagtcat   9600
aaaattaatg cccaatataa ctctcctcaa taactgcacg agggtagaga ttgcagaata   9660
caggagacta ctgagaacag ttttggaacc aattagagat gcacttaatg caatgaccca   9720
gaatataaga ccggttcaga gtgtagcttc aagtaggaga cacaagagat ttgcgggagt   9780
agtcctggca ggtgcggccc taggcgttgc cacagctgct cagataacag ccggcattgc   9840
acttcaccag tccatgctga actctcaagc catcgacaat ctgagagcga gcctggaaac   9900
tactaatcag gcaattgaga caatcagaca agcagggcag gagatgatat tggctgttca   9960
gggtgtccaa gactacatca ataatgagct gataccgtct atgaaccaac tatcttgtga  10020
tttaatcggc cagaagctcg ggctcaaatt gctcagatac tatacagaaa tcctgtcatt  10080
atttggcccc agtttacggg accccatatc tgcggagata tctatccagg ctttgagcta  10140
tgcgcttgga ggagacatca ataaggtgtt agaaaagctc ggatacagtg gaggtgattt  10200
actgggcatc ttagagagcg gaggaataaa ggcccggata actcacgtcg acacagagtc  10260
ctacttcatt gtcctcagta tagcctatcc gacgctgtcc gagattaagg gggtgattgt  10320
ccaccggcta gagggggtct cgtacaacat aggctctcaa gagtggtata ccactgtgcc  10380
caagtatgtt gcaacccaag ggtaccttat ctcgaatttt gatgagtcat cgtgtacttt  10440
catgccagag gggactgtgt gcagccaaaa tgccttgtac ccgatgagtc ctctgctcca  10500
agaatgcctc cgggggtaca ccaagtcctg tgctcgtaca ctcgtatccg ggtcttttgg  10560
gaaccggttc attttatcac aagggaacct aatagccaat tgtgcatcaa tcctttgcaa  10620
gtgttacaca acaggaacga tcattaatca agaccctgac aagatcctaa catacattgc  10680
tgccgatcac tgcccggtag tcgaggtgaa cggcgtgacc atccaagtcg ggagcaggag  10740
gtatccagac gctgtgtact tgcacagaat tgacctcggt cctcccatat cattggagag  10800
gttggacgta gggacaaatc tggggaatgc aattgctaag ttggaggatg ccaaggaatt  10860
gttggagtca tcggaccaga tattgaggag tatgaaaggt ttatcgagca ctagcatagt  10920
ctacatcctg attgcagtgt gtcttggagg gttgataggg atccccgctt taatatgttg  10980
ctgcaggggg cgttgtaaca aaaagggaga acaagttggt atgtcaagac caggcctaaa  11040
gcctgatctt acgggaacat caaaatccta tgtaaggtcg ctctgatcct ctacaactct  11100
tgaaacacaa atgtcccaca agtctcctct tcgtcatcaa gcaaccaccg cacccagcat  11160
caagcccacc tgaaattatc tccggcttcc ctctggccga acaatatcgg tagttaatca  11220
```

```
aaacttaggg tgcaagatca tccacaatgt caccacaacg agaccggata aatgccttct  11280
acaaagataa cccccatccc aagggaagta ggatagtcat taacagagaa catcttatga  11340
ttgatagacc ttatgttttg ctggctgttc tgtttgtcat gtttctgagc ttgatcgggt  11400
tgctagccat tgcaggcatt agacttcatc gggcagccat ctacaccgca gagatccata  11460
aaagcctcag caccaatcta gatgtaacta actcaatcga gcatcaggtc aaggacgtgc  11520
tgacaccact cttcaaaatc atcggtgatg aagtgggcct gaggacacct cagagattca  11580
ctgacctagt gaaattaatc tctgacaaga ttaaattcct taatccggat agggagtacg  11640
acttcagaga tctcacttgg tgtatcaacc cgccagagag aatcaaattg gattatgatc  11700
aatactgtgc agatgtggct gctgaagagc tcatgaatgc attggtgaac tcaactctac  11760
tggagaccag aacaaccaat cagttcctag ctgtctcaaa gggaaactgc tcagggccca  11820
ctacaatcag aggtcaattc tcaaacatgt cgctgtccct gttagacttg tatttaggtc  11880
gaggttacaa tgtgtcatct atagtcacta tgacatccca gggaatgtat gggggaactt  11940
acctagtgga aaagcctaat ctgagcagca aaaggtcaga gttgtcacaa ctgagcatgt  12000
accgagtgtt tgaagtaggt gttatcagaa atccgggttt gggggctccg gtgttccata  12060
tgacaaacta tcttgagcaa ccagtcagta atgatctcag caactgtatg gtggctttgg  12120
gggagctcaa actcgcagcc ctttgtcacg gggaagattc tatcacaatt ccctatcagg  12180
gatcagggaa aggtgtcagc ttccagctcg tcaagctagg tgtctggaaa tccccaaccg  12240
acatgcaatc ctgggtcccc ttatcaacgg atgatccagt gatagacagg ctttacctct  12300
catctcacag aggtgttatc gctgacaatc aagcaaaatg ggctgtcccg acaacacgaa  12360
cagatgacaa gttgcgaatg gagacatgct tccaacaggc gtgtaagggt aaaatccaag  12420
cactctgcga gaatcccgag tgggcaccat tgaaggataa caggattcct tcatacgggg  12480
tcttgtctgt tgatctgagt ctgacagttg agcttaaaat caaaattgct tcgggattcg  12540
ggccattgat cacacacggt tcagggatgg acctatacaa atccaaccac aacaatgtgt  12600
attggctgac tatcccgcca atgaagaacc tagccttagg tgtaatcaac acattggagt  12660
ggataccgag attcaaggtt agtccctacc tcttcactgt cccaattaag gaagcaggcg  12720
aagactgcca tgccccaaca tacctacctg cggaggtgga tggtgatgtc aaactcagtt  12780
ccaatctggt gattctacct ggtcaagatc tccaatatgt tttggcaacc tacgatactt  12840
ccagggttga acatgctgtg gtttattacg tttacagccc aagccgctca ttttcttact  12900
tttatccttt taggttgcct ataaaggggg tccccatcga attacaagtg gaatgcttca  12960
catgggacca aaaactctgg tgccgtcact tctgtgtgct tgcggactca gaatctggtg  13020
gacatatcac tcactctggg atggtgggca tgggagtcag ctgcacagtc acccgggaag  13080
atggaaccaa tcgcagatag ggctgctagt gaaccaatca catgatgtca cccagacatc  13140
aggcataccc actagtgtga aatagacatc agaattaaga aaaacgtagg gtccaagtgg  13200
ttccccgtta tggactcgct atctgtcaac cagatcttat accctgaagt tcacctagat  13260
agcccgatag ttaccaataa gatagtagcc atcctggagt atgctcgagt ccctcacgct  13320
tacagcctgg aggaccctac actgtgtcag aacatcaagc accgcctaaa aaacggattt  13380
tccaaccaaa tgattataaa caatgtggaa gttgggaatg tcatcaagtc caagcttagg  13440
agttatccgg cccactctca tattccatat ccaaattgta atcaggattt atttaacata  13500
gaagacaaag agtcaacgag gaagatccgt gaactcctca aaaaggggaa ttcgctgtac  13560
```

-continued

```
tccaaagtca gtgataaggt tttccaatgc ttaagggaca ctaactcacg gcttggccta  13620

ggctccgaat tgagggagga catcaaggag aaagttatta acttgggagt ttacatgcac  13680

agctcccagt ggtttgagcc ctttctgttt tggtttacag tcaagactga gatgaggtca  13740

gtgattaaat cacaaaccca tacttgccat aggaggagac acacacctgt attcttcact  13800

ggtagttcag ttgagttgct aatctctcgt gaccttgttg ctataatcag taaagagtct  13860

caacatgtat attacctgac atttgaactg gttttgatgt attgtgatgt catagagggg  13920

aggttaatga cagagaccgc tatgactatt gatgctaggt atacagagct tctaggaaga  13980

gtcagataca tgtggaaact gatagatggt ttcttccctg cactcgggaa tccaacttat  14040

caaattgtag ccatgctgga gcctctttca cttgcttacc tgcagctgag ggatataaca  14100

gtagaactca gaggtgcttt ccttaaccac tgctttactg aaatacatga tgttcttgac  14160

caaaacgggt tttctgatga aggtacttat catgagttaa ctgaagctct agattacatt  14220

ttcataactg atgacataca tctgacaggg gagattttct catttttcag aagtttcggc  14280

caccccagac ttgaagcagt aacggctgct gaaaatgtta ggaaatacat gaatcagcct  14340

aaagtcattg tgtatgagac tctgatgaaa ggtcatgcca tattttgtgg aatcataatc  14400

aacggctatc gtgacaggca cggaggcagt tggccaccgc tgaccctccc cctgcatgct  14460

gcagacacaa tccggaatgc tcaagcttca ggtgaagggt taacacatga gcagtgcgtt  14520

gataactgga aatcttttgc tggagtgaaa tttggctgct ttatgcctct tagcctggat  14580

agtgatctga caatgtacct aaaggacaag gcacttgctg ctctccaaag ggaatgggat  14640

tcagtttacc cgaaagagtt cctgcgttac gaccctccca agggaaccgg gtcacggagg  14700

cttgtagatg ttttccttaa tgattcgagc tttgacccat atgatgtgat aatgtatgtt  14760

gtaagtggag cttacctcca tgaccctgag ttcaacctgt cttacagcct gaaagaaaag  14820

gagatcaagg aaacaggtag actttttgct aaaatgactt acaaaatgag ggcatgccaa  14880

gtgattgctg aaaatctaat ctcaaacggg attggcaaat attttaagga caatgggatg  14940

gccaaggatg agcacgattt gactaaggca ctccacactc tagctgtctc aggagtcccc  15000

aaagatctca aagaaagtca caggggggggg ccagtcttaa aaacctactc ccgaagccca  15060

gtccacacaa gtaccaggaa cgtgagagca gcaaaagggt ttatagggtt ccctcaagta  15120

attcggcagg accaagacac tgatcatccg gagaatatgg aagcttacga gacagtcagt  15180

gcatttatca cgactgatct caagaagtac tgccttaatt ggagatatga gaccatcagc  15240

ttgtttgcac agaggctaaa tgagatttac ggattgccct catttttcca gtggctgcat  15300

aagaggcttg agacctctgt cctgtatgta agtgaccctc attgcccccc cgaccttgac  15360

gcccatatcc cgttatataa agtccccaat gatcaaatct tcattaagta ccctatggga  15420

ggtatagaag ggtattgtca gaagctgtgg accatcagca ccattcccta tctatacctg  15480

gctgcttatg agagcggagt aaggattgct tcgttagtgc aaggggacaa tcagaccata  15540

gccgtaacaa aaagggtacc cagcacatgg ccctacaacc ttaagaaacg ggaagctgct  15600

agagtaacta gagattactt tgtaattctt aggcaaaggc tacatgatat tggccatcac  15660

ctcaaggcaa atgagacaat tgtttcatca catttttttg tctattcaaa aggaatatat  15720

tatgatgggc tacttgtgtc ccaatcactc aagagcatcg caagatgtgt attctggtca  15780

gagactatag ttgatgaaac aagggcagca tgcagtaata ttgctacaac aatggctaaa  15840

agcatcgaga gaggttatga ccgttacctt gcatattccc tgaacgtcct aaaagtgata  15900

cagcaaattc tgatctctct tggcttcaca atcaattcaa ccatgacccg ggatgtagtc  15960
```

```
atacccctcc tcacaaacaa cgacctctta ataaggatgg cactgttgcc cgctcctatt  16020
ggggggatga attatctgaa tatgagcagg ctgtttgtca gaaacatcgg tgatccagta  16080
acatcatcaa ttgctgatct caagagaatg attctcgcct cactaatgcc tgaagagacc  16140
ctccatcaag taatgacaca acaaccgggg gactcttcat tcctagactg ggctagcgac  16200
ccttactcag caaatcttgt atgtgtccag agcatcacta gactcctcaa gaacataact  16260
gcaaggtttg tcctgatcca tagtccaaac ccaatgttaa aaggattatt ccatgatgac  16320
agtaaagaag aggacgaggg actggcggca ttcctcatgg acaggcatat tatagtacct  16380
agggcagctc atgaaatcct ggatcatagt gtcacagggg caagagagtc tattgcaggc  16440
atgctggata ccacaaaagg cttgattcga gccagcatga ggaagggggg gttaacctct  16500
cgagtgataa ccagattgtc caattatgac tatgaacaat tcagagcagg gatggtgcta  16560
ttgacaggaa gaaagagaaa tgtcctcatt gacaaagagt catgttcagt gcagctggcg  16620
agagctctaa gaagccatat gtgggcgagg ctagctcgag gacggcctat ttacggcctt  16680
gaggtccctg atgtactaga atctatgcga ggccacctta ttcggcgtca tgagacatgt  16740
gtcatctgcg agtgtggatc agtcaactac ggatggtttt ttgtcccctc gggttgccaa  16800
ctggatgata ttgacaagga aacatcatcc ttgagagtcc catatattgg ttctaccact  16860
gatgagagaa cagacatgaa gcttgccttc gtaagagccc caagtcgatc cttgcgatct  16920
gctgttagaa tagcaacagt gtactcatgg gcttacggtg atgatgatag ctcttggaac  16980
gaagcctggt tgttggctag gcaaagggcc aatgtgagcc tggaggagct aagggtgatc  17040
actcccatct caacttcgac taatttagcg cataggttga gggatcgtag cactcaagtg  17100
aaatactcag gtacatccct tgtccgagtg gcgaggtata ccacaatctc caacgacaat  17160
ctctcatttg tcatatcaga taagaaggtt gatactaact ttatatacca acaaggaatg  17220
cttctagggt tgggtgtttt agaaacattg tttcgactcg agaaagatac cggatcatct  17280
aacacggtat tacatcttca cgtcgaaaca gattgttgcg tgatcccgat gatagatcat  17340
cccaggatac ccagctcccg caagctagag ctgagggcag agctatgtac caacccattg  17400
atatatgata atgcaccttt aattgacaga gatgcaacaa ggctatacac ccagagccat  17460
aggaggcacc ttgtggaatt tgttacatgg tccacacccc aactatatca cattttagct  17520
aagtccacag cactatctat gattgacctg gtaacaaaat ttgagaagga ccatatgaat  17580
gaaatttcag ctctcatagg ggatgacgat atcaatagtt tcataactga gtttctgctc  17640
atagagccaa gattattcac tatctacttg ggccagtgtg cggccatcaa ttgggcattt  17700
gatgtacatt atcatagacc atcagggaaa tatcagatgg gtgagctgtt gtcatcgttc  17760
ctttctagaa tgagcaaagg agtgtttaag gtgcttgtca atgctctaag ccacccaaag  17820
atctacaaga aattctggca ttgtggtatt atagagccta tccatggtcc ttcacttgat  17880
gctcaaaact tgcacacaac tgtgtgcaac atggtttaca catgctatat gacctacctc  17940
gacctgttgt tgaatgaaga gttagaagag ttcacatttc tcttgtgtga aagcgacgag  18000
gatgtagtac cggacagatt cgacaacatc caggcaaaac acttatgtgt tctggcagat  18060
ttgtactgtc aaccagggac ctgcccacca attcgaggtc taagaccggt agagaaatgt  18120
gcagttctaa ccgaccatat caaggcagag gctatgttat ctccagcagg atcttcgtgg  18180
aacataaatc caattattgt agaccattac tcatgctctc tgacttatct ccggcgagga  18240
tcgatcaaac agataagatt gagagttgat ccaggattca ttttcgacgc cctcgctgag  18300
```

```
gtaaatgtca gtcagccaaa gatcggcagc aacaacatct caaatatgag catcaaggct  18360
ttcagacccc cacacgatga tgttgcaaaa ttgctcaaag atatcaacac aagcaagcac  18420
aatcttccca tttcaggggg caatctcgcc aattatgaaa tccatgcttt ccgcagaatc  18480
gggttgaact catctgcttg ctacaaagct gttgagatat caacattaat taggagatgc  18540
cttgagccag gggaggacgg cttgttcttg ggtgagggat cgggttctat gttgatcact  18600
tataaagaga tacttaaact aaacaagtgc ttctataata gtggggtttc cgccaattct  18660
agatctggtc aaagggaatt agcaccctat ccctccgaag ttggccttgt cgaacacaga  18720
atgggagtag gtaatattgt caaagtgctc tttaacggga ggcccgaagt cacgtgggta  18780
ggcagtgtag attgcttcaa tttcatagtt agtaatatcc ctacctctag tgtggggttt  18840
atccattcag atatagagac cttgcctgac aaagatacta tagagaagct agaggaattg  18900
gcagccatct tatcgatggc tctgctcctg ggcaaaatag gatcaatact ggtgattaag  18960
cttatgcctt tcagcgggga ttttgttcag ggatttataa gttatgtagg gtctcattat  19020
agagaagtga accttgtata ccctagatac agcaacttca tctctactga atcttatttg  19080
gttatgacag atctcaaggc taaccggcta atgaatcctg aaaagattaa gcagcagata  19140
attgaatcat ctgtgaggac ttcacctgga cttataggtc acatcctatc cattaagcaa  19200
ctaagctgca tacaagcaat tgtgggagac gcagttagta gaggtgatat caatcctact  19260
ctgaaaaaac ttacacctat agagcaggtg ctgatcaatt gcgggttggc aattaacgga  19320
cctaagctgt gcaaagaatt gatccaccat gatgttgcct cagggcaaga tggattgctt  19380
aattctatac tcatcctcta cagggagttg gcaagattca aagacaacca aagaagtcaa  19440
caagggatgt tccacgctta ccccgtattg gtaagtagca ggcaacgaga acttatatct  19500
aggatcaccc gcaaattctg gggcacatt cttctttact ccgggaacaa aaagttgata  19560
aataagttta tccagaatct caagtccggc tatctgatac tagacttaca ccagaatatc  19620
ttcgttaaga atctatccaa gtcagagaaa cagattatta tgacgggggg tttgaaacgt  19680
gagtgggttt ttaaggtaac agtcaaggag accaaagaat ggtataagtt agtcggatac  19740
agtgccctga ttaaggacta attggttgaa ctccggaacc ctaatcctgc cctaggtggt  19800
taggcattat ttgcaatata ttaaagaaaa ctttgaaaat acgaagtttc tattcccagc  19860
tttgtctggt ggccggcatg gtcccagcct cctcgctggc gccggctggg caacattccg  19920
aggggaccgt cccctcggta atggcgaatg ggacgcggcc gatccggctg ctaacaaagc  19980
ccgaaaggaa gctgagttgg ctgctgccac cgctgagcaa taactagcat aaccccttgg  20040
ggcctctaaa cgggtcttga ggggtttttt gctgaaagga ggaactatat ccggatgcgg  20100
ccgcgggccc tatggtaccc agcttttgtt ccctttagtg agggttaatt ccgagcttgg  20160
cgtaatcatg gtcatagctg tttcctgtgt gaaattgtta tccgctcaca attccacaca  20220
acataggagc cggaagcata aagtgtaaag cctggggtgc ctaatgagtg aggtaactca  20280
cattaattgc gttgcgctca ctgcccgctt tccagtcggg aaacctgtcg tgccagctgc  20340
attaatgaat cggccaacgc gcggggagag gcggtttgcg tattgggcgc tcttccgctt  20400
cctcgctcac tgactcgctg cgctcggtcg ttcggctgcg gcgagcggta tcagctcact  20460
caaaggcggt aatacggtta tccacagaat caggggataa cgcaggaaag aacatgtgag  20520
caaaaggcca gcaaaaggcc aggaaccgta aaaaggccgc gttgctggcg tttttccata  20580
ggctcggccc ccctgacgag catcacaaaa atcgacgctc aagtcagagg tggcgaaacc  20640
cgacaggact ataaagatac caggcgttcc cccctggaag ctccctcgtg cgctctcctg  20700
```

```
ttccgaccct gccgcttacc ggatacctgt ccgcctttct cccttcggga agcgtggcgc  20760
tttctcaatg ctcacgctgt aggtatctca gttcggtgta ggtcgttcgc tccaagctgg  20820
gctgtgtgca cgaacccccc gttcagcccg accgctgcgc cttatccggt aactatcgtc  20880
ttgagtccaa cccggtaaga cacgacttat cgccactggc agcagccact ggtaacagga  20940
ttagcagagc gaggtatgta ggcggtgcta cagagttctt gaagtggtgg cctaactacg  21000
gctacactag aaggacagta tttggtatct gcgctctgct gaagccagtt accttcggaa  21060
aaagagttgg tagctcttga tccggcaaac aaaccaccgc tggtagcggt ggtttttttg  21120
tttgcaagca gcagattacg cgcagaaaaa aaggatctca agaagatcct ttgatctttt  21180
ctacggggtc tgacgctcag tggaacgaaa actcacgtta agggattttg gtcatgagat  21240
tatcaaaaag gatcttcacc tagatccttt taaattaaaa atgaagtttt aaatcaatct  21300
aaagtatata tgagtaaact tggtctgaca gttaccaatg cttaatcagt gaggcaccta  21360
tctcagcgat ctgtctattt cgttcatcca tagttgcctg actgcccgtc gtgtagataa  21420
ctacgatacg ggagggctta ccatctggcc ccagtgctgc aatgataccg cgagacccac  21480
gctcaccggc tccagattta tcagcaataa accagccagc cggaagggcc gagcgcagaa  21540
gtggtcctgc aactttatcc gcctccatcc agtctattaa ttgttgccgg gaagctagag  21600
taagtagttc gccagttaat agtttgcgca acgttgttgc cattgctaca ggcatcgtgg  21660
tgtcacgctc gtcgtttggt atggcttcat tcagctccgg ttcccaacga tcaaggcgag  21720
ttacatgatc ccccatgttg tgaaaaaaag cggttagctc cttcggtcct ccgatcgttg  21780
tcagaagtaa gttggccgca gtgttatcac tcatgcttat ggcagcactg cataattctc  21840
ttactgtcat gccatccgta agatgctttt ctgtgactgg tgagtactca accaagtcat  21900
tctgagaata gtgtatgcgg cgaccgagtt gctcttgccc ggcgtcaata cgggataata  21960
ccgcgccaca tagcagaact ttaaaagtgc tcatcattgg aaaacgttct tcggggcgaa  22020
aactctcaag gatcttaccg ctgttgagat ccagttcgat gtaacccact cgtgcaccca  22080
actgatcttc agcatctttt actttcacca gcgtttctgg gtgagcaaaa acaggaaggc  22140
aaaatgccgc aaaaaaggga ataagggcga cacggaaatg ttgaatactc atactcttcc  22200
tttttcaata ttattgaagc atttatcagg gttattgtct catgagcgga tacatatttg  22260
aatgtattta gaaaaataaa caaatagggg ttccgcgcac atttccccga aaagtgccac  22320
ctgaaattgt aaacgttaat attttgttaa aattcgcgtt aaatttttgt taaatcagct  22380
cattttttaa ccaataggcc gaaatcggca aaatccctta taaatcaaaa gaatagaccg  22440
agatagggtt gagtgttgtt ccagtttgga acaagagtcc actattaaag aacgtggact  22500
ccaacgtcaa agggcgaaaa accgtctatc agggcgatgg cccactacgt gaaccatcac  22560
cctaatcaag ttttttgggg tcgaggtgcc gtaaagcact aaatcggaac cctaaaggga  22620
gcccccgatt tagagcttga cggggaaagc cggcgaacgt ggcgagaaag gaagggaaga  22680
aagcgaaagg agcgggcgct agggcgctgg caagtgtagc ggtcacgctg cgcgtaacca  22740
ccacacccgc cgcgcttaat gcgccgctac agggcgcgtc ccattcgcca ttcaggctgc  22800
gcaactgttg ggaagggcga tcggtgcggg cctcttcgct attacgccag ccaccgcggt  22860
g                                                                  22861
```

<210> SEQ ID NO 14
<211> LENGTH: 22861
<212> TYPE: DNA

```
<213> ORGANISM: Artificial Sequence
<220> FEATURE:
<223> OTHER INFORMATION: Plasmide MeV-Z+mNP+GPC

<400> SEQUENCE: 14

gcggccgcta atacgactca ctatagggcc aactttgttt ggtctgatga gtccgtgagg     60
acgaaacccg gagtcccggg tcaccaaaca aagttgggta aggatagttc aatcaatgat    120
catcttctag tgcacttagg attcaagatc ctattatcag ggacaagagc aggattaggg    180
atatccgaga cgcgtacgat gggcaataag caggcaaagg cacccgaaag caaggattca    240
cctagagcat cactgattcc cgacgcaact catctggggc cacagttctg caaatcctgt    300
tggttcgaga acaaaggcct ggtggagtgc aataaccact acctgtgcct gaactgtctg    360
acactgctgc tgagtgtgag caacagatgc ccaatctgca agatgcctct gccaacaaag    420
ctgaggcctt ctgctgcacc caccgcacca ccaactggag ccgcagacag cattagaccc    480
cccccatact caccataagc gcgcagcgct tagacgtctc gcgatcgatt agtgcgagag    540
gccgagggcc agaacaacat ccgcctacca tccatcattg ttataaaaaa cttaggattc    600
aagatcctat tatcagggac aagagcagga ttagggatat ccgagatggc cacacttta     660
aggagcttag cattgttcaa aagaaacaag gacaaaccac ccattacatc aggatccggt    720
ggagccatca gaggaatcaa acacattatt atagtaccaa tccctggaga ttcctcaatt    780
accactcgat ccagacttct ggaccggttg gtgaggttaa ttggaaaccc ggatgtgagc    840
gggcccaaac taacaggggc actaataggt atattatcct tatttgtgga gtctccaggt    900
caattgattc agaggatcac cgatgaccct gacgttagca taaggctgtt agaggttgtc    960
cagagtgacc agtcacaatc tggccttacc ttcgcatcaa gaggtaccaa catggaggat   1020
gaggcggacc aatacttttc acatgatgat ccaattagta gtgatcaatc caggttcgga   1080
tggttcggga acaaggaaat ctcagatatt gaagtgcaag accctgaggg attcaacatg   1140
attctgggta ccatcctagc ccaaatttgg gtcttgctcg caaaggcggt tacggcccca   1200
gacacggcag ctgattcgga gctaagaagg tggataaagt acacccaaca aagaagggta   1260
gttggtgaat ttagattgga gagaaaatgg ttggatgtgg tgaggaacag gattgccgag   1320
gacctctcct tacgccgatt catggtcgct ctaatcctgg atatcaagag aacacccgga   1380
aacaaaccca ggattgctga aatgatatgt gacattgata catatatcgt agaggcagga   1440
ttagccagtt ttatcctgac tattaagttt gggatagaaa ctatgtatcc tgctcttgga   1500
ctgcatgaat ttgctggtga gttatccaca cttgagtcct tgatgaacct ttaccagcaa   1560
atgggggaaa ctgcacccta catggtaatc ctggagaact caattcagaa caagttcagt   1620
gcaggatcat accctctgct ctggagctat gccatgggag taggagtgga acttgaaaac   1680
tccatgggag gtttgaactt tggccgatct tactttgatc cagcatattt tagattaggg   1740
caagagatgg taaggaggtc agctggaaag gtcagttcca cattggcatc tgaactcggt   1800
atcactgccg aggatgcaag gcttgtttca gagattgcaa tgcatactac tgaggacaag   1860
atcagtagag cggttggacc cagacaagcc caagtatcat ttctacacgg tgatcaaagt   1920
gagaatgagc taccgagatt ggggggcaag gaagatagga gggtcaaaca gagtcgagga   1980
gaagccaggg agagctacag agaaaccggg cccagcagag caagtgatgc gagagctgcc   2040
catcttccaa ccggcacacc cctagacatt gacactgcaa cggagtccag ccaagatccg   2100
caggacagtc gaaggtcagc tgacgccctg cttaggctgc aagccatggc aggaatctcg   2160
gaagaacaag gctcagacac ggacacccct atagtgtaca atgacagaaa tcttctagac   2220
```

-continued taggtgcgag aggccgaggg ccagaacaac atccgcctac catccatcat tgttataaaa 2280
aacttaggaa ccaggtccac acagccgcca gcccatcaac catccactcc cacgattgga 2340
gccaatggca gaagagcagg cacgccatgt caaaaacgga ctggaatgca tccgggctct 2400
caaggccgag cccatcggct cactggccat cgaggaagct atggcagcat ggtcagaaat 2460
atcagacaac ccaggacagg agcgagccac ctgcagggaa gagaaggcag gcagttcggg 2520
tctcagcaaa ccatgcctct cagcaattgg atcaactgaa ggcggtgcac ctcgcatccg 2580
cggtcaggga cctggagaga gcgatgacga cgctgaaact ttgggaatcc ccccaagaaa 2640
tctccaggca tcaagcactg ggttacagtg ttattacgtt tatgatcaca gcggtgaagc 2700
ggttaaggga atccaagatg ctgactctat catggttcaa tcaggccttg atggtgatag 2760
caccctctca ggaggagaca atgaatctga aaacagcgat gtggatattg gcgaacctga 2820
taccgaggga tatgctatca ctgaccgggg atctgctccc atctctatgg ggttcagggc 2880
ttctgatgtt gaaactgcag aaggagggga gatccacgag ctcctgagac tccaatccag 2940
aggcaacaac tttccgaagc ttgggaaaac tctcaatgtt cctccgcccc cggaccccgg 3000
tagggccagc acttccggga cacccattaa aaagggcaca gacgcgagat tagcctcatt 3060
tggaacggag atcgcgtctt tattgacagg tggtgcaacc caatgtgctc gaaagtcacc 3120
ctcggaacca tcagggccag gtgcacctgc ggggaatgtc cccgagtgtg tgagcaatgc 3180
cgcactgata caggagtgga cacccgaatc tggtaccaca atctccccga gatcccagaa 3240
taatgaagaa gggggagact attatgatga tgagctgttc tctgatgtcc aagatattaa 3300
aacagccttg gccaaaatac acgaggataa tcagaagata atctccaagc tagaatcact 3360
gctgttattg aagggagaag ttgagtcaat taagaagcag atcaacaggc aaaatatcag 3420
catatccacc ctggaaggac acctctcaag catcatgatc gccattcctg gacttgggaa 3480
ggatcccaac gaccccactg cagatgtcga aatcaatccc gacttgaaac ccatcatagg 3540
cagagattca ggccgagcac tggccgaagt tctcaagaaa cccgttgcca gccgacaact 3600
ccaaggaatg acaaatggac ggaccagttc cagaggacag ctgctgaagg aatttcagct 3660
aaagccgatc gggaaaaaga tgagctcagc cgtcgggttt gttcctgaca ccggccctgc 3720
atcacgcagt gtaatccgct ccattataaa atccagccgg ctagaggagg atcggaagcg 3780
ttacctgatg actctccttg atgatatcaa aggagccaat gatcttgcca agttccacca 3840
gatgctgatg aagataataa tgaagtagct acagctcaac ttacctgcca accccatgcc 3900
agtcgaccca actagcctac cctccatcat tgttataaaa aacttaggaa ccaggtccac 3960
acagccgcca gcccatcaac gcgtacgatg agtgccagca aagaaatcaa gagcttcctg 4020
tggacccaga gtctgcggag ggaactgagc ggatactgta gcaacatcaa actgcaggtg 4080
gtcaaggacg ctcaggcact gctgcatggg ctggacttct ccgaggtgtc taatgtgcag 4140
cggctgatgc ggaaagaacg gagggacgat aatgacctga agcgactgcg cgacctgaac 4200
caggcagtga acaatctggt cgagctgaag agcacccagc agaaatcaat cctgcgggtc 4260
gggacactga catctgacga cctgctgatc ctggctgcag acctggagaa gctgaaatcg 4320
aaagtgatcc gcaccgaaag gccactgtcc gccggggtct acatgggcaa tctgtcttcc 4380
cagcagctgg accagaggcg ggctctgctg aacatgattg ggatgtccgg aggaaatcag 4440
ggagctagag ccgggaggga cggagtcgtg cgggtctggg acgtgaagaa tgccgaactg 4500
ctgaacaacc agttcgggac catgccaagt ctgacactgg catgcctgac taaacagggc 4560

```
caggtggatc tgaatgatgc agtccaggct ctgaccgacc tgggcctgat ctacaccgcc   4620

aagtacccca atactagcga cctggataga ctgacccaga gccaccccat cctgaacatg   4680

atcgacacta agaagtcctc actgaacatc agtggctata atttctccct gggggcagca   4740

gtcaaggctg gcgcatgcat gctggacggc gggaatatgc tggaaaccat caaagtgtct   4800

ccccagacca tggatggcat cctgaaatct attctgaaag tcaagaaggc cctgggaatg   4860

tttatttcag acaccccccgg cgagaggaat ccatatgaga acattctgta taagatttgc   4920

ctgagtggcg acgggtggcc atacattgca agccggacat caattaccgg aagagcttgg   4980

gagaatacag tcgtggacct ggaaagcgac ggcaagcccc agaaggccga ctcaaacaac   5040

tcctcaaaga gtctgcagtc agctggcttc acagcagggc tgacttactc ccagctgatg   5100

acactgaagg acgcaatgct gcagctggac ccaaacgcta agacatggat ggccatcgag   5160

gcccggccag aagatccagt ggaaatcgca ctgtatcagc catcatccgg atgctatatc   5220

catttcttcc gggaaccaac tgatctgaag cagttcaagc aggatgcaaa gtactcccac   5280

ggaatcgatg tcaccgatct gttcgcaacc cagccaggac tgacatcagc cgtcatcgat   5340

gccctgccta ggaacatggt cattacttgc cagggctccg acgatattag gaagctgctg   5400

gagagccagg gacggaagga tatcaaactg atcgatattg ccctgtctaa gactgatagc   5460

cggaaatatg agaatgcagt ctgggatcag tacaaggacc tgtgccatat gcataccgga   5520

gtggtcgtcg agaagaagaa gaggggcgga aaggaagaga tcacacccca ctgtgccctg   5580

atggattgca tcatgttcga cgcagccgtg tccgggggcc tgaacacctc agtcctgagg   5640

gctgtcctgc caagagatat ggtgtttaga acttcaaccc caagagtcgt cctgtaattc   5700

gaactacagc tcaacttacc tgccaacccc atgccagtcg acccaactag tacaacctaa   5760

atccattata aaaaacttag gaaccaggtc cacacagccg ccagcccatc aaccatccac   5820

tcccacgatt ggaggccggc catgggccag attgtcacat tctttcagga agtgccacac   5880

gtcattgagg aggtcatgaa catcgtgctg attgctctgt cagtgctggc agtgctgaaa   5940

ggactgtaca acttcgctac ctgtggactg gtgggactgg tcacattcct gctgctgtgc   6000

ggcagaagtt gcactacctc actgtacaaa ggagtgtacg agctgcagac tctggaactg   6060

aacatggaga cactgaatat gacaatgcct ctgagctgca ccaagaataa tagccaccac   6120

tatatcatgg tcgggaacga aaccggcctg gaactgaccc tgacaaacac cagcatcatt   6180

aaccacaagt tctgcaatct gagcgacgct cacaagaaga acctgtatga ccacgctctg   6240

atgtccatca tcagtacctt tcacctgtcc atccccaatt tcaaccagta cgaggcaatg   6300

tcatgcgact tcaacggggg caagatcagt gtccagtaca acctgagcca ctcctacgcc   6360

ggcgacgcag ccaaccactg cggaactgtc gccaatggcg tgctgcagac attcatgagg   6420

atggcatggg ggggatctta catcgcactg gatagcggca ggggcaattg ggattgcatc   6480

atgacttcct atcagtatct gattatccag aatactacat gggaggatca ttgccagttc   6540

agtcggccca gccctattgg atatctgggg ctgctgtcac agagaacacg ggatatctat   6600

atttcaagac gcctgctggg cacattcact tggacactgt cagacagtga gggcaaggat   6660

actccagggg gctactgcct gacacgatgg atgctgatcg aagcagagct gaaatgcttc   6720

ggcaataccg cagtggccaa gtgcaacgag aaacacgacg aggagttctg cgacatgctg   6780

aggctgttcg acttcaacaa acaggctatc cagagactga aggcagaagc ccagatgtca   6840

atccagctga tcaacaaggc agtgaacgcc ctgatcaacg accagctgat catgaagaac   6900

cacctgagag acattatggg catcccctac tgtaattaca gcaagtattg gtacctgaac   6960
```

```
cacactacaa ccgggagaac atccctgccc aagtgctggc tggtcagcaa tgggagttat   7020
ctgaatgaaa cccatttcag cgacgatatc gaacagcagg ctgacaacat gatcacagag   7080
atgctgcaga aagagtacat ggaaagacag ggcaagacac cactgggact ggtcgatctg   7140
ttcgtcttct ccactagctt ctatctgatt tccatcttcc tgcacctggt gaagatcccc   7200
actcataggc acattgtcgg caagagttgc cctaaacccc ataggctgaa tcacatgggg   7260
atttgtagtt gcggcctgta taagcagcct ggcgtgcctg tgaagtggaa gagatgagcg   7320
cgcagcgctt agacgtctcg cgatcgatac tagtacaacc taaatccatt ataaaaaact   7380
taggagcaaa gtgattgcct cccaaggtcc acaatgacag agacctacga cttcgacaag   7440
tcggcatggg acatcaaagg gtcgatcgct ccgatacaac ccaccaccta cagtgatggc   7500
aggctggtgc cccaggtcag agtcatagat cctggtctag gcgacaggaa ggatgaatgc   7560
tttatgtaca tgtttctgct gggggttgtt gaggacagcg attccctagg gcctccaatc   7620
gggcgagcat ttgggttcct gcccttaggt gttggcagat ccacagcaaa gcccgaaaaa   7680
ctcctcaaag aggccactga gcttgacata gttgttagac gtacagcagg gctcaatgaa   7740
aaactggtgt tctacaacaa caccccacta actctcctca caccttggag aaaggtccta   7800
acaacaggga gtgtcttcaa cgcaaaccaa gtgtgcaatg cggttaatct gataccgctc   7860
gataccccgc agaggttccg tgttgtttat atgagcatca cccgtctttc ggataacggg   7920
tattacaccg ttcctagaag aatgctggaa ttcagatcgg tcaatgcagt ggccttcaac   7980
ctgctggtga cccttaggat tgacaaggcg ataggccctg ggaagatcat cgacaataca   8040
gagcaacttc ctgaggcaac atttatggtc cacatcggga acttcaggag aaagaagagt   8100
gaagtctact ctgccgatta ttgcaaaatg aaaatcgaaa agatgggcct ggtttttgca   8160
cttggtggga tagggggcac cagtcttcac attagaagca caggcaaaat gagcaagact   8220
ctccatgcac aactcgggtt caagaagacc ttatgttacc cgctgatgga tatcaatgaa   8280
gaccttaatc gattactctg gaggagcaga tgcaagatag taagaatcca ggcagttttg   8340
cagccatcag ttcctcaaga attccgcatt tacgacgacg tgatcataaa tgatgaccaa   8400
ggactattca aagttctgta gaccgtagtg cccagcaatg cccgaaaacg acccccctca   8460
caatgacagc cagaaggccc ggacaaaaaa gccccctccg aaagactcca cggaccaagc   8520
gagaggccag ccagcagccg acggcaagcg cgaacaccag gcggccccag cacagaacag   8580
ccctgacaca aggccaccac cagccacccc aatctgcatc ctcctcgtgg gacccccgag   8640
gaccaacccc caaggctgcc cccgatccaa accaccaacc gcatccccac cacccccggg   8700
aaagaaaccc ccagcaattg gaaggcccct cccccctcttc ctcaacacaa gaactccaca   8760
accgaaccgc acaagcgacc gaggtgaccc aaccgcaggc atccgactcc ctagacagat   8820
cctctctccc cggcaaacta aacaaaactt agggccaagg aacatacaca cccaacagaa   8880
cccagacccc ggcccacggc gccgcgcccc caacccccga caaccagagg gagcccccaa   8940
ccaatcccgc cggctccccc ggtgcccaca ggcagggaca ccaacccccg aacagaccca   9000
gcacccaacc atcgacaatc caagacgggg gggccccccc aaaaaaaggc ccccaggggc   9060
cgacagccag caccgcgagg aagcccaccc accccacaca cgaccacggc aaccaaacca   9120
gaacccagac caccctgggc caccagctcc cagactcggc catcaccccg cagaaaggaa   9180
aggccacaac ccgcgcaccc cagccccgat ccggcgggga gccacccaac ccgaaccagc   9240
acccaagagc gatccccgaa ggacccccga accgcaaagg acatcagtat cccacagcct   9300
```

-continued

```
ctccaagtcc cccggtctcc tcctcttctc gaagggacca aaagatcaat ccaccacacc   9360
cgacgacact caactcccca cccctaaagg agacaccggg aatcccagaa tcaagactca   9420
tccaatgtcc atcatgggtc tcaaggtgaa cgtctctgcc atattcatgg cagtactgtt   9480
aactctccaa acacccaccg gtcaaatcca ttggggcaat ctctctaaga taggggtggt   9540
aggaatagga agtgcaagct acaaagttat gactcgttcc agccatcaat cattagtcat   9600
aaaattaatg cccaatataa ctctcctcaa taactgcacg agggtagaga ttgcagaata   9660
caggagacta ctgagaacag ttttggaacc aattagagat gcacttaatg caatgaccca   9720
gaatataaga ccggttcaga gtgtagcttc aagtaggaga cacaagagat ttgcgggagt   9780
agtcctggca ggtgcggccc taggcgttgc cacagctgct cagataacag ccggcattgc   9840
acttcaccag tccatgctga actctcaagc catcgacaat ctgagagcga gcctggaaac   9900
tactaatcag gcaattgaga caatcagaca agcagggcag gagatgatat tggctgttca   9960
gggtgtccaa gactacatca ataatgagct gataccgtct atgaaccaac tatcttgtga  10020
tttaatcggc cagaagctcg ggctcaaatt gctcagatac tatacagaaa tcctgtcatt  10080
atttggcccc agtttacggg accccatatc tgcggagata tctatccagg ctttgagcta  10140
tgcgcttgga ggagacatca ataaggtgtt agaaaagctc ggatacagtg gaggtgattt  10200
actgggcatc ttagagagcg gaggaataaa ggcccggata actcacgtcg acacagagtc  10260
ctacttcatt gtcctcagta tagcctatcc gacgctgtcc gagattaagg gggtgattgt  10320
ccaccggcta gaggggtct cgtacaacat aggctctcaa gagtggtata ccactgtgcc  10380
caagtatgtt gcaacccaag ggtaccttat ctcgaatttt gatgagtcat cgtgtacttt  10440
catgccagag ggactgtgt gcagccaaaa tgccttgtac ccgatgagtc ctctgctcca  10500
agaatgcctc cgggggtaca ccaagtcctg tgctcgtaca ctcgtatccg ggtcttttgg  10560
gaaccggttc attttatcac aagggaacct aatagccaat tgtgcatcaa tcctttgcaa  10620
gtgttacaca acaggaacga tcattaatca agaccctgac aagatcctaa catacattgc  10680
tgccgatcac tgcccggtag tcgaggtgaa cggcgtgacc atccaagtcg ggagcaggag  10740
gtatccagac gctgtgtact tgcacagaat tgacctcggt cctcccatat cattggagag  10800
gttggacgta gggacaaatc tggggaatgc aattgctaag ttggaggatg ccaaggaatt  10860
gttggagtca tcggaccaga tattgaggag tatgaaaggt ttatcgagca ctagcatagt  10920
ctacatcctg attgcagtgt gtcttggagg gttgataggg atccccgctt taatatgttg  10980
ctgcaggggg cgttgtaaca aaaagggaga acaagttggt atgtcaagac caggcctaaa  11040
gcctgatctt acgggaacat caaaatccta tgtaaggtcg ctctgatcct ctacaactct  11100
tgaaacacaa atgtcccaca agtctcctct tcgtcatcaa gcaaccaccg cacccagcat  11160
caagcccacc tgaaattatc tccggcttcc ctctggccga acaatatcgg tagttaatca  11220
aaacttaggg tgcaagatca tccacaatgt caccacaacg agaccggata aatgccttct  11280
acaaagataa cccccatccc aagggaagta ggatagtcat taacagagaa catcttatga  11340
ttgatagacc ttatgttttg ctggctgttc tgtttgtcat gtttctgagc ttgatcgggt  11400
tgctagccat tgcaggcatt agacttcatc gggcagccat ctacaccgca gagatccata  11460
aaagcctcag caccaatcta gatgtaacta actcaatcga gcatcaggtc aaggacgtgc  11520
tgacaccact cttcaaaatc atcggtgatg aagtgggcct gaggacacct cagagattca  11580
ctgacctagt gaaattaatc tctgacaaga ttaaattcct taatccggat agggagtacg  11640
acttcagaga tctcacttgg tgtatcaacc cgccagagag aatcaaattg gattatgatc  11700
```

```
aatactgtgc agatgtggct gctgaagagc tcatgaatgc attggtgaac tcaactctac  11760
tggagaccag aacaaccaat cagttcctag ctgtctcaaa gggaaactgc tcagggccca  11820
ctacaatcag aggtcaattc tcaaacatgt cgctgtccct gttagacttg tatttaggtc  11880
gaggttacaa tgtgtcatct atagtcacta tgacatccca gggaatgtat gggggaactt  11940
acctagtgga aaagcctaat ctgagcagca aaaggtcaga gttgtcacaa ctgagcatgt  12000
accgagtgtt tgaagtaggt gttatcagaa atccgggttt gggggctccg gtgttccata  12060
tgacaaacta tcttgagcaa ccagtcagta atgatctcag caactgtatg gtggctttgg  12120
gggagctcaa actcgcagcc ctttgtcacg gggaagattc tatcacaatt ccctatcagg  12180
gatcagggaa aggtgtcagc ttccagctcg tcaagctagg tgtctggaaa tccccaaccg  12240
acatgcaatc ctgggtcccc ttatcaacgg atgatccagt gatagacagg ctttacctct  12300
catctcacag aggtgttatc gctgacaatc aagcaaaatg ggctgtcccg acaacacgaa  12360
cagatgacaa gttgcgaatg gagacatgct tccaacaggc gtgtaagggt aaaatccaag  12420
cactctgcga gaatcccgag tgggcaccat tgaaggataa caggattcct tcatacgggg  12480
tcttgtctgt tgatctgagt ctgacagttg agcttaaaat caaaattgct tcgggattcg  12540
ggccattgat cacacacggt tcagggatgg acctatacaa atccaaccac aacaatgtgt  12600
attggctgac tatcccgcca atgaagaacc tagccttagg tgtaatcaac acattggagt  12660
ggataccgag attcaaggtt agtccctacc tcttcactgt cccaattaag gaagcaggcg  12720
aagactgcca tgccccaaca tacctacctg cggaggtgga tggtgatgtc aaactcagtt  12780
ccaatctggt gattctacct ggtcaagatc tccaatatgt tttggcaacc tacgatactt  12840
ccagggttga acatgctgtg gtttattacg tttacagccc aagccgctca ttttcttact  12900
tttatccttt taggttgcct ataaaggggg tccccatcga attacaagtg gaatgcttca  12960
catgggacca aaaactctgg tgccgtcact tctgtgtgct tgcggactca gaatctggtg  13020
gacatatcac tcactctggg atggtgggca tgggagtcag ctgcacagtc acccgggaag  13080
atggaaccaa tcgcagatag ggctgctagt gaaccaatca catgatgtca cccagacatc  13140
aggcataccc actagtgtga aatagacatc agaattaaga aaaacgtagg gtccaagtgg  13200
ttccccgtta tggactcgct atctgtcaac cagatcttat accctgaagt tcacctagat  13260
agcccgatag ttaccaataa gatagtagcc atcctggagt atgctcgagt ccctcacgct  13320
tacagcctgg aggaccctac actgtgtcag aacatcaagc accgcctaaa aaacggattt  13380
tccaaccaaa tgattataaa caatgtggaa gttgggaatg tcatcaagtc caagcttagg  13440
agttatccgg cccactctca tattccatat ccaaattgta atcaggattt atttaacata  13500
gaagacaaag agtcaacgag gaagatccgt gaactcctca aaaggggaa ttcgctgtac  13560
tccaaagtca gtgataaggt tttccaatgc ttaagggaca ctaactcacg gcttggccta  13620
ggctccgaat tgagggagga catcaaggag aaagttatta acttgggagt ttacatgcac  13680
agctcccagt ggtttgagcc ctttctgttt tggtttacag tcaagactga gatgaggtca  13740
gtgattaaat cacaaaccca tacttgccat aggaggagac acacacctgt attcttcact  13800
ggtagttcag ttgagttgct aatctctcgt gaccttgttg ctataatcag taaagagtct  13860
caacatgtat attacctgac atttgaactg gttttgatgt attgtgatgt catagagggg  13920
aggttaatga cagagaccgc tatgactatt gatgctaggt atacagagct tctaggaaga  13980
gtcagataca tgtggaaact gatagatggt ttcttccctg cactcgggaa tccaacttat  14040
```

```
caaattgtag ccatgctgga gcctctttca cttgcttacc tgcagctgag ggatataaca  14100
gtagaactca gaggtgcttt ccttaaccac tgctttactg aaatacatga tgttcttgac  14160
caaaacgggt tttctgatga aggtacttat catgagttaa ctgaagctct agattacatt  14220
ttcataactg atgacataca tctgacaggg gagattttct catttttcag aagtttcggc  14280
caccccagac ttgaagcagt aacggctgct gaaaatgtta ggaaatacat gaatcagcct  14340
aaagtcattg tgtatgagac tctgatgaaa ggtcatgcca tattttgtgg aatcataatc  14400
aacggctatc gtgacaggca cggaggcagt tggccaccgc tgaccctccc cctgcatgct  14460
gcagacacaa tccggaatgc tcaagcttca ggtgaagggt taacacatga gcagtgcgtt  14520
gataactgga aatcttttgc tggagtgaaa tttggctgct ttatgcctct tagcctggat  14580
agtgatctga caatgtacct aaaggacaag gcacttgctg ctctccaaag ggaatgggat  14640
tcagtttacc cgaaagagtt cctgcgttac gaccctccca agggaaccgg gtcacggagg  14700
cttgtagatg ttttccttaa tgattcgagc tttgacccat atgatgtgat aatgtatgtt  14760
gtaagtggag cttacctcca tgaccctgag ttcaacctgt cttacagcct gaaagaaaag  14820
gagatcaagg aaacaggtag actttttgct aaaatgactt acaaaatgag ggcatgccaa  14880
gtgattgctg aaaatctaat ctcaaacggg attggcaaat attttaagga caatgggatg  14940
gccaaggatg agcacgattt gactaaggca ctccacactc tagctgtctc aggagtcccc  15000
aaagatctca aagaaagtca caggggggg ccagtcttaa aaacctactc ccgaagccca  15060
gtccacacaa gtaccaggaa cgtgagagca gcaaaagggt ttatagggtt ccctcaagta  15120
attcggcagg accaagacac tgatcatccg gagaatatgg aagcttacga gacagtcagt  15180
gcatttatca cgactgatct caagaagtac tgccttaatt ggagatatga gaccatcagc  15240
ttgtttgcac agaggctaaa tgagatttac ggattgccct catttttcca gtggctgcat  15300
aagaggcttg agacctctgt cctgtatgta agtgaccctc attgcccccc cgaccttgac  15360
gcccatatcc cgttatataa agtccccaat gatcaaatct tcattaagta ccctatggga  15420
ggtatagaag ggtattgtca gaagctgtgg accatcagca ccattcccta tctatacctg  15480
gctgcttatg agagcggagt aaggattgct tcgttagtgc aaggggacaa tcagaccata  15540
gccgtaacaa aaagggtacc cagcacatgg ccctacaacc ttaagaaacg ggaagctgct  15600
agagtaacta gagattactt tgtaattctt aggcaaaggc tacatgatat tggccatcac  15660
ctcaaggcaa atgagacaat tgtttcatca catttttttg tctattcaaa aggaatatat  15720
tatgatgggc tacttgtgtc ccaatcactc aagagcatcg caagatgtgt attctggtca  15780
gagactatag ttgatgaaac aagggcagca tgcagtaata ttgctacaac aatggctaaa  15840
agcatcgaga gaggttatga ccgttacctt gcatattccc tgaacgtcct aaaagtgata  15900
cagcaaattc tgatctctct tggcttcaca atcaattcaa ccatgacccg ggatgtagtc  15960
atacccctcc tcacaaacaa cgacctctta ataaggatgg cactgttgcc cgctcctatt  16020
ggggggatga attatctgaa tatgagcagg ctgtttgtca gaaacatcgg tgatccagta  16080
acatcatcaa ttgctgatct caagagaatg attctcgcct cactaatgcc tgaagagacc  16140
ctccatcaag taatgacaca acaaccgggg gactcttcat tcctagactg ggctagcgac  16200
ccttactcag caaatcttgt atgtgtccag agcatcacta gactcctcaa gaacataact  16260
gcaaggtttg tcctgatcca tagtccaaac ccaatgttaa aaggattatt ccatgatgac  16320
agtaaagaag aggacgaggg actggcggca ttcctcatgg acaggcatat tatagtacct  16380
agggcagctc atgaaatcct ggatcatagt gtcacagggg caagagagtc tattgcaggc  16440
```

```
atgctggata ccacaaaagg cttgattcga gccagcatga ggaagggggg gttaacctct  16500
cgagtgataa ccagattgtc caattatgac tatgaacaat tcagagcagg gatggtgcta  16560
ttgacaggaa gaaagagaaa tgtcctcatt gacaaagagt catgttcagt gcagctggcg  16620
agagctctaa gaagccatat gtgggcgagg ctagctcgag gacggcctat ttacggcctt  16680
gaggtccctg atgtactaga atctatgcga ggccacctta ttcggcgtca tgagacatgt  16740
gtcatctgcg agtgtggatc agtcaactac ggatggtttt ttgtcccctc gggttgccaa  16800
ctggatgata ttgacaagga aacatcatcc ttgagagtcc catatattgg ttctaccact  16860
gatgagagaa cagacatgaa gcttgccttc gtaagagccc caagtcgatc cttgcgatct  16920
gctgttagaa tagcaacagt gtactcatgg gcttacggtg atgatgatag ctcttggaac  16980
gaagcctggt tgttggctag gcaaagggcc aatgtgagcc tggaggagct aagggtgatc  17040
actcccatct caacttcgac taatttagcg cataggttga gggatcgtag cactcaagtg  17100
aaatactcag gtacatccct tgtccgagtg gcgaggtata ccacaatctc caacgacaat  17160
ctctcatttg tcatatcaga taagaaggtt gatactaact ttatatacca acaaggaatg  17220
cttctagggt tgggtgtttt agaaacattg tttcgactcg agaaagatac cggatcatct  17280
aacacggtat tacatcttca cgtcgaaaca gattgttgcg tgatcccgat gatagatcat  17340
cccaggatac ccagctcccg caagctagag ctgagggcag agctatgtac caacccattg  17400
atatatgata atgcaccttt aattgacaga gatgcaacaa ggctatacac ccagagccat  17460
aggaggcacc ttgtggaatt tgttacatgg tccacacccc aactatatca cattttagct  17520
aagtccacag cactatctat gattgacctg gtaacaaaat ttgagaagga ccatatgaat  17580
gaaatttcag ctctcatagg ggatgacgat atcaatagtt tcataactga gtttctgctc  17640
atagagccaa gattattcac tatctacttg ggccagtgtg cggccatcaa ttgggcattt  17700
gatgtacatt atcatagacc atcagggaaa tatcagatgg gtgagctgtt gtcatcgttc  17760
ctttctagaa tgagcaaagg agtgtttaag gtgcttgtca atgctctaag ccacccaaag  17820
atctacaaga aattctggca ttgtggtatt atagagccta tccatggtcc ttcacttgat  17880
gctcaaaact tgcacacaac tgtgtgcaac atggtttaca catgctatat gacctacctc  17940
gacctgttgt tgaatgaaga gttagaagag ttcacatttc tcttgtgtga aagcgacgag  18000
gatgtagtac cggacagatt cgacaacatc caggcaaaac acttatgtgt tctggcagat  18060
ttgtactgtc aaccagggac ctgcccacca attcgaggtc taagaccggt agagaaatgt  18120
gcagttctaa ccgaccatat caaggcagag gctatgttat ctccagcagg atcttcgtgg  18180
aacataaatc caattattgt agaccattac tcatgctctc tgacttatct ccggcgagga  18240
tcgatcaaac agataagatt gagagttgat ccaggattca ttttcgacgc cctcgctgag  18300
gtaaatgtca gtcagccaaa gatcggcagc aacaacatct caaatatgag catcaaggct  18360
ttcagacccc cacacgatga tgttgcaaaa ttgctcaaag atatcaacac aagcaagcac  18420
aatcttccca tttcaggggg caatctcgcc aattatgaaa tccatgcttt ccgcagaatc  18480
gggttgaact catctgcttg ctacaaagct gttgagatat caacattaat taggagatgc  18540
cttgagccag gggaggacgg cttgttcttg ggtgagggat cgggttctat gttgatcact  18600
tataaagaga tacttaaact aaacaagtgc ttctataata gtggggtttc cgccaattct  18660
agatctggtc aaagggaatt agcaccctat ccctccgaag ttggccttgt cgaacacaga  18720
atgggagtag gtaatattgt caaagtgctc tttaacggga ggcccgaagt cacgtgggta  18780
```

```
ggcagtgtag attgcttcaa tttcatagtt agtaatatcc ctacctctag tgtggggttt  18840
atccattcag atatagagac cttgcctgac aaagatacta tagagaagct agaggaattg  18900
gcagccatct tatcgatggc tctgctcctg ggcaaaatag gatcaatact ggtgattaag  18960
cttatgcctt tcagcgggga ttttgttcag ggatttataa gttatgtagg gtctcattat  19020
agagaagtga accttgtata ccctagatac agcaacttca tctctactga atcttatttg  19080
gttatgacag atctcaaggc taaccggcta atgaatcctg aaaagattaa gcagcagata  19140
attgaatcat ctgtgaggac ttcacctgga cttataggtc acatcctatc cattaagcaa  19200
ctaagctgca tacaagcaat tgtgggagac gcagttagta gaggtgatat caatcctact  19260
ctgaaaaaac ttacacctat agagcaggtg ctgatcaatt gcgggttggc aattaacgga  19320
cctaagctgt gcaaagaatt gatccaccat gatgttgcct cagggcaaga tggattgctt  19380
aattctatac tcatcctcta cagggagttg gcaagattca aagacaacca aagaagtcaa  19440
caagggatgt tccacgctta ccccgtattg gtaagtagca ggcaacgaga acttatatct  19500
aggatcaccc gcaaattctg gggcacatt cttctttact ccgggaacaa aaagttgata  19560
aataagttta tccagaatct caagtccggc tatctgatac tagacttaca ccagaatatc  19620
ttcgttaaga atctatccaa gtcagagaaa cagattatta tgacgggggg tttgaaacgt  19680
gagtgggttt ttaaggtaac agtcaaggag accaaagaat ggtataagtt agtcggatac  19740
agtgccctga ttaaggacta attggttgaa ctccggaacc ctaatcctgc cctaggtggt  19800
taggcattat ttgcaatata ttaaagaaaa ctttgaaaat acgaagtttc tattcccagc  19860
tttgtctggt ggccggcatg gtcccagcct cctcgctggc gccggctggg caacattccg  19920
aggggaccgt cccctcggta atggcgaatg ggacgcggcc gatccggctg ctaacaaagc  19980
ccgaaaggaa gctgagttgg ctgctgccac cgctgagcaa taactagcat aaccccttgg  20040
ggcctctaaa cgggtcttga ggggtttttt gctgaaagga ggaactatat ccggatgcgg  20100
ccgcgggccc tatggtaccc agcttttgtt ccctttagtg agggttaatt ccgagcttgg  20160
cgtaatcatg gtcatagctg tttcctgtgt gaaattgtta tccgctcaca attccacaca  20220
acataggagc cggaagcata aagtgtaaag cctggggtgc ctaatgagtg aggtaactca  20280
cattaattgc gttgcgctca ctgcccgctt tccagtcggg aaacctgtcg tgccagctgc  20340
attaatgaat cggccaacgc gcggggagag gcggtttgcg tattgggcgc tcttccgctt  20400
cctcgctcac tgactcgctg cgctcggtcg ttcggctgcg gcgagcggta tcagctcact  20460
caaaggcggt aatacggtta tccacagaat caggggataa cgcaggaaag aacatgtgag  20520
caaaaggcca gcaaaaggcc aggaaccgta aaaaggccgc gttgctggcg tttttccata  20580
ggctcggccc ccctgacgag catcacaaaa atcgacgctc aagtcagagg tggcgaaacc  20640
cgacaggact ataaagatac caggcgttcc ccctggaag ctccctcgtg cgctctcctg  20700
ttccgaccct gccgcttacc ggatacctgt ccgcctttct cccttcggga agcgtggcgc  20760
tttctcaatg ctcacgctgt aggtatctca gttcggtgta ggtcgttcgc tccaagctgg  20820
gctgtgtgca cgaacccccc gttcagcccg accgctgcgc cttatccggt aactatcgtc  20880
ttgagtccaa cccggtaaga cacgacttat cgccactggc agcagccact ggtaacagga  20940
ttagcagagc gaggtatgta ggcggtgcta cagagttctt gaagtggtgg cctaactacg  21000
gctacactag aaggacagta tttggtatct gcgctctgct gaagccagtt accttcggaa  21060
aaagagttgg tagctcttga tccggcaaac aaaccaccgc tggtagcggt ggtttttttg  21120
tttgcaagca gcagattacg cgcagaaaaa aaggatctca agaagatcct ttgatctttt  21180
```

ctacggggtc tgacgctcag tggaacgaaa actcacgtta agggattttg gtcatgagat 21240
tatcaaaaag gatcttcacc tagatccttt taaattaaaa atgaagtttt aaatcaatct 21300
aaagtatata tgagtaaact tggtctgaca gttaccaatg cttaatcagt gaggcaccta 21360
tctcagcgat ctgtctattt cgttcatcca tagttgcctg actgcccgtc gtgtagataa 21420
ctacgatacg ggagggctta ccatctggcc ccagtgctgc aatgataccg cgagacccac 21480
gctcaccggc tccagattta tcagcaataa accagccagc cggaagggcc gagcgcagaa 21540
gtggtcctgc aactttatcc gcctccatcc agtctattaa ttgttgccgg gaagctagag 21600
taagtagttc gccagttaat agtttgcgca acgttgttgc cattgctaca ggcatcgtgg 21660
tgtcacgctc gtcgtttggt atggcttcat tcagctccgg ttcccaacga tcaaggcgag 21720
ttacatgatc ccccatgttg tgaaaaaaag cggttagctc cttcggtcct ccgatcgttg 21780
tcagaagtaa gttggccgca gtgttatcac tcatgcttat ggcagcactg cataattctc 21840
ttactgtcat gccatccgta agatgctttt ctgtgactgg tgagtactca accaagtcat 21900
tctgagaata gtgtatgcgg cgaccgagtt gctcttgccc ggcgtcaata cgggataata 21960
ccgcgccaca tagcagaact ttaaaagtgc tcatcattgg aaaacgttct tcggggcgaa 22020
aactctcaag gatcttaccg ctgttgagat ccagttcgat gtaacccact cgtgcaccca 22080
actgatcttc agcatctttt actttcacca gcgtttctgg gtgagcaaaa acaggaaggc 22140
aaaatgccgc aaaaaaggga ataagggcga cacggaaatg ttgaatactc atactcttcc 22200
tttttcaata ttattgaagc atttatcagg gttattgtct catgagcgga tacatatttg 22260
aatgtattta gaaaaataaa caaatagggg ttccgcgcac atttccccga aaagtgccac 22320
ctgaaattgt aaacgttaat attttgttaa aattcgcgtt aaatttttgt taaatcagct 22380
cattttttaa ccaataggcc gaaatcggca aaatccctta taaatcaaaa gaatagaccg 22440
agatagggtt gagtgttgtt ccagtttgga acaagagtcc actattaaag aacgtggact 22500
ccaacgtcaa agggcgaaaa accgtctatc agggcgatgg cccactacgt gaaccatcac 22560
cctaatcaag ttttttgggg tcgaggtgcc gtaaagcact aaatcggaac cctaaaggga 22620
gcccccgatt tagagcttga cggggaaagc cggcgaacgt ggcgagaaag gaagggaaga 22680
aagcgaaagg agcgggcgct agggcgctgg caagtgtagc ggtcacgctg cgcgtaacca 22740
ccacacccgc cgcgcttaat gcgccgctac agggcgcgtc ccattcgcca ttcaggctgc 22800
gcaactgttg ggaagggcga tcggtgcggg cctcttcgct attacgccag ccaccgcggt 22860
g 22861

<210> SEQ ID NO 15
<211> LENGTH: 18967
<212> TYPE: DNA
<213> ORGANISM: Artificial Sequence
<220> FEATURE:
<223> OTHER INFORMATION: Plasmide pTM1-MVSchwarz pTM-MVSchw (GenBank: FW366202.1)

<400> SEQUENCE: 15
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300

```
ccaatccctg gagattcctc aattaccact cgatccagac ttctggaccg gttggtgagg    360
ttaattggaa acccggatgt gagcgggccc aaactaacag gggcactaat aggtatatta    420
tccttatttg tggagtctcc aggtcaattg attcagagga tcaccgatga ccctgacgtt    480
agcataaggc tgttagaggt tgtccagagt gaccagtcac aatctggcct taccttcgca    540
tcaagaggta ccaacatgga ggatgaggcg gaccaatact tttcacatga tgatccaatt    600
agtagtgatc aatccaggtt cggatggttc gggaacaagg aaatctcaga tattgaagtg    660
caagaccctg agggattcaa catgattctg ggtaccatcc tagcccaaat ttgggtcttg    720
ctcgcaaagg cggttacggc cccagacacg gcagctgatt cggagctaag aaggtggata    780
aagtacaccc aacaaagaag ggtagttggt gaatttagat tggagagaaa atggttggat    840
gtggtgagga acaggattgc cgaggacctc tccttacgcc gattcatggt cgctctaatc    900
ctggatatca agagaacacc cggaaacaaa cccaggattg ctgaaatgat atgtgacatt    960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga acctttacca gcaaatgggg gaaactgcac cctacatggt aatcctggag   1140
aactcaattc agaacaagtt cagtgcagga tcataccctc tgctctggag ctatgccatg   1200
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg gacccagaca agcccaagta   1440
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca cacccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
```

-continued aacccaatgt gctcgaaagt caccctcgga accatcaggg ccaggtgcac ctgcggggaa 2700
tgtccccgag tgtgtgagca atgccgcact gatacaggag tggacacccg aatctggtac 2760
cacaatctcc ccgagatccc agaataatga agaaggggga gactattatg atgatgagct 2820
gttctctgat gtccaagata ttaaaacagc cttggccaaa atacacgagg ataatcagaa 2880
gataatctcc aagctagaat cactgctgtt attgaaggga gaagttgagt caattaagaa 2940
gcagatcaac aggcaaaata tcagcatatc caccctggaa ggacacctct caagcatcat 3000
gatcgccatt cctggacttg ggaaggatcc caacgacccc actgcagatg tcgaaatcaa 3060
tcccgacttg aaacccatca taggcagaga ttcaggccga gcactggccg aagttctcaa 3120
gaaacccgtt gccagccgac aactccaagg aatgacaaat ggacggacca gttccagagg 3180
acagctgctg aaggaatttc agctaaagcc gatcgggaaa aagatgagct cagccgtcgg 3240
gtttgttcct gacaccggcc ctgcatcacg cagtgtaatc cgctccatta taaaatccag 3300
ccggctagag gaggatcgga agcgttacct gatgactctc cttgatgata tcaaaggagc 3360
caatgatctt gccaagttcc accagatgct gatgaagata ataatgaagt agctacagct 3420
caacttacct gccaacccca tgccagtcga cccaactagt acaacctaaa tccattataa 3480
aaaacttagg agcaaagtga ttgcctccca aggtccacaa tgacagagac ctacgacttc 3540
gacaagtcgg catgggacat caaagggtcg atcgctccga tacaacccac cacctacagt 3600
gatggcaggc tggtgcccca ggtcagagtc atagatcctg gtctaggcga caggaaggat 3660
gaatgcttta tgtacatgtt tctgctgggg gttgttgagg acagcgattc cctagggcct 3720
ccaatcgggc gagcatttgg gttcctgccc ttaggtgttg gcagatccac agcaaagccc 3780
gaaaaactcc tcaaagaggc cactgagctt gacatagttg ttagacgtac agcagggctc 3840
aatgaaaaac tggtgttcta caacaacacc ccactaactc tcctcacacc ttggagaaag 3900
gtcctaacaa cagggagtgt cttcaacgca aaccaagtgt gcaatgcggt taatctgata 3960
ccgctcgata ccccgcagag gttccgtgtt gtttatatga gcatcacccg tctttcggat 4020
aacgggtatt acaccgttcc tagaagaatg ctggaattca gatcggtcaa tgcagtggcc 4080
ttcaacctgc tggtgaccct taggattgac aaggcgatag gccctgggaa gatcatcgac 4140
aatacagagc aacttcctga ggcaacattt atggtccaca tcgggaactt caggagaaag 4200
aagagtgaag tctactctgc cgattattgc aaaatgaaaa tcgaaaagat gggcctggtt 4260
tttgcacttg gtgggatagg gggcaccagt cttcacatta gaagcacagg caaaatgagc 4320
aagactctcc atgcacaact cgggttcaag aagaccttat gttacccgct gatggatatc 4380
aatgaagacc ttaatcgatt actctggagg agcagatgca agatagtaag aatccaggca 4440
gttttgcagc catcagttcc tcaagaattc cgcatttacg acgacgtgat cataaatgat 4500
gaccaaggac tattcaaagt tctgtagacc gtagtgccca gcaatgcccg aaaacgaccc 4560
ccctcacaat gacagccaga aggcccggac aaaaaagccc cctccgaaag actccacgga 4620
ccaagcgaga ggccagccag cagccgacgg caagcgcgaa caccaggcgg ccccagcaca 4680
gaacagccct gacacaaggc caccaccagc caccccaatc tgcatcctcc tcgtgggacc 4740
cccgaggacc aacccccaag gctgcccccg atccaaacca ccaaccgcat ccccaccacc 4800
cccgggaaag aaacccccag caattggaag gcccctcccc ctcttcctca acacaagaac 4860
tccacaaccg aaccgcacaa gcgaccgagg tgacccaacc gcaggcatcc gactccctag 4920
acagatcctc tctccccggc aaactaaaca aaacttaggg ccaaggaaca tacacaccca 4980
acagaaccca gaccccggcc cacggcgccg cgcccccaac cccgacaacc cagagggagc 5040

```
ccccaaccaa tcccgccggc tcccccggtg cccacaggca gggacaccaa cccccgaaca   5100
gacccagcac ccaaccatcg acaatccaag acgggggggc ccccccaaaa aaaggccccc   5160
aggggccgac agccagcacc gcgaggaagc ccacccaccc cacacacgac cacggcaacc   5220
aaaccagaac ccagaccacc ctgggccacc agctcccaga ctcggccatc accccgcaga   5280
aaggaaaggc cacaacccgc gcaccccagc cccgatccgg cggggagcca cccaacccga   5340
accagcaccc aagagcgatc cccgaaggac ccccgaaccg caaaggacat cagtatccca   5400
cagcctctcc aagtcccccg gtctcctcct cttctcgaag ggaccaaaag atcaatccac   5460
cacacccgac gacactcaac tccccacccc taaaggagac accgggaatc ccagaatcaa   5520
gactcatcca atgtccatca tgggtctcaa ggtgaacgtc tctgccatat tcatggcagt   5580
actgttaact ctccaaacac ccaccggtca aatccattgg ggcaatctct ctaagatagg   5640
ggtggtagga ataggaagtg caagctacaa agttatgact cgttccagcc atcaatcatt   5700
agtcataaaa ttaatgccca atataactct cctcaataac tgcacgaggg tagagattgc   5760
agaatacagg agactactga gaacagtttt ggaaccaatt agagatgcac ttaatgcaat   5820
gacccagaat ataagaccgg ttcagagtgt agcttcaagt aggagacaca agagatttgc   5880
gggagtagtc ctggcaggtg cggccctagg cgttgccaca gctgctcaga taacagccgg   5940
cattgcactt caccagtcca tgctgaactc tcaagccatc gacaatctga gagcgagcct   6000
ggaaactact aatcaggcaa ttgagacaat cagacaagca gggcaggaga tgatattggc   6060
tgttcagggt gtccaagact acatcaataa tgagctgata ccgtctatga accaactatc   6120
ttgtgattta atcggccaga agctcgggct caaattgctc agatactata cagaaatcct   6180
gtcattattt ggccccagtt tacgggaccc catatctgcg gagatatcta tccaggcttt   6240
gagctatgcg cttggaggag acatcaataa ggtgttagaa aagctcggat acagtggagg   6300
tgatttactg ggcatcttag agagcggagg aataaaggcc cggataactc acgtcgacac   6360
agagtcctac ttcattgtcc tcagtatagc ctatccgacg ctgtccgaga ttaagggggt   6420
gattgtccac cggctagagg gggtctcgta caacataggc tctcaagagt ggtataccac   6480
tgtgcccaag tatgttgcaa cccaagggta ccttatctcg aattttgatg agtcatcgtg   6540
tactttcatg ccagagggga ctgtgtgcag ccaaaatgcc ttgtacccga tgagtcctct   6600
gctccaagaa tgcctccggg ggtacaccaa gtcctgtgct cgtacactcg tatccgggtc   6660
ttttgggaac cggttcattt tatcacaagg gaacctaata gccaattgtg catcaatcct   6720
ttgcaagtgt tacacaacag gaacgatcat taatcaagac cctgacaaga tcctaacata   6780
cattgctgcc gatcactgcc cggtagtcga ggtgaacggc gtgaccatcc aagtcgggag   6840
caggaggtat ccagacgctg tgtacttgca cagaattgac ctcggtcctc ccatatcatt   6900
ggagaggttg gacgtaggga caaatctggg gaatgcaatt gctaagttgg aggatgccaa   6960
ggaattgttg gagtcatcgg accagatatt gaggagtatg aaaggtttat cgagcactag   7020
catagtctac atcctgattg cagtgtgtct tggagggttg atagggatcc ccgctttaat   7080
atgttgctgc agggggcgtt gtaacaaaaa gggagaacaa gttggtatgt caagaccagg   7140
cctaaagcct gatcttacgg gaacatcaaa atcctatgta aggtcgctct gatcctctac   7200
aactcttgaa acacaaatgt cccacaagtc tcctcttcgt catcaagcaa ccaccgcacc   7260
cagcatcaag cccacctgaa attatctccg gcttccctct ggccgaacaa tatcggtagt   7320
taatcaaaac ttagggtgca agatcatcca caatgtcacc acaacgagac cggataaatg   7380
```

-continued

```
ccttctacaa agataacccc catcccaagg gaagtaggat agtcattaac agagaacatc   7440
ttatgattga tagaccttat gttttgctgg ctgttctgtt tgtcatgttt ctgagcttga   7500
tcgggttgct agccattgca ggcattagac ttcatcgggc agccatctac accgcagaga   7560
tccataaaag cctcagcacc aatctagatg taactaactc aatcgagcat caggtcaagg   7620
acgtgctgac accactcttc aaaatcatcg gtgatgaagt gggcctgagg acacctcaga   7680
gattcactga cctagtgaaa ttaatctctg acaagattaa attccttaat ccggataggg   7740
agtacgactt cagagatctc acttggtgta tcaacccgcc agagagaatc aaattggatt   7800
atgatcaata ctgtgcagat gtggctgctg aagagctcat gaatgcattg gtgaactcaa   7860
ctctactgga gaccagaaca accaatcagt tcctagctgt ctcaaaggga aactgctcag   7920
ggcccactac aatcagaggt caattctcaa acatgtcgct gtccctgtta gacttgtatt   7980
taggtcgagg ttacaatgtg tcatctatag tcactatgac atcccaggga atgtatgggg   8040
gaacttacct agtggaaaag cctaatctga gcagcaaaag gtcagagttg tcacaactga   8100
gcatgtaccg agtgtttgaa gtaggtgtta tcagaaatcc gggtttgggg gctccggtgt   8160
tccatatgac aaactatctt gagcaaccag tcagtaatga tctcagcaac tgtatggtgg   8220
ctttggggga gctcaaactc gcagcccttt gtcacgggga agattctatc acaattccct   8280
atcagggatc agggaaaggt gtcagcttcc agctcgtcaa gctaggtgtc tggaaatccc   8340
caaccgacat gcaatcctgg gtccccttat caacggatga tccagtgata gacaggcttt   8400
acctctcatc tcacagaggt gttatcgctg acaatcaagc aaaatgggct gtcccgacaa   8460
cacgaacaga tgacaagttg cgaatggaga catgcttcca acaggcgtgt aagggtaaaa   8520
tccaagcact ctgcgagaat cccgagtggg caccattgaa ggataacagg attccttcat   8580
acggggtctt gtctgttgat ctgagtctga cagttgagct taaaatcaaa attgcttcgg   8640
gattcgggcc attgatcaca cacggttcag ggatggacct atacaaatcc aaccacaaca   8700
atgtgtattg gctgactatc ccgccaatga agaacctagc cttaggtgta atcaacacat   8760
tggagtggat accgagattc aaggttagtc cctacctctt cactgtccca attaaggaag   8820
caggcgaaga ctgccatgcc ccaacatacc tacctgcgga ggtggatggt gatgtcaaac   8880
tcagttccaa tctggtgatt ctacctggtc aagatctcca atatgttttg gcaacctacg   8940
atacttccag ggttgaacat gctgtggttt attacgttta cagcccaagc cgctcatttt   9000
cttactttta tccttttagg ttgcctataa agggggtccc catcgaatta caagtggaat   9060
gcttcacatg ggaccaaaaa ctctggtgcc gtcacttctg tgtgcttgcg gactcagaat   9120
ctggtggaca tatcactcac tctgggatgg tgggcatggg agtcagctgc acagtcaccc   9180
gggaagatgg aaccaatcgc agatagggct gctagtgaac caatcacatg atgtcaccca   9240
gacatcaggc atacccacta gtgtgaaata gacatcagaa ttaagaaaaa cgtagggtcc   9300
aagtggttcc ccgttatgga ctcgctatct gtcaaccaga tcttataccc tgaagttcac   9360
ctagatagcc cgatagttac caataagata gtagccatcc tggagtatgc tcgagtccct   9420
cacgcttaca gcctggagga ccctacactg tgtcagaaca tcaagcaccg cctaaaaaac   9480
ggattttcca accaaatgat tataaacaat gtggaagttg ggaatgtcat caagtccaag   9540
cttaggagtt atccggccca ctctcatatt ccatatccaa attgtaatca ggatttattt   9600
aacatagaag acaaagagtc aacgaggaag atccgtgaac tcctcaaaaa ggggaattcg   9660
ctgtactcca aagtcagtga taaggttttc caatgcttaa gggacactaa ctcacggctt   9720
ggcctaggct ccgaattgag ggaggacatc aaggagaaag ttattaactt gggagtttac   9780
```

```
atgcacagct cccagtggtt tgagcccttt ctgttttggt ttacagtcaa gactgagatg   9840
aggtcagtga ttaaatcaca aacccatact tgccatagga ggagacacac acctgtattc   9900
ttcactggta gttcagttga gttgctaatc tctcgtgacc ttgttgctat aatcagtaaa   9960
gagtctcaac atgtatatta cctgacattt gaactggttt tgatgtattg tgatgtcata  10020
gaggggaggt taatgacaga gaccgctatg actattgatg ctaggtatac agagcttcta  10080
ggaagagtca gatacatgtg gaaactgata gatggtttct tccctgcact cgggaatcca  10140
acttatcaaa ttgtagccat gctggagcct ctttcacttg cttacctgca gctgagggat  10200
ataacagtag aactcagagg tgctttcctt aaccactgct ttactgaaat acatgatgtt  10260
cttgaccaaa acgggttttc tgatgaaggt acttatcatg agttaactga agctctagat  10320
tacattttca taactgatga catacatctg acaggggaga ttttctcatt tttcagaagt  10380
ttcggccacc ccagacttga agcagtaacg gctgctgaaa atgttaggaa atacatgaat  10440
cagcctaaag tcattgtgta tgagactctg atgaaaggtc atgccatatt ttgtggaatc  10500
ataatcaacg gctatcgtga caggcacgga ggcagttggc caccgctgac cctcccccctg 10560
catgctgcag acacaatccg gaatgctcaa gcttcaggtg aagggttaac acatgagcag  10620
tgcgttgata actggaaatc ttttgctgga gtgaaatttg gctgctttat gcctcttagc  10680
ctggatagtg atctgacaat gtacctaaag gacaaggcac ttgctgctct ccaaagggaa  10740
tgggattcag tttacccgaa agagttcctg cgttacgacc ctcccaaggg aaccgggtca  10800
cggaggcttg tagatgtttt ccttaatgat tcgagctttg acccatatga tgtgataatg  10860
tatgttgtaa gtggagctta cctccatgac cctgagttca acctgtctta cagcctgaaa  10920
gaaaaggaga tcaaggaaac aggtagactt tttgctaaaa tgacttacaa aatgagggca  10980
tgccaagtga ttgctgaaaa tctaatctca aacgggattg gcaaatattt taaggacaat  11040
gggatggcca aggatgagca cgatttgact aaggcactcc acactctagc tgtctcagga  11100
gtccccaaag atctcaaaga aagtcacagg ggggggccag tcttaaaaac ctactcccga  11160
agcccagtcc acacaagtac caggaacgtg agagcagcaa aagggtttat agggttccct  11220
caagtaattc ggcaggacca agacactgat catccggaga atatggaagc ttacgagaca  11280
gtcagtgcat ttatcacgac tgatctcaag aagtactgcc ttaattggag atatgagacc  11340
atcagcttgt ttgcacagag gctaaatgag atttacggat tgccctcatt tttccagtgg  11400
ctgcataaga ggcttgagac ctctgtcctg tatgtaagtg accctcattg cccccccgac  11460
cttgacgccc atatcccgtt atataaagtc cccaatgatc aaatcttcat taagtaccct  11520
atgggaggta tagaagggta ttgtcagaag ctgtggacca tcagcaccat tccctatcta  11580
tacctggctg cttatgagag cggagtaagg attgcttcgt tagtgcaagg ggacaatcag  11640
accatagccg taacaaaaag ggtacccagc acatggccct acaaccttaa gaaacgggaa  11700
gctgctagag taactagaga ttactttgta attcttaggc aaaggctaca tgatattggc  11760
catcacctca aggcaaatga gacaattgtt tcatcacatt tttttgtcta ttcaaaagga  11820
atatattatg atgggctact tgtgtcccaa tcactcaaga gcatcgcaag atgtgtattc  11880
tggtcagaga ctatagttga tgaaacaagg gcagcatgca gtaatattgc tacaacaatg  11940
gctaaaagca tcgagagagg ttatgaccgt taccttgcat attccctgaa cgtcctaaaa  12000
gtgatacagc aaattctgat ctctcttggc ttcacaatca attcaaccat gacccgggat  12060
gtagtcatac ccctcctcac aaacaacgac ctcttaataa ggatggcact gttgcccgct  12120
```

```
cctattgggg ggatgaatta tctgaatatg agcaggctgt ttgtcagaaa catcggtgat  12180
ccagtaacat catcaattgc tgatctcaag agaatgattc tcgcctcact aatgcctgaa  12240
gagaccctcc atcaagtaat gacacaacaa ccgggggact cttcattcct agactgggct  12300
agcgaccctt actcagcaaa tcttgtatgt gtccagagca tcactagact cctcaagaac  12360
ataactgcaa ggtttgtcct gatccatagt ccaaacccaa tgttaaaagg attattccat  12420
gatgacagta aagaagagga cgagggactg gcggcattcc tcatggacag gcatattata  12480
gtacctaggg cagctcatga aatcctggat catagtgtca caggggcaag agagtctatt  12540
gcaggcatgc tggataccac aaaaggcttg attcgagcca gcatgaggaa ggggggggtta  12600
acctctcgag tgataaccag attgtccaat tatgactatg aacaattcag agcagggatg  12660
gtgctattga caggaagaaa gagaaatgtc ctcattgaca aagagtcatg ttcagtgcag  12720
ctggcgagag ctctaagaag ccatatgtgg gcgaggctag ctcgaggacg gcctatttac  12780
ggccttgagg tccctgatgt actagaatct atgcgaggcc accttattcg gcgtcatgag  12840
acatgtgtca tctgcgagtg tggatcagtc aactacggat ggtttttttgt cccctcgggt  12900
tgccaactgg atgatattga caaggaaaca tcatccttga gagtcccata tattggttct  12960
accactgatg agagaacaga catgaagctt gccttcgtaa gagccccaag tcgatccttg  13020
cgatctgctg ttagaatagc aacagtgtac tcatgggctt acggtgatga tgatagctct  13080
tggaacgaag cctggttgtt ggctaggcaa agggccaatg tgagcctgga ggagctaagg  13140
gtgatcactc ccatctcaac ttcgactaat ttagcgcata ggttgaggga tcgtagcact  13200
caagtgaaat actcaggtac atcccttgtc cgagtggcga ggtataccac aatctccaac  13260
gacaatctct catttgtcat atcagataag aaggttgata ctaactttat ataccaacaa  13320
ggaatgcttc tagggttggg tgttttagaa acattgtttc gactcgagaa agataccgga  13380
tcatctaaca cggtattaca tcttcacgtc gaaacagatt gttgcgtgat cccgatgata  13440
gatcatccca ggatacccag ctcccgcaag ctagagctga gggcagagct atgtaccaac  13500
ccattgatat atgataatgc acctttaatt gacagagatg caacaaggct atacacccag  13560
agccatagga ggcaccttgt ggaatttgtt acatggtcca caccccaact atatcacatt  13620
ttagctaagt ccacagcact atctatgatt gacctggtaa caaaatttga gaaggaccat  13680
atgaatgaaa tttcagctct catagggggat gacgatatca atagtttcat aactgagttt  13740
ctgctcatag agccaagatt attcactatc tacttgggcc agtgtgcggc catcaattgg  13800
gcatttgatg tacattatca tagaccatca gggaaatatc agatgggtga gctgttgtca  13860
tcgttccttt ctagaatgag caaaggagtg tttaaggtgc ttgtcaatgc tctaagccac  13920
ccaaagatct acaagaaatt ctggcattgt ggtattatag agcctatcca tggtccttca  13980
cttgatgctc aaaacttgca cacaactgtg tgcaacatgg tttacacatg ctatatgacc  14040
tacctcgacc tgttgttgaa tgaagagtta gaagagttca catttctctt gtgtgaaagc  14100
gacgaggatg tagtaccgga cagattcgac aacatccagg caaaacactt atgtgttctg  14160
gcagatttgt actgtcaacc agggacctgc ccaccaattc gaggtctaag accggtagag  14220
aaatgtgcag ttctaaccga ccatatcaag gcagaggcta tgttatctcc agcaggatct  14280
tcgtggaaca taaatccaat tattgtagac cattactcat gctctctgac ttatctccgg  14340
cgaggatcga tcaaacagat aagattgaga gttgatccag gattcatttt cgacgccctc  14400
gctgaggtaa atgtcagtca gccaaagatc ggcagcaaca acatctcaaa tatgagcatc  14460
aaggctttca gacccccaca cgatgatgtt gcaaaattgc tcaaagatat caacacaagc  14520
```

```
aagcacaatc ttcccatttc agggggcaat ctcgccaatt atgaaatcca tgctttccgc  14580
agaatcgggt tgaactcatc tgcttgctac aaagctgttg agatatcaac attaattagg  14640
agatgccttg agccagggga ggacggcttg ttcttgggtg agggatcggg ttctatgttg  14700
atcacttata aagagatact taaactaaac aagtgcttct ataatagtgg ggtttccgcc  14760
aattctagat ctggtcaaag ggaattagca ccctatccct ccgaagttgg ccttgtcgaa  14820
cacagaatgg gagtaggtaa tattgtcaaa gtgctcttta acgggaggcc cgaagtcacg  14880
tgggtaggca gtgtagattg cttcaatttc atagttagta atatccctac ctctagtgtg  14940
gggtttatcc attcagatat agagaccttg cctgacaaag atactataga gaagctagag  15000
gaattggcag ccatcttatc gatggctctg ctcctgggca aaataggatc aatactggtg  15060
attaagctta tgcctttcag cggggatttt gttcagggat ttataagtta tgtagggtct  15120
cattatagag aagtgaacct tgtataccct agatacagca acttcatctc tactgaatct  15180
tatttggtta tgacagatct caaggctaac cggctaatga atcctgaaaa gattaagcag  15240
cagataattg aatcatctgt gaggacttca cctggactta taggtcacat cctatccatt  15300
aagcaactaa gctgcataca agcaattgtg ggagacgcag ttagtagagg tgatatcaat  15360
cctactctga aaaaacttac acctatagag caggtgctga tcaattgcgg gttggcaatt  15420
aacggaccta agctgtgcaa agaattgatc caccatgatg ttgcctcagg gcaagatgga  15480
ttgcttaatt ctatactcat cctctacagg gagttggcaa gattcaaaga caaccaaaga  15540
agtcaacaag ggatgttcca cgcttacccc gtattggtaa gtagcaggca acgagaactt  15600
atatctagga tcacccgcaa attctggggg cacattcttc tttactccgg gaacaaaaag  15660
ttgataaata agtttatcca gaatctcaag tccggctatc tgatactaga cttacaccag  15720
aatatcttcg ttaagaatct atccaagtca gagaaacaga ttattatgac ggggggtttg  15780
aaacgtgagt gggtttttaa ggtaacagtc aaggagacca aagaatggta taagttagtc  15840
ggatacagtg ccctgattaa ggactaattg gttgaactcc ggaaccctaa tcctgcccta  15900
ggtggttagg cattatttgc aatatattaa agaaaacttt gaaaatacga agtttctatt  15960
cccagctttg tctggtggcc ggcatggtcc cagcctcctc gctggcgccg gctgggcaac  16020
attccgaggg gaccgtcccc tcggtaatgg cgaatgggac gcggccgatc cggctgctaa  16080
caaagcccga aaggaagctg agttggctgc tgccaccgct gagcaataac tagcataacc  16140
ccttggggcc tctaaacggg tcttgagggg ttttttgctg aaaggaggaa ctatatccgg  16200
atgcggccgc gggccctatg gtacccagct tttgttccct ttagtgaggg ttaattccga  16260
gcttggcgta atcatggtca tagctgtttc ctgtgtgaaa ttgttatccg ctcacaattc  16320
cacacaacat aggagccgga agcataaagt gtaaagcctg gggtgcctaa tgagtgaggt  16380
aactcacatt aattgcgttg cgctcactgc ccgctttcca gtcgggaaac ctgtcgtgcc  16440
agctgcatta atgaatcggc caacgcgcgg ggagaggcgg tttgcgtatt gggcgctctt  16500
ccgcttcctc gctcactgac tcgctgcgct cggtcgttcg gctgcggcga gcggtatcag  16560
ctcactcaaa ggcggtaata cggttatcca cagaatcagg ggataacgca ggaaagaaca  16620
tgtgagcaaa aggccagcaa aaggccagga accgtaaaaa ggccgcgttg ctggcgtttt  16680
tccataggct ccgcccccct gacgagcatc acaaaaatcg acgctcaagt cagaggtggc  16740
gaaacccgac aggactataa agataccagg cgtttccccc tggaagctcc ctcgtgcgct  16800
ctcctgttcc gaccctgccg cttaccggat acctgtccgc ctttctccct tcgggaagcg  16860
```

```
tggcgctttc tcaatgctca cgctgtaggt atctcagttc ggtgtaggtc gttcgctcca  16920
agctgggctg tgtgcacgaa ccccccgttc agcccgaccg ctgcgcctta tccggtaact  16980
atcgtcttga gtccaacccg gtaagacacg acttatcgcc actggcagca gccactggta  17040
acaggattag cagagcgagg tatgtaggcg gtgctacaga gttcttgaag tggtggccta  17100
actacggcta cactagaagg acagtatttg gtatctgcgc tctgctgaag ccagttacct  17160
tcggaaaaag agttggtagc tcttgatccg gcaaacaaac caccgctggt agcggtggtt  17220
tttttgtttg caagcagcag attacgcgca gaaaaaaagg atctcaagaa gatcctttga  17280
tcttttctac ggggtctgac gctcagtgga acgaaaactc acgttaaggg attttggtca  17340
tgagattatc aaaaaggatc ttcacctaga tccttttaaa ttaaaaatga agttttaaat  17400
caatctaaag tatatatgag taaacttggt ctgacagtta ccaatgctta atcagtgagg  17460
cacctatctc agcgatctgt ctatttcgtt catccatagt tgcctgactg cccgtcgtgt  17520
agataactac gatacgggag ggcttaccat ctggccccag tgctgcaatg ataccgcgag  17580
acccacgctc accggctcca gatttatcag caataaacca gccagccgga agggccgagc  17640
gcagaagtgg tcctgcaact ttatccgcct ccatccagtc tattaattgt tgccgggaag  17700
ctagagtaag tagttcgcca gttaatagtt tgcgcaacgt tgttgccatt gctacaggca  17760
tcgtggtgtc acgctcgtcg tttggtatgg cttcattcag ctccggttcc caacgatcaa  17820
ggcgagttac atgatccccc atgttgtgaa aaaaagcggt tagctccttc ggtcctccga  17880
tcgttgtcag aagtaagttg gccgcagtgt tatcactcat gcttatggca gcactgcata  17940
attctcttac tgtcatgcca tccgtaagat gcttttctgt gactggtgag tactcaacca  18000
agtcattctg agaatagtgt atgcggcgac cgagttgctc ttgcccggcg tcaatacggg  18060
ataataccgc gccacatagc agaactttaa aagtgctcat cattggaaaa cgttcttcgg  18120
ggcgaaaact ctcaaggatc ttaccgctgt tgagatccag ttcgatgtaa cccactcgtg  18180
cacccaactg atcttcagca tcttttactt tcaccagcgt ttctgggtga gcaaaaacag  18240
gaaggcaaaa tgccgcaaaa aagggaataa gggcgacacg gaaatgttga atactcatac  18300
tcttcctttt tcaatattat tgaagcattt atcagggtta ttgtctcatg agcggataca  18360
tatttgaatg tatttagaaa aataaacaaa taggggttcc gcgcacattt ccccgaaaag  18420
tgccacctga aattgtaaac gttaatattt tgttaaaatt cgcgttaaat ttttgttaaa  18480
tcagctcatt ttttaaccaa taggccgaaa tcggcaaaat cccttataaa tcaaaagaat  18540
agaccgagat agggttgagt gttgttccag tttggaacaa gagtccacta ttaaagaacg  18600
tggactccaa cgtcaaaggg cgaaaaaccg tctatcaggg cgatggccca ctacgtgaac  18660
catcacccta atcaagtttt ttggggtcga ggtgccgtaa agcactaaat cggaacccta  18720
aagggagccc ccgatttaga gcttgacggg gaaagccggc gaacgtggcg agaaaggaag  18780
ggaagaaagc gaaaggagcg ggcgctaggg cgctggcaag tgtagcggtc acgctgcgcg  18840
taaccaccac acccgccgcg cttaatgcgc cgctacaggg cgcgtcccat tcgccattca  18900
ggctgcgcaa ctgttgggaa gggcgatcgg tgcgggcctc ttcgctatta cgccagccac  18960
cgcggtg                                                            18967
```

<210> SEQ ID NO 16
<211> LENGTH: 115
<212> TYPE: DNA
<213> ORGANISM: Artificial Sequence
<220> FEATURE:
<223> OTHER INFORMATION: ATU sequence without insert

```
<400> SEQUENCE: 16

cttaggaacc aggtccacac agccgccagc ccatcaacgc gtacgatgta ggcgcgcagc     60

gcttagacgt ctcgcgatcg atactagtac aacctaaatc cattataaaa aactt         115


<210> SEQ ID NO 17
<211> LENGTH: 1591
<212> TYPE: DNA
<213> ORGANISM: Artificial Sequence
<220> FEATURE:
<223> OTHER INFORMATION: ATU sequence with codon-optimized cDNA GPC
      insert

<400> SEQUENCE: 17

cttaggaacc aggtccacac agccgccagc ccatcaacgc gtacgatgat gggccagatt     60

gtcacattct ttcaggaagt gccacacgtc attgaggagg tcatgaacat cgtgctgatt    120

gctctgtcag tgctggcagt gctgaaagga ctgtacaact tcgctacctg tggactggtg    180

ggactggtca cattcctgct gctgtgcggc agaagttgca ctacctcact gtacaaagga    240

gtgtacgagc tgcagactct ggaactgaac atggagacac tgaatatgac aatgcctctg    300

agctgcacca agaataatag ccaccactat atcatggtcg ggaacgaaac cggcctggaa    360

ctgaccctga caaacaccag catcattaac cacaagttct gcaatctgag cgacgctcac    420

aagaagaacc tgtatgacca cgctctgatg tccatcatca gtacctttca cctgtccatc    480

cccaatttca accagtacga ggcaatgtca tgcgacttca acgggggcaa gatcagtgtc    540

cagtacaacc tgagccactc ctacgccggc gacgcagcca accactgcgg aactgtcgcc    600

aatggcgtgc tgcagacatt catgaggatg gcatgggggg gatcttacat cgcactggat    660

agcggcaggg gcaattggga ttgcatcatg acttcctatc agtatctgat tatccagaat    720

actacatggg aggatcattg ccagttcagt cggcccagcc ctattggata tctggggctg    780

ctgtcacaga gaacacggga tatctatatt tcaagacgcc tgctgggcac attcacttgg    840

acactgtcag acagtgaggg caaggatact ccagggggct actgcctgac acgatggatg    900

ctgatcgaag cagagctgaa atgcttcggc aataccgcag tggccaagtg caacgagaaa    960

cacgacgagg agttctgcga catgctgagg ctgttcgact tcaacaaaca ggctatccag   1020

agactgaagg cagaagccca gatgtcaatc cagctgatca acaaggcagt gaacgccctg   1080

atcaacgacc agctgatcat gaagaaccac ctgagagaca ttatgggcat cccctactgt   1140

aattacagca agtattggta cctgaaccac actacaaccg ggagaacatc cctgcccaag   1200

tgctggctgg tcagcaatgg gagttatctg aatgaaaccc atttcagcga cgatatcgaa   1260

cagcaggctg acaacatgat cacagagatg ctgcagaaag agtacatgga aagacagggc   1320

aagacaccac tgggactggt cgatctgttc gtcttctcca ctagcttcta tctgatttcc   1380

atcttcctgc acctggtgaa gatccccact cataggcaca ttgtcggcaa gagttgccct   1440

aaaccccata ggctgaatca catggggatt tgtagttgcg gcctgtataa gcagcctggc   1500

gtgcctgtga aatggaagag atgataggcg cgcagcgctt agacgtctcg cgatcgatac   1560

tagtacaacc taaatccatt ataaaaaact t                                  1591
```